US012588644B2

(12) United States Patent
Frijters et al.

(10) Patent No.: US 12,588,644 B2
(45) Date of Patent: Mar. 31, 2026

(54) ROOT-KNOT NEMATODE RESISTANCE CONFERRING GENE

(71) Applicant: RIJK ZWAAN ZAADTEELT EN ZAADHANDEL B.V., De Lier (NL)

(72) Inventors: Raoul Jacobus Johannes Maria Frijters, De Lier (NL); Jonathan Kalisvaart, De Lier (NL); Adriaan Verhage, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 240 days.

(21) Appl. No.: 18/064,456

(22) Filed: Dec. 12, 2022

(65) Prior Publication Data

US 2023/0287062 A1      Sep. 14, 2023

Related U.S. Application Data

(63) Continuation-in-part of application No. PCT/EP2021/066682, filed on Jun. 18, 2021.

(30) Foreign Application Priority Data

Jun. 18, 2020    (WO) ................ PCT/EP2020/067028

(51) Int. Cl.
    *A01H 6/82*       (2018.01)
    *A01H 1/00*       (2006.01)
(52) U.S. Cl.
    CPC ........... *A01H 6/825* (2018.05); *A01H 1/1265* (2021.01)
(58) Field of Classification Search
    CPC .... C07K 14/415; A01H 1/1265; A01H 6/825; C12Q 1/6895; C12Q 2600/13; Y02A 40/146; C12N 15/8269
    See application file for complete search history.

(56) References Cited

FOREIGN PATENT DOCUMENTS

CN        102 268 482 B        1/2013
WO          01/94601 A2       12/2001
WO      WO-2019108619 A1 *     6/2019

OTHER PUBLICATIONS

Lüdke, Daniel et al. A root-specific NLR network confers resistance to plant parasitic nematodes, 2023, bioRxiv 2023.12.14.571630 (Year: 2023) (Year: 2023).*

Sharma et al., A Solanum lycopersicum x Solanum pimpinellifolium linkage map of tomato displaying genomic locations of R-genes, RGAs, and candidate resistance/defense-response ESTs., 2008 International journal of plant genomics vol. 926090 (Year: 2008) (Year: 2008).*

Falk, Duane E. Generating and maintaining diversity at the elite level in crop breeding. (2010) Genome vol. 53, 11 : 982-91. (Year: 2010).*

Pinheiro, J. B et al., "Resistance Sources to Root-Knot Nematode Meloidogyne Enterolobii in *Solanum* Species". Emirates Journal of Food and Agriculture, vol. 32, No. 4, Apr. 2020, pp. 303-308, (Year: 2020).*

Förderer, Alexander, and Jiorgos Kourelis. "NLR immune receptors: structure and function in plant disease resistance." Biochemical Society transactions vol. 51,4 (2023): 1473-1483. doi:10.1042/BST20221087 (Year: 2023).*

S. Seah, et al., The nematode-resistance gene, Mi-1, is associated with an inverted chromosomal segment in susceptible compared to resistant tomato, Theor Appl Genet (2004) 108:1635-1642.

Sergio Molinari, Natural genetic and induced plant resistance, as a control strategy to plant-parasitic nematodes alternative to pesticides, Plant Cell Rep (2011) 30:31 1-323.

International Search Report and Written Opinion issued Sep. 22, 2001 in Int'l App. No. PCT/EP2021/066682.

Alysson J. da Silva, et al., Search for sources of resistance to Meloidogyne enterolobii in commercial and wild tomatoes, Hortic, bras., Brasilia (Apr.-Jun. 2019) vol. 37, No. 2, p. 188-198.

Chih-Hang Wu, et al., NLR network mediates immunity to diverse plant pathogens, PNAS (Jul. 25, 2017) vol. 114, No. 30, p. 8113-8118.

English translation of JP Office Action mailed Apr. 1, 2025 in co-pending JP Application No. 2022-578622.

* cited by examiner

*Primary Examiner* — Amjad Abraham
*Assistant Examiner* — Christian Jose Ordaz
(74) *Attorney, Agent, or Firm* — Duane Morris LLP; Thomas J. Kowalski

(57)        ABSTRACT

A nucleic acid encoding an MeR1 protein, which confers resistance to root-knot nematode when present in a Solanaceae plant is provided. Said nucleic acid has a nucleotide sequence that may comprise a coding sequence according to SEQ ID NO: 2, 3, 4, 5, 6, 7, 8 or 9, or a coding sequence having at least 90% sequence identity with SEQ ID NO: 2, 3, 4, 5, 6, 7, 8 or 9; or a nucleotide sequence encoding a protein having an amino acid sequence according to SEQ ID NO: 10, 11, 12, 13, 14, 15, 16 or 17, or a protein having an amino acid sequence having at least 85% sequence identity with SEQ ID NO: 10, 11, 12, 13, 14, 15, 16 or 17. The invention further relates to plants and seeds which may comprise the nucleic acid, methods for making and identifying such plants and use of the nucleic acid.

18 Claims, 1 Drawing Sheet
Specification includes a Sequence Listing.

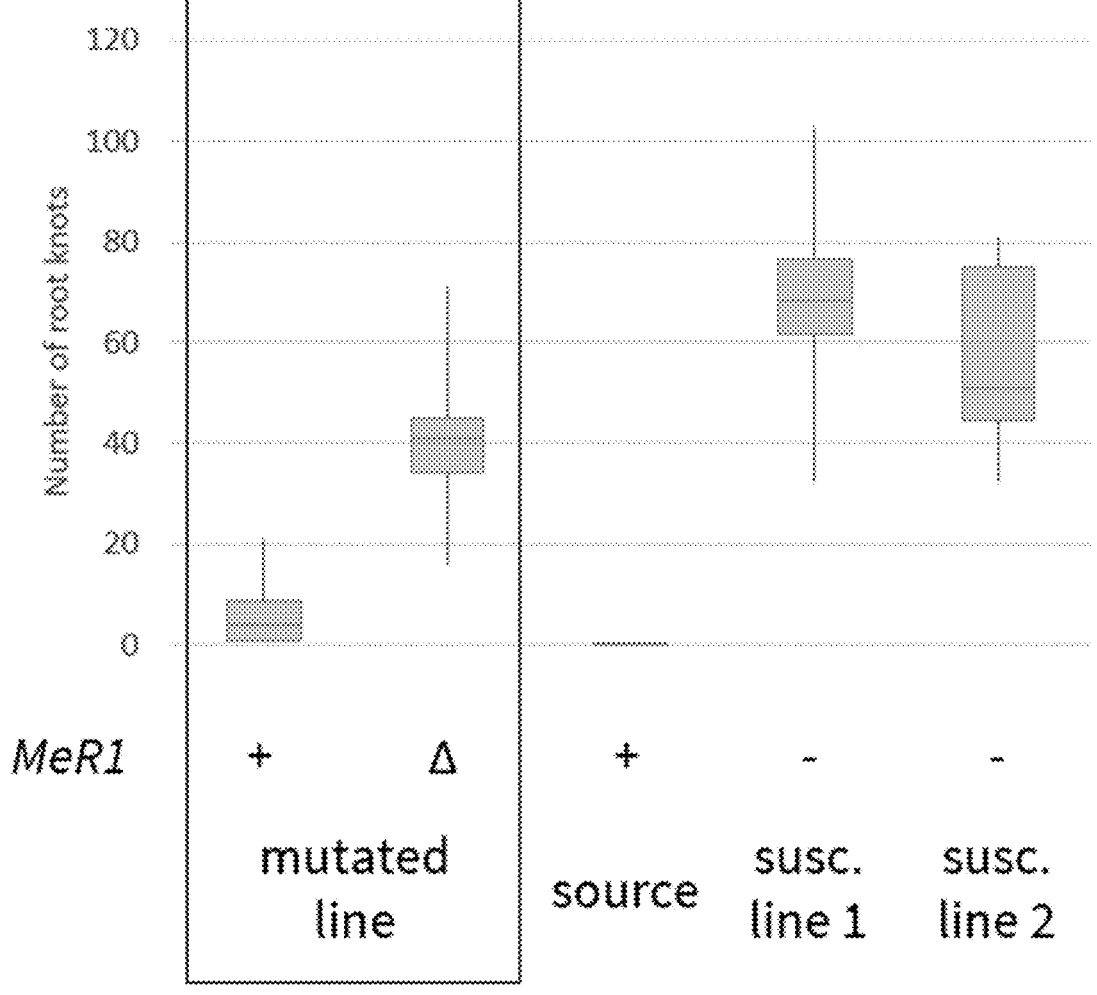

ROOT-KNOT NEMATODE RESISTANCE CONFERRING GENE

RELATED APPLICATIONS AND INCORPORATION BY REFERENCE

This application is a continuation-in-part application of international patent application Serial No. PCT/EP2021/066682 filed 18 Jun. 2021, which published as PCT Publication No. WO 2021/255272 on 23 Dec. 2021, which claims benefit of international patent application Serial No. PCT/EP2020/067028 filed 18 Jun. 2020.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing, which has been submitted electronically and is hereby incorporated by reference in its entirety. Said XML copy, was created Dec. 9, 2022, is named Y7954_00560SL.xml and is 120,906 bytes in size.

FIELD OF THE INVENTION

The present invention relates to a nucleic acid molecule providing resistance to a root-knot nematode and to a root-knot nematode resistant plant of the Solanaceae family which may comprise the nucleic acid molecule(s), and a method for the identification of the presence of the nucleic acid molecule(s) in a plant. The invention further relates to a method for producing such plant and methods for identification and selection of such a plant. The invention also relates to a seed of the root-knot nematode resistant plant of the Solanaceae family.

BACKGROUND OF THE INVENTION

One of the problems that is encountered when growing plants of the Solanaceae family is the occurrence of various plant parasitic nematodes. A number of resistance genes against some nematode species have been identified, which resistances are incorporated in suitable varieties through breeding. This allows the growers to obtain a good yield even when a certain nematode is present during production.

Regularly, however, new nematodes or strains of known nematodes are identified, that in certain instances can break the available resistance. For instance in tomato (*Solanum lycopersicum*) the known Mi1-2 resistance gene confers resistance against some nematodes, but not against the root-knot nematode *Meloidogyne enterolobii* (*M. enterolobii*).

Citation or identification of any document in this application is not an admission that such document is available as prior art to the present invention.

SUMMARY OF THE INVENTION

The nematodes to which the invention relates use the plant root for their life and therefore the infection by root-knot nematodes such as *M. enterolobii* leads to root galls that can lead to the death of the infected plant or to a reduction of yield.

Surprisingly, it was found after extensive research that an NBS-LRR gene, herein called MeR1 (*Meloidogyne enterolobii* resistant 1) is expressed in the root and is responsible for the resistance to a root-knot nematode in a plant of the Solanaceae family.

The invention relates to a nucleic acid molecule encoding an MeR1 protein, which confers resistance to root-knot nematode, in particular to *M. enterolobii*, when present in a plant of the Solanaceae family, in particular in a *Solanum lycopersicum* plant, wherein said nucleic acid molecule has a nucleotide sequence which is:

a) a nucleotide sequence which may comprise a coding sequence according to SEQ ID NO: 2, 3, 4, 5, 6, 7, 8 or 9, or a coding sequence which has in order of increased preference 90%, 91%, 92%, 93%, 94%, 95%, 96%, 97%, 98%, 99% sequence identity with the sequence according to SEQ ID NO: 2, 3, 4, 5, 6, 7, 8 or 9; or b) a nucleotide sequence encoding a protein having an amino acid sequence according to SEQ ID NO: 10, 11, 12, 13, 14, 15, 16 or 17, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 10, 11, 12, 13, 14, 15, 16 or 17.

The invention relates in particular to a nucleic acid molecule encoding an MeR1 protein, which confers resistance to root-knot nematode, in particular to *M. enterolobii*, when present in a plant of the Solanaceae family, in particular in a *Solanum lycopersicum* plant, wherein said nucleic acid molecule has a nucleotide sequence which is:

a) a nucleotide sequence which may comprise a coding sequence according to SEQ ID NO: 2, or a coding sequence which has in order of increased preference 90%, 91%, 92%, 93%, 94%, 95%, 96%, 97%, 98%, 99% sequence identity with the sequence according to SEQ ID NO: 2; or b) a nucleotide sequence encoding a protein having an amino acid sequence according to SEQ ID NO: 10, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 10; or a) a nucleotide sequence which may comprise a coding sequence according to SEQ ID NO: 3, or a coding sequence which has in order of increased preference 90%, 91%, 92%, 93%, 94%, 95%, 96%, 97%, 98%, 99% sequence identity with the sequence according to SEQ ID NO: 3; or b) a nucleotide sequence encoding a protein having an amino acid sequence according to SEQ ID NO: 11, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 11; or a) a nucleotide sequence which may comprise a coding sequence according to SEQ ID NO: 4, or a coding sequence which has in order of increased preference 90%, 91%, 92%, 93%, 94%, 95%, 96%, 97%, 98%, 99% sequence identity with the sequence according to SEQ ID NO: 4; or b) a nucleotide sequence encoding a protein having an amino acid sequence according to SEQ ID NO: 12, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 12; or a) a nucleotide sequence which may comprise a coding sequence according to SEQ ID NO: 5, or a coding sequence which has in order of increased preference 90%, 91%, 92%, 93%, 94%, 95%, 96%, 97%, 98%, 99% sequence identity with the sequence according to SEQ ID NO: 5; or b) a nucleotide sequence encoding a protein having an amino acid sequence according to SEQ ID NO: 13, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 13; or a) a nucleotide sequence which may comprise a coding sequence according to SEQ ID NO: 6, or a coding sequence which has in order of increased preference 90%, 91%, 92%, 93%, 94%, 95%, 96%, 97%, 98%, 99% sequence identity with the sequence according to SEQ ID NO: 6; or b) a nucleotide sequence encoding a protein having an amino acid sequence according to SEQ ID NO: 14, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 14; or a) a nucleotide sequence which may comprise a coding sequence according to SEQ ID NO: 7, or a coding sequence which has in order of increased preference 90%, 91%, 92%, 93%, 94%, 95%, 96%, 97%, 98%, 99% sequence identity with the sequence according to SEQ ID NO: 7; or b) a nucleotide sequence encoding a protein having an amino acid sequence according to SEQ ID NO: 15, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 15; or a) a nucleotide sequence which may comprise a coding sequence according to SEQ ID NO: 8, or a coding sequence which has in order of increased preference 90%, 91%, 92%, 93%, 94%, 95%, 96%, 97%, 98%, 99% sequence identity with the sequence according to SEQ ID NO: 8; or b) a nucleotide sequence encoding a protein having an amino acid sequence according to SEQ ID NO: 16, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 16; or a) a nucleotide sequence which may comprise a coding sequence according to SEQ ID NO: 9, or a coding sequence which has in order of increased preference 90%, 91%, 92%, 93%, 94%, 95%, 96%, 97%, 98%, 99% sequence identity with the sequence according to SEQ ID NO: 9; or b) a nucleotide sequence encoding a protein having an amino acid sequence according to SEQ ID NO: 17, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 17.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposit

Seed of tomato *Solanum lycopersicum* comprising the nucleic acid molecules of the invention homozygously, resulting in a *M. enterolobii* resistant plant, was deposited with NCIMB Ltd, Ferguson Building, Craibstone Estate, Bucksburn, Aberdeen AB21 9YA, UK on Nov. 18, 2019, under deposit accession numbers NCIMB 43515.

The Deposits with NCIMB Ltd, under deposit accession number NCIMB 43515 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Results of the *M. enterolobii* disease testing of plants with a modified MeR1 gene of the invention; Amount of root knots on the source, susceptible line 1 and 2 and the mutated lines with the deletion leading to a non-functional MeR1 gene (A) and without the deletion with a functional MeR1 gene (+).

DETAILED DESCRIPTION OF THE INVENTION

During the research leading to the invention it has been found that the MeR1 gene which may comprise the nucleic acid molecule having the genomic sequence according to SEQ ID NO: 1 was found in wild tomato species, in particular in *Solanum* pimpinellifolium species. When this nucleic acid molecule was transferred to a root-knot nematode susceptible *Solanum lycopersicum* plant, the *Solanum lycopersicum* plant became resistant to the root-knot nematode, in particular to *M. enterolobii*. Therefore, the MeR1 gene is capable of encoding a protein which confers resistance to a root-knot nematode to a plant of the Solanaceae family. In particular, the MeR1 gene is capable of encoding a protein which confers resistance to *M. enterolobii* to a *Solanum lycopersicum* plant. The genomic sequence which may comprise SEQ ID NO: 1 leads to 8 different isoforms which may comprise the coding sequence (CDS sequence) selected from the group consisting of SEQ ID Nos. 2, 3, 4, 5, 6, 7, 8 and 9. The isoforms are different splice variants of the gene. After splicing the genomic sequence which may comprise SEQ ID NO: 1 of the MeR1 gene of the invention leads to the 8 different isoforms which may comprise the coding sequence (CDS sequence) of the MeR1 gene of the invention selected from the group consisting of SEQ ID Nos. 2, 3, 4, 5, 6, 7, 8 and 9. These CDS sequences encode a protein which may comprise the amino acid sequence selected from the group consisting of SEQ ID Nos 10, 11, 12, 13, 14, 15, 16 and 17; SEQ ID NO: 2 encodes the MeR1 protein with an amino acid sequence which may comprise SEQ ID NO: 10, SEQ ID NO: 3 encodes the MeR1 protein with an amino acid sequence which may comprise SEQ ID NO: 11, SEQ ID NO: 4 encodes the MeR1 protein with an amino acid sequence which may comprise SEQ ID NO: 12, SEQ ID NO: 5 encodes the MeR1 protein with an amino acid sequence which may comprise SEQ ID NO: 13, SEQ ID NO: 6 encodes the MeR1 protein with an amino acid sequence which may comprise SEQ ID NO: 14, SEQ ID NO: 7 encodes the MeR1 protein with an amino acid sequence which may comprise SEQ ID NO: 15, SEQ ID NO: 8 encodes the MeR1 protein with an amino acid sequence which may comprise SEQ ID NO: 16 and SEQ ID NO: 9 encodes the MeR1 protein with an amino acid sequence which may comprise SEQ ID NO: 17.

During the research leading to the invention it was found that the MeR1 gene of the invention segregates together with another resistance gene called NRL (Nucleotide-binding domain and leucine-rich repeat) required for cell death 6 (NRC6). The genome of a *Solanum lycopersicum* plant can comprise one or more NRC6 gene(s) herein called NRC6-

2a, NRC6-2b etc. The nucleic acid molecules NRC6-2a, NRC6-2c, NRC6-2b, NRC6-3 and NRC6-1a are alleles of the NRC6 gene which encode a protein which when present with the MeR1 gene of the invention contributes to resistance to a root-knot nematode to a plant of the Solanaceae family. The nucleic acid molecule NRC6-2a which may comprise the genomic sequence according to SEQ ID NO: 18, encodes a protein which when present with the MeR1 gene of the invention contributes to resistance to a root-knot nematode within a plant of the Solanaceae family. The CDS sequence of the NRC6-2a allele of the invention may comprise SEQ ID NO: 19 and encodes the NRC6 protein with the amino acid sequence which may comprise SEQ ID NO: 20. The nucleic acid molecule NRC6-2c which may comprise the genomic sequence according to SEQ ID NO: 21 encodes a protein which when present with the MeR1 gene of the invention contributes to resistance to a root-knot nematode to a plant of the Solanaceae family. The CDS sequence of the NRC6-2c allele of the invention may comprise SEQ ID NO: 22 and encodes the NRC6 protein with the amino acid sequence which may comprise SEQ ID NO: 23. The nucleic acid molecule NRC6-2b which may comprise the CDS sequence according to SEQ ID NO: 24 encodes an NRC6 protein with the amino acid sequence which may comprise SEQ ID NO: 25, which when present with the MeR1 gene of the invention contributes to resistance to a root-knot nematode to a plant of the Solanaceae family. The nucleic acid molecule NRC6-3 which may comprise the CDS sequence according to SEQ ID NO: 26 encodes an NRC6 protein with the amino acid sequence which may comprise SEQ ID NO: 27, which when present with the MeR1 gene of the invention contributes to resistance to a root-knot nematode to a plant of the Solanaceae family. The nucleic acid molecule NRC6-la which may comprise the CDS sequence according to SEQ ID NO: 28 encodes an NRC6 protein with the amino acid sequence which may comprise SEQ ID NO: 29, which when present with the MeR1 gene of the invention contributes to resistance to a root-knot nematode to a plant of the Solanaceae family.

The invention further relates to a nucleic acid molecule encoding a NRC6 protein, which contributes to resistance to root-knot nematode, in particular to *M. enterolobii*, when present in a plant of the Solanaceae family, in particular in a *Solanum lycopersicum* plant, together with the nucleic acid molecule encoding an MeR1 protein as defined above, wherein said nucleic acid molecule has a nucleotide sequence which is:

a) a nucleotide sequence which may comprise a coding sequence according to SEQ ID NO: 19, or a coding sequence having 98%, preferably 99% sequence identity with the sequence according to SEQ ID NO: 19; or b) a nucleotide sequence encoding a protein having an amino acid sequence according to SEQ ID NO: 20, or a protein having an amino acid sequence which has 98%, preferably 99% sequence identity with the amino acid sequence according to SEQ ID NO: 20.

In one embodiment the invention relates to a nucleic acid molecule encoding a NRC6 protein, which contributes to resistance to root-knot nematode, in particular to *M. enterolobii*, when present in a plant of the Solanaceae family, in particular in a *Solanum lycopersicum* plant, together with the nucleic acid molecule encoding an MeR1 protein as defined above, wherein said nucleic acid molecule has a nucleotide sequence which is:

a) a nucleotide sequence which may comprise a coding sequence according to SEQ ID NO: 22, or a coding sequence having 98%, preferably 99% sequence identity with the sequence according to SEQ ID NO: 22; or b) a nucleotide sequence encoding a protein having an amino acid sequence according to SEQ ID NO: 23, or a protein having an amino acid sequence which has 98%, preferably 99% sequence identity with the amino acid sequence according to SEQ ID NO: 23.

In a further embodiment, the invention relates to a nucleic acid molecule encoding a NRC6 protein, which contributes to resistance to root-knot nematode, in particular to *M. enterolobii*, when present in a plant of the Solanaceae family, in particular in a *Solanum lycopersicum* plant, together with the nucleic acid molecule encoding an MeR1 protein as defined above, wherein said nucleic acid molecule has a nucleotide sequence which is:

a) a nucleotide sequence which may comprise a coding sequence according to SEQ ID NO: 24, or a coding sequence having 98%, preferably 99% sequence identity with the sequence according to SEQ ID NO: 24; or b) a nucleotide sequence encoding a protein having an amino acid sequence according to SEQ ID NO: 25, or a protein having an amino acid sequence which has 98%, preferably 99% sequence identity with the amino acid sequence according to SEQ ID NO: 25.

In a further embodiment, the invention relates to a nucleic acid molecule encoding a NRC6 protein, which contributes to resistance to root-knot nematode, in particular to *M. enterolobii*, when present in a plant of the Solanaceae family, in particular in a *Solanum lycopersicum* plant, together with the nucleic acid molecule encoding an MeR1 protein as defined above, wherein said nucleic acid molecule has a nucleotide sequence which is:

a) a nucleotide sequence which may comprise a coding sequence according to SEQ ID NO: 26, or a coding sequence having 98%, preferably 99% sequence identity with the sequence according to SEQ ID NO: 26; or b) a nucleotide sequence encoding a protein having an amino acid sequence according to SEQ ID NO: 27, or a protein having an amino acid sequence which has 98%, preferably 99% sequence identity with the amino acid sequence according to SEQ ID NO: 27.

In a further embodiment, the invention relates to a nucleic acid molecule encoding a NRC6 protein, which contributes to resistance to root-knot nematode, in particular to *M. enterolobii*, when present in a plant of the Solanaceae family, in particular in a *Solanum lycopersicum* plant, together with the nucleic acid molecule encoding an MeR1 protein as defined above, wherein said nucleic acid molecule has a nucleotide sequence which is:

a) a nucleotide sequence which may comprise a coding sequence according to SEQ ID NO: 28, or a coding sequence having 98%, preferably 99% sequence identity with the sequence according to SEQ ID NO: 28; or b) a nucleotide sequence encoding a protein having an amino acid sequence according to SEQ ID NO: 29, or a protein having an amino acid sequence which has 98%, preferably 99% sequence identity with the amino acid sequence according to SEQ ID NO: 29.

The nucleic acid molecules MeR1 and NRC6 of the invention each encode an NBS-LRR protein, which is also called NLR protein, and may comprise a nucleotide binding site and a leucine rich repeat domain. In recent research, it was shown that NBS-LRR proteins in the plant often communicate with each other to induce an immunity response to a pathogen, therefore in the plant genome so called "sensor" NBS-LRR proteins exist which detect the pathogen and need a "helper" NB S-LRR to induce the immune response after binding of the pathogen effector to the sensor NLR. The genomes of the Solanaceae plants comprise numerous NBS-LRR proteins and the network is very complex. It is therefore difficult to predict if an NBS-LRR protein is a helper or a sensor protein and which NBS-LRR helper protein interacts with which NBS-LRR sensor protein(s). Recently, it has been discovered by Adachi et al. ((2019) *An N-terminal motif in NLR immune receptors is functionally conserved across distantly related plant* species; Elife. 27; 8) that the so-called helper NLR proteins comprise a specific motif: the MADA-motif (SEQ ID NO:30). When analyzing the sequences of NRC6 it was found that the encoded protein may comprise the MADA-motif and can therefore be characterized as being a helper NLR protein. The MeR1 protein does not comprise the motif and can therefore be considered as a candidate for the sensor NLR protein which is able to communicate with a helper NLR protein.

The invention also relates to a plant of the Solanaceae family, in particular a *Solanum lycopersicum* plant, which may comprise the nucleic acid molecule encoding an MeR1 protein, which confers resistance to root-knot nematode, in particular to *M. enterolobii*, when present in a plant of the Solanaceae family, wherein said nucleic acid molecule has a nucleotide sequence which is:

a) a nucleotide sequence which may comprise a coding sequence according to SEQ ID NO: 2, 3, 4, 5, 6, 7, 8 or 9, or a coding sequence which has in order of increased preference 90%, 91%, 92%, 93%, 94%, 95%, 96%, 97%, 98%, 99% sequence identity with the sequence according to SEQ ID NO: 2, 3, 4, 5, 6, 7, 8 or 9; or b) a nucleotide sequence encoding a protein having an amino acid sequence according to SEQ ID NO: 10, 11, 12, 13, 14, 15, 16 or 17, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 10, 11, 12, 13, 14, 15, 16 or 17;

and optionally at least one nucleic acid molecule encoding an NRC6-2a protein, wherein said nucleic acid molecule has a nucleotide sequence which is:

a) a nucleotide sequence which may comprise a coding sequence according to SEQ ID NO: 19, or a coding sequence having 98%, preferably 99% sequence identity with the sequence according to SEQ ID NO: 19; or b) a nucleotide sequence encoding an NRC6-2a protein having an amino acid sequence according to SEQ ID NO: 20, or a protein having an amino acid sequence which has 98%, preferably 99% sequence identity with the amino acid sequence according to SEQ ID NO: 20;

and/or a nucleic acid molecule encoding an NRC6-2c protein, wherein said nucleic acid molecule has a nucleotide sequence which is:

a) a nucleotide sequence which may comprise a coding sequence according to SEQ ID NO: 22, or a coding sequence having 98%, preferably 99% sequence identity with the sequence according to SEQ ID NO: 22; or b) a nucleotide sequence encoding an NRC6-2c protein having an amino acid sequence according to SEQ ID NO: 23, or a protein having an amino acid sequence which has 98%, preferably 99% sequence identity with the amino acid sequence according to SEQ ID NO: 23;

and/or a nucleic acid molecule encoding an NRC6-2b protein, wherein said nucleic acid molecule has a nucleotide sequence which is:

a) a nucleotide sequence which may comprise a coding sequence according to SEQ ID NO: 24, or a coding sequence having 98%, preferably 99% sequence identity with the sequence according to SEQ ID NO: 24; or b) a nucleotide sequence encoding an NRC6-2b protein having an amino acid sequence according to SEQ ID NO: 25, or a protein having an amino acid sequence which has 98%, preferably 99% sequence identity with the amino acid sequence according to SEQ ID NO: 25;

and/or a nucleic acid molecule encoding an NRC6-3 protein, wherein said nucleic acid molecule has a nucleotide sequence which is:

a) a nucleotide sequence which may comprise a coding sequence according to SEQ ID NO: 26, or a coding sequence having 98%, preferably 99% sequence identity with the sequence according to SEQ ID NO: 26; or b) a nucleotide sequence encoding an NRC6-3 protein having an amino acid sequence according to SEQ ID NO: 27, or a protein having an amino acid sequence which has 98%, preferably 99% sequence identity with the amino acid sequence according to SEQ ID NO: 27;

and/or a nucleic acid molecule encoding an NRC6-1a protein, wherein said nucleic acid molecule has a nucleotide sequence which is:

a) a nucleotide sequence which may comprise a coding sequence according to SEQ ID NO: 28, or a coding sequence having 98%, preferably 99% sequence identity with the sequence according to SEQ ID NO: 28; or b) a nucleotide sequence encoding an NRC6-1a protein having an amino acid sequence according to SEQ ID NO: 29, or a protein having an amino acid sequence which has 98%, preferably 99% sequence identity with the amino acid sequence according to SEQ ID NO: 29.

In particular, the invention relates to a plant of the Solanaceae family, in particular a *Solanum lycopersicum* plant, which may comprise a nucleic acid molecule encoding an MeR1 protein, which confers resistance to root-knot nematode, in particular to *M. enterolobii*, when present in a plant of the Solanaceae family, wherein said nucleic acid molecule has a nucleotide sequence which is:

a) a nucleotide sequence which may comprise a coding sequence according to SEQ ID NO: 2, 3, 4, 5, 6, 7, 8 or 9, or a coding sequence which has in order of increased preference 90%, 91%, 92%, 93%, 94%, 95%, 96%, 97%, 98%, 99% sequence identity with the sequence according to SEQ ID NO: 2, 3, 4, 5, 6, 7, 8 or 9; or b) a nucleotide sequence encoding a protein having an amino acid sequence according to SEQ ID NO: 10, 11, 12, 13, 14, 15, 16 or 17, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 10, 11, 12, 13, 14, 15, 16 or 17;

and a nucleic acid molecule encoding an NRC6-2a protein, wherein said nucleic acid molecule has a nucleotide sequence which is:

a) a nucleotide sequence which may comprise a coding sequence according to SEQ ID NO: 19, or a coding sequence having 98%, preferably 99% sequence identity with the sequence according to SEQ ID NO: 19; or b) a nucleotide sequence encoding an NRC6-2a protein having an amino acid sequence according to SEQ ID NO: 20, or a protein having an amino acid sequence which has 98%, preferably 99% sequence identity with the amino acid sequence according to SEQ ID NO: 20;

and a nucleic acid molecule encoding an NRC6-2c protein, wherein said nucleic acid molecule has a nucleotide sequence which is:

a) a nucleotide sequence which may comprise a coding sequence according to SEQ ID NO: 22, or a coding sequence having 98%, preferably 99% sequence identity with the sequence according to SEQ ID NO: 22; or b) a nucleotide sequence encoding an NRC6-2c protein having an amino acid sequence according to SEQ ID NO: 23, or a protein having an amino acid sequence which has 98%, preferably 99% sequence identity with the amino acid sequence according to SEQ ID NO: 23.

The invention also relates to a plant of the Solanaceae family, in particular a *Solanum lycopersicum* plant, which may comprise the nucleic acid molecule encoding an MeR1 protein as described herein, which confers resistance to root-knot nematode, in particular to *M. enterolobii*, when present in a plant of the Solanaceae family, and one NRC6 gene as described herein and selected from the group consisting of NRC6-2a, NRC6-2c, NRC6-2b, NRC6-3 and NRC6-1a.

The invention also relates to a plant of the Solanaceae family, in particular a *Solanum lycopersicum* plant, which may comprise the nucleic acid molecule encoding an MeR1 protein as described herein, which confers resistance to root-knot nematode, in particular to *M. enterolobii*, when present in a plant of the Solanaceae family, and two NRC6 genes as described herein and selected from the group consisting of NRC6-2a, NRC6-2c, NRC6-2b, NRC6-3 and NRC6-1a.

The invention also relates to a plant of the Solanaceae family, in particular a *Solanum lycopersicum* plant, which may comprise the nucleic acid molecule encoding an MeR1 protein as described herein, which confers resistance to root-knot nematode, in particular to *M. enterolobii*, when present in a plant of the Solanaceae family, and three NRC6 genes as described herein and selected from the group consisting of NRC6-2a, NRC6-2c, NRC6-2b, NRC6-3 and NRC6-1a.

The invention also relates to a plant of the Solanaceae family, in particular a *Solanum lycopersicum* plant, which may comprise the nucleic acid molecule encoding an MeR1 protein as described herein, which confers resistance to root-knot nematode, in particular to *M. enterolobii*, when present in a plant of the Solanaceae family, and four NRC6 genes as described herein and selected from the group consisting of NRC6-2a, NRC6-2c, NRC6-2b, NRC6-3 and NRC6-1a.

The invention also relates to a plant of the Solanaceae family, in particular a *Solanum lycopersicum* plant, which may comprise the nucleic acid molecule encoding an MeR1 protein as described herein, which confers resistance to root-knot nematode, in particular to *M. enterolobii*, when present in a plant of the Solanaceae family, and five NRC6 genes as described herein and selected from the group consisting of NRC6-2a, NRC6-2c, NRC6-2b, NRC6-3 and NRC6-1a.

A plant of the Solanaceae family, can be a plant of the species *Solanum lycopersicum, Capsicum annuum, Solanum melongena, Solanum tuberosum*, or *Nicotiana tabacum*.

Preferably, the invention also relates to a *Solanum lycopersicum* plant which may comprise one or more of the NRC6 alleles as defined above which allele(s) contribute(s) to resistance to *M. enterolobii* when present in said plant together with the MeR1 nucleic acid molecule of the invention. In this application the term tomato and *Solanum lycopersicum* are used interchangeably.

The phenotype of the invention inherits in a dominant manner. As used herein, dominant means that when the nucleic acid molecule(s) of the invention is/are heterozygously present in a plant, the resistance level to root-knot nematode of the plant is the same as if the nucleic acid molecule(s) of the invention would be homozygously present in a plant. A *Solanum lycopersicum* plant that has the nucleic acid molecules of the invention homozygously can be grown from seed deposited as NCIMB 43515. Such plants show *M. enterolobii* resistance.

A *Solanum lycopersicum* plant which may comprise the MeR1 gene of the invention and two NRC6 alleles (NRC6-2a and NRC6-2c) can be grown from a seed, a representative sample of which was deposited with the NCIMB under deposit number NCIMB 43515.

The presence of resistance to a root-knot nematode can be determined through a bioassay as described in Example 1. Determining resistance of a *Solanum lycopersicum* plant to *M. enterolobii* is done by counting the egg masses. The *Solanum lycopersicum* plants to be tested are sown in trays in a greenhouse, after 2 weeks the plants are transferred to 660 cc pots filled with a sandy soil mixture. As a susceptible control plant Dometica RZ is introduced in the test and as a positive control a plant grown from for a seed of the deposit NCIMB 43515 is introduced in the test. Next to the roots, holes are made with a 1 ml pipet tip and filled with 1 ml suspension which may comprise 500 of the second stage juveniles (J2) *M. enterolobii* inoculum per plant. After inoculation, the plants are grown in a growth chamber (23° C., 14 h. light) and watered three times a week. Six weeks after inoculation the plants are removed from the soil and the roots are washed with tap water. The egg masses are counted and the scoring is done according to the symptoms as presented in Table 2. An *M. enterolobii* resistant tomato plant has a score of 0, 1 or 2, preferably 0 or 1, when scoring according to Table 2 is used.

A plant of the present invention is optionally a cultivated plant having improved agronomic characteristics that make it suitable for commercial cultivation. This is thus an agronomically elite plant. The invention also relates to a fruit of a plant of the Solanaceae family harvested from a plant of the invention, wherein the fruit may comprise the nucleic acid molecule(s) of the invention in its genome which leads to resistance to a root-knot nematode, in particular to *M. enterolobii*, in the plant. This fruit is also referred to herein as 'the fruit of the invention'. Preferably, the fruit is a tomato fruit of a *Solanum lycopersicum* plant.

The present invention relates to a rootstock or scion of a plant of the Solanaceae family which may comprise the nucleic acid molecule(s) of the invention. Said rootstock or scion can be used in a grafting process to develop a grafted plant of the Solanaceae family which shows the phenotype of the invention and which grafted plant is also part of the invention. In one embodiment, the invention further relates to a rootstock which results from an interspecific cross between plants belonging to different species of the Solanaceae family wherein one parent plant of the interspecific cross is preferably a plant of the species *Solanum lycopersicum* which may comprise the nucleic acid molecule(s) of the invention and the other parent is selected from the group consisting of *Solanum Arcanum, Solanum cheesmaniae, Solanum chilense, Solanum chmielewskii, Solanum corneliomulleri, Solanum galapagense, Solanum habrochaites, Solanum huaylasense, Solanum juglandifolium, Solanum lycopersicum cerasiforme, Solanum lycopersicoides, Sola-*

*num neorickii, Solanum ochrantum, Solanum pennellii, Solanum peruvianum, Solanum pimpinellifolium* and *Solanum sitiens*.

The present invention further relates to the use of the plant of the invention in a grafting process, wherein the plant of the invention can either be used as a scion or preferably as a rootstock in the grafting process. The other plant used in the grafting process can be any plant of the Solanaceae family and preferably belongs to the *Solanum* genus.

The present invention relates to a method for producing plant of the Solanaceae family which is resistant to a root-knot nematode, in particular to *M. enterolobii*, which may comprise introducing the nucleic acid molecule(s) of the invention into the plant.

The nucleic acid molecule(s) of the invention can be introduced from another plant, which may comprise the nucleic acid molecule(s), through commonly used breeding techniques, such as crossing and selection, when the plants are sexually compatible. Such introduction can be from a plant of the same species, that usually can be crossed easily, or from a plant of a related species. Difficulties in crossing can be overcome through techniques known in the art such as embryo rescue, or cis-genesis. Suitably methods for the identification of the nucleic acid molecule are used to follow the incorporation of the nucleic acid molecule into another plant.

Alternatively, the nucleic acid molecule(s) of the invention can be transferred or introduced from another, sexually incompatible, plant, for example by using a transgenic approach. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention. The CRISPR/Cas system may, for example, comprise a Cas9, Cpf1, Cms1, MAD7, C2c2, CasX and/or CasY protein.

The invention further relates to a plant of the invention which may comprise the nucleic acid molecule(s) of the invention leading to resistance to a root-knot nematode, in particular to *M. enterolobii*, either homozygously or heterozygously, which plant is a plant of an inbred line, a hybrid, a doubled haploid, or a plant of a segregating population. Preferably, the plant of the invention is a non-transgenic plant.

The invention also relates to a seed of a plant of the Solanaceae family which may comprise the nucleic acid molecule(s) of the invention, wherein the plant of the Solanaceae family grown from the seed is a plant of the invention that is resistant to a root-knot nematode, in particular to *M. enterolobii*. Preferably, the plant is a *Solanum lycopersicum* plant. The invention also relates to seed produced by a plant of the invention wherein the seed harbors the nucleic acid molecule(s) of the invention, and as such, a plant grown from said seed is a plant of the invention.

Moreover, the invention also relates to a food product or a processed food product which may comprise the fruit of the invention or part thereof. The food product may have undergone one or more processing steps. Such a processing step might comprise but is not limited to any one of the following treatments or combinations thereof: peeling, cutting, washing, juicing, cooking, cooling. A processed food product may also be a salad mixture which may comprise the fruit of the invention. The fruit is a fruit of a plant of a species of the Solanaceae family, in particular pepper, egg-plant, potato, tomato. Preferably, the fruit is a tomato fruit of the invention. The processed form that is obtained is also part of this invention.

The invention also relates to propagation material suitable for producing a plant of the invention, wherein the propagation material is suitable for sexual reproduction, and is in particular selected from a microspore, pollen, an ovary, an ovule, an embryo sac, and an egg cell; or is suitable for vegetative reproduction, and is in particular selected from a cutting, a root, a stem, a cell, a protoplast; or is suitable for tissue culture of regenerable cells, and is in particular selected from a leaf, pollen, an embryo, a cotyledon, a hypocotyl, a meristematic cell, a root, a root tip, an anther, a flower, a seed, a rootstock and a stem; wherein the plant produced from the propagation material may comprise the nucleic acid molecule(s) of the invention that confers resistance to a root-knot nematode, preferably resistance to *M. enterolobii*. A plant of the invention may be used as a source of the propagation material.

The invention further relates to a cell which may comprise the nucleic acid molecule(s) of the invention as defined herein. A cell of the invention can be obtained from, or be present in, a plant of the invention. Such a cell may either be in isolated form, or is a part of a complete plant, or from a part thereof, and still constitutes a cell of the invention because such a cell may comprise the nucleic acid molecule(s) that encode(s) the protein(s) that confer(s) resistance to a root-knot nematode, in particular to *M. enterolobii*, to a cultivated plant of the invention. Each cell of a plant of the invention carries the nucleic acid molecule(s) encoding the protein(s) conferring resistance to a root-knot nematode, in particular to *M. enterolobii*, to a plant. A cell of the invention may also be a regenerable cell that can regenerate into a new plant of the invention.

The invention further relates to plant tissue of a plant of the invention, which may comprise the nucleic acid molecule(s) of the invention. The tissue can be undifferentiated tissue or already differentiated tissue. Undifferentiated tissue is for example a stem tip, an anther, a petal, pollen, and can be used in micropropagation to obtain new plantlets that are grown into new plants of the invention. The tissue can also be grown from a cell of the invention.

The invention further relates to tissue culture of a plant of the invention, which is also propagation material and which may comprise the nucleic acid molecule(s) of the invention in its genome. The tissue culture may comprise regenerable cells. Such tissue culture can be selected or derived from any part of the plant, in particular from a leaf, pollen, an embryo, a cotyledon, a hypocotyl, a meristematic cell, a root, a root tip, an anther, a flower, a seed, a stem or a rootstock. The tissue culture can be regenerated into a plant of the invention which may comprise the nucleic acid molecule(s) of the invention, wherein the regenerated plant expresses resistance to a root-knot nematode, in particular to *M. enterolobii*, and is also part of the invention.

The invention additionally relates to the use of a plant of the invention in plant breeding. The invention thus also relates to a breeding method for the development of a cultivated plant of the invention that is resistant to a root-knot nematode, in particular to *M. enterolobii*, wherein a plant which may comprise the nucleic acid molecule(s) of the invention for conferring said resistance to another plant is used. Preferably, the plant of the invention used in plant breeding is a *Solanum lycopersium* plant. Seed of a *Solanum lycopersium* being representative for a plant that can be used in plant breeding to develop another plant with resistance to a root-knot nematode, in particular to *M. enterolobii*, was deposited with the NCIMB under accession numbers NCIMB 43515.

The invention also concerns the use of the nucleic acid molecule(s) of the invention for the development of a plant that has resistance to a root-knot nematode. Preferably, the developed plant is a *Solanum lycopersicum* plant that has resistance to *M. enterolobii*.

The invention also relates to a method of testing a plant for the presence in its genome of the nucleic acid molecule(s) of the invention, which may comprise detecting the presence of the nucleic acid molecule(s) of the invention in the genome of a plant.

The method of testing a plant for the presence in its genome of the nucleic acid molecule(s) of the invention encoding the protein(s) conferring resistance to a root-knot nematode, in particular to *M. enterolobii*, optionally further may comprise selecting a plant that may comprise said nucleic acid molecule(s) as a plant resistant to a root-knot nematode.

The present invention relates to a method for selecting a root-knot nematode resistant plant of the Solanaceae family, in particular a *Solanum lycopersicum* plant, wherein the selection may comprise determining the presence of a nucleic acid molecule(s) of the invention in the genome of a plant of the Solanaceae family, and selecting the plant if it may comprise the nucleic acid molecule(s) of the invention. A plant in which the nucleic acid molecule(s) is identified is subsequently selected as a plant resistant to a root-knot nematode. In one embodiment, the root-knot nematode is *M. enterolobii* which can be detected by performing a bio-assay as described in Example 1. The selected plant obtained by such method is also a part of this invention. The invention further relates to a method for selecting a plant of the Solanaceae family, in particular a *Solanum lycopersicum* plant, carrying the nucleic acid molecule(s) of the invention, which may comprise determining the presence of the nucleic acid molecule(s) of the invention by determining its genomic nucleotide sequence or a functional part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence identity to a SEQ ID NO: selected from the group consisting of SEQ ID NO:1, 18 and 21.

The invention further relates to a method for selecting a plant of the Solanaceae family, in particular a *Solanum lycopersicum* plant, carrying the nucleic acid molecule(s) of the invention, which may comprise determining the presence of the nucleic acid molecule(s) of the invention by determining its coding sequence or a part thereof in the plant, wherein said sequence has in order of increased preference 90%, 91%, 92%, 93%, 94%, 95%, 96%, 97%, 98%, 99%, 100% sequence identity to a SEQ ID NO: selected from the group consisting of SEQ ID NO: 2, 3, 4, 5, 6, 7, 8, 9, 19, 22, 24, 26 and 28.

The invention further relates to a method for selecting a plant of the Solanaceae, in particular a *Solanum lycopersicum* plant, family carrying the nucleic acid molecule(s) of the invention, which may comprise determining the presence of the nucleic acid molecule(s) of the invention by determining the amino acid sequence of the encoded protein(s), wherein said sequence has in order of increased preference 85%, 86%, 87%, 88%, 89%, 90%, 91%, 92%, 93%, 94%, 95%, 96%, 97%, 98%, 99%, 100% sequence identity to a SEQ ID NO: selected from the group consisting of SEQ ID NO: 10, 11, 12, 13, 14, 14, 16, 17, 20, 23, 25, 27 and 29.

The invention also relates to a method for the production of a plant, which is resistant to a root-knot nematode, in particular to *M. enterolobii*, said method which may comprise:

crossing a plant of the invention, which may comprise the nucleic acid molecule(s) of the invention, with another plant;

optionally performing one or more rounds of selfing and/or crossing of the plant resulting from the cross to obtain a further generation population;

selecting from the plants resulting from the cross, or from the further generation population, a plant that may comprise the nucleic acid molecule(s) of the invention, which plant is resistant against a root-knot nematode, in particular against *M. enterolobii*.

Selection of a plant which may comprise the nucleic acid molecule(s) of the invention is suitably done by comparing the sequences to any one of the sequences selected from the group consisting of SEQ ID Nos 1, 2, 3, 4, 5, 6, 7, 8, 9, 18, 19, 21, 22, 24, 26 and 28. The plant can alternatively, or in addition, be phenotypically selected for having resistance to a root-knot nematode, in particular by performing a bioassay for *M. enterolobii* resistance.

In one embodiment of the invention, the plant of the invention used in the method for the production of a plant, which is resistant against a root-knot nematode, is a *Solanum lycopersicum* plant. In a further embodiment of the invention, the plant of the invention used in the method for the production of a *Solanum lycopersicum* plant which is resistant against *M. enterolobii*, is a plant grown from seed deposited under NCIMB accession number NCIMB 43515, or a progeny plant thereof which is a direct or further descendant through crossing a plant grown from the deposited seed with itself or with another plant for one or more subsequent generations.

The invention additionally provides for a method of introducing another desired trait into a plant which may comprise resistance to a root-knot nematode, in particular to *M. enterolobii*, which may comprise:

crossing a plant of the invention which may comprise the nucleic acid molecule(s) of the invention with a second plant that may comprise the other desired trait to produce F1 progeny;

optionally selecting in the F1 for a plant that may comprise resistance to a root-knot nematode and the other desired trait;

crossing the optionally selected F1 progeny with either parent, to produce backcross progeny;

selecting backcross progeny which may comprise resistance to a root-knot nematode and the other desired trait; and optionally repeating steps c) and d) one or more times in succession to produce selected fourth or higher backcross progeny that may comprise the other desired trait and has resistance to a root-knot-nematode. Backcrossing is optionally done until the backcross progeny is stable and can be used as a parent line, which can be reached after up to 10 backcrosses.

In one embodiment of the invention, the plant of the invention used in the method of introducing another desired trait into a plant which may comprise resistance to a root-knot nematode is a *Solanum lycopersicum* plant which may comprise resistance to *M. enterolobii*. In a further embodiment of the invention, the *Solanum lycopersicum* plant of the invention used in the method of introducing another desired trait into a plant which may comprise resistance to *M. enterolobii* is a plant grown from seed deposited under NCIMB accession number NCIMB 43515, or a progeny plant thereof which is a direct or further descendant through crossing a plant grown from the deposited seed with itself or with another plant for one or more subsequent generations.

Optionally, selfing steps are performed after any of the crossing or backcrossing steps. Selection of a plant which may comprise the nucleic acid molecule(s) of the invention that leads to resistance to a root-knot nematode and the other desired trait can alternatively be done following any crossing or selfing step of the method. The other desired trait can be selected from, but is not limited to, the following group: resistance to bacterial, fungal or viral diseases, insect or pest resistance, improved germination, plant size, plant type, improved shelf-life, water stress and heat stress tolerance, and male sterility. The invention includes a plant produced by this method and the fruit obtained therefrom.

The invention further relates to a method for the production of a plant which may comprise the nucleic acid molecule(s) of the invention, wherein the presence of said nucleic acid molecule(s) leads to resistance to a root-knot nematode, in particular to *M. enterolobii*, by using vegetative reproduction, by using tissue culture of the plant material that may comprise the nucleic acid molecule(s) of the invention or by using a doubled haploid generation technique to generate a doubled haploid line and wherein the method may comprise growing a seed which may comprise said nucleic acid molecule into the said plant.

The invention further relates to a method for seed production which may comprise growing a plant from a seed of the invention, allowing the plant to produce a fruit with seed, harvesting the fruit, and extracting the seed. Production of the seed is suitably done by crossing with itself or with another plant that is optionally also a plant of the invention. The seed that is so produced has the capability to grow into a plant that may comprise the nucleic acid molecule(s) of the invention and is resistant to a root-knot nematode, in particular to *M. enterolobii*.

The invention further relates to hybrid seed and to a method for producing said hybrid seed, which may comprise crossing a first parent plant with a second parent plant and harvesting the resultant hybrid seed, wherein the first parent plant and/or the second parent plant is a plant of the invention which may comprise the nucleic acid molecule(s) of the invention. The resulting hybrid plant that can be grown from the hybrid seed, which may comprise said nucleic acid molecule(s), which hybrid plant has resistance to a root-knot nematode, in particular to *M. enterolobii*, is also a plant of the invention.

The parent that provides the resistance to a root-knot nematode, in particular to *M. enterolobii*, can be a plant grown directly from the deposited seed. The parent can also be a progeny plant from the deposited seed which is a direct or further descendant obtained by crossing with itself or with another plant one or more times, or a progeny plant from seed that is identified to have obtained the nucleic acid molecule(s) of the invention and thereby the resistance to a root-knot nematode, in particular to *M. enterolobii*, by other means.

Introgression of the nucleic acid molecule(s) of the invention as used herein means introduction of the nucleic acid molecule(s) of the invention from a donor plant which may comprise said nucleic acid molecule(s) into a recipient plant not carrying said nucleic acid molecule(s) by standard breeding techniques, wherein selection for plants which may comprise the nucleic acid molecule(s) of the invention can be performed phenotypically by means of observation of the resistance to a root-knot nematode, in particular to *M. enterolobii*, or selection can be performed by comparing the sequence to the any one of the sequences selected from the group consisting of SEQ ID Nos 1, 2, 3, 4, 5, 6, 7, 8, 9, 18, 19, 21, 22, 24, 26 and 26, as described herein.

The nucleic acid molecule(s) of the invention is/are introgressed into a plant of the Solanaceae family from another plant of the Solanaceae family. In one embodiment, the nucleic acid molecule(s) of the invention is/are introgressed into *Solanum lycopersicum* from a plant of the species *Solanum pimpinellifolium*. In another embodiment, the nucleic acid molecule(s) is/are introgressed from a *Solanum lycopersicum* plant which may comprise the nucleic acid molecule(s) of the invention into a *Solanum lycopersicum* plant lacking the nucleic acid molecule(s) of the invention. In a further embodiment of the invention, the nucleic acid molecule(s) is/are introgressed from a *Solanum lycopersicum* plant or a *Solanum pimpinellifolium*, which may comprise the nucleic acid molecule(s) of the invention, into a plant lacking the nucleic acid molecule(s) of the invention and wherein the plant is selected from the group consisting of *Solanum Arcanum, Solanum cheesmaniae, Solanum chilense, Solanum chmielewskii, Solanum corneliomulleri, Solanum galapagense, Solanum habrochaites, Solanum huaylasense, Solanum juglandifolium, Solanum lycopersicum cerasiforme, Solanum lycopersicoides, Solanum neorickii, Solanum ochrantum, Solanum pennellii, Solanum peruvianum, Solanum pimpinellifolium* and *Solanum sitiens*. In particular the MeR1 gene of the invention is introgressed into a plant of the Solanaceae family from another plant of the Solanaceae family. In one particular embodiment, the MeR1 gene of the invention is introgressed into *Solanum lycopersicum* from a plant of the species *Solanum pimpinellifolium*.

As used herein, the "phenotype of the invention", "the resistance of the invention" is resistance to a root-knot nematode. Preferably, the resistance to a root-knot nematode is resistance to the root-knot nematode *Meloidogyne enterolobii* (Yang & Eisenback, 1983). A synonym of *M. enterolobii* is *Meloidogyne mayaguensis* or *M. mayaguensis*.

As used herein the term "nucleic acid molecule" is used to designate the nucleotide sequence of a gene or of an allele of the gene which is a specific sequence of a gene linked to as a specific phenotype, i.e. the phenotype of the invention. Optionally, the nucleic acid molecule is isolated. As used herein "MeR1 gene of the invention" or "MeR1 nucleic acid molecule of the invention" is used to designate the MeR1 gene, which leads to the phenotype of the invention. The invention relates to a gene or an allele, which encodes a functional protein leading to the resistance. More specifically, "MeR1 gene of the invention" or "MeR1 nucleic acid molecule of the invention" is used to designate a nucleic acid molecule encoding an MeR1 protein, which confers resistance to root-knot nematode, in particular to *M. enterolobii*, when present in a plant of the Solanaceae family, in particular in a *Solanum lycopersicum* plant, wherein said nucleic acid molecule has a nucleotide sequence which is:

a) a nucleotide sequence which may comprise a coding sequence according to SEQ ID NO: 2, 3, 4, 5, 6, 7, 8 or 9, or a coding sequence which has in order of increased preference 90%, 91%, 92%, 93%, 94%, 95%, 96%, 97%, 98%, 99% sequence identity with the sequence according to SEQ ID NO: 2, 3, 4, 5, 6, 7, 8 or 9; or b) a nucleotide sequence encoding a protein having an amino acid sequence according to SEQ ID NO: 10, 11, 12, 13, 14, 15, 16 or 17, or a protein having an amino acid sequence which has in order of increased preference 85%, 86%, 87%, 88%, 89%, 90%, 91%, 92%, 93%, 94%, 95%, 96%, 97%, 98%, 99% sequence identity with the amino acid sequence according to SEQ ID NO: 10, 11, 12, 13, 14, 15, 16 or 17.

As used herein the term "NRC6 allele" is used to designate an allele of the NRC6 gene which contributes to root-knot nematode resistance, in particular to *M. enterolobii*, in a plant when present together with the MeR1 gene of the invention. More specifically, "NRC6 allele" is used to designate nucleic acid molecule encoding a protein, which contributes to resistance to root-knot nematode, in particular to *M. enterolobii*, when present in a plant of the Solanaceae family, in particular a *Solanum lycopersicum*, together with the MeR1 nucleic acid molecule of the invention, wherein said nucleic acid molecule has a nucleotide sequence which is:

a) a nucleotide sequence which may comprise a coding sequence according to SEQ ID NO: 19, 22, 24, 26 or 28 or a coding sequence having 98%, preferably 99% sequence identity with the sequence according to SEQ ID NO: 19, 22, 24, 26 or 28; or b) a nucleotide sequence encoding a protein having an amino acid sequence according to SEQ ID NO: 20, 23, 25, 27 or 29 or a protein having an amino acid sequence which has 98%, preferably 99% sequence identity with the amino acid sequence according to SEQ ID NO: 20, 23, 25, 27 or 29.

In general the plants of the *Solanum* genus and in particular the *Solanum lycopersicum* plants comprise an NRC6 allele of the NRC6 gene. Examples of alleles are given herein. The presence of a NRC6 gene alone in a plant does not lead to *M. enterolobii* resistance. For having a plant of the Solanaceae family, in particular a *Solanum lycopersicum*, resistant to root-knot nematode, in particular to *M. enterolobii*, at least the MeR1 gene of the invention should be present in said plant and preferably in combination with a NRC6 gene.

As used herein, sequence identity is the percentage of nucleotides or amino acids that is identical between two sequences after proper alignment of those sequences. The person skilled in the art is aware of how to align sequences, for example by using a sequence alignment tool such as BLAST®, which can be used for both nucleotide sequences and protein sequences. To obtain the most significant result, the best possible alignment that gives the highest sequence identity score should be obtained. The percentage sequence identity is calculated through comparison over the length of the shortest sequence in the assessment, whereby in the present case a sequence represents a gene or an allele that at least may comprise a start codon and a stop codon, or a complete protein encoded by such a gene or allele.

In the context of this invention "nucleic acid molecules of the invention" is used to designate the nucleic acid molecule defined as "MeR1 gene of the invention" as defined above and at least one nucleic acid molecule defined as "NRC6 allele" as defined above, which can be the NRC6-2a, NRC6-2c, NRC6-2b, NRC6-3 or NRC6-1a allele as defined herein or any combination thereof.

As used herein "nucleic acid molecule(s) of the invention" means the MeR1 gene of the invention or the MeR1 gene of the invention optionally in combination with at least one NRC6 allele which can be the NRC6-2a, NRC6-2c, NRC6-2b, NRC6-3 or NRC6-1a allele as defined herein or any combination thereof.

As used herein, the "plant of the invention" is a plant of the family of the Solanaceae family, which may comprise the nucleic acid molecule(s) of the invention and which is resistant to root-knot nematode, preferably the plant of the invention belongs to the genus *Solanum*, even more preferably the plant is a *Solanum lycopersicum* plant, which is resistant to *M. enterolobii*.

As used herein "progeny" is intended to mean the first and all further descendants from a cross with a plant of the invention, wherein a cross may comprise a cross with itself or a cross with another plant, and wherein a descendant that is determined to be progeny may comprise the nucleic acid molecule(s) of the invention as defined herein leading to resistance to a root-knot nematode, in particular to *M. enterolobii*. "Progeny" also encompasses a plant that carries the nucleic acid molecule(s) of the invention and is resistant to a root-knot nematode, in particular to *M. enterolobii*, and is obtained from another plant, or progeny of a plant, of the invention by vegetative propagation or another form of multiplication.

TABLE 1

Sequence information
The genomic sequences correspond to the mRNA with +2 kb upstream and downstream
from the start and the end.

| | |
|---|---|
| SEQ ID NO:<br>1: genomic<br>MeR1MeR1 | TTTCGCACTTCACTGAAACATTAAATTGGGCAACATTACTCTGT<br>TATACTAATAATACAGATTTTAGGTGCCTTGATATCAAACATA<br>GAGTAAATTCAATTATTTTCGTGTTCATCACATTCCTCATCTAT<br>TTTTCTCTTACTTATTTTCCTCCTTTTTAGCAGGAGAGTATCGAG<br>GCATGGTGATGCATTTGCAGTCTCAGTTTTGATTACCTGTTCCA<br>ATAAAGAAACTTGTTACAAGTATGTTTTGTTGATTCAAACATG<br>CCAAGTTTGAAAACGAAGTTTTATATTAATGTTTTTGCGTTTTC<br>TTTCAGTGCTGAATAATTTGTCTAATCTGTAGTTGATGTTTGGA<br>TATCTATGTATTGTTCGATTGACACGAGTTGTTTATACTATCAT<br>TTGTTGTTTATGAATATGTAAAACATATTTGATTTATGTTTGCA<br>ACGTCAACGTGAACATTCAATTAGTCTAATCAAAGTCTAGATC<br>TAAAATTGATTAATTTAAGTTCATAATTTATTTTGAATTATTAT<br>CTAAAACCGAAGACTTTCTACTCGAAAATCGAAATCATAGCTG<br>ACAGTCTCCATAAATATATTTGCAATTGAATAACATAATAAGC<br>ATTTATCAGTTAATTTTATGGAGTTTCTGGATTTACGTGATATT<br>CAAACATCTCCCGCGCATATTAATTATGTGAAGTAATGAAGTG<br>TGTAACATAAGTCAAAAGGTGCATAAATAAAGAGTCAAGGGT<br>AATAAGACTTTAGTTTACTTTAGGTGTGTCTCTGAAATTTCGAT<br>TATAATCTACGATATATTGTGTCTTGTCCCAACATTTAAATAAA<br>ATGAACAAATAATTTTAATTACCAAATGGATCCATAGTCTGTTT<br>AGTTGACTAATGGAAAGATTTATAGGAAGGTGAGATTGTTTTA<br>TCCCTGATTAGAGGTTTTGGTTCGAGTTTTGTGTATACGAAAAA<br>ATTGTGTTGAAAGCGTCACTTATGAATAGGCCCTATAATGTAT<br>GATTCGAATTTAGTCTGAGTTCTAATATGAATTTTGAACACATT<br>GAAAAATTATATCCTTTGTTAAATTTCATGGTTTTAACATCTTG<br>GAAGTAAAGAAAAAGGTAAAATATTTTTTTTTTCTATTTCATTT<br>TTTTACATGTAATATTTGAATTCAAAGGCTGAGAGAGTAATAC<br>CCCCCTTTTATTTTTATTTGTGGATTACATATATACATAAGAAC<br>TAGAAAAATGTTTATATTTTCGACTTGACAATGATAGAATGTA<br>AATGTTGGATATATAGAATAATTTGTTGGAGCTTCTACCATTTT<br>TTGCTTACCGTCTTAAGGTTGAAGGCGTAGATGTTTATTATCCG<br>AATAATTCCTTTTTGTCGATAATCAAGCATCAATATTAGATTAG<br>TAGCCGACCCTCTTCTCTTACCTCTCTAAACAATTTTTCAATAT<br>TTCCATTTTGGTTGGTAAAAATATTAGAGAACATTTTCTCTATA<br>GAAATATCATGTGTTTATTCAGAATTGTTATTGACTCCATATAT<br>TTTTAATAATCCAAAACCTATAAATTTAATAGTTTACATTCACA<br>ATTATTGCTTGTTGCTGTTCTTTTACCTTGTGTTTCTAATTTTTA<br>CCGTTATTAAATATGCATGTGATTAGTTGAAATATTAAATCTCT<br>AGAAATTGAAGGCTGGCTCGAGGTTAGAGATTAAATGGAAAA<br>ATGAAAGTCAACGAAGCATGGTAGCTGTCAAATACGCTCCAAC<br>TCAAAGCATTACTGTCATGATGGAGTTCCTATTGATCCATCGTG<br>AAAAATTGAACGATATGTTGGCACATGTCGGAATACTTAAAAT<br>ATCGAATTAATATAATTGAATTTAACTTTGAAAATTAATCAAA<br>TTAACTTTCGAAAAGCGCTACCTGACAATTAAAAATACAAGGA<br>GTGAGCAGTGAACTTAAACTAATCTATTTCAGATCTCTAGGCTT<br>TGATAAACTAATTGACAGTTCAACATTTGCAGATCTAACTTCA<br>ACGTTTGCTTCTTGTAGATCTGCAACAAGGCAAACTACCATTTG<br>AGAGTAAAGAAAAAGGTATAATATAATGTTTTTCTAGTTTTCA<br>TTTTACATGTATTTTTGTGATTCACTTGATTTGAATGAAACATA<br>CATTACAAGAACTAGAAAACGAATTTGTATTTTTGACTTAGAT<br>AATTATAAAATGTTAGATGATTTTGTCATAATTTGTAGTATTCA<br>CTCTTGTTTTTAGTAAATATACCTCTTTCTTAAATGTGATTGATT<br>TACAGATTATATATTTAGAATTTTTGCTTATTAAAAGAAAAAT<br>TAATTAGTGGCGGAAATTTGAGGTGAATTTGTGAAGAATGGAA<br>GAAGTTGGAAATTCGAGAGTTTGTTCATGTGTTTTTTAAGGTAG<br>AAGAAACAAAAAAAATCCATTTGATCTAAAATTCCAATTGAAA<br>TGTATTACAAGTTGTTTGGGGTAAAAAATAATGACATGAATGT<br>GTTTTTCTCAAATGATAATGACATAGATGAGCCAAAGTTTTAA<br>CTGATGACATAAATGAACCTTTCTTTTTCTACAAAGTTCGATAA<br>CATATTTGAGCCAAAATTTAGAATTTATAACAGCTGACATTCTT |

TABLE 1-continued

Sequence information
The genomic sequences correspond to the mRNA with +2 kb upstream and downstream
from the start and the end.

```
TTAACTCTTTCTTCTTGCTGTTACTTTTACTTGTGTTTCTAATTC
TTTTATCCTTATTAAATGTGGATGTGATTAGTTTGAAAAATCAA
ATTTTGTAGATATTGAAGGCTGGTTGGATGGAAAAAGGAGAAA
AATCATTGGTATGTCTATTGTCTACCAATACTGTAGTTTCTAGC
GTTAAGAGCCAATATTTTCAACTGAATTTTGCTGATGCATATGT
TTTTGATTTAGCAGCTACTATTTGAGGAACAAAAAACAAGAAT
CACGAATCTTATTGATGATTTCTTGATTCGCTTGAAGCAAATAA
AGAATGAATTCATTGCTTCAAAATTGGATGCCTTTGAAAATCT
AAGAATGGAACTGAGATTCCTAAGAACATTTGTCCTGTTTGGG
AATTCGATGAATTTGGATGACTTTTATGAGAGGATGTCACTGA
GTATAAGCAAATTCGATCAATCTACGGAGTACGTAGATAAAAT
AATCCTAGAGAAATACAACATGGAATGTCTTGCCCCTCTGCTG
CTTGAAGAGATAAGAAATTATTTGAGTTTGAAGAATGATTATG
TAGCCACAACTACAGAGATAAAATTGTTTGAATACCTCATCAG
AAACCTCCATGATCTACCAAAGTATTGTTCTGATTTGCTTCTAC
CACTCATGAGTGAATACAAGATTCTTCGGCAAGTATGCACACA
TCTCAGAGATTTCTATCAGTTGGAATGCAACAAAACAACAAAA
ACAGAATTTCTCTATACTCGGTATCAAGTGACAGCCGATAGAG
TAACACAATTCTGTTTTGATCTTTGGACAGGAATGTATAAATAC
TCTGACAATGAGTATGCCTTCTCTGAATGTTCTTCCAAGATCAC
TTCTCTACTCATTGACATAATCCCTCTTGAGTTGGAGGTTCTAT
ACATTTCTACTTCTAAGCTCATCAAAGAGTCAACGTCAAAAGA
ACTAGAAGGATTTGTTAAGCAAATCTTAAAAGCATCTCCAAGG
ATTCTTCAACATTATCTCATTCATCTCCAAGGACGCATGGCCGG
TGTAGAAGCCGTCAATTTCGCTCCAACTCGAAGCATTAGTGTC
ATGATGGAGTTCCTATTGATCTTTCTCACCGATATGCCAAAGCG
GTTTATCCATCGTGAAAAATTGAACGATATGTTGGCACATGTC
AGAATACTTACAAGGAAAATATCTACTCTGGTGAGTAAACTGT
TGGAGGAGATCTCTGAGGATAATATCAATGAAGCGGACTTTTC
AGCTCCGGACTTTTTGCAAGAAATTGAACAAATGAAGGGAGAT
ATCAGACACATCTTTTTAAAAGCTCCTGAGTCATCTCAACTTCG
GTTTCCTATGGATGATGGTTTCCTCTTCATGAATCTTCTACTCA
GACATTTAAATGATTTACTCATTTCCAATGCTTATTCAGTTTTT
CTCATAAAAAAGAAATTGGGATGGTGAAAGAAAGCCTTGAA
TTCCTAATATCATCTTTCAGGAAAGTCAGGCAAACATTGGATG
AGAGTACTAGTGGAGTAGTTAAAAATTGTTGGGTGCGTGCTTT
GGATGTGGCATATGAGGCAGAACATATCATTAATTCCATTCTT
GTCAGAGATAAAGCTCTCTCACATCTCCTCTTCTCACTTCCGAG
TGTCACTGATAAGATCAAACTTATCGTGGAACAAGTCACCAGG
TTTCAGCTGGAGGATAAGAATGGGGATGGCCCCCTTGATGCAA
AGTCTTCCTTCGAGCCAACTCAGTCAACTTCATCACCTTTTGTT
GAGGTAACAGTAGGTCACGAGAAAGAAGAATCCCAGATCATT
GACCAGCTCCTTGATGAACATGAATCTGAGCTTGATGTCATTTC
CATTGTCGGAATGCCAGGACTCGGTAAAACTACTCTGGCCAAC
AAAGTGTATAAAGATACATTAGTTGCTAGGCATTTCCATGTCC
GTGCTTGGTGCACTGTTTCGCAAAGTATAACAAGTCAAAGGT
GTTGCGGGAGATTCTTCAGCAAGTTACTGGCTCGGGAGGAAAA
GAAAGTGAAGATGACCTGGCTGAAAAGCTACGAAGAGCACTA
CTCGATAAAAGGTACCTAATCGTCTTGGATGATGTGTGGGATA
TTGCAACAGGGGAGATGTTAATAGCATGTTTTCCTAAGGGTAA
GAGAGGAAATAGAATCATCTTAACTAGCCGAAGTAGAAAGGT
AGGTTTGAAAGTTAAATGCCGTAGTGATCCTCTCGACCTTAAA
CTTTTAACATCTGAAGAAAGTTGGGATTTATTCGAAAAAAGGG
TATTTGGAGATGAAGGAAGCTGCCCTGCTGAACTGTCCGAAGT
TGGACACCAAATAGTTGAGAAATGTAAGGGTCTTCCCTTGGCT
ATTGTTTTAATTGCTGGAGTAATTGTTAGAGGGAAGAAAAAGG
AAAAGGATTTTTGGCTTAAGATACTGCATAATCTGGATTCCTTT
ATTTCTACCAACATCAATTTGGTTATGCAATTAAGTTATGACCA
TTTACCATGCCACCTGAAGCCGTTGCTGCTTTACTTTGCAACAA
CTCAAAAGAGCCAACAAACTCCAGTCTCTACATTGATGCAGTT
GTGGATGGCCGAAGGGTTTGTGGATCATGATAGTTTAGAGGAA
GTAACTCAAAGTTACTTGGATGCTCTAATTTCCAGTAGCCTGAT
AATGGTGGATCATATCCCCTCCAAGAGTTATTGGTGGACGTCT
TTAATGATCAAGGTTTGCTATGTGCATGATGTTGTGCACGATTT
TTGTTCAGAAAAAGCCAAAAAGGAGAAGTTTCTCAAGTTAATC
AATTCAGGTGATCCATTTCATGCTTCAGATTTCCTACACCATCG
TCTAACCATTCATACTGACAACGGCCAACTCCACAAAAAATGT
GTTTTATTCAATTCTAATAAGTGCTTAGCTGTTAGTAAGCATGT
CATATCTTTGAAAGTGAGTGGTCCACTAGATGAGTTCAGGTAT
ATCTGTCACACAAGACACTTTGGACTTGTTAGAGTGTTGCAAC
TGGATGACATCATTCTGGAAGATTCTTTAATGGAAGAAATAGG
GTCCCTATTTCATTTGAGGTTCTTAAGCATTGAGACTGCTGTAG
GTGTAATAGCTATCCCAGTGTCGTGGTTGAACCTCCAGAATCT
GGAAACGCTGTTGATTTATACAACTTATTCCACCATGGTATTAC
TGCCCAGAATATTGCAACTGTCAAAGCTGAAACATGTGAAAAT
TAAGGAATGTTCTTTCTTTGAAGAGAAAGAGGATATCCAACGT
```

TABLE 1-continued

Sequence information
The genomic sequences correspond to the mRNA with +2 kb upstream and downstream
from the start and the end.

```
AGAATATTGGAAGCTGGGAATTCTTCAAACTTGACAACTCTAT
CCGGAGTTGTTATCTCATATTCTGAAGGCATGAGTGATGATGC
TCTGGAGAAGTTCCCAATTCTTCAGCACCTTGATTGCATCATCA
TGGAATCGCAGAATGCTCCTACACACGACTATTGGTTTCTCAA
GCTTGATGTACTTAATAAACTCGAATCATTCGTAGCAAGATAC
AAGCGCAATGGACATCCCTCGTTAAACCGACAACCGTATGGAT
TTCACTTCCCTACAAGCTTGAAAGAGTTACGGTTGACTGGTTTT
TTCCTGAGACCTGATTTGTTGTCAGTAATCGCAGCGTTGCCTGA
GCTTGAGATTATGGAGTTTTCCGGCTGTTATTTCGTGGATACTA
AATGGGACGCAAGTGAGGACATCTATCTAAGTCTTAAGACTTT
GATTTTGCGAGATGTCCATTTATCAGAATGGCAAGTTGAGGGG
GGAACTTTTCCCAAGCTTGAGAAATTAATACTAAAATTTTGTTC
CACACTTGGGGAGATCCCTTGTGCATTTATGGATGTAGAAACT
TTAAAGTCCATTGATTTAAGTTTTGTTGGGCGTAAGCTTCGAGA
TTCAGCCATTGAGATTAAGAAAAATGTAGCAGATTTCACAGGA
GAGGACAGAGTTGATGTCCACACATCACATTTGTTTGCAACCA
ACGTGAAAGAACAGATTATGAGAATGACGGGTATGGGAAATA
TACAGGGAAGGAGAGGAATTTAAAAAGTTTAGAACTTGAAAG
GTTGGGAACTTGAAAAGTACTCTAATGCTTTATTGAAAAAGAT
AATAGTCCCTCATCGGTAATGGAAATGAAAATAGGAGAGTTTA
AATAAATAAACACTCCTATTAAATTATTTTTTTTTACAAATAAA
TTTCTGTTCATCTTATTTACTGGTTCTAAAAATCTCAGTTACTTC
GTGTTTCTGAATTATTTATTATAACCAGTAACTTCTGATTTTCTT
AACACAGATTGGCAACAGAGATAACTAAGTTCGTTTAATTTAT
ATAATTTGCATTTGTGTAGTGTGTTCATTGAAGTTGTTAGTAGA
GTTCATTCTTCTTTCTGCACACACTACCACAAAAACAACTTTTT
AGAGGCAATAAACAAATCATCCACTGATTTGACTAGTCGTAAC
ATTATGAGAAAATTCAATGGATTTGTTTTGTATTGCAGGTGGA
GAATGTACTTGTGAAGAACTATAATACTTAGATCCTGAATGTT
TGATTTGTGCTTATACATAGTTGGTGGAGTGATTGCACTGATTC
TCGTGGTTATGAATCGCAGTGGTTGATGAAGTTGGATTTCTCAT
GGAAAAATCACAACAATGAAGAACGAAACAACGCAACGCCTC
CATCTGATTACTGCTTCCAATAAACAAACTTGTTACTGGTTTTC
TCATTGCTGGTTCTGGACGTATTTTGATCTAATGTGTCGTGTGT
TTTCTTTCCTGTTTTTTTTGTTAGTTATGAATCTTATTTCGTCTGT
AATCTCTCATATAAGATTCTAGTTTGTTTGTTTTTTTTAATTGGA
AGGTTTCAATGCCAAATTGTGAATCAATATAGGTCCCATTTGG
CATGAAAAAGGCAACTAACTATCCACTATTGATATGGACAGTTA
ATTAGATAACTACTGTGCCAACAAGCATTGTGGTGGAGAGGCA
GTACTCTCTGATCCTTAATCAGAGGTCTCGCGTTCGAGCCCTAC
CAGATATAGAATCGCCTATGTATGTCTTACTCTCAATGTGATAC
TATTTTTCAATATTAAATATGTATCAAATATAGAATATAATTAT
CGAAACTATCTTAAATCCTTGCAATTAGGTCCTAAACTATTATT
ATTATTATTATATAATAAACTAATAAAGTAACATCAAACTTGC
CATTTTTTATTCTTGTCACCTAATTACATGATTGAATAATGTTTT
TTCCCGACTATTATTGATCCACTAGCAAATATTTATATGGACAG
TAGGAAATTATATAGAAAGACTTTGCTTTAATAATTCAAAATC
ATAGTAAACTTTGCTTAAACTAATCTATTICACATCTAGTCTTT
AATTGCTTCTTGCTTTTGCTCACTCAATTTTGTCAGTGAAAGTT
TTGTAAATCTGCAAACTACCATTTAGGATGAAGTAACTCTTTTA
ACAGCTGACATTCTTTTAACTCTTTCTTCTTGCTGTTACTTTTAC
TTGTGTTTCTAATTCTTTTATCCTTATTACAAGTGCATGTGATTA
GTTTGAAAAATCAAATTTTGTAGATATTGAAGGCTGGTTGGAT
GGAAAAGGGAGAAAAATCATTGGTATGTCTATTGTCTACCAAT
ACTGTAGTTTCTAGCGTTAAGAGCCAATATTTTCAACTGAATTT
TGCTGATGAATATGTTTTTGATTTAGCAGCTACTATTTGAGGAA
CAAAAAACAAGAATCACGAATCTTATTGATGATTTCTTGATTC
GCTTGAAGCAAATAAAGAATGAATTCATTGCTTCAAAATTGGA
TGCCTTTGAAAATCTAAGAATGGAACTGAGATTCCTAAGAACA
TTTGTCCTGTTTGGGAATTCGATGAATTTGGATGACTTTTATGA
GAGGATGTCACTGAGTATAAGCAAATTCGATCAATCTACGGAG
TACGTAGATAAAATAATCCTAGAGAAATACAACATGGAATGCC
TTGCCCCTCTGCTGCTTGAAGAGATAAGAAATTATTTGAGTTTG
AAGAATGATTATGTAGCCACAACTACAGAGATAAAATTGTTTG
AATACCTCATCAGAAACCTCCATGATCTACCAAAGTATTGTTCT
GATTTGCTTCTACCACTCATGAGTGAATACAAGATTCTTCGGCA
AGTATGCACACATCTCAGAGATTTCTATCAGTTGGAATGCAAC
AAAACAACAAAAACAGAATTTCTCTATACTCGGTATCAAGTGA
CAGTTAATAGAGTAACACAATTCTGTTTTGATCTTTGGACAAG
AAAGTATAAAGACTTTGACAATGAGTATGCCTTCTCTGAATGT
TCTTCCAAGATCACTTCTCTACTCATCGACATAATCCCTCTTGA
GTTGGAGGTTCTACACATTTCTACACATTGTTAAGCAAATCCTA
AAAGCATCTCCAAGGATTCTTCAAAAGCATCTCATTCATCTCC
AAGGACGCATGGTAGCCGTCAGTTACTCTACAACTCAAAGCAT
TAATGTCATGATGGAGTTCCTATTGATCTTTCTCACTGATATAC
CAAAGCGCTTTATCCATCGTGGCAAATTGAACTCTATGTTGGC
```

TABLE 1-continued

Sequence information
The genomic sequences correspond to the mRNA with +2 kb upstream and downstream
from the start and the end.

```
              ACATGTCGGACTACTTACAAGGAAGATATCTATTCTCATGGAA
              GAGAGCTCTAATATGAATGAAGCAGACTTTTCAGCTACATACT
              TGTTGCAAGAAATCGAACGAATGAAGAGAGAGATATCAAACAGA
              TTATTTTGAAAGCGCCAGAGTCATCCCAACTTTGCCTTCCTATG
              GATGATGGTTTCCTCTTCATGAATCTTCTACTCCGACATTTAAA
              TGATTTACTCACTTCCAATTCTTATTCAGTTTCTCTGATAAAAA
              AAGAAATTGAGATGGTGAAACAATGCCTTGAATTCCTAACAAC
              ATCTTTCAGGCAAACATTGGATGAGAGCACTAGTGGAGTTGTT
              AAAGATTGTTGGATGCGTGCTTTGGATG

SEQ ID NO:    ATGGAAAAAGGAGAAAAATCATTGCTACTATTTGAGGAACAA
2:            AAAACAAGAATCACGAATCTTATTGATGATTTCTTGATTCGCTT
CDS MeR1      GAAGCAAATAAAGAATGAATTCATTGCTTCAAAATTGGATGCC
(isoform 1)   TTTGAAAATCTAAGAATGGAACTGAGATTCCTAAGAACATTTG
              TCCTGTTTGGGAATTCGATGAATTTGGATGACTTTTATGAGAGG
              ATGTCACTGAGTATAAGCAAATTCGATCAATCTACGGAGTACG
              TAGATAAAATAATCCTAGAGAAATACAACATGGAATGTCTTGC
              CCCTCTGCTGCTTGAAGAGATAAGAAATTATTTGAGTTTGAAG
              AATGATTATGTAGCCACAACTACAGAGATAAAATTGTTTGAAT
              ACCTCATCAGAAACCTCCATGATCTACCAAAGTATTGTTCTGAT
              TTGCTTCTACCACTCATGAGTGAATACAAGATTCTTCGGCAAGT
              ATGCACACATCTCAGAGATTTCTATCAGTTGGAATGCAACAAA
              ACAACAAAAACAGAATTTCTCTATACTCGGTATCAAGTGACAG
              CCGATAGAGTAACACAATTCTGTTTTGATCTTTGGACAGGAAT
              GTATAAATACTCTGACAATGAGTATGCCTTCTCTGAATGTTCTT
              CCAAGATCACTTCTCTACTCATTGACATAATCCCTCTTGAGTTG
              GAGGTTCTATACATTTCTACTTCTAAGCTCATCAAAGAGTCAAC
              GTCAAAAGAACTAGAAGGATTTGTTAAGCAAATCTTAAAAGCA
              TCTCCAAGGATTCTTCAACATTATCTCATTCATCTCCAAGGACG
              CATGGCCGGTGTAGAAGCCGTCAATTTCGCTCCAACTCGAAGC
              ATTAGTGTCATGATGGAGTTCCTATTGATCTTTCTCACCGATAT
              GCCAAAGCGGTTTATCCATCGTGAAAAATTGAACGATATGTTG
              GCACATGTCAGAATACTTACAAGGAAAATATCTACTCTGGTGA
              GTAAACTGTTGGAGGAGATCTCTGAGGATAATATCAATGAAGC
              GGACTTTTCAGCTCCGGACTTTTTGCAAGAAATTGAACAAATG
              AAGGGAGATATCAGACACATCTTTTTAAAAGCTCCTGAGTCAT
              CTCAACTTCGGTTTCCTATGGATGATGGTTTCCTCTTCATGAAT
              CTTCTACTCAGACATTTAAATGATTTACTCATTTCCAATGCTTA
              TTCAGTTTTTCTCATAAAAAAAGAAATTGGGATGGTGAAAGAA
              AGCCTTGAATTCCTAATATCATCTTTCAGGAAAGTCAGGCAAA
              CATTGGATGAGAGTACTAGTGGAGTAGTTAAAAATTGTTGGGT
              GCGTGCTTTGGATGTGGCATATGAGGCAGAACATATCATTAAT
              TCCATTCTTGTCAGAGATAAAGCTCTCTCACATCTCCTCTTCTC
              ACTTCCGAGTGTCACTGATAAGATCAAACTTATCGTGGAACAA
              GTCACCAGGTTTCAGCTGGAGGATAAGAATGGGGATGGCCCCC
              TTGATGCAAAGTCTTCCTTCGAGCCAACTCAGTCAACTTCATCA
              CCTTTTGTTGAGGTAACAGTAGGTCACGAGAAAGAAGAATCCC
              AGATCATTGACCAGCTCCTTGATGAACATGAATCTGAGCTTGA
              TGTCATTTCCATTGTCGGAATGCCAGGACTCGGTAAAACTACT
              CTGGCCAACAAAGTGTATAAAGATACATTAGTTGCTAGGCATT
              TCCATGTCCGTGCTTGGTGCACTGTTTCGCAAAAGTATAACAA
              GTCAAAGGTGTTGCGGGAGATTCTTCAGCAAGTTACTGGCTCG
              GGAGGAAAAGAAAGTGAAGATGACCTGGCTGAAAAGCTACGA
              AGAGCACTACTCGATAAAAGGTACCTAATCGTCTTGGATGATG
              TGTGGGATATTGCAACAGGGGAGATGTTAATAGCATGTTTTCC
              TAAGGGTAAGAGAGGGAAATAGAATCATCTTAACTAGCCGAAG
              TAGAAAGGTAGGTTTGAAAGTTAAATGCCGTAGTGATCCTCTC
              GACCTTAAACTTTTAACATCTGAAGAAAGTTGGGATTTATTCG
              AAAAAAGGGTATTTGGAGATGAAGGAAGCTGCCCTGCTGAAC
              TGTCCGAAGTTGGACACCAAATAGTTGAGAAATGTAAGGGTCT
              TCCCTTGGCTATTGTTTTAATTGCTGGAGTAATTGTTAGAGGGA
              AGAAAAAGGAAAAGGATTTTTGGCTTAAGATACTGCATAATCT
              GGATTCCTTTATTTCTACCAACATCAATTTGGTTATGCAATTAA
              GTTATGACCATTTACCATGCCACCTGAAGCCGTTGCTGCTTTAC
              TTTGCAACAACTCAAAAGAGCCAACAAACTCCAGTCTCTACAT
              TGATGCAGTTGTGGATGGCCGAAGGGTTTGTGGATCATGATAG
              TTTAGAGGAAGTAACTCAAAGTTACTTGGATGCTCTAATTTCC
              AGTAGCCTGATAATGGTGGATCATATCCCCTCCAAGAGTTATT
              GGTGGACGTCTTTAATGATCAAGGTTTGCTATGTGCATGATGTT
              GTGCACGATTTTTGTTCAGAAAAAGCCAAAAAGGAGAAGTTTC
              TCAAGTTAATCAATTCAGGTGATCCATTTCATGCTTCAGATTTC
              CTACACCATCGTCTAACCATTCATACTGACAACGGCCAACTCC
              ACAAAAAATGTGTTTATTCAATTCTAATAAGTGCTTAGCTGTT
              AGTAAGCATGTCATATCTTTGAAAGTGAGTGGTCCACTAGATG
              AGTTCAGGTATATCTGTCACACAAGACACTTTGGACTTGTTAG
              AGTGTTGCAACTGGATGACATCATTCTGGAAGATTCTTTAATG
```

TABLE 1-continued

Sequence information
The genomic sequences correspond to the mRNA with +2 kb upstream and downstream
from the start and the end.

```
                GAAGAAATAGGGTCCCTATTTCATTTGAGGTTCTTAAGCATTG
                AGACTGCTGTAGGTGTAATAGCTATCCCAGTGTCGTGGTTGAA
                CCTCCAGAATCTGGAAACGCTGTTGATTTATACAACTTATTCCA
                CCATGGTATTACTGCCCAGAATATTGCAACTGTCAAAGCTGAA
                ACATGTGAAAATTAAGGAATGTTCTTTCTTTGAAGAGAAAGAG
                GATATCCAACGTAGAATATTGGAAGCTGGGAATTCTTCAAACT
                TGACAACTCTATCCGGAGTTGTTATCTCATATTCTGAAGGCATG
                AGTGATGATGCTCTGGAGAAGTTCCCAATTCTTCAGCACCTTG
                ATTGCATCATCATGGAATCGCAGAATGCTCCTACACACGACTA
                TTGGTTTCTCAAGCTTGATGTACTTAATAAACTCGAATCATTCG
                TAGCAAGATACAAGCGCAATGGACATCCCTCGTTAAACCGACA
                ACCGTATGGATTTCACTTCCCTACAAGCTTGAAAGAGTTACGG
                TTGACTGGTTTTTTCCTGAGACCTGATTTGTTGTCAGTAATCGC
                AGCGTTGCCTGAGCTTGAGATTATGGAGTTTTCCGGCTGTTATT
                TCGTGGATACTAAATGGGACGCAAGTGAGGACATCTATCTAAG
                TCTTAAGACTTTGATTTTGCGAGATGTCCATTTATCAGAATGGC
                AAGTTGAGGGGGGAACTTTTCCCAAGCTTGAGAAATTAATACT
                AAAATTTTGTTCCACACTTGGGGAGATCCCTTGTGCATTTATGG
                ATGTAGAAACTTTAAAGTCCATTGATTTAAGTTTTGTTGGGCGT
                AAGCTTCGAGATTCAGCCATTGAGATTAAGAAAAATGTAGCAG
                ATTTCACAGGAGAGGACAGAGTTGATGTCCACACATCACATTT
                GTTTGCAACCAACGTGAAAGAACAGATTATGAGAATGACGGG
                TATGGGAAATATCAGGGAAGGAGAGGAATTTAA
```

```
SEQ ID NO:     ATGGAAAAAGGAGAAAAATCATTGCAGCTACTATTTGAGGAA
3:             CAAAAAACAAGAATCACGAATCTTATTGATGATTTCTTGATTC
CDS MeR1       GCTTGAAGCAAATAAAGAATGAATTCATTGCTTCAAAATTGGA
(isoform 2)    TGCCTTTGAAAATCTAAGAATGGAACTGAGATTCCTAAGAACA
               TTTGTCCTGTTTGGGAATTCGATGAATTGGATGACTTTTATGA
               GAGGATGTCACTGAGTATAAGCAAATTCGATCAATCTACGGAG
               TACGTAGATAAAATAATCCTAGAGAAATACAACATGGAATGTC
               TTGCCCCTCTGCTGCTTGAAGAGATAAGAAATTATTTGAGTTTG
               AAGAATGATTATGTAGCCACAACTACAGAGATAAAATTGTTTG
               AATACCTCATCAGAAACCTCCATGATCTACCAAAGTATTGTTCT
               GATTTGCTTCTACCACTCATGAGTGAATACAAGATTCTTCGGCA
               AGTATGCACACATCTCAGAGATTTCTATCAGTTGGAATGCAAC
               AAAACAACAAAAACAGAATTTCTCTATACTCGGTATCAAGTGA
               CAGCCGATAGAGTAACACAATTCTGTTTTGATCTTTGGACAGG
               AATGTATAAATACTCTGACAATGAGTATGCCTTCTCTGAATGTT
               CTTCCAAGATCACTTCTCTACTCATTGACATAATCCCTCTTGAG
               TTGGAGGTTCTATACATTTCTACTTCTAAGCTCATCAAAGAGTC
               AACGTCAAAAGAACTAGAAGGATTTGTTAAGCAAATCTTAAAA
               GCATCTCCAAGGATTCTTCAACATTATCTCATTCATCTCCAAGG
               ACGCATGGCCGGTGTAGAAGCCGTCAATTTCGCTCCAACTCGA
               AGCATTAGTGTCATGATGGAGTTCCTATTGATCTTTCTCACCGA
               TATGCCAAAGCGGTTTATCCATCGTGAAAAATTGAACGATATG
               TTGGCACATGTCAGAATACTTACAAGGAAAATATCTACTCTGG
               TGAGTAAACTGTTGGAGGAGATCTCTGAGGATAATATCAATGA
               AGCGGACTTTTCAGCTCCGGACTTTTTGCAAGAAATTGAACAA
               ATGAAGGGAGATATCAGACACATCTTTTTAAAAGCTCCTGAGT
               CATCTCAACTTCGGTTTCCTATGGATGATGGTTCCTCTTCATG
               AATCTTCTACTCAGACATTTAAATGATTTACTCATTTCCAATGC
               TTATTCAGTTTTTCTCATAAAAAAAGAAATTGGGATGGTGAAA
               GAAAGCCTTGAATTCCTAATATCATCTTTCAGGAAAGTCAGGC
               AAACATTGGATGAGAGTACTAGTGGAGTAGTTAAAAATTGTTG
               GGTGCGTGCTTTGGATGTGGCATATGAGGCAGAACATATCATT
               AATTCCATTCTTGTCAGAGATAAAGCTCTCTCACATCTCCTCTT
               CTCACTTCCGAGTGTCACTGATAAGATCAAACTTATCGTGGAA
               CAAGTCACCAGGTTTCAGCTGGAGGATAAGAATGGGGATGGC
               CCCCTTGATGCAAAGTCTTCCTTCGAGCCAACTCAGTCAACTTC
               ATCACCTTTTGTTGAGGTAACAGTAGGTCACGAGAAAGAAGAA
               TCCCAGATCATTGACCAGCTCCTTGATGAACATGAATCTGAGC
               TTGATGTCATTTCCATTGTCGGAATGCCAGGACTCGGTAAAAC
               TACTCTGGCCAACAAAGTGTATAAAGATACATTAGTTGCTAGG
               CATTTCCATGTCCGTGCTTGGTGCACTGTTTCGCAAAAGTATAA
               CAAGTCAAAGGTGTTGCGGGAGATTCTTCAGCAAGTTACTGGC
               TCGGGAGGAAAAGAAAGTGAAGATGACCTGGCTGAAAAGCTA
               CGAAGAGCACTACTCGATAAAAGGTACCTAATCGTCTTGGATG
               ATGTGTGGGATATTGCAACAGGGGAGATGTTAATAGCATGTTT
               TCCTAAGGGTAAGAGAGGAAATAGAATCATCTTAACTAGCCGA
               AGTAGAAAGGTAGGTTTGAAAGTTAAATGCCGTAGTGATCCTC
               TCGACCTTAAACTTTTAACATCTGAAGAAAGTTGGGATTTATTC
               GAAAAAAGGGTATTTGGAGATGAAGGGAAGCTGCCCTGCTGAA
               CTGTCCGAAGTTGGACACCAAATAGTTGAGAAATGTAAGGGTC
               TTCCCTTGGCTATTGTTTTAATTGCTGGAGTAATTGTTAGAGGG
               AAGAAAAAGGAAAAGGATTTTTGGCTTAAGATACTGCATAATC
```

TABLE 1-continued

Sequence information
The genomic sequences correspond to the mRNA with +2 kb upstream and downstream
from the start and the end.

```
                  TGGATTCCTTTATTTCTACCAACATCAATTTGGTTATGCAATTA
                  AGTTATGACCATTTACCATGCCACCTGAAGCCGTTGCTGCTTTA
                  CTTTGCAACAACTCAAAAGAGCCAACAAACTCCAGTCTCTACA
                  TTGATGCAGTTGTGGATGGCCGAAGGGTTTGTGGATCATGATA
                  GTTTAGAGGAAGTAACTCAAAGTTACTTGGATGCTCTAATTTC
                  CAGTAGCCTGATAATGGTGGATCATATCCCCTCCAAGAGTTAT
                  TGGTGGACGTCTTTAATGATCAAGGTTTGCTATGTGCATGATGT
                  TGTGCACGATTTTTGTTCAGAAAAAGCCAAAAAGGAGAAGTTT
                  CTCAAGTTAATCAATTCAGGTGATCCATTTCATGCTTCAGATTT
                  CCTACACCATCGTCTAACCATTCATACTGACAACGGCCAACTC
                  CACAAAAAATGTGTTTTATTCAATTCTAATAAGTGCTTAGCTGT
                  TAGTAAGCATGTCATATCTTTGAAAGTGAGTGGTCCACTAGAT
                  GAGTTCAGGTATATCTGTCACACAAGACACTTTGGACTTGTTA
                  GAGTGTTGCAACTGGATGACATCATTCTGGAAGATTCTTTAAT
                  GGAAGAAATAGGGTCCCTATTTCATTTGAGGTTCTTAAGCATT
                  GAGACTGCTGTAGGTGTAATAGCTATCCCAGTGTCGTGGTTGA
                  ACCTCCAGAATCTGGAAACGCTGTTGATTTATACAACTTATTCC
                  ACCATGGTATTACTGCCCAGAATATTGCAACTGTCAAAGCTGA
                  AACATGTGAAAATTAAGGAATGTTCTTTCTTTGAAGAGAAAGA
                  GGATATCCAACGTAGAATATTGGAAGCTGGGAATTCTTCAAAC
                  TTGACAACTCTATCCGGAGTTGTTATCTCATATTCTGAAGGCAT
                  GAGTGATGATGCTCTGGAGAAGTTCCCAATTCTTCAGCACCTT
                  GATTGCATCATCATGGAATCGCAGAATGCTCCTACACACGACT
                  ATTGGTTTCTCAAGCTTGATGTACTTAATAAACTCGAATCATTC
                  GTAGCAAGATACAAGCGCAATGGACATCCCTCGTTAAACCGAC
                  AACCGTATGGATTTCACTTCCCTACAAGCTTGAAAGAGTTACG
                  GTTGACTGGTTTTTTCCTGAGACCTGATTTGTTGTCAGTAATCG
                  CAGCGTTGCCTGAGCTTGAGATTATGGAGTTTTCCGGCTGTTAT
                  TTCGTGGATACTAAATGGGACGCAAGTGAGGACATCTATCTAA
                  GTCTTAAGACTTTGATTTTGCGAGATGTCCATTTATCAGAATGG
                  CAAGTTGAGGGGGGAACTTTTCCCAAGCTTGAGAAATTAATAC
                  TAAAATTTTGTTCCACACTTGGGGAGATCCCTTGTGCATTTATG
                  GATGTAGAAACTTTAAAGTCCATTGATTTAAGTTTTGTTGGGCG
                  TAAGCTTCGAGATTCAGCCATTGAGATTAAGAAAAATGTAGCA
                  GATTTCACAGGAGAGGACAGAGTTGATGTCCACACATCACATT
                  TGTTTGCAACCAACGTGAAAGAACAGATTATGAGAATGACGG
                  GTATGGGAAATATACAGGGAAGGAGAGGAATTTAA

SEQ ID NO:   ATGGAAAAAGGAGAAAAATCATTGCTACTATTTGAGGAACAA
4:           AAAACAAGAATCACGAATCTTATTGATGATTTCTTGATTCGCTT
CDS MeR1     GAAGCAAATAAAGAATGAATTCATTGCTTCAAAATTGGATGCC
(isoform 3)  TTTGAAAATCTAAGAATGGAACTGAGATTCCTAAGAACATTTG
             TCCTGTTTGGGAATTCGATGAATTTGGATGACTTTTATGAGAGG
             ATGTCACTGAGTATAAGCAAATTCGATCAATCTACGGAGTACG
             TAGATAAAATAATCCTAGAGAAATACAACATGGAATGTCTTGC
             CCCTCTGCTGCTTGAAGAGATAAGAAATTATTTGAGTTTGAAG
             AATGATTATGTAGCCACAACTACAGAGATAAAATTGTTTGAAT
             ACCTCATCAGAAACCTCCATGATCTACCAAAGTATTGTTCTGAT
             TTGCTTCTACCACTCATGAGTGAATACAAGATTCTTCGGCAAGT
             ATGCACACATCTCAGAGATTTCTATCAGTTGGAATGCAACAAA
             ACAACAAAAACAGAATTTCTCTATACTCGGTATCAAGTGACAG
             CCGATAGAGTAACACAATTCTGTTTTGATCTTTGGACAGGAAT
             GTATAAATACTCTGACAATGAGTATGCCTTCTCTGAATGTTCTT
             CCAAGATCACTTCTCTACTCATTGACATAATCCCTCTTGAGTTG
             GAGGTTCTATACATTTCTACTTCTAAGCTCATCAAAGAGTCAAC
             GTCAAAAGAACTAGAAGGATTTGTTAAGCAAATCTTAAAAGCA
             TCTCCAAGGATTCTTCAACATTATCTCATTCATCTCCAAGGACG
             CATGGCCGGTGTAGAAGCCGTCAATTTCGCTCCAACTCGAAGC
             ATTAGTGTCATGATGGAGTTCCTATTGATCTTTCTCACCGATAT
             GCCAAAGCGGTTTATCCATCGTGAAAAATTGAACGATATGTTG
             GCACATGTCAGAATACTTACAAGGAAAATATCTACTCTGGTGA
             GTAAACTGTTGGAGGAGATCTCTGAGGATAATATCAATGAAGC
             GGACTTTTCAGCTCCGGACTTTTTGCAAGAAATTGAACAAATG
             AAGGGAGATATCAGACACATCTTTTTAAAAGCTCCTGAGTCAT
             CTCAACTTCGGTTTCCTATGGATGATGGTTTCCTCTTCATGAAT
             CTTCTACTCAGACATTTAAATGATTTACTCATTTCCAATGCTTA
             TTCAGTTTTTCTCATAAAAAAAGAAATTGGGATGGTGAAAGAA
             AGCCTTGAATTCCTAATATCATCTTTCAGGAAAGTCAGGCAAA
             CATTGGATGAGAGTACTAGTGGAGTAGTTAAAAATTGTTGGGT
             GCGTGCTTTGGATGTGGCATATGAGGCAGAACATATCATTAAT
             TCCATTCTTGTCAGAGATAAAGCTCTCTCACATCTCCTCTTCTC
             ACTTCCGAGTGTCACTGATAAGATCAAACTTATCGTGGAACAA
             GTCACCAGGTTTCAGCTGGAGGATAAGAATGGGGATGGCCCCC
             TTGATGCAAAGTCTTCCTTCGAGCCAACTCAGTCAACTTCATCA
             CCTTTTGTTGAGGTAACAGTAGGTCACGAGAAAGAAGAATCCC
             AGATCATTGACCAGCTCCTTGATGAACATGAATCTGAGCTTGA
```

TABLE 1-continued

Sequence information
The genomic sequences correspond to the mRNA with +2 kb upstream and downstream
from the start and the end.

```
                TGTCATTTCCATTGTCGGAATGCCAGGACTCGGTAAAACTACT
                CTGGCCAACAAAGTGTATAAAGATACATTAGTTGCTAGGCATT
                TCCATGTCCGTGCTTGGTGCACTGTTTCGCAAAAGTATAACAA
                GTCAAAGGTGTTGCGGGAGATTCTTCAGCAAGTTACTGGCTCG
                GGAGGAAAAGAAAGTGAAGATGACCTGGCTGAAAAGCTACGA
                AGAGCACTACTCGATAAAAGGTACCTAATCGTCTTGGATGATG
                TGTGGGATATTGCAACAGGGGAGATGTTAATAGCATGTTTTCC
                TAAGGGTAAGAGAGGAAATAGAATCATCTTAACTAGCCGAAG
                TAGAAAGGTAGGTTTGAAAGTTAAATGCCGTAGTGATCCTCTC
                GACCTTAAACTTTTAACATCTGAAGAAAGTTGGGATTTATTCG
                AAAAAAGGGTATTTGGAGATGAAGGAAGCTGCCCTGCTGAAC
                TGTCCGAAGTTGGACACCAAATAGTTGAGAAATGTAAGGGTCT
                TCCCTTGGCTATTGTTTTAATTGCTGGAGTAATTGTTAGAGGGA
                AGAAAAAGGAAAAGGATTTTTGGCTTAAGATACTGCATAATCT
                GGATTCCTTTATTTCTACCAACATCAATTTGGTTATGCAATTAA
                GTTATGACCATTTACCATGCCACCTGAAGCCGTTGCTGCTTTAC
                TTTGCAACAACTCAAAAGAGCCAACAAACTCCAGTCTCTACAT
                TGATGCAGTTGTGGATGGCCGAAGGGTTTGTGGATCATGATAG
                TTTAGAGGAAGTAACTCAAAGTTACTTGGATGCTCTAATTTCC
                AGTAGCCTGATAATGGTGGATCATATCCCCTCCAAGAGTTATT
                GGTGGACGTCTTTAATGATCAAGGTTTGCTATGTGCATGATGTT
                GTGCACGATTTTTGTTCAGAAAAAGCCAAAAAGGAGAAGTTTC
                TCAAGTTAATCAATTCAGGTGATCCATTTCATGCTTCAGATTTC
                CTACACCATCGTCTAACCATTCATACTGACAACGGCCAACTCC
                ACAAAAAATGTGTTTTATTCAATTCTAATAAGTGCTTAGCTGTT
                AGTAAGCATGTCATATCTTTGAAAGTGAGTGGTCCACTAGATG
                AGTTCAGGTATATCTGTCACACAAGACACTTTGGACTTGTTAG
                AGTGTTGCAACTGGATGACATCATTCTGGAAGATTCTTTAATG
                GAAGAAATAGGGTCCCTATTTCATTTGAGGTTCTTAAGCATTG
                AGACTGCTGTAGGTGTAATAGCTATCCCAGTGTCGTGGTTGAA
                CCTCCAGAATCTGGAAACGCTGTTGATTTATACAACTTATTCCA
                CCATGGTATTACTGCCCAGAATATTGCAACTGTCAAAGCTGAA
                ACATGTGAAAATTAAGGAATGTTCTTTCTTTGAAGAGAAAGAG
                GATATCCAACGTAGAATATTGGAAGCTGGGAATTCTTCAAACT
                TGACAACTCTATCCGGAGTTGTTATCTCATATTCTGAAGGCATG
                AGTGATGATGCTCTGGAGAAGTTCCCAATTCTTCAGCACCTTG
                ATTGCATCATCATGGAATCGCAGAATGCTCCTACACACGACTA
                TTGGTTTCTCAAGCTTGATGTACTTAATAAACTCGAATCATTCG
                TAGCAAGATACAAGCGCAATGGACATCCCTCGTTAAACCGACA
                ACCGTATGGATTTCACTTCCCTACAAGCTTGAAAGAGTTACGG
                TTGACTGGTTTTTTCCTGAGACCTGATTTGTTGTCAGTAATCGC
                AGCGTTGCCTGAGCTTGAGATTATGGAGTTTTCCGGCTGTTATT
                TCGTGGATACTAAATGGGACGCAAGTGAGGACATCTATCTAAG
                TCTTAAGACTTTGATTTTGCGAGATGTCCATTTATCAGAATGGC
                AAGTTGAGGGGGGAACTTTTCCCAAGCTTGAGAAATTAATACT
                AAAATTTTGTTCCACACTTGGGGAGATCCCTTGTGCATTTATGG
                ATGTAGAAACTTTAAAGTCCATTGATTTAAGTTTTGTTGGGCGT
                AAGCTTCGAGATTCAGCCATTGAGATTAAGAAAAATGTAGCAG
                ATTTCACAGGAGAGGACAGAGTTGATGTCCACACATCACATTT
                GTTTGCAACCAACGTGAAAGAACAGATTATGAGAATGACGGG
                TGGAGAATGTACTTGTGAAGAACTATAA

SEQ ID NO:    ATGGAAAAAGGAGAAAAATCATTGCAGCTACTATTTGAGGAA
5             CAAAAAACAAGAATCACGAATCTTATTGATGATTTCTTGATTC
CDS MeR1      GCTTGAAGCAAATAAAGAATGAATTCATTGCTTCAAAATTGGA
(isoform 4)   TGCCTTTGAAAATCTAAGAATGGAACTGAGATTCCTAAGAACA
              TTTGTCCTGTTTGGGAATTCGATGAATTTGGATGACTTTTATGA
              GAGGATGTCACTGAGTATAAGCAAATTCGATCAATCTACGGAG
              TACGTAGATAAAATAATCCTAGAGAAATACAACATGGAATGTC
              TTGCCCCTCTGCTGCTTGAAGAGATAAGAAATTATTTGAGTTTG
              AAGAATGATTATGTAGCCACAACTACAGAGATAAAATTGTTTG
              AATACCTCATCAGAAACCTCCATGATCTACCAAAGTATTGTTCT
              GATTTGCTTCTACCACTCATGAGTGAATACAAGATTCTTCGGCA
              AGTATGCACACATCTCAGAGATTTCTATCAGTTGGAATGCAAC
              AAAACAACAAAAACAGAATTTCTCTATACTCGGTATCAAGTGA
              CAGCCGATAGAGTAACACAATTCTGTTTTGATCTTTGGACAGG
              AATGTATAAATACTCTGACAATGAGTATGCCTTCTCTGAATGTT
              CTTCCAAGATCACTTCTCTACTCATTGACATAATCCCTCTTGAG
              TTGGAGGTTCTATACATTTCTACTTCTAAGCTCATCAAAGAGTC
              AACGTCAAAAGAACTAGAAGGATTTGTTAAGCAAATCTTAAAA
              GCATCTCCAAGGATTCTTCAACATTATCTCATTCATCTCCAAGG
              ACGCATGGCCGGTGTAGAAGCCGTCAATTTCGCTCCAACTCGA
              AGCATTAGTGTCATGATGGAGTTCCTATTGATCTTTCTCACCGA
              TATGCCAAAGCGGTTTATCCATCGTGAAAAATTGAACGATATG
              TTGGCACATGTCAGAATACTTACAAGGAAAATATCTACTCTGG
              TGAGTAAACTGTTGGAGGAGATCTCTGAGGATAATATCAATGA
```

TABLE 1-continued

Sequence information
The genomic sequences correspond to the mRNA with +2 kb upstream and downstream
from the start and the end.

```
AGCGGACTTTTCAGCTCCGGACTTTTTGCAAGAAATTGAACAA
ATGAAGGGAGATATCAGACACATCTTTTTAAAAGCTCCTGAGT
CATCTCAACTTCGGTTTCCTATGGATGATGGTTTCCTCTTCATG
AATCTTCTACTCAGACATTTAAATGATTTACTCATTTCCAATGC
TTATTCAGTTTTTCTCATAAAAAAAGAAATTGGGATGGTGAAA
GAAAGCCTTGAATTCCTAATATCATCTTTCAGGAAAGTCAGGC
AAACATTGGATGAGAGTACTAGTGGAGTAGTTAAAAATTGTTG
GGTGCGTGCTTTGGATGTGGCATATGAGGCAGAACATATCATT
AATTCCATTCTTGTCAGAGATAAAGCTCTCTCACATCTCCTCTT
CTCACTTCCGAGTGTCACTGATAAGATCAAACTTATCGTGGAA
CAAGTCACCAGGTTTCAGCTGGAGGATAAGAATGGGGATGGC
CCCCTTGATGCAAAGTCTTCCTTCGAGCCAACTCAGTCAACTTC
ATCACCTTTTGTTGAGGTAACAGTAGGTCACGAGAAAGAAGAA
TCCCAGATCATTGACCAGCTCCTTGATGAACATGAATCTGAGC
TTGATGTCATTTCCATTGTCGGAATGCCAGGACTCGGTAAAAC
TACTCTGGCCAACAAAGTGTATAAAGATACATTAGTTGCTAGG
CATTTCCATGTCCGTGCTTGGTGCACTGTTTCGCAAAGTATAA
CAAGTCAAAGGTGTTGCGGGAGATTCTTCAGCAAGTTACTGGC
TCGGGAGGAAAAGAAAGTGAAGATGACCTGGCTGAAAAGCTA
CGAAGAGCACTACTCGATAAAAGGTACCTAATCGTCTTGGATG
ATGTGTGGGATATTGCAACAGGGGGAGATGTTAATAGCATGTTT
TCCTAAGGGTAAGAGAGGAAATAGAATCATCTTAACTAGCCGA
AGTAGAAAGGTAGGTTTGAAAGTTAAATGCCGTAGTGATCCTC
TCGACCTTAAACTTTTAACATCTGAAGAAAGTTGGGATTTATTC
GAAAAAGGGTATTTGGAGATGAAGGAAGCTGCCCTGCTGAA
CTGTCCGAAGTTGGACACCAAATAGTTGAGAAATGTAAGGGTC
TTCCCTTGGCTATTGTTTTAATTGCTGGAGTAATTGTTAGAGGG
AAGAAAAAGGAAAAGGATTTTTGGCTTAAGATACTGCATAATC
TGGATTCCTTTATTTCTACCAACATCAATTTGGTTATGCAATTA
AGTTATGACCATTTACCATGCCACCTGAAGCCGTTGCTGCTTTA
CTTTGCAACAACTCAAAAGAGCCAACAAACTCCAGTCTCTACA
TTGATGCAGTTGTGGATGGCCGAAGGGTTTGTGGATCATGATA
GTTTAGAGGAAGTAACTCAAAGTTACTTGGATGCTCTAATTTC
CAGTAGCCTGATAATGGTGGATCATATCCCCTCCAAGAGTTAT
TGGTGGACGTCTTTAATGATCAAGGTTTGCTATGTGCATGATGT
TGTGCACGATTTTTGTTCAGAAAAAGCCAAAAAGGAGAAGTTT
CTCAAGTTAATCAATTCAGGTGATCCATTTCATGCTTCAGATTT
CCTACACCATCGTCTAACCATTCATACTGACAACGGCCAACTC
CACAAAAAATGTGTTTTATTCAATTCTAATAAGTGCTTAGCTGT
TAGTAAGCATGTCATATCTTTGAAAGTGAGTGGTCCACTAGAT
GAGTTCAGGTATATCTGTCACACAAGACACTTTGGACTTGTTA
GAGTGTTGCAACTGGATGACATCATTCTGGAAGATTCTTTAAT
GGAAGAAATAGGGTCCCTATTTCATTTGAGGTTCTTAAGCATT
GAGACTGCTGTAGGTGTAATAGCTATCCCAGTGTCGTGGTTGA
ACCTCCAGAATCTGGAAACGCTGTTGATTTATACAACTTATTCC
ACCATGGTATTACTGCCCAGAATATTGCAACTGTCAAAGCTGA
AACATGTGAAAATTAAGGAATGTTCTTTCTTTGAAGAGAAAGA
GGATATCCAACGTAGAATATTGGAAGCTGGGAATTCTTCAAAC
TTGACAACTCTATCCGGAGTTGTTATCTCATATTCTGAAGGCAT
GAGTGATGATGCTCTGGAGAAGTTCCCAATTCTTCAGCACCTT
GATTGCATCATCATGGAATCGCAGAATGCTCCTACACACGACT
ATTGGTTTCTCAAGCTTGATGTACTTAATAAACTCGAATCATTC
GTAGCAAGATACAAGCGCAATGGACATCCCTCGTTAAACCGAC
AACCGTATGGATTTCACTTCCCTACAAGCTTGAAAGAGTTACG
GTTGACTGGTTTTTTCCTGAGACCTGATTTGTTGTCAGTAATCG
CAGCGTTGCCTGAGCTTGAGATTATGGAGTTTTCCGGCTGTTAT
TTCGTGGATACTAAATGGGACGCAAGTGAGGACATCTATCTAA
GTCTTAAGACTTTGATTTTGCGAGATGTCCATTTATCAGAATGG
CAAGTTGAGGGGGGAACTTTTCCCAAGCTTGAGAAATTAATAC
TAAAATTTTGTTCCACACTTGGGGAGATCCCTTGTGCATTTATG
GATGTAGAAACTTTAAAGTCCATTGATTTAAGTTTTGTTGGGCG
TAAGCTTCGAGATTCAGCCATTGAGATTAAGAAAAATGTAGCA
GATTTCACAGGAGAGGACAGAGTTGATGTCCACACATCACATT
TGTTTGCAACCAACGTGAAAGAACAGATTATGAGAATGACGG
GTGGAGAATGTACTTGTGAAGAACTATAA
```

```
SEQ ID NO:    ATGGAAAAAGGAGAAAAATCATTGCTACTATTTGAGGAACAA
6:            AAAACAAGAATCACGAATCTTATTGATGATTTCTTGATTCGCTT
CDS MeR1      GAAGCAAATAAAGAATGAATTCATTGCTTCAAAATTGGATGCC
(isoform 5)   TTTGAAAATCTAAGAATGGAACTGAGATTCCTAAGAACATTTG
              TCCTGTTTGGGAATTCGATGAATTTGGATGACTTTTATGAGAGG
              ATGTCACTGAGTATAAGCAAATTCGATCAATCTACGGAGTACG
              TAGATAAAATAATCCTAGAGAAATACAACATGGAATGTCTTGC
              CCCTCTGCTGCTTGAAGAGATAAGAAATTATTTGAGTTTGAAG
              AATGATTATGTAGCCACAACTACAGAGATAAAATTGTTTGAAT
              ACCTCATCAGAAACCTCCATGATCTACCAAAGTATTGTTCTGAT
```

TABLE 1-continued

Sequence information
The genomic sequences correspond to the mRNA with +2 kb upstream and downstream
from the start and the end.

```
               TTGCTTCTACCACTCATGAGTGAATACAAGATTCTTCGGCAAGT
               ATGCACACATCTCAGAGATTTCTATCAGTTGGAATGCAACAAA
               ACAACAAAAACAGAATTTCTCTATACTCGGTATCAAGTGACAG
               CCGATAGAGTAACACAATTCTGTTTTGATCTTTGGACAGGAAT
               GTATAAATACTCTGACAATGAGTATGCCTTCTCTGAATGTTCTT
               CCAAGATCACTTCTCTACTCATTGACATAATCCCTCTTGAGTTG
               GAGGTTCTATACATTTCTACTTCTAAGCTCATCAAAGAGTCAAC
               GTCAAAAGAACTAGAAGGATTTGTTAAGCAAATCTTAAAAGCA
               TCTCCAAGGATTCTTCAACATTATCTCATTCATCTCCAAGGACG
               CATGGCCGGTGTAGAAGCCGTCAATTTCGCTCCAACTCGAAGC
               ATTAGTGTCATGATGGAGTTCCTATTGATCTTTCTCACCGATAT
               GCCAAAGCGGTTTATCCATCGTGAAAAATTGAACGATATGTTG
               GCACATGTCAGAATACTTACAAGGAAAATATCTACTCTGGTGA
               GTAAACTGTTGGAGGAGATCTCTGAGGATAATATCAATGAAGC
               GGACTTTTCAGCTCCGGACTTTTTGCAAGAAATTGAACAAATG
               AAGGGAGATATCAGACACATCTTTTTAAAAGCTCCTGAGTCAT
               CTCAACTTCGGTTTCCTATGGATGATGGTTTCCTCTTCATGAAT
               CTTCTACTCAGACATTTAAATGATTTACTCATTTCCAATGCTTA
               TTCAGTTTTTCTCATAAAAAAAGAAATTGGGATGGTGAAAGAA
               AGCCTTGAATTCCTAATATCATCTTTCAGGAAAGTCAGGCAAA
               CATTGGATGAGAGTACTAGTGGAGTAGTTAAAAATTGTTGGGT
               GCGTGCTTTGGATGTGGCATATGAGGCAGAACATATCATTAAT
               TCCATTCTTGTCAGAGATAAAGCTCTCTCACATCTCCTCTTCTC
               ACTTCCGAGTGTCACTGATAAGATCAAACTTATCGTGGAACAA
               GTCACCAGGTTTCAGCTGGAGGATAAGAATGGGGATGGCCCCC
               TTGATGCAAAGTCTTCCTTCGAGCCAACTCAGTCAACTTCATCA
               CCTTTTGTTGAGGTAACAGTAGGTCACGAGAAAGAAGAATCCC
               AGATCATTGACCAGCTCCTTGATGAACATGAATCTGAGCTTGA
               TGTCATTTCCATTGTCGGAATGCCAGGACTCGGTAAAACTACT
               CTGGCCAACAAAGTGTATAAAGATACATTAGTTGCTAGGCATT
               TCCATGTCCGTGCTTGGTGCACTGTTTCGCAAAAGTATAACAA
               GTCAAAGGTGTTGCGGGAGATTCTTCAGCAAGTTACTGGCTCG
               GGAGGAAAAGAAAGTGAAGATGACCTGGCTGAAAAGCTACGA
               AGAGCACTACTCGATAAAAGGTGGAGAATGTACTTGTGA
```

```
SEQ ID NO:    ATGGAAAAAGGAGAAAAATCATTGCAGCTACTATTTGAGGAA
7:            CAAAAAACAAGAATCACGAATCTTATTGATGATTTCTTGATTC
CDS MeR1      GCTTGAAGCAAATAAAGAATGAATTCATTGCTTCAAAATTGGA
(isoform 6)   TGCCTTTGAAAATCTAAGAATGGAACTGAGATTCCTAAGAACA
              TTTGTCCTGTTTGGGAATTCGATGAATTTGGATGACTTTTATGA
              GAGGATGTCACTGAGTATAAGCAAATTCGATCAATCTACGGAG
              TACGTAGATAAAATAATCCTAGAGAAATACAACATGGAATGTC
              TTGCCCCTCTGCTGCTTGAAGAGATAAGAAATTATTTGAGTTTG
              AAGAATGATTATGTAGCCACAACTACAGAGATAAAATTGTTTG
              AATACCTCATCAGAAACCTCCATGATCTACCAAAGTATTGTTCT
              GATTTGCTTCTACCACTCATGAGTGAATACAAGATTCTTCGGCA
              AGTATGCACACATCTCAGAGATTTCTATCAGTTGGAATGCAAC
              AAAACAACAAAAACAGAATTTCTCTATACTCGGTATCAAGTGA
              CAGCCGATAGAGTAACACAATTCTGTTTTGATCTTTGGACAGG
              AATGTATAAATACTCTGACAATGAGTATGCCTTCTCTGAATGTT
              CTTCCAAGATCACTTCTCTACTCATTGACATAATCCCTCTTGAG
              TTGGAGGTTCTATACATTTCTACTTCTAAGCTCATCAAAGAGTC
              AACGTCAAAAGAACTAGAAGGATTTGTTAAGCAAATCTTAAAA
              GCATCTCCAAGGATTCTTCAACATTATCTCATTCATCTCCAAGG
              ACGCATGGCCGGTGTAGAAGCCGTCAATTTCGCTCCAACTCGA
              AGCATTAGTGTCATGATGGAGTTCCTATTGATCTTTCTCACCGA
              TATGCCAAAGCGGTTTATCCATCGTGAAAAATTGAACGATATG
              TTGGCACATGTCAGAATACTTACAAGGAAAATATCTACTCTGG
              TGAGTAAACTGTTGGAGGAGATCTCTGAGGATAATATCAATGA
              AGCGGACTTTTCAGCTCCGGACTTTTTGCAAGAAATTGAACAA
              ATGAAGGGAGATATCAGACACATCTTTTTAAAAGCTCCTGAGT
              CATCTCAACTTCGGTTTCCTATGGATGATGGTTTCCTCTTCATG
              AATCTTCTACTCAGACATTTAAATGATTTACTCATTTCCAATGC
              TTATTCAGTTTTTCTCATAAAAAAAGAAATTGGGATGGTGAAA
              GAAAGCCTTGAATTCCTAATATCATCTTTCAGGAAAGTCAGGC
              AAACATTGGATGAGAGTACTAGTGGAGTAGTTAAAAATTGTTG
              GGTGCGTGCTTTGGATGTGGCATATGAGGCAGAACATATCATT
              AATTCCATTCTTGTCAGAGATAAAGCTCTCTCACATCTCCTCTT
              CTCACTTCCGAGTGTCACTGATAAGATCAAACTTATCGTGGAA
              CAAGTCACCAGGTTTCAGCTGGAGGATAAGAATGGGGATGGC
              CCCCTTGATGCAAAGTCTTCCTTCGAGCCAACTCAGTCAACTTC
              ATCACCTTTTGTTGAGGTAACAGTAGGTCACGAGAAAGAAGAA
              TCCCAGATCATTGACCAGCTCCTTGATGAACATGAATCTGAGC
              TTGATGTCATTTCCATTGTCGGAATGCCAGGACTCGGTAAAAC
              TACTCTGGCCAACAAAGTGTATAAAGATACATTAGTTGCTAGG
              CATTTCCATGTCCGTGCTTGGTGCACTGTTTCGCAAAAGTATAA
```

TABLE 1-continued

Sequence information
The genomic sequences correspond to the mRNA with +2 kb upstream and downstream
from the start and the end.

```
                  CAAGTCAAAGGTGTTGCGGGAGATTCTTCAGCAAGTTACTGGC
                  TCGGGAGGAAAAGAAAGTGAAGATGACCTGGCTGAAAAGCTA
                  CGAAGAGCACTACTCGATAAAAGGTGGAGAATGTACTTGTGA

SEQ ID NO:        ATGGAAAAAGGAGAAAAATCATTGCTACTATTTGAGGAACAA
8:                AAAACAAGAATCACGAATCTTATTGATGATTTCTTGATTCGCTT
CDS MeR1          GAAGCAAATAAAGAATGAATTCATTGCTTCAAAATTGGATGCC
(isoform 7)       TTTGAAAATCTAAGAATGGAACTGAGATTCCTAAGAACATTTG
                  TCCTGTTTGGGAATTCGATGAATTTGGATGACTTTTATGAGAGG
                  ATGTCACTGAGTATAAGCAAATTCGATCAATCTACGGAGTACG
                  TAGATAAAATAATCCTAGAGAAATACAACATGGAATGTCTTGC
                  CCCTCTGCTGCTTGAAGAGATAAGAAATTATTTGAGTTTGAAG
                  AATGATTATGTAGCCACAACTACAGAGATAAAATTGTTTGAAT
                  ACCTCATCAGAAACCTCCATGATCTACCAAAGTATTGTTCTGAT
                  TTGCTTCTACCACTCATGAGTGAATACAAGATTCTTCGGCAAGT
                  ATGCACACATCTCAGAGATTTCTATCAGTTGGAATGCAACAA
                  ACAACAAAAACAGAATTTCTCTATACTCGGTATCAAGTGACAG
                  CCGATAGAGTAACACAATTCTGTTTTGATCTTTGGACAGGAAT
                  GTATAAATACTCTGACAATGAGTATGCCTTCTCTGAATGTTCTT
                  CCAAGATCACTTCTCTACTCATTGACATAATCCCTCTTGAGTTG
                  GAGGTTCTATACATTTCTACTTCTAAGCTCATCAAAGAGTCAAC
                  GTCAAAAGAACTAGAAGGATTTGTTAAGCAAATCTTAAAAGCA
                  TCTCCAAGGATTCTTCAACATTATCTCATTCATCTCCAAGGACG
                  CATGGCCGGTGTAGAAGCCGTCAATTTCGCTCCAACTCGAAGC
                  ATTAGTGTCATGATGGAGTTCCTATTGATCTTTCTCACCGATAT
                  GCCAAAGCGGTTTATCCATCGTGAAAAATTGAACGATATGTTG
                  GCACATGTCAGAATACTTACAAGGAAAATATCTACTCTGGTGA
                  GTAAACTGTTGGAGGAGATCTCTGAGGATAATATCAATGAAGC
                  GGACTTTTCAGCTCCGGACTTTTTGCAAGAAATTGAACAAATG
                  AAGGGAGATATCAGACACATCTTTTTAAAAGCTCCTGAGTCAT
                  CTCAACTTCGGTTTCCTATGGATGATGGTTTCCTCTTCATGAAT
                  CTTCTACTCAGACATTTAAATGATTTACTCATTTCCAATGCTTA
                  TTCAGTTTTTCTCATAAAAAAAGAAATTGGGATGGTGAAAGAA
                  AGCCTTGAATTCCTAATATCATCTTTCAGGAAAGTCAGGCAAA
                  CATTGGATGAGAGTACTAGTGGAGTAGTTAAAAATTGTTGGGT
                  GCGTGCTTTGGATGTGGCATATGAGGCAGAACATATCATTAAT
                  TCCATTCTTGTCAGAGATAAAGCTCTCTCACATCTCCTCTTCTC
                  ACTTCCGAGTGTCACTGATAAGATCAAACTTATCGTGGAACAA
                  GTCACCAGGTTTCAGCTGGAGGATAAGAATGGGGATGGCCCCC
                  TTGATGCAAAGTCTTCCTTCGAGCCAACTCAGTCAACTTCATCA
                  CCTTTTGTTGAGGTAACAGTAGGTCACGAGAAAGAAGAATCCC
                  AGATCATTGACCAGCTCCTTGATGAACATGAATCTGAGCTTGA
                  TGTCATTTCCATTGTCGGAATGCCAGGACTCGGTAAAACTACT
                  CTGGCCAACAAAGTGTATAAAGATACATTAGTTGCTAGGCATT
                  TCCATGTCCGTGCTTGGTGCACTGTTTCGCAAAAGTATAACAA
                  GTCAAAGGTGTTGCGGGAGATTCTTCAGCAAGTTACTGGCTCG
                  GGAGGAAAAGAAAGTGAAGATGACCTGGCTGAAAAGCTACGA
                  AGAGCACTACTCGATAAAAGGTACCTAATCGTCTTGGATGATG
                  TGTGGGATATTGCAACAGGGGAGATGTTAATAGCATGTTTTCC
                  TAAGGGTAAGAGAGGAAATAGAATCATCTTAACTAGCCGAAG
                  TAGAAAGGTAGGTTTGAAAGTTAAATGCCGTAGTGATCCTCTC
                  GACCTTAAACTTTTAACATCTGAAGAAAGTTGGGATTTATTCG
                  AAAAAAGGGTATTTGGAGATGAAGGAAGCTGCCCTGCTGAAC
                  TGTCCGAAGTTGGACACCAAATAGTTGAGAAATGTAAGGGTCT
                  TCCCTTGGCTATTGTTTTAATTGCTGGAGTAATTGTTAGAGGGA
                  AGAAAAAGGAAAAGGATTTTTGGCTTAAGATACTGCATAATCT
                  GGATTCCTTTATTTCTACCAACATCAATTTGGTTATGCAATTAA
                  GTTATGACCATTTACCATGCCACCTGAAGCCGTTGCTGCTTTAC
                  TTTGCAACAACTCAAAAGAGCCAACAAACTCCAGTCTCTACAT
                  TGATGCAGTTGTGGATGGCCGAAGGGTTTGTGGATCATGATAG
                  TTTAGAGGAAGTAACTCAAAGTTACTTGGATGCTCTAATTTCC
                  AGTAGCCTGATAATGGTGGATCATATCCCCTCCAAGAGTTATT
                  GGTGGACGTCTTTAATGATCAAGGTTTGCTATGTGCATGATGTT
                  GTGCACGATTTTTGTTCAGAAAAAGCCAAAAAGGAGAAGTTTC
                  TCAAGTTAATCAATTCAGGTGATCCATTTCATGCTTCAGATTTC
                  CTACACCATCGTCTAACCATTCATACTGACAACGGCCAACTCC
                  ACAAAAAATGTGTTTTATTCAATTCTAATAAGTGCTTAGCTGTT
                  AGTAAGCATGTCATATCTTTGAAAGTGAGTGGTCCACTAGATG
                  AGTTCAGGTATATCTGTCACACAAGACACTTTGGACTTGTTAG
                  AGTGTTGCAACTGGATGACATCATTCTGGAAGATTCTTTAATG
                  GAAGAAATAGGGTCCCTATTTCATTTGAGGTTCTTAAGCATTG
                  AGACTGCTGTAGGTGTAATAGCTATCCCAGTGTCGTGGTTGAA
                  CCTCCAGAATCTGGAAACGCTGTTGATTTATACAACTTATTCCA
                  CCATGGTATTACTGCCCAGAATATTGCAACTGTCAAAGCTGAA
                  ACATGTGAAAATTAAGGAATGTTCTTTCTTTGAAGAGAAAGAG
                  GATATCCAACGTAGAATATTGGAAGCTGGGAATTCTTCAAACT
```

TABLE 1-continued

Sequence information
The genomic sequences correspond to the mRNA with +2 kb upstream and downstream
from the start and the end.

```
                  TGACAACTCTATCCGGAGTTGTTATCTCATATTCTGAAGGCATG
                  AGTGATGATGCTCTGGAGAAGTTCCCAATTCTTCAGCACCTTG
                  ATTGCATCATCATGGAATCGCAGAATGCTCCTACACACGACTA
                  TTGGTTTCTCAAGCTTGATGTACTTAATAAACTCGAATCATTCG
                  TAGCAAGATACAAGCGCAATGGACATCCCTCGTTAAACCGACA
                  ACCGTATGGATTTCACTTCCCTACAAGCTTGAAAGAGTTACGG
                  TTGACTGGTTTTTTCCTGAGACCTGATTTGTTGTCAGTAATCGC
                  AGCGTTGCCTGAGCTTGAGATTATGGAGTTTTCCGGCTGTTATT
                  TCGTGGATACTAAATGGGACGCAAGTGAGGACATCTATCTAAG
                  TCTTAAGACTTTGATTTTGCGAGATGTCCATTTATCAGAATGGC
                  AAGTTGAGGGGGGAACTTTTCCCAAGCTTGAGAAATTAATACT
                  AAAATTTTGTTCCACACTTGGGGAGATCCCTTGTGCATTTATGG
                  ATGTAGAAACTTTAAAGTCCATTGATTTAAGTTTTGTTGGGCGT
                  AAGCTTCGAGATTCAGCCATTGAGATTAAGAAAAATGTAGCAG
                  ATTTCACAGGAGAGGACAGAGTTGATGTCCACACATCACATTT
                  GTTTGCAACCAACGTGAAAGAACAGATTATGAGAATGACGGT
                  GGTTGATGAAGTTGGATTTCTCATGGAAAAATCACAACAATGA

SEQ ID NO:   ATGGAAAAAGGAGAAAAATCATTGCAGCTACTATTTGAGGAA
9:           CAAAAAACAAGAATCACGAATCTTATTGATGATTTCTTGATTC
CDS MeR1     GCTTGAAGCAAATAAAGAATGAATTCATTGCTTCAAAATTGGA
(isoform 8)  TGCCTTTGAAAATCTAAGAATGGAACTGAGATTCCTAAGAACA
                  TTTGTCCTGTTTGGGAATTCGATGAATTTGGATGACTTTTATGA
                  GAGGATGTCACTGAGTATAAGCAAATTCGATCAATCTACGGAG
                  TACGTAGATAAAATAATCCTAGAGAAATACAACATGGAATGTC
                  TTGCCCCTCTGCTGCTTGAAGAGATAAGAAATTATTTGAGTTTG
                  AAGAATGATTATGTAGCCACAACTACAGAGATAAAATTGTTTG
                  AATACCTCATCAGAAACCTCCATGATCTACCAAAGTATTGTTCT
                  GATTTGCTTCTACCACTCATGAGTGAATACAAGATTCTTCGGCA
                  AGTATGCACACATCTCAGAGATTTCTATCAGTTGGAATGCAAC
                  AAAACAACAAAAACAGAATTTCTCTATACTCGGTATCAAGTGA
                  CAGCCGATAGAGTAACACAATTCTGTTTTGATCTTTGGACAGG
                  AATGTATAAATACTCTGACAATGAGTATGCCTTCTCTGAATGTT
                  CTTCCAAGATCACTTCTCTACTCATTGACATAATCCCTCTTGAG
                  TTGGAGGTTCTATACATTTCTACTTCTAAGCTCATCAAAGAGTC
                  AACGTCAAAAGAACTAGAAGGATTTGTTAAGCAAATCTTAAAA
                  GCATCTCCAAGGATTCTTCAACATTATCTCATTCATCTCCAAGG
                  ACGCATGGCCGGTGTAGAAGCCGTCAATTTCGCTCCAACTCGA
                  AGCATTAGTGTCATGATGGAGTTCCTATTGATCTTTCTCACCGA
                  TATGCCAAAGCGGTTTATCCATCGTGAAAAATTGAACGATATG
                  TTGGCACATGTCAGAATACTTACAAGGAAAATATCTACTCTGG
                  TGAGTAAACTGTTGGAGGAGATCTCTGAGGATAATATCAATGA
                  AGCGGACTTTTCAGCTCCGGACTTTTTGCAAGAAATTGAACAA
                  ATGAAGGGAGATATCAGACACATCTTTTTAAAAGCTCCTGAGT
                  CATCTCAACTTCGGTTTCCTATGGATGATGGTTTCCTCTTCATG
                  AATCTTCTACTCAGACATTTAAATGATTTACTCATTTCCAATGC
                  TTATTCAGTTTTTTCTCATAAAAAAAGAAATTGGGATGGTGAAA
                  GAAAGCCTTGAATTCCTAATATCATCTTTCAGGAAAGTCAGGC
                  AAACATTGGATGAGAGTACTAGTGGAGTAGTTAAAAATTGTTG
                  GGTGCGTGCTTTGGATGTGGCATATGAGGCAGAACATATCATT
                  AATTCCATTCTTGTCAGAGATAAAGCTCTCTCACATCTCCTCTT
                  CTCACTTCCGAGTGTCACTGATAAGATCAAACTTATCGTGGAA
                  CAAGTCACCAGGTTTCAGCTGGAGGATAAGAATGGGGATGGC
                  CCCCTTGATGCAAAGTCTTCCTTCGAGCCAACTCAGTCAACTTC
                  ATCACCTTTTGTTGAGGTAACAGTAGGTCACGAGAAAGAAGAA
                  TCCCAGATCATTGACCAGCTCCTTGATGAACATGAATCTGAGC
                  TTGATGTCATTTCCATTGTCGGAATGCCAGGACTCGGTAAAAC
                  TACTCTGGCCAACAAAGTGTATAAAGATACATTAGTTGCTAGG
                  CATTTCCATGTCCGTGCTTGGTGCACTGTTTCGCAAAAGTATAA
                  CAAGTCAAAGGTGTTGCGGGAGATTCTTCAGCAAGTTACTGGC
                  TCGGGAGGAAAAGAAAGTGAAGATGACCTGGCTGAAAAGCTA
                  CGAAGAGCACTACTCGATAAAAGGTACCTAATCGTCTTGGATG
                  ATGTGTGGGATATTGCAACAGGGGAGATGTTAATAGCATGTTT
                  TCCTAAGGGTAAGAGAGGAAATAGAATCATCTTAACTAGCCGA
                  AGTAGAAAGGTAGGTTTGAAAGTTAAATGCCGTAGTGATCCTC
                  TCGACCTTAAACTTTTAACATCTGAAGAAAGTTGGGATTTATTC
                  GAAAAAAGGGTATTTGGAGATGAAGGAAGCTGCCCTGCTGAA
                  CTGTCCGAAGTTGGACACCAAATAGTTGAGAAATGTAAGGGTC
                  TTCCCTTGGCTATTGTTTTAATTGCTGGAGTAATTGTTAGAGGG
                  AAGAAAAAGGAAAAGGATTTTTGGCTTAAGATACTGCATAATC
                  TGGATTCCTTTATTTCTACCAACATCAATTTGGTTATGCAATTA
                  AGTTATGACCATTTACCATGCCACCTGAAGCCGTTGCTGCTTTA
                  CTTTGCAACAACTCAAAAGAGCCAACAAACTCCAGTCTCTACA
                  TTGATGCAGTTGTGGATGGCCGAAGGGGTTTGTGGATCATGATA
                  GTTTAGAGGAAGTAACTCAAAGTTACTTGGATGCTCTAATTTC
                  CAGTAGCCTGATAATGGTGGATCATATCCCCTCCAAGAGTTAT
```

TABLE 1-continued

Sequence information
The genomic sequences correspond to the mRNA with +2 kb upstream and downstream
from the start and the end.

```
TGGTGGACGTCTTTAATGATCAAGGTTTGCTATGTGCATGATGT
TGTGCACGATTTTTGTTCAGAAAAAGCCAAAAAGGAGAAGTTT
CTCAAGTTAATCAATTCAGGTGATCCATTTCATGCTTCAGATTT
CCTACACCATCGTCTAACCATTCATACTGACAACGGCCAACTC
CACAAAAAATGTGTTTTATTCAATTCTAATAAGTGCTTAGCTGT
TAGTAAGCATGTCATATCTTTGAAAGTGAGTGGTCCACTAGAT
GAGTTCAGGTATATCTGTCACACAAGACACTTTGGACTTGTTA
GAGTGTTGCAACTGGATGACATCATTCTGGAAGATTCTTTAAT
GGAAGAAATAGGGTCCCTATTTCATTTGAGGTTCTTAAGCATT
GAGACTGCTGTAGGTGTAATAGCTATCCCAGTGTCGTGGTTGA
ACCTCCAGAATCTGGAAACGCTGTTGATTTATACAACTTATTCC
ACCATGGTATTACTGCCCAGAATATTGCAACTGTCAAAGCTGA
AACATGTGAAAATTAAGGAATGTTCTTTCTTTGAAGAGAAAGA
GGATATCCAACGTAGAATATTGGAAGCTGGGAATTCTTCAAAC
TTGACAACTCTATCCGGAGTTGTTATCTCATATTCTGAAGGCAT
GAGTGATGATGCTCTGGAGAAGTTCCCAATTCTTCAGCACCTT
GATTGCATCATCATGGAATCGCAGAATGCTCCTACACACGACT
ATTGGTTTCTCAAGCTTGATGTACTTAATAAACTCGAATCATTC
GTAGCAAGATACAAGCGCAATGGACATCCCTCGTTAAACCGAC
AACCGTATGGATTTCACTTCCCTACAAGCTTGAAAGAGTTACG
GTTGACTGGTTTTTTCCTGAGACCTGATTTGTTGTCAGTAATCG
CAGCGTTGCCTGAGCTTGAGATTATGGAGTTTTCCGGCTGTTAT
TTCGTGGATACTAAATGGGACGCAAGTGAGGACATCTATCTAA
GTCTTAAGACTTTGATTTTGCGAGATGTCCATTTATCAGAATGG
CAAGTTGAGGGGGGAACTTTTCCCAAGCTTGAGAAATTAATAC
TAAAATTTTGTTCCACACTTGGGGAGATCCCTTGTGCATTTATG
GATGTAGAAACTTTAAAGTCCATTGATTTAAGTTTTGTTGGGCG
TAAGCTTCGAGATTCAGCCATTGAGATTAAGAAAAATGTAGCA
GATTTCACAGGAGAGGACAGAGTTGATGTCCACACATCACATT
TGTTTGCAACCAACGTGAAAGAACAGATTATGAGAATGACGGT
GGTTGATGAAGTTGGATTTCTCATGGAAAAATCACAACAATGA
```

| SEQ ID NO: 10: protein MeR1 (isoform 1) | MEKGEKSLLLFEEQKTRITNLIDDFLIRLKQIKNEFIASKLDAFENL |
| | RMELRFLRTFVLFGNSMNLDDFYERMSLSISKFDQSTEYVDKIILE |
| | KYNMECLAPLLLEEIRNYLSLKNDYVATTTEIKLFEYLIRNLHDLP |
| | KYCSDLLLPLMSEYKILRQVCTHLRDFYQLECNKTTKTEFLYTRY |
| | QVTADRVTQFCFDLWTGMYKYSDNEYAFSECSSKITSLLIDIIPLE |
| | LEVLYISTSKLIKESTSKELEGFVKQILKASPRILQHYLIHLQGRMA |
| | GVEAVNFAPTRSISVMMEFLLIFLTDMPKRFIHREKLNDMLAHVRI |
| | LTRKISTLVSKLLEEISEDNINEADFSAPDFLQEIEQMKGDIRHIFLK |
| | APESSQLRFPMDDGFLFMNLLLRHLNDLLISNAYSVFLIKKEIGMV |
| | KESLEFLISSFRKVRQTLDESTSGVVKNCWVRALDVAYEAEHIINS |
| | ILVRDKALSHLLFSLPSVTDKIKLIVEQVTRFQLEDKNGDGPLDAK |
| | SSFEPTQSTSSPFVEVTVGHEKEESQIIDQLLDEHESELDVISIVGMP |
| | GLGKTTLANKVYKDTLVARHFHVRAWCTVSQKYNKSKVLREIL |
| | QQVTGSGGKESEDDLAEKLRRALLDKRYLIVLDDVWDIATGEML |
| | IACFPKGKRGNRIILTSRSRKVGLKVKCRSDPLDLKLLTSEESWDL |
| | FEKRVFGDEGSCPAELSEVGHQIVEKCKGLPLAIVLIAGVIVRGKK |
| | KEKDFWLKILHNLDSFISTNINLVMQLSYDHLPCHLKPLLLYFATT |
| | QKSQQTPVSTLMQLWMAEGFVDHDSLEEVTQSYLDALISSSLIMV |
| | DHIPSKSYWWTSLMIKVCYVHDVVHDFCSEKAKKEKFLKLINSG |
| | DPFHASDFLHHRLTIHTDNGQLHKKCVLFNSNKCLAVSKHVISLK |
| | VSGPLDEFRYICHTRHFGLVRVLQLDDIILEDSLMEEIGSLFHLRFL |
| | SIETAVGVIAIPVSWLNLQNLETLLIYTTYSTMVLLPRILQLSKLKH |
| | VKIKECSFFEEKEDIQRRILEAGNSSNLTTLSGVVISYSEGMSDDAL |
| | EKFPILQHLDCIIMESQNAPTHDYWFLKLDVLNKLESFVARYKRN |
| | GHPSLNRQPYGFHFPTSLKELRLTGFFLRPDLLSVIAALPELEIMEF |
| | SGCYFVDTKWDASEDIYLSLKTLILRDVHLSEWQVEGGTFPKLEK |
| | LILKFCSTLGEIPCAFMDVETLKSIDLSFVGRKLRDSAIEIKKNVAD |
| | FTGEDRVDVHTSHLFATNVKEQIMRMTGMGNIQGRRGI |

| SEQ ID NO: 11: protein MeR1 (isoform 2) | MEKGEKSLQLLFEEQKTRITNLIDDFLIRLKQIKNEFIASKLDAFEN |
| | LRMELRFLRTFVLFGNSMNLDDFYERMSLSISKFDQSTEYVDKIIL |
| | EKYNMECLAPLLLEEIRNYLSLKNDYVATTTEIKLFEYLIRNLHDL |
| | PKYCSDLLLPLMSEYKILRQVCTHLRDFYQLECNKTTKTEFLYTR |
| | YQVTADRVTQFCFDLWTGMYKYSDNEYAFSECSSKITSLLIDIIPL |
| | ELEVLYISTSKLIKESTSKELEGFVKQILKASPRILQHYLIHLQGRM |
| | AGVEAVNFAPTRSISVMMEFLLIFLTDMPKRFIHREKLNDMLAHV |
| | RILTRKISTLVSKLLEEISEDNINEADFSAPDFLQEIEQMKGDIRHIF |
| | LKAPESSQLRFPMDDGFLFMNLLLRHLNDLLISNAYSVFLIKKEIG |
| | MVKESLEFLISSFRKVRQTLDESTSGVVKNCWVRALDVAYEAEHI |
| | INSILVRDKALSHLLFSLPSVTDKIKLIVEQVTRFQLEDKNGDGPLD |
| | AKSSFEPTQSTSSPFVEVTVGHEKEESQIIDQLLDEHESELDVISIVG |
| | MPGLGKTTLANKVYKDTLVARHFHVRAWCTVSQKYNKSKVLRE |
| | ILQQVTGSGGKESEDDLAEKLRRALLDKRYLIVLDDVWDIATGE |
| | MLIACFPKGKRGNRIILTSRSRKVGLKVKCRSDPLDLKLLTSEESW |

TABLE 1-continued

Sequence information
The genomic sequences correspond to the mRNA with +2 kb upstream and downstream
from the start and the end.

```
                    DLFEKRVFGDEGSCPAELSEVGHQIVEKCKGLPLAIVLIAGVIVRG
                    KKKEKDFWLKILHNLDSFISTNINLVMQLSYDHLPCHLKPLLLYF
                    ATTQKSQQTPVSTLMQLWMAEGFVDHDSLEEVTQSYLDALISSSL
                    IMVDHIPSKSYWWTSLMIKVCYVHDVVHDFCSEKAKKEKFLKLI
                    NSGDPFHASDFLHHRLTIHTDNGQLHKKCVLFNSNKCLAVSKHVI
                    SLKVSGPLDEFRYICHTRHFGLVRVLQLDDIILEDSLMEEIGSLFHL
                    RFLSIETAVGVIAIPVSWLNLQNLETLLIYTTYSTMVLLPRILQLSK
                    LKHVKIKECSFFEEKEDIQRRILEAGNSSNLTTLSGVVISYSEGMSD
                    DALEKFPILQHLDCIIMESQNAPTHDYWFLKLDVLNKLESFVARY
                    KRNGHPSLNRQPYGFHFPTSLKELRLTGFFLRPDLLSVIAALPELEI
                    MEFSGCYFVDTKWDASEDIYLSLKTLILRDVHLSEWQVEGGTFPK
                    LEKLILKFCSTLGEIPCAFMDVETLKSIDLSFVGRKLRDSAIEIKKN
                    VADFTGEDRVDVHTSHLFATNVKEQIMRMTGMGNIQGRRGI

SEQ ID NO:          MEKGEKSLLLFEEQKTRITNLIDDFLIRLKQIKNEFIASKLDAFENL
12:                 RMELRFLRTFVLFGNSMNLDDFYERMSLSISKFDQSTEYVDKIILE
protein MeR1        KYNMECLAPLLLEEIRNYLSLKNDYVATTTEIKLFEYLIRNLHDLP
(isoform 3)         KYCSDLLLPLMSEYKILRQVCTHLRDFYQLECNKTTKTEFLYTRY
                    QVTADRVTQFCFDLWTGMYKYSDNEYAFSECSSKITSLLIDIIPLE
                    LEVLYISTSKLIKESTSKELEGFVKQILKASPRILQHYLIHLQGRMA
                    GVEAVNFAPTRSISVMMEFLLIFLTDMPKRFIHREKLNDMLAHVRI
                    LTRKISTLVSKLLEEISEDNINEADFSAPDFLQEIEQMKGDIRHIFLK
                    APESSQLRFPMDDGFLFMNLLLRHLNDLLISNAYSVFLIKKEIGMV
                    KESLEFLISSFRKVRQTLDESTSGVVKNCWVRALDVAYEAEHIINS
                    ILVRDKALSHLLFSLPSVTDKIKLIVEQVTRFQLEDKNGDGPLDAK
                    SSFEPTQSTSSPFVEVTVGHEKEESQIIDQLLDEHESELDVISIVGMP
                    GLGKTTLANKVYKDTLVARHFHVRAWCTVSQKYNKSKVLREIL
                    QQVTGSGGKESEDDLAEKLRRALLDKRYLIVLDDVWDIATGEML
                    IACFPKGKRGNRIILTSRSRKVGLKVKCRSDPLDLKLLTSEESWDL
                    FEKRVFGDEGSCPAELSEVGHQIVEKCKGLPLAIVLIAGVIVRGKK
                    KEKDFWLKILHNLDSFISTNINLVMQLSYDHLPCHLKPLLLYFATT
                    QKSQQTPVSTLMQLWMAEGFVDHDSLEEVTQSYLDALISSSLIMV
                    DHIPSKSYWWTSLMIKVCYVHDVVHDFCSEKAKKEKFLKLINSG
                    DPFHASDFLHHRLTIHTDNGQLHKKCVLFNSNKCLAVSKHVISLK
                    VSGPLDEFRYICHTRHFGLVRVLQLDDIILEDSLMEEIGSLFHLRFL
                    SIETAVGVIAIPVSWLNLQNLETLLIYTTYSTMVLLPRILQLSKLKH
                    VKIKECSFFEEKEDIQRRILEAGNSSNLTTLSGVVISYSEGMSDDAL
                    EKFPILQHLDCIIMESQNAPTHDYWFLKLDVLNKLESFVARYKRN
                    GHPSLNRQPYGFHFPTSLKELRLTGFFLRPDLLSVIAALPELEIMEF
                    SGCYFVDTKWDASEDIYLSLKTLILRDVHLSEWQVEGGTFPKLEK
                    LILKFCSTLGEIPCAFMDVETLKSIDLSFVGRKLRDSAIEIKKNVAD
                    FTGEDRVDVHTSHLFATNVKEQIMRMTGGECTEEL SEQ ID NO:          MEKGEKSLQLLFEEQKTRITNLIDDFLIRLKQIKNEFIASKLDAFEN
13:                 LRMELRFLRTFVLFGNSMNLDDFYERMSLSISKFDQSTEYVDKIIL
protein MeR1        EKYNMECLAPLLLEEIRNYLSLKNDYVATTTEIKLFEYLIRNLHDL
(isoform 4)         PKYCSDLLLPLMSEYKILRQVCTHLRDFYQLECNKTTKTEFLYTR
                    YQVTADRVTQFCFDLWTGMYKYSDNEYAFSECSSKITSLLIDIIPL
                    ELEVLYISTSKLIKESTSKELEGFVKQILKASPRILQHYLIHLQGRM
                    AGVEAVNFAPTRSISVMMEFLLIFLTDMPKRFIHREKLNDMLAHV
                    RILTRKISTLVSKLLEEISEDNINEADFSAPDFLQEIEQMKGDIRHIF
                    LKAPESSQLRFPMDDGFLFMNLLLRHLNDLLISNAYSVFLIKKEIG
                    MVKESLEFLISSFRKVRQTLDESTSGVVKNCWVRALDVAYEAEHI
                    INSILVRDKALSHLLFSLPSVTDKIKLIVEQVTRFQLEDKNGDGPLD
                    AKSSFEPTQSTSSPFVEVTVGHEKEESQIIDQLLDEHESELDVISIVG
                    MPGLGKTTLANKVYKDTLVARHFHVRAWCTVSQKYNKSKVLRE
                    ILQQVTGSGGKESEDDLAEKLRRALLDKRYLIVLDDVWDIATGE
                    MLIACFPKGKRGNRIILTSRSRKVGLKVKCRSDPLDLKLLTSEESW
                    DLFEKRVFGDEGSCPAELSEVGHQIVEKCKGLPLAIVLIAGVIVRG
                    KKKEKDFWLKILHNLDSFISTNINLVMQLSYDHLPCHLKPLLLYF
                    ATTQKSQQTPVSTLMQLWMAEGFVDHDSLEEVTQSYLDALISSSL
                    IMVDHIPSKSYWWTSLMIKVCYVHDVVHDFCSEKAKKEKFLKLI
                    NSGDPFHASDFLHHRLTIHTDNGQLHKKCVLFNSNKCLAVSKHVI
                    SLKVSGPLDEFRYICHTRHFGLVRVLQLDDIILEDSLMEEIGSLFHL
                    RFLSIETAVGVIAIPVSWLNLQNLETLLIYTTYSTMVLLPRILQLSK
                    LKHVKIKECSFFEEKEDIQRRILEAGNSSNLTTLSGVVISYSEGMSD
                    DALEKFPILQHLDCHIMESQNAPTHDYWFLKLDVLNKLESFVARY
                    KRNGHPSLNRQPYGFHFPTSLKELRLTGFFLRPDLLSVIAALPELEI
                    MEFSGCYFVDTKWDASEDIYLSLKTLILRDVHLSEWQVEGGTFPK
                    LEKLILKFCSTLGEIPCAFMDVETLKSIDLSFVGRKLRDSAIEIKKN
                    VADFTGEDRVDVHTSHLFATNVKEQIMRMTGGECTEEL SEQ ID NO:          MEKGEKSLLLFEEQKTRITNLIDDFLIRLKQIKNEFIASKLDAFENL
14:                 RMELRFLRTFVLFGNSMNLDDFYERMSLSISKFDQSTEYVDKIILE
protein MeR1        KYNMECLAPLLLEEIRNYLSLKNDYVATTTEIKLFEYLIRNLHDLP
(isoform 5)         KYCSDLLLPLMSEYKILRQVCTHLRDFYQLECNKTTKTEFLYTRY
```

TABLE 1-continued

Sequence information
The genomic sequences correspond to the mRNA with +2 kb upstream and downstream
from the start and the end.

```
                QVTADRVTQFCFDLWTGMYKYSDNEYAFSECSSKITSLLIDIIPLE
                LEVLYISTSKLIKESTSKELEGFVKQILKASPRILQHYLIHLQGRMA
                GVEAVNFAPTRSISVMMEFLLIFLTDMPKRFIHREKLNDMLAHVRI
                LTRKISTLVSKLLEEISEDNINEADFSAPDFLQEIEQMKGDIRHIFLK
                APESSQLRFPMDDGFLFMNLLLRHLNDLLISNAYSVFLIKKEIGMV
                KESLEFLISSFRKVRQTLDESTSGVVKNCWVRALDVAYEAEHIINS
                ILVRDKALSHLLFSLPSVTDKIKLIVEQVTRFQLEDKNGDGPLDAK
                SSFEPTQSTSSPFVEVTVGHEKEESQIIDQLLDEHESELDVISIVGMP
                GLGKTTLANKVYKDTLVARHFHVRAWCTVSQKYNKSKVLREIL
                QQVTGSGGKESEDDLAEKLRRALLDKRWRMYL

SEQ ID NO:     MEKGEKSLQLLFEEQKTRITNLIDDFLIRLKQIKNEFIASKLDAFEN
15:            LRMELRFLRTFVLFGNSMNLDDFYERMSLSISKFDQSTEYVDKIIL
protein MeR1   EKYNMECLAPLLLEEIRNYLSLKNDYVATTTEIKLFEYLIRNLHDL
(isoform 6)    PKYCSDLLLPLMSEYKILRQVCTHLRDFYQLECNKTTKTEFLYTR
                YQVTADRVTQFCFDLWTGMYKYSDNEYAFSECSSKITSLLIDIIPL
                ELEVLYISTSKLIKESTSKELEGFVKQILKASPRILQHYLIHLQGRM
                AGVEAVNFAPTRSISVMMEFLLIFLTDMPKRFIHREKLNDMLAHV
                RILTRKISTLVSKLLEEISEDNINEADFSAPDFLQEIEQMKGDIRHIF
                LKAPESSQLRFPMDDGFLFMNLLLRHLNDLLISNAYSVFLIKKEIG
                MVKESLEFLISSFRKVRQTLDESTSGVVKNCWVRALDVAYEAEHI
                INSILVRDKALSHLLFSLPSVTDKIKLIVEQVTRFQLEDKNGDGPLD
                AKSSFEPTQSTSSPFVEVTVGHEKEESQIIDQLLDEHESELDVISIVG
                MPGLGKTTLANKVYKDTLVARHFHVRAWCTVSQKYNKSKVLRE
                ILQQVTGSGGKESEDDLAEKLRRALLDKRWRMYL SEQ ID NO:     MEKGEKSLLLLFEEQKTRITNLIDDFLIRLKQIKNEFIASKLDAFENL
16:            RMELRFLRTFVLFGNSMNLDDFYERMSLSISKFDQSTEYVDKIILE
protein MeR1   KYNMECLAPLLLEEIRNYLSLKNDYVATTTEIKLFEYLIRNLHDLP
(isoform 7)    KYCSDLLLPLMSEYKILRQVCTHLRDFYQLECNKTTKTEFLYTRY
                QVTADRVTQFCFDLWTGMYKYSDNEYAFSECSSKITSLLIDIIPLE
                LEVLYISTSKLIKESTSKELEGFVKQILKASPRILQHYLIHLQGRMA
                GVEAVNFAPTRSISVMMEFLLIFLTDMPKRFIHREKLNDMLAHVRI
                LTRKISTLVSKLLEEISEDNINEADFSAPDFLQEIEQMKGDIRHIFLK
                APESSQLRFPMDDGFLFMNLLLRHLNDLLISNAYSVFLIKKEIGMV
                KESLEFLISSFRKVRQTLDESTSGVVKNCWVRALDVAYEAEHIINS
                ILVRDKALSHLLFSLPSVTDKIKLIVEQVTRFQLEDKNGDGPLDAK
                SSFEPTQSTSSPFVEVTVGHEKEESQIIDQLLDEHESELDVISIVGMP
                GLGKTTLANKVYKDTLVARHFHVRAWCTVSQKYNKSKVLREIL
                QQVTGSGGKESEDDLAEKLRRALLDKRYLIVLDDVWDIATGEML
                IACFPKGKRGNRIILTSRSRKVGLKVKCRSDPLDLKLLTSEESWDL
                FEKRVFGDEGSCPAELSEVGHQIVEKCKGLPLAIVLIAGVIVRGKK
                KEKDFWLKILHNLDSFISTNINLVMQLSYDHLPCHLKPLLLYFATT
                QKSQQTPVSTLMQLWMAEGFVDHDSLEEVTQSYLDALISSSLIMV
                DHIPSKSYWWTSLMIKVCYVHDVVHDFCSEKAKKEKFLKLINSG
                DPFHASDFLHHRLTIHTDNGQLHKKCVLFNSNKCLAVSKHVISLK
                VSGPLDEFRYICHTRHFGLVRVLQLDDIILEDSLMEEIGSLFHLRFL
                SIETAVGVIAIPVSWLNLQNLETLLIYTTYSTMVLLPRILQLSKLKH
                VKIKECSFFEEKEDIQRRILEAGNSSNLTTLSGVVISYSEGMSDDAL
                EKFPILQHLDCIIMESQNAPTHDYWFLKLDVLNKLESFVARYKRN
                GHPSLNRQPYGFHFPTSLKELRLTGFFLRPDLLSVIAALPELEIMEF
                SGCYFVDTKWDASEDIYLSLKTLILRDVHLSEWQVEGGTFPKLEK
                LILKFCSTLGEIPCAFMDVETLKSIDLSFVGRKLRDSAIEIKKNVAD
                FTGEDRVDVHTSHLFATNVKEQIMRMTVVDEVGFLMEKSQQ SEQ ID NO:     MEKGEKSLQLLFEEQKTRITNLIDDFLIRLKQIKNEFIASKLDAFEN
17:            LRMELRFLRTFVLFGNSMNLDDFYERMSLSISKFDQSTEYVDKIIL
protein MeR 1  EKYNMECLAPLLLEEIRNYLSLKNDYVATTTEIKLFEYLIRNLHDL
(isoform 8)    PKYCSDLLLPLMSEYKILRQVCTHLRDFYQLECNKTTKTEFLYTR
                YQVTADRVTQFCFDLWTGMYKYSDNEYAFSECSSKITSLLIDIIPL
                ELEVLYISTSKLIKESTSKELEGFVKQILKASPRILQHYLIHLQGRM
                AGVEAVNFAPTRSISVMMEFLLIFLTDMPKRFIHREKLNDMLAHV
                RILTRKISTLVSKLLEEISEDNINEADFSAPDFLQEIEQMKGDIRHIF
                LKAPESSQLRFPMDDGFLFMNLLLRHLNDLLISNAYSVFLIKKEIG
                MVKESLEFLISSFRKVRQTLDESTSGVVKNCWVRALDVAYEAEHI
                INSILVRDKALSHLLFSLPSVTDKIKLIVEQVTRFQLEDKNGDGPLD
                AKSSFEPTQSTSSPFVEVTVGHEKEESQIIDQLLDEHESELDVISIVG
                MPGLGKTTLANKVYKDTLVARHFHVRAWCTVSQKYNKSKVLRE
                ILQQVTGSGGKESEDDLAEKLRRALLDKRYLIVLDDVWDIATGE
                MLIACFPKGKRGNRIILTSRSRKVGLKVKCRSDPLDLKLLTSEESW
                DLFEKRVFGDEGSCPAELSEVGHQIVEKCKGLPLAIVLIAGVIVRG
                KKKEKDFWLKILHNLDSFISTNINLVMQLSYDHLPCHLKPLLLYF
                ATTQKSQQTPVSTLMQLWMAEGFVDHDSLEEVTQSYLDALISSSL
                IMVDHIPSKSYWWTSLMIKVCYVHDVVHDFCSEKAKKEKFLKLI
                NSGDPFHASDFLHHRLTIHTDNGQLHKKCVLFNSNKCLAVSKHVI
                SLKVSGPLDEFRYICHTRHFGLVRVLQLDDIILEDSLMEEIGSLFHL
```

TABLE 1-continued

Sequence information
The genomic sequences correspond to the mRNA with +2 kb upstream and downstream
from the start and the end.

RFLSIETAVGVIAIPVSWLNLQNLETLLIYTTYSTMVLLPRILQLSK
LKHVKIKECSFFEEKEDIQRRILEAGNSSNLTTLSGVVISYSEGMSD
DALEKFPILQHLDCIIMESQNAPTHDYWFLKLDVLNKLESFVARY
KRNGHPSLNRQPYGFHFPTSLKELRLTGFFLRPDLLSVIAALPELEI
MEFSGCYFVDTKWDASEDIYLSLKTLILRDVHLSEWQVEGGTFPK
LEKLILKFCSTLGEIPCAFMDVETLKSIDLSFVGRKLRDSAIEIKKN
VADFTGEDRVDVHTSHLFATNVKEQIMRMTVVDEVGFLMEKSQ
Q

SEQ ID NO: 18: Genomic NRC6-2a

ATTCAATTTTAAAAAATTATTCAGTAAAATTATTAAATTTTATT
TTGTATCGTTAAAATTACTCAATTTTGATATATTTAAATCAGTG
AAATTATTAAACTAAATTTATCATTAAAATAATAAAATAATTTT
TTAAATATATAATTACAAATAAAATAATAAATAAATACTTAAA
ATTACTACTTTATTATATATTGTAAGATAAAATAATAAAAGAT
AATTTTATCAATTTCATTTGGTACACTGCTTCATTATTGCAATG
ACGACTGTCGATTTTGCTCCGGTAGTTTAATCAATTTGTAGTGG
TTTAATCAATTTTTTGTTTGTGTGAATCCCTTATTTAATTTTTTT
TTAAAAAAAATAAATAAAGTGAGGTTTCATGTATCAATGGTAG
TTTGGACAATTTTGAGTAGTTTGATAAATTTATTTTTTGTTTTGA
ATTTTTATTATTTTATAATGAAATAGTAATTTCGAGTCATGTAC
TATGTAGTTTAATCATAAACATAGATTGAGTGATTTTAATGATA
TAAAAACCTAAATTGAGTATTTTACTGGTACAAAATGAAGTTT
AGTTGCTAGATATATTTCAAAGTTGAGTGACCTTTTGAGAAA
TTAACTCCTCTGTCAGATCTCCTAATTTGATAAATTTTCAAAC
TTCATAATATAACATTTTCCTTTTTTATAATGATTACAAACTAT
ATCAAACGACGAGTTCCCCCTGTCACTTATACTTTTAATTCACA
AATTCCTCTTATCAGTGTGACCACATCCCCACAACCATACTTGT
TACGATCCAAAAATGAGCGTGATGACACTCGTCTTATTCACAT
AGATTAGTCAGCCTAAAACTCAATTATTATGAAGAAGAGAGGA
AATAAACTATAAAGTGGAATCAGATTCATGAGTTGTGTTTGAG
TCTGAATTATTGAATATTAAAGTCTGATCAATTAAAGTCGAGA
GTAATTAGTCTGTATAATTTGTTCTATGTTTATTACTGAGTTGT
AATAATTTCTATATTTTGTAACCAAAAACGGATTTGACTTTTTG
AAGAGAGTTTGAGAGAATTGTAACAAGAAATGTGTTTGACTTA
TCGCAGAGTAGAGTTAAGAGAGAGTTAGAGAGAATTGTAATA
AGAAATGAGTTTGACTTCTTAGTGAGTAGAGAGTTGAGAGAGA
GTTTGAGAGAATTATAACAAGAAGTTTGACTTCTTGGAGAATA
GAGTTTCCGATTATAATTAATCGTTGAAGAGTAAAGATACTAG
ACTTAGTCCCTTTGATGATTGAATTGTTATTGAAGTTAATAAAA
TTGTGATGTGATTTTTTCCTTCCTTGAGGGAGGAAGGCTTCCAC
GGTAAATTAAGTGTTGTTTAAATTCTGTTCTAAACGACTATAGG
AACCAGGTTCCTAGAAATAATTGTTGGCGCATAGTATCTTTCA
AGGAAAAATGCAGAATGCCACGTAAGCTCGAAAAGGGTAGAA
AATTATCTATAAAATAAGTTCGGGTGGAAGGATAATAAGAGTT
GTATAAGTGTGTCTCTGAAATTTGAGACATAGATTAGGAGGTA
CTTATGTATTTTCCCTTCTTCCAGTTATTTGTTTCACCTCTTCCA
TAATGTCAAATCCTTAATTATATATGTCTACCTCTGTACGTCAT
ATTATAGATAGAGAAACAATTTAAATGTGTCTTTATAATCAAT
ATCACTGAAAGCTCTAGCGACGTTAAATACAACAATATTATTT
TTTTATTTTGCTACCTTGAATAATAATTCTCAATTGTTTACAAG
CTTTCCAACAACACCCATTTATTTCAACCAATGTGAACCTCTTT
CCAACAACACTTAATTTGTTTTCTAGTAATTTTTCAATCAACAT
GAACTTAATTATTCAAATGTTAGCTGTCATTGGATTATTAAATT
GTTAATGTTGTAAGGTGATGGTGTATTATATTAAGAATTAACA
AATAATACTTAAAGACTTGGTTAATCTAATTCAGAGTCAACTT
GAAGTTATTTCATTCCACATGTTTATAAACACACAACTATGGC
AATAACAACATAGCAATTGTCATCTCTAAATTACTACTACTATT
CTTCTTCTCCATCAATTTAATCCTCAGAAATGGATCCGTTTACG
GCGGCTGCATTAACCACTGCGGTGACAGCCACGGTGAGCCTTC
TGGTGGAGAACTTGTCGCATCTTATAAGTTATAATTGGAAGTT
GTATACAGGATTGAAGAAATCATGCGAAGATTTGTATGATGAA
GTGAAGCGATTAAATGCATTTTTAGTCGATAACGCGAATCAGA
GAAGTAATAGTACGCAATGGGATGTATTAGTCGATAAAATTCG
ACGTACAGTATATAAAGCAGAGGATGTTGTTGATAAATTATTG
ATTCAGGGCAAGTTAGACCAAGAGAGTAATATAGCTAAAAAG
ATGTTTCACAAAACTTACAAAAACAGGAATTTTACTGAGGAAA
TCAATGAGATACTTGTAGAGGTGAGGAAAATCCTTGAGGAAA
ATCAACATCTGTTTGAGGCAAACCCGACGATTGATCATCATCA
GCCTGAAAAAGTTGTCCAGGAGGAACAGGTACGTTTACACGA
AATTTCGATTTTAATGTGATTTATTGAAATATGAAATGAACTAT
GATTTGCTCGTTCAGTAAAACTGTATAAGAGTTGGGAGAAATAG
TACTTCCTCTGTTTTAATATGCATTATTTGTTTGAACTTAGTTAA
AGTTTAATCTAAATTATTCAGATCTAGGACAAGGCATTAGGCA
TAAGTAAGGCAAAGGGTAGAAGTACCTTTCTAGATTATGACTC
AAAATTCCGTAGAATTTTACTTTAGTTAAGGTGTGTCTCTGAAAT
TCAGACAATTAAAGGTCACCACCAACCATTATTACATGCACAA

TABLE 1-continued

Sequence information
The genomic sequences correspond to the mRNA with +2 kb upstream and downstream
from the start and the end.

```
ATCACTATCGATAATTGCCACCATTGGTCAACATTATATATCGC
TGACCTCCATCTATCATTAACTGTCAGTATGATTCCACTATTAA
TTATCAAATGGTCATCAACAACAACCACAATTAATCACTAAGG
CCAATCACTATACTGTCCACAACCACTATCATCTGTCAACACTA
TCTAAAATCGATACACACAATCACTATCATTAGTCATTACCAC
CACCGATTGTCACATTTTCTTGTAGTGAATGATGGGGATTGAA
AATATGAAGAATAAAATAGACATGCATAGGATAAGGGGACAT
ATTTTTCATAGTTGAATGGGACATTGAAAATTAATAACTTTCAC
ATGATCATAACTCATTTGGTACCTGATGGAATAATTTCTTGTTA
TGATGATACAATCAAGACAAGTAGCCTTAATAACTTGTTTAAT
TTGTCCATCTTACAGGGTTCGTCATTGGAAAATCACGAAGTGG
TTGGATTTGATGAAGAAGCAACGAAAGTGATCAATCGTCTGGT
TGAAGGAGCAGAGTGTCTAGATGTTATCCCGGTTGTAGGAATG
CCGGGACTTGGTAAAACCACACTGGCAAGAAAAATCTTTAATG
ATCCTAAGATTTCGCGAGAATTTTTCAGCTACATTTGGGTTTTC
ATCGGACAATCAACGTGTGTAAAAAGGGATATCCTTTTTAATA
TTCTGAAAGGGTTCACAAATTCATTTGATGAATTCAAAAACAG
AAATGAGGCAAGCATAACTGATGAAATACGTAAGCGTGTGGC
TAATGGAGGTAAATGTCTCATTGTCTTGGATGATGTGTGGGAT
ACAAATGTTGTAGATATTGTCAAGACAGTTTTCCCTGATAACA
AAAAAGCCCACAGGATCATGATGACCACTCGACACGAAGACA
TTGCTAGATCTGTCAATAAATATCCCCACAATCTGAAATTTCTG
GATGGAGACGAAAGTTTCCAGCTGCTAGAAAAGAGAGCTTTTG
GCGTTAGCCGTTGTCCTGTTGAGTTAGTAGAACATGGAGAAGC
CATTGTAGCAAAATGTAGTGGAGTACCACTTACAATTGTGGTA
ATTGCAGGAGCTTTAAGAGGTCGTACGAGTGAAATTGATTGGA
AAGTAGTTAGGGAAAATGTGGGGAAGCATCTTATACAAGAAG
ACAAACTTCAGAGATGTGTGAATGTTGTGAGATTGAGTTACAA
TCATTTGCCTCAAGAAAAAAATCTTGCTTCTTGTATTTTGGTG
CCTTTCCTCAAGGATTTGATATCCCCGCTTGGAAATTGATTCGA
CTCTGGATTGCTGAGGGACTCATAATGTCCAAGTTGTCGGGCA
ACGAAATTGAAGAGATAGCAGAGTATTATCTTAATGACTTTGC
CAACAGGAACTTAGTGATGGTGATGAAAAGAAATCTAATGA
TCGAATAAAAACATGTCGTGTTCACGACATGTTACATGAGTTT
TGCGTTGAAGAGGCTACTAGATTGACTCTTTTCAAACAAGTAT
GTCTCACATCTGATCAAGACATACAGAACTCAATTACTTGTCG
TCGTGTCTCTATTCAATCATCTGTTCCTCAAAACTTCATCTCAA
AAAAGACAGTTGAAGAACATGTTAGGTCATTGTTATGTTTTTC
CTCAAAACAAAAACAAGTTGACTTTTCTAATATCGACGTCAAG
CTCATCCCTACCGCATTTCCACTTATGAGAGTCTTAGACATTGA
ATCCGTCAAGTTTAGTATTCCCAGGGAATTTTACCAGCTATTGC
ACTTGAGGTATATCGCTATGTCAGGTGATTTCGAGCAACTTCCT
AAACTCTTTACTTCTTTCTGTAATGCACAAACTCTCATTCTAAA
TACTTCCAAGCCCACCCTTGATATAAAAGCTGACATATGGAAC
ATGCCACGTTTGCGTCATCTGCACACCAACAAACCTGCAATCT
TACCACCCCCTACAAGTAGTAGTAGTAGTAGTACAAATTCTTG
TTTGTTGCAAACTCTATCTCTGGTTACACCAGAAAGCTGCAAG
GGAAACGTTCTTTCAAAGGCTCGTAATGTCAAGAAAATGAGTG
TTAAAGGTAATTTGACACCTTTTCTTGAAACTAGCAAGGGTGA
ATTTTTCAGCAATTTTCAAGTGCTAAAGCTCCTGGAAAGTTTAA
CACTGCTAAATGATGATAAGAGTAATAAATCTCTTCACCTTCC
GTCAGCATTCTCCGAATGTTTACCAAATTTGAAGAAGTTAACT
CTATCAAAAACAAGGTTTGACTGGAATCAGGCATATAGATTAG
GGCAGGTGAAAAATCTCCAGGTCCTAAAACTGAAAGAAAATG
CATTCACGGGGCCGTCCTGGAGGATGGAGCCAGGAGGTTTCAA
GAAACTTCAGGTCTTGTGGATTGAAATGGCAGATTTCGTGTCG
TGGGAGGCATCAAACTGTCCTTTCCCAAGACTTAGGAGCCTTT
TCCTGATCTCCTGTCTTAATCTTGAGGCTGTGCCACTCGATCTT
TCCCATTTGGATAACCTTCAAGAGATGACGTTGGAAAACACAA
GCAAAGCAAGCAAATCTGCAAGAGAAATAGAATGCGAGAAAA
AGAAGAAGCAAGCTGATGATCCAGAAACTGGCAAATTCAAGC
TCACTATTCCCTACTGAAGCTGATTTCAATGCCACAAAGTGAA
GTTGTTATAAGGTTAGTCCAATTCTCTCCCTCTCGTATCAGTAA
ATATCGAATAAGATATTTTTCAATAAGATTGCATCTATCCCTAT
AGTCTCTCCACGCAGAATTAGTAGGTAGCAGTGTGTTGTCTTG
CTGTCTCGTTCATATCAATAGTCATAGTATTGCTCCTATAGTTT
CTTATCCTTCGATTTTTCGTTACTATACGTTGTCCCTTATACCTC
GATATTAGTAATGCTTGTTGTAGTTTCTCTTATGTTACTATCTG
CTGTTTTTGTTATTACCTGTTGTTTCTTGTATTTCCGTCATTTCTT
TTTGGGACTCCTTTGAACTTTCTCCTTGAGACAAAGGTCAATCG
GAAACAACCTACCTCTCTTTCTTTGAGATAAGGTTCCTCCCCGA
CTCTATTTTGTGGGACTACACTGAGTATATTGTTTGGGTTTCG
CACTTCACTGAAACATTAAATTGGGCAACATTACTCTGTTATAC
TAATAATACAGATTTTAGGTGCCTTGATATCAAACATAGAGTA
AATTCAATTATTTTCGTGTTCATCACATTCCTCATCTATTTTTCT
CTTACTTATTTTCCTCCTTTTTAGCAGGAGAGTATCGAGGCATG
```

TABLE 1-continued

Sequence information
The genomic sequences correspond to the mRNA with +2 kb upstream and downstream
from the start and the end.

```
              GTGATGCATTTGCAGTCTCAGTTTTGATTACCTGTTCCAATAAA
              GAAACTTGTTACAAGTATGTTTTGTTGATTCAAACATGCCAAGT
              TTGAAAACGAAGTTTTATATTAATGTTTTTGCGTTTTCTTTCAG
              TGCTGAATAATTTGTCTAATCTGTAGTTGATGTTTGGATATCTA
              TGTATTGTTCGATTGACACGAGTTGTTTATACTATCATTTGTTG
              TTTATGAATATGTAAAACATATTTGATTTATGTTTGCAACGTCA
              ACGTGAACATTCAATTAGTCTAATCAAAGTCTAGATCTAAAAT
              TGATTAATTTAAGTTCATAATTTATTTTGAATTATTATCTAAAA
              CCGAAGACTTTCTACTCGAAAATCGAAATCATAGCTGACAGTC
              TCCATAAATATATTTGCAATTGAATAACATAATAAGCATTTATC
              AGTTAATTTTATGGAGTTTCTGGATTTACGTGATATTCAAACAT
              CTCCCGCGCATATTAATTATGTGAAGTAATGAAGTGTGTAACA
              TAAGTCAAAAGGTGCATAAATAAAGAGTCAAGGGTAATAAGA
              CTTTAGTTTACTTTAGGTGTGTCTCTGAAATTTCGATTATAATC
              TACGATATATTGTGTCTTGTCCCAACATTTAAATAAAATGAAC
              AAATAATTTTAATTACCAAATGGATCCATAGTCTGTTTAGTTGA
              CTAATGGAAAGATTTATAGGAAGGTGAGATTGTTTTATCCCTG
              ATTAGAGGTTTTGGTTCGAGTTTTGTGTATACGAAAAAATTGTG
              TTGAAAGCGTCACTTATGAATAGGCCCTATAATGTATGATTCG
              AATTTAGTCTGAGTTCTAATATGAATTTTGAACACATTGAAAA
              ATTATATCCTTTGTTAAATTTCATGGTTTTAACATCTTGGAAGT
              AAAGAAAAAGGTAAAATATTTTTTTTTTCTATTTCATTTTTTTA
              CATGTAATATTTGAATTCAAAGGCTGAGAGAGTAATACCCCCC
              TTTTATTTTTATTTGTGGATTACATATATACATAAGAACTAGAA
              AAATGTTTATATTTTCGACTTGACAATGATAGAATGTAAATGTT
              GGATATATAGAATAATTTGTTGGAGCTTCTACCATTTTTTGCTT
              ACCGTCTTAAGGTTGAAGGCGTAGATGTTTATTATCCGAATAA
              TTCCTTTTTGTCGATAATCAAGCATCAATATTAGATTAGTAGCC
              GACCCTCTTCTCTTACCTCTCTAAACAATTTTTCAATATTTCCAT
              TTTGGTTGGTAAAAATATTAGAGAACATTTTCTCTATAGAAAT
              ATCATGTGTTTATTCAGAATTGTTATTGACTCCATATATTTTTA
              ATAATCCAAAACCTATAAATTTAATAGTTTACATTCACAATTAT
              TGCTTGTTGCTGTTCTTTTACCTTGTGTTTCTAATTTTTACCGTT
              ATTAAATATGCATGTGATTAGTTGAAATATTAAATCTCTAGAA
              ATTGAAGGCTGGCTCGAGGTTAGAGATTAAATGGAAAAATGA
              AAGTCAACGAAGCATGGTAGCTGTCAAATACGCTCCAACTCAA
              AGCATTACTGTCATGATGGAGTTCCTATTGATCCATCGTGAAA
              AATTGAACGATATGTTGGCACATGTCGGAATACTTAAAATATC
              GAATTAATATAATTGAATTTAACTTTGAAAATTAATCAAATTA
              ACTTTCGAAAAGCGCTACCTGACAATTAAAAATACAAGGAGTG
              AGCAGTGAACTTAAACTAATCTATTTCAGATCTCTAGGCTTTGA
              TAAACTAATTGACAGTTCAACATTTGCAGATCTAACTTCAACG
              TTTGCTTCTTGTAGATCTGCAACAAGGCAAACTACCATTTGAG
              AGTAAAGAAAAAGGTATAATATAATGTTTTTCTAGTTTTCATTT
              TACATGTATTTTTGTGATTCACTTGATTTGAATGAAACATACAT
              TACAAGAACTAGAAAACGAATTTGTATTTTTGACTTAGATAAT
              TATAAAATGTTAGATGATTTTGTCATAAATTTGTAGTATTCACTC
              TTGTTTTTAGTAAATATACCTCTTTCTTAAATGTGATTGATTTAC
              AGATTATATATTTTAGAATTTTTGCTTATTAAAAGAAAAATTAA
              TTAGTGGCGGAAATTTGAGGTGAATTTGTGAAGAATGGAAGAA
              GTTGGAAATTC

SEQ ID NO:   ATGGATCCGTTTACGGCGGCTGCATTAACCACTGCGGTGACAG
19:          CCACGGTGAGCCTTCTGGTGGAGAACTTGTCGCATCTTATAAG
CDS NRC6-    TTATAATTGGAAGTIGTATACAGGATTGAAGAAATCATGCGAA
2a           GATTTGTATGATGAAGTGAAGCGATTAAATGCATTTTTAGTCG
              ATAACGCGAATCAGAGAAGTAATAGTACGCAATGGGATGTATT
              AGTCGATAAAATTCGACGTACAGTATATAAAGCAGAGGATGTT
              GTTGATAAATTATTGATTCAGGGCAAGTTAGACCAAGAGAGTA
              ATATAGCTAAAAAGATGTTTCACAAAACTTACAAAAACAGGA
              ATTTTACTGAGGAAATCAATGAGATACTTGTAGAGGTGAGGAA
              AATCCTTGAGGAAATCAACATCTGTTTGAGGCAAACCCGACG
              ATTGATCATCATCAGCCTGAAAAAGTTGTCCAGGAGGAACAGG
              GTTCGTCATTGGAAAATCACGAAGTGGTTGGATTTGATGAAGA
              AGCAACGAAAGTGATCAATCGTCTGGTTGAAGGAGCAGAGTG
              TCTAGATGTTATCCCGGTTGTAGGAATGCCGGGACTTGGTAAA
              ACCACACTGGCAAGAAAAATCTTTAATGATCCTAAGATTTCGC
              GAGAATTTTTCAGCTACATTTGGGTTTTCATCGGACAATCAACG
              TGTGTAAAAAGGGGATATCCTTTTTAATATTCTGAAAGGGTTCA
              CAAATTCATTTGATGAATTCAAAAACAGAAATGAGGCAAGCAT
              AACTGATGAAATACGTAAGCGTGTGGCTAATGGAGGTAAATGT
              CTCATTGTCTTGGATGATGTGTGGGATACAAATGTTGTAGATAT
              TGTCAAGACAGTTTTCCCTGATAACAAAAAAGCCCACAGGATC
              ATGATGACCACTCGACACGAAGACATTGCTAGATCTGTCAATA
              AATATCCCCACAATCTGAAATTTCTGGATGGAGACGAAAGTTT
              CCAGCTGCTAGAAAAGAGAGCTTTTGGCGTTAGCCGTTGTCCT
```

TABLE 1-continued

Sequence information
The genomic sequences correspond to the mRNA with +2 kb upstream and downstream
from the start and the end.

```
                    GTTGAGTTAGTAGAACATGGAGAAGCCATTGTAGCAAAATGTA
                    GTGGAGTACCACTTACAATTGTGGTAATTGCAGGAGCTTTAAG
                    AGGTCGTACGAGTGAAATTGATTGGAAAGTAGTTAGGGAAAA
                    TGTGGGGAAGCATCTTATACAAGAAGACAAACTTCAGAGATGT
                    GTGAATGTTGTGAGATTGAGTTACAATCATTTGCCTCAAGAAA
                    AAAAATCTTGCTTCTTGTATTTTGGTGCCTTTCCTCAAGGATTT
                    GATATCCCCGCTTGGAAATTGATTCGACTCTGGATTGCTGAGG
                    GACTCATAATGTCCAAGTTGTCGGGCAACGAAATTGAAGAGAT
                    AGCAGAGTATTATCTTAATGACTTTGCCAACAGGAACTTAGTG
                    ATGGTGATGAAAAAGAAATCTAATGATCGAATAAAAACATGT
                    CGTGTTCACGACATGTTACATGAGTTTTGCGTTGAAGAGGCTA
                    CTAGATTGACTCTTTTCAAACAAGTATGTCTCACATCTGATCAA
                    GACATACAGAACTCAATTACTTGTCGTCGTGTCTCTATTCAATC
                    ATCTGTTCCTCAAAACTTCATCTCAAAAAAGACAGTTGAAGAA
                    CATGTTAGGTCATTGTTATGTTTTTCCTCAAAACAAAAACAAGT
                    TGACTTTTCTAATATCGACGTCAAGCTCATCCCTACCGCATTTC
                    CACTTATGAGAGTCTTAGACATTGAATCCGTCAAGTTTAGTATT
                    CCCAGGGAATTTTACCAGCTATTGCACTTGAGGTATATCGCTAT
                    GTCAGGTGATTTCGAGCAACTTCCTAAACTCTTTACTTCTTTCT
                    GTAATGCACAAACTCTCATTCTAAATACTTCCAAGCCCACCCTT
                    GATATAAAAGCTGACATATGGAACATGCCACGTTTGCGTCATC
                    TGCACACCAACAAACCTGCAATCTTACCACCCCCTACAAGTAG
                    TAGTAGTAGTAGTACAAATTCTTGTTTGTTGCAAACTCTATCTC
                    TGGTTACACCAGAAAGCTGCAAGGGAAACGTTCTTTCAAAGGC
                    TCGTAATGTCAAGAAAATGAGTGTTAAAGGTAATTTGACACCT
                    TTTCTTGAAACTAGCAAGGGTGAATTTTTCAGCAATTTTCAAGT
                    GCTAAAGCTCCTGGAAAGTTTAACACTGCTAAATGATGATAAG
                    AGTAATAAATCTCTTCACCTTCCGTCAGCATTCTCCGAATGTTT
                    ACCAAATTTGAAGAAGTTAACTCTATCAAAAACAAGGTTTGAC
                    TGGAATCAGGCATATAGATTAGGGCAGGTGAAAAATCTCCAG
                    GTCCTAAAACTGAAAGAAAATGCATTCACGGGGCCGTCCTGGA
                    GGATGGAGCCAGGAGGTTTCAAGAAACTTCAGGTCTTGTGGAT
                    TGAAATGGCAGATTTCGTGTCGTGGGAGGCATCAAACTGTCCT
                    TTCCCAAGACTTAGGAGCCTTTTCCTGATCTCCTGTCTTAATCT
                    TGAGGCTGTGCCACTCGATCTTTCCCATTTGGATAACCTTCAAG
                    AGATGACGTTGGAAAACACAAGCAAAGCAAGCAAATCTGCAA
                    GAGAAATAGAATGCGAGAAAAAGAAGAAGCAAGCTGATGATC
                    CAGAAACTGGCAAATTCAAGCTCACTATTCCCTACTGA
```

SEQ ID NO:    MDPFTAAALTTAVTATVSLLVENLSHLISYNWKLYTGLKKSCEDL
20:           YDEVKRLNAFLVDNANQRSNSTQWDVLVDKIRRTVYKAEDVVD
Protein       KLLIQGKLDQESNIAKKMFHKTYKNRNFTEEINEILVEVRKILEEN
NRC6-2a       QHLFEANPTIDHHQPEKVVQEEQGSSLENHEVVGFDEEATKVINR
              LVEGAECLDVIPVVGMPGLGKTTLARKIFNDPKISREFFSYIWVFI
              GQSTCVKRDILFNILKGFTNSFDEFKNRNEASITDEIRKRVANGGK
              CLIVLDDVWDTNVVDIVKTVFPDNKKAHRIMMTTRHEDIARSVN
              KYPHNLKFLDGDESFQLLEKRAFGVSRCPVELVEHGEAIVAKCSG
              VPLTIVVIAGALRGRTSEIDWKVVRENVGKHLIQEDKLQRCVNVV
              RLSYNHLPQEKKSCFLYFGAFPQGFDIPAWKLIRLWIAEGLIMSKL
              SGNEIEEIAEYYLNDFANRNLVMVMKKKSNDRIKTCRVHDMLHE
              FCVEEATRLTLFKQVCLTSDQDIQNSITCRRVSIQSSVPQNFISKKT
              VEEHVRSLLCFSSKQKQVDFSNIDVKLIPTAFPLMRVLDIESVKFSI
              PREFYQLLHLRYIAMSGDFEQLPKLFTSFCNAQTLILNTSKPTLDIK
              ADIWNMPRLRHLHTNKPAILPPPTSSSSSSSTNSCLLQTLSLVTPESC
              KGNVLSKARNVKKMSVKGNLTPFLETSKGEFFSNFQVLKLLESLT
              LLNDDKSNKSLHLPSAFSECLPNLKKLTLSKTRFDWNQAYRLGQ
              VKNLQVLKLKENAFTGPSWRMEPGGFKKLQVLWIEMADFVSWE
              ASNCPFPRLRSLFLISCLNLEAVPLDLSHLDNLQEMTLENTSKASK
              SAREIECEKKKKQADDPETGKFKLTIPY SEQ ID NO:    AGTTTGTCAAATCATCAAAACTACAAATAACAGTTTTGATTTTG
21: Genomic   GACTCTCTTTTTTTTAAAAAAATTTTAATATTATATTATATTTTT
NRC6-2c       AAATTAATTTTTTATTGGCCCACGGGCCGGCCCTACCAATATTT
              CTCAAGCCCCCCAAATGAGCAGGCTTATTCAGGCTGGACAAAA
              AAATCATTTTCTTAAATGGGTTCCAAAAATCTTAGCCCAATCCT
              ATTAAATCTCGGGTTAGGCCAGGCCGACCCAACGGACCTAGCC
              CATATTGACGGCTCTAGTTAGAACCATGAAAATTATGTGATAT
              ATTTTGGTCAAATGTTTCTCACAATGAAACTTAAAAACCTAAT
              GAAGGCTAGCTTGAATATATGGCCATACAACAAAATAAAATG
              ACAAAACTGATCCCTTATCTTTGCTAGTAGTTTCAATATAGTCC
              TTTTAAGTATCAATCAAATACTTTTGATCATTTTTAGTAAGATA
              AATTTTGTAGATAAATAACAAATTCGTTGCTAATTCTGTTTAGT
              GATAAATTATCAAAGATATTTTTTAACCACAAGCAATTTAACG
              ATGAAATTCGTACCTAATTCTATTTTATTTTTTATATAAAATATT
              ATCGAAACTTTAATGTTTTAAATTCAATTTAAACTGTGAAAATA
              TTTTTAAAAAATCTATTTATTTTATTCTTCTATATTTTGTGCTCA TABLE 1-continued Sequence information
The genomic sequences correspond to the mRNA with +2 kb upstream and downstream
from the start and the end.

```
ATATAGTTGGATGTAGTTCACACTTCACAATTGTATTACATAAT
TTTCTTATATCCTTAATCTTTCTTGCATTGTTTTGGGAAAAAAA
TGCAATTTTATAATAATAATTATCGTCATAATAATAATAATTAG
TCAAGTGAATAATAAAAATAATTTCTGTTAAGAATTATTTTAAT
CAAATTATCCACCTTCTTAAGAATCTCATCATTTCAAGTAAACG
TGGATCTGCCAATAAGATAAAGGACCTAGGAAGTGATGATAA
AAAATATTTATTTCAAATTGGGATGATTTCAATAAACGAATAA
AATTCTTGTAACTTAGGAATTAATTTTTAACTTTTTCTTTTATA
ACAACTCTATTATAAGACTGAATAAAATAATGACTACATTACC
CCCCACTATATTAATTAATTCTATTTAATATAAACTTTACAGAA
AAACCTCGGCAAAGCGAACACCTTGTTTCCCGTGCTCACCAAC
CACAACAATTACGCGGTTAATATCTCAAATGGTTATACAATTTT
AAAAAATTATTCGGTAAAATCATTAAATTTTATTTTATATTATT
AGAGTTACTCAATTTAAGTATATTTAAATCGGTGAAATCACTA
AACTAAATTTATCGATAAATTAAGTGTTGTTAAAATTTTGTTCT
AAACGACTATAGGAAATAGGTTTCTACAAATAACTGTCGGCGC
ATAGTTTCTTTCAAGGAAAAATGCAGAGTGCCAAGTAAGGCCG
AAAAGGGTAAAAAATTATCTATAAAATAAGTCCGGATGGGGG
AATAATAAGACTTGTATAAGTGTGTCTCTGAAATTTCGGACAT
AAATTAGGAGATACTTATGTATTTTCCTTTGTTTCAGTTATTTG
TTTCACCTCTTCCATAATGTTAAATCCTTAATTATATATGTCTA
CCTCTGTACGTCATATTATAGATAGAAAAAAAAATTAAATATG
TGTCTTTATAATCAACACTCTATATAAGTATCACTGAAAGATCT
AGCGACGTTAAATACAACTAAATATTTTTTATTTTGCTACCTTG
AATAATAATTCTCAATTGTTTACAAGCTTTCCAACAACACCCAT
TTATTTTCAACCAATGTGAACCTCTTTCCAACAACACTTAATTT
TTCTATCAATATGAACTTAATTATTCAAATGTTAGCTGTCATTG
GATTATTAAATTGTTAATGTTGTAAGGTGATGGTGTATTATATT
AAGAATTAACTAATAATACTTAAAGACTTGGTTAATCTAATTC
AGAGTCAACATAAAGTTAATTCATTCCACATCTTTATATACAC
ACAACTATGGCAATAACAACATAGCAATTGTCATCTCTAAATT
ACTACTACTATTCTTCTTCTTCATCAATTTAATCCTCAGAAATG
GATCCGTTTACGGCCGCTGCCTTAACCACTGCAGTGACAGCCA
CGGTGAGTCTTCTGGTGGAGAACTTGTCGCATCTTATAAGTTAT
AATTGGAAGTTGTATACAGGATTGAAGAAATCATGCGAAGATT
TGTATGATGAAGTGAAGCGATTAAATGCATTTTTAGCCGATAA
CGCGAATCAGAGAAGTAATAGTACGCAATGGGATGTATTAGTC
GATAAAATTCGACGTACAGTATATAAAGCAGAGGATGTTGTTG
ATAAATTATTGATTCAGGGCAAGTTAGACCAAGAGAGTAATAT
AGCTAGAAAAATGTTTCACAAAACTTACAAAAACAGGAATTTT
ACTGAGGAAATCAATGAGATACTTGTAGAGGTGAGGAAAATC
CTTGATGAAAATCAACATCTGTTTGAGGCAAACCCGACGATTG
ATCATCATCAGCCTGAAAAAGTTGTCCAGGAGGAACAGGTACG
TTTACACGAAATTTCGATTTTAATGTGATTTATTGAAATATGAA
ATGAACTATGATTTGCTCGTTTAGTAAAACTGTATAAGAGTTG
GAGAAATAGTACTTCCTCTGTTTTAATATGCATTATTTGTTTGA
ACTTAGTTAAAGTTTAATCTAAATTATTCAGATCTAGGACAAG
GCATAAGTAAGGCAAAGGATAGAAGTACCTTTCTAGATTATGA
CTCAAATTCCGTAGAATTTTACTTTAGTTAAGGTGTGTCTCTGA
AATTCAGACAATTAAAGGTCACCACCAACCATTATTACATGCA
CAAATCACTATCGATAATTGCCACCATTGGTCAACATTATATAT
CGCTGACCTCCATCTATCATTAACTGTCAGTATGATTCCACTAT
TAATTATCAAATGGTCACCAACAACAACCACAATTAATCACTA
AGGCCAATCACTATACTGTTCACAACCACTATCATCTGTCAAC
ACTATCTAAAATCGATACACACAATCACTATCATTAGTCATTA
CCACCACCGATTGTCACATTTTCTTGTAGTGAATGATGGGGATT
GAAAATATGAAGAATAAAATAGACATGCATAGGATAAGGGGA
CATATTTTTCATAGTTGAATGGGACATTGAAAATTAATAACTTT
CACATGATCATAACTCATTTGGTACCTGATGGAATAATTTCTTG
TTATGATGATACAATCAAGACAAGTAGCCTTAATAAATTGTTT
AATTTGTCCATCTTACAGGGTTCGTCATTGGAAAATCACGAAG
TGGTTGGATTTGATGAAGAAGCAACGAAAGTGATCAATCGTCT
GGTTGAAGGAGCAGAGTGTCTAGATGTTATCCCGGTTGTAGGA
ATGCCGGGACTTGGTAAAACCACACTGGCAAGAAAAATCTTTA
ATGATCCTAAGATTTCGCGAGAATTTTTCAGCTACATTTGGGTT
TTCATCGGACAATCAACGTGTGTAAAAAGGGATATCCTTTTTA
ATATTCTGAAAGGGTTCACAAATTCATTTGATGAATTCAAAAA
CAGAAATGAGGCAAGCATAACTGATGAAATACGTAAGCGTGT
GGCTAATGGAGGTAAATGTCTCATTGTCTTGGATGATGTGTGG
GATACAAATGTTGTAGATATTGTCAAGACAGTTTTCCCTGATA
ACAAAAAAGCCCACAGGATCATGATGACCACTCGACACGAAG
ACATTGCTAGATCTGTCAATAAATATCCCCACAATCTGAAATTT
CTGGATGGAGATGAAAGTTTCCAGCTGCTAGAAAAGAGAGCTT
TTGGCGTTAGCCGTTGTCCTGTTGAGTTAGTAGAACATGGAGA
AGCCATTGTAGCAAAATGTAGTGGAGTACCACTTACAATTGTG
GTAATTGCAGGAGCTTTAAGAGGTCGTACGAGTGAAATTGATT
```

TABLE 1-continued

Sequence information
The genomic sequences correspond to the mRNA with +2 kb upstream and downstream
from the start and the end.

```
GGAAAGTAGTTAGGGAAAATGTGGGGAAGCATCTTATACAAG
AAGACAAACTTCAGAGATGTGTGAATGTTGTGAGATTGAGTTA
CAATCATTTGCCTCAAGAAAAAAAATCTTGCTTCTTGTATTTTG
GTGCCTTTCCTCAAGGATTTGATATCCCCGCTTGGAAATTGATT
CGACTCTGGATTGCTGAGGGACTCATAATGTCCAAGTTGTCGG
GCAACGAAATTGAAGAGATAGCAGAGTATTATCTTAATGACTT
TGCCAACAGGAACTTAGTGATGGTGATGAAAAAGAAATCTAAT
GATCGAATAAAAACATGTCGTGTTCACGACATGTTACATGAGT
TTTGCGTTGAAGAGGCTACTAGATTGACTCTTTTCAAACAAGT
ATGTCTCACATCTGATCAAGACATACAGAACTCAATTACTTGT
CGTCGTGTCTCTATTCAATCATCTGTTCCTCAAAACTTCATCTC
AAAAAAGACAGTTGAAGAACATGTTAGGTCATTGTTATGTTTT
TCCTCAAAACAAAAACAAGTTGACTTTTCTAATATCGACGTCA
AGCTCATCCCTACCGCATTTCCACTTATGAGAGTCTTAGACATT
GAATCCGTCAAGTTTAGTATTCCCAGGGAATTTTACCAGCTATT
GCACTTGAGGTATATCGCTATGTCAGGTGATTTCGAGCAACTT
CCTAAACTCTTTACTTCTTTCTGTAATGCACAAACTCTCATTCT
AAATACTTCCAAGCCCACCCTTGATATAAAAGCTGACATATGG
AACATGCCACGTTTGCGTCATCTGCACACCAACAAACCTGCAA
TCTTACCACCCCCTACAAGTAGTAGTAGTAGTAGTACAAATTC
TTGTTTGTTGCAAACTCTATCTCTGGTTACACCAGAAAGCTGCA
AGGGAAACGTTCTTTCAAAGGCTCGTAATGTCAAGAAAATGAG
TGTTAAAGGTAATTTGACACCTTTTCTTGAAACTAGCAAGGGT
GAATTTTTCAGCAATTTTCAAGTGCTAAAGCTCCTGGAAAGTTT
AACACTGCTAAATGATGATAAGAGTAATAAATCTCTTCACCTT
CCGTCAGCATTCTCCGAATGTTTACCAAATTTGAAGAAGTTAA
CTCTATCAAAAACAAGGTTTGACTGGAATCAGGCATATAGATT
AGGGCAGGTGAAAAATCTCCAGGTCCTAAAACTGAAAGAAAA
TGCATTCACGGGGCCGTCCTGGAGGATGGAGCCAGGAGGTTTC
AAGAAACTTCAGGTCTTGTGGATTGAAATGGCAGATTTCGTGT
CGTGGGAGGCATCAAACTGTCCTTTCCCAAGACTTAGGAGCCT
TTTCCTGATCTCCTGTCTTAATCTTGAGGCTGTGCCACTCGATC
TTTCCCATTTGGATAACCTTCAAGAGATGACGTTGGAAAACAC
AAGCAAAGCAAGCAAATCTGCAAGAGAAATAGAATGCGAGAA
AAAGAAGAAGCAAGCTGATCATCCAGAAACTGGCAAATTCAA
GCTCACTATTCCCTACTGAAGCTGATTTCAATGCCACAAAGTG
AAGTTGTTATAAGGTTAGTCCAATTCTCTCCCTCTCGTATCAGT
AAATATCGAATAAGATATTTTTCAATAAGATTGCATCTATCCCT
ATAGTCTCTCCACGCAGAATTAGTAGGTAGCAGTGTGTTGTCTT
GCTGTCTCGTTCATATCAATAGTCATAGTATTGCTCCTATAGTT
TCTTATCCTTCGATTTTTCGTTACTATACGTTGTCCCTTATACCT
CGATATTAGTAATGCTTGTTGTAGTTTCTCTTATGTTACTATCT
GCTGTTTTTGTTATTACCTGTTGTTTCTTGTATTTCCGTCATTTC
TTTTTGGGACTCCTTTGAACTTTCTCCTTGAGACAAAGGTCAAT
CGGAAACAACCTACCTCTCTTTCTTTGAGATAAGGTTCCTCCCC
AGACTCTATTTTGTGGGACTACACTGAGTATATTGTTTTGGGTT
TCGCACTTCACTGAAACATTAAATTGGGCAACATTACTCTGTTA
TACTAATAATACAGATTTTAGGTGCCTTGATATCAAACATAGA
GTAAATTCAATTATTTTCGTGTTCATCACATTCCTCATCTATTTT
TCTCTTACTTATTTTCCTCCTTTTTAGCAGGAGAGTATCGAGGC
ATGGTGATGCATTTGCAGTCTCAGTTTTGATTACCTGTTCCAAT
AAAGAAACTTGTTACAAGTATGTTTTGTTGATTCAAACATGCC
AAGTTTGAAAACGAAGTTTTATATTAATGTTTTTGCGTTTTCTT
TCAGTGCTGAATAATTTGTCTAATCTGTAGTTGATGTTTGGATA
TCTATGTATTGTTCGATTGACACGAGTTGTTTATACTATCATTT
GTTGTTTATGAATATGTAAAACATATTTGATTTATGTTTGCAAC
GTCAACGTGAACATTCAATTAGTCTAATCAAAGTCTAGATCTA
AAATTGATTAATTTAAGTTTATAATTTATTTTGAATTATTATCT
AAAACCGAAGACTTTCTACTCGAAAATCGAAATCATAGCTGAC
AGTCTCCATAAATATATTTGCAATTGAATAACATAATAAGCAT
TTATCAGTTAATTTTATGGAGTTTTTGGATTTACGTGATATTCA
AACATCTCCCGCGCATATTAATTATGTGAAGTAATGAAGTGTG
TAACATAAGTCAAAAGGTGCATAAATAAAGAGTCAAGGGTAA
TAAGACTTTAGTTTACTTTAGGTGTGTCTCTGAAATTTCGATTA
TAATCTACGAGATATTGTGTCTTGTCCCAACATTTAAATAAAAT
GAACAAATAATTTTAATTACCAAATGGATCCATAGTCTGTTTA
GTTGACTAATGGAAAGATTTATAGGAAGGTGAGATTGTTTTAT
CCCTGATTAGAGGTTTTGGTTCGAGTTTTGTGTATACGAAAAA
ATTGTGTTGAAAGCGTCACTTATGAATAGGCCCTATAATGTAT
GATTCGAATTTAGTCTGAGTTCTAATATGAATTTTGAACACATT
GAAAAATTATATCCTTTGTTAAATTTCATGGTTTTAACATCTTG
GAAGTAAAGAAAAAGGTAAAATATTTTTTTTTTCTATTTCATTT
TTTTACATGTAATATTTGAATTCAAAGGCAGAGAGAGTAATAC
CCCCCTTTTATTTTTATTTGTGGATTACATATATACATAAGAAC
TAGAAAAATGTTTATATTTTCGACTTGACAATGATAGAATGTA
AATGTTGGATATATAGAATAATTTGTTGGAGCTTCTACCATTTT
```

TABLE 1-continued

Sequence information
The genomic sequences correspond to the mRNA with +2 kb upstream and downstream
from the start and the end.

```
                  TTGCTTACCGTCTTAAGGTTGAAGGCGTAGATGTTTATTATCCG
                  AATAATTCCTTTTTGTCGATAATCAAGCATCAATATTAGATTAG
                  TAGCCGACCCTCTTCTCTTACCTCTCTAAACAATTTTTCAATAT
                  TTCCATTTTGGTTGGTAAAAATATTAGAGAACATTTTCTCTATA
                  GAAATATCATGTGTTTATTCAGAATTGTTATTTACTACATATAT
                  TTTTAATAATTAAAAACCTATAAATTTAATAGTTTACATTCACA
                  ATTATTGCTTGTTGCTGTTCTTTTGCCTTGTGTTTCTAATTTTTA
                  CCGTTATTAAATATGCATGTGATTAGTTGAAATATCAAATCTCA
                  TATTAAATGGAAAAATGAAAGTCAACGAAGCATGGTAGCTGTC
                  AAATACGCTCCAACTCAAAGCATTACTGTCATGATGGATTTCC
                  TATTGATCCATCGTGAAAAATTGAACGATATGTTGGCACATGT
                  CAGAATGCTTAAAATATCGAATTAATATAATTGAATTTAACTTT
                  GAAAATTAATCAAATTAACTTTCGAAAAGCGCTACCTGACAAT
                  TAAAAATAGAAGGAGTGAGCAGTGAACTTAAACTAATCTATTT
                  CAGATCTCTAGAGTTTGATAAACTAATTGACAGTTCAACATTT
                  GCAGATCTAACTTCAACATTTGCTTCTTGTAAATCTGCAACAAG
                  GCAAACTACCATTTGAGAGTAAAGAAAAAGGTATAATATAAT
                  GTTTTTCTAGTTTTCATTTTACATGTATTTTTGTGATTCACTTGA
                  TTTGAATGAAACATACATTACAAGAACTAGAAAACGAATTTGT
                  ATTTTTGACTTAGATAATTATAAAATGTTAGATGATTGTCATAA
                  TTTGTAGTATTCACTCTTGTTTTTAGTAAATATACTCTTTCTTAA
                  ATGTGATTGATTTACAGATTATATATTTTAGAATTTTTGCTTAT
                  TAAAAGAAAAATTAATTAGTGGCGGAAATTTGAGGTGAATTCG
                  TGAAGAATGGAAGAAGTTGGAAATTTGAGAGTTTTACATGTGT
                  TTTTTAAGGTAGAAGAAACAAAAAGAATCCATTTGATCTAAAA
                  TTCCAATTGAAAAGTATTAAAAGTTGTTTGGGATCT

SEQ ID NO:   ATGGATCCGTTTACGGCCGCTGCCTTAACCACTGCAGTGACAG
22:          CCACGGTGAGTCTTCTGGTGGAGAACTTGTCGCATCTTATAAG
CDS NRC6-    TTATAATTGGAAGTIGTATACAGGATTGAAGAAATCATGCGAA
2c           GATTTGTATGATGAAGTGAAGCGATTAAATGCATTTTTAGCCG
             ATAACGCGAATCAGAGAAGTAATAGTACGCAATGGGATGTATT
             AGTCGATAAAATTCGACGTACAGTATATAAAGCAGAGGATGTT
             GTTGATAAATTATTGATTCAGGGCAAGTTAGACCAAGAGAGTA
             ATATAGCTAGAAAAATGTTTCACAAAACTTACAAAAACAGGA
             ATTTTACTGAGGAAATCAATGAGATACTTGTAGAGGTGAGGAA
             AATCCTTGATGAAAATCAACATCTGTTTGAGGCAAACCCGACG
             ATTGATCATCATCAGCCTGAAAAAGTTGTCCAGGAGGAACAGG
             GTTCGTCATTGGAAAATCACGAAGTGGTTGGATTTGATGAAGA
             AGCAACGAAAGTGATCAATCGTCTGGTTGAAGGAGCAGAGTG
             TCTAGATGTTATCCCGGTTGTAGGAATGCCGGGACTTGGTAAA
             ACCACACTGGCAAGAAAAATCTTTAATGATCCTAAGATTTCGC
             GAGAATTTTTCAGCTACATTTGGGTTTTCATCGGACAATCAACG
             TGTGTAAAAAGGGATATCCTTTTTAATATTCTGAAAGGGTTCA
             CAAATTCATTTGATGAATTCAAAAACAGAAATGAGGCAAGCAT
             AACTGATGAAATACGTAAGCGTGTGGCTAATGGAGGTAAATGT
             CTCATTGTCTTGGATGATGTGTGGGATACAAATGTTGTAGATAT
             TGTCAAGACAGTTTTCCCTGATAACAAAAAAGCCCACAGGATC
             ATGATGACCACTCGACACGAAGACATTGCTAGATCTGTCAATA
             AATATCCCCACAATCTGAAATTTCTGGATGGAGATGAAAGTTT
             CCAGCTGCTAGAAAAGAGAGCTTTTGGCGTTAGCCGTTGTCCT
             GTTGAGTTAGTAGAACATGGAGAAGCCATTGTAGCAAAATGTA
             GTGGAGTACCACTTACAATTGTGGTAATTGCAGGAGCTTTAAG
             AGGTCGTACGAGTGAAATTGATTGGAAAGTAGTTAGGGAAAA
             TGTGGGGAAGCATCTTATACAAGAAGACAAACTTCAGAGATGT
             GTGAATGTTGTGAGATTGAGTTACAATCATTTGCCTCAAGAAA
             AAAAATCTTGCTTCTTGTATTTTGGTGCCTTTCCTCAAGGATTT
             GATATCCCCGCTTGGAAATTGATTCGACTCTGGATTGCTGAGG
             GACTCATAATGTCCAAGTTGTCGGGCAACGAAATTGAAGAGAT
             AGCAGAGTATTATCTTAATGACTTTGCCAACAGGAACTTAGTG
             ATGGTGATGAAAAGAAATCTAATGATCGAATAAAAACATGT
             CGTGTTCACGACATGTTACATGAGTTTTGCGTTGAAGAGGCTA
             CTAGATTGACTCTTTTCAAACAAGTATGTCTCACATCTGATCAA
             GACATACAGAACTCAATTACTTGTCGTCGTGTCTCTATTCAATC
             ATCTGTTCCTCAAAACTTCATCTCAAAAAAGACAGTTGAAGAA
             CATGTTAGGTCATTGTTATGTTTTTCCTCAAAACAAAAACAAGT
             TGACTTTTCTAATATCGACGTCAAGCTCATCCCTACCGCATTTC
             CACTTATGAGAGTCTTAGACATTGAATCCGTCAAGTTTAGTATT
             CCCAGGGAATTTTACCAGCTATTGCACTTGAGGTATATCGCTAT
             GTCAGGTGATTTCGAGCAACTTCCTAAACTCTTTACTTCTTTCT
             GTAATGCACAAACTCTCATTCTAAATACTTCCAAGCCCACCCTT
             GATATAAAAGCTGACATATGGAACATGCCACGTTTGCGTCATC
             TGCACACCAACAAACCTGCAATCTTACCACCCCCTACAAGTAG
             TAGTAGTAGTAGTACAAATTCTTGTTTGTTGCAAACTCTATCTC
             TGGTTACACCAGAAAGCTGCAAGGGAAACGTTCTTTCAAAGGC
             TCGTAATGTCAAGAAAATGAGTGTTAAAGGTAATTTGACACCT
```

TABLE 1-continued

Sequence information
The genomic sequences correspond to the mRNA with +2 kb upstream and downstream
from the start and the end.

```
            TTTCTTGAAACTAGCAAGGGTGAATTTTTCAGCAATTTTCAAGT
            GCTAAAGCTCCTGGAAAGTTTAACACTGCTAAATGATGATAAG
            AGTAATAAATCTCTTCACCTTCCGTCAGCATTCTCCGAATGTTT
            ACCAAATTTGAAGAAGTTAACTCTATCAAAAACAAGGTTTGAC
            TGGAATCAGGCATATAGATTAGGGCAGGTGAAAAATCTCCAG
            GTCCTAAAACTGAAAGAAAATGCATTCACGGGGCCGTCCTGGA
            GGATGGAGCCAGGAGGTTTCAAGAAACTTCAGGTCTTGTGGAT
            TGAAATGGCAGATTTCGTGTCGTGGGAGGCATCAAACTGTCCT
            TTCCCAAGACTTAGGAGCCTTTTCCTGATCTCCTGTCTTAATCT
            TGAGGCTGTGCCACTCGATCTTTCCCATTTGGATAACCTTCAAG
            AGATGACGTTGGAAAACACAAGCAAAGCAAGCAAATCTGCAA
            GAGAAATAGAATGCGAGAAAAGAAGAAGCAAGCTGATCATC
            CAGAAACTGGCAAATTCAAGCTCACTATTCCCTACTGA

SEQ ID NO:   MDPFTAAALTTAVTATVSLLVENLSHLISYNWKLYTGLKKSCEDL
23: Protein  YDEVKRLNAFLADNANQRSNSTQWDVLVDKIRRTVYKAEDVVD
NRC6-2c      KLLIQGKLDQESNIARKMFHKTYKNRNFTEEINEILVEVRKILDEN
            QHLFEANPTIDHHQPEKVVQEEQGSSLENHEVVGFDEEATKVINR
            LVEGAECLDVIPVVGMPGLGKTTLARKIFNDPKISREFFSYIWVFI
            GQSTCVKRDILFNILKGFTNSFDEFKNRNEASITDEIRKRVANGGK
            CLIVLDDVWDTNVVDIVKTVFPDNKKAHRIMMTTRHEDIARSVN
            KYPHNLKFLDGDESFQLLEKRAFGVSRCPVELVEHGEAIVAKCSG
            VPLTIVVIAGALRGRTSEIDWKVVRENVGKHLIQEDKLQRCVNVV
            RLSYNHLPQEKKSCFLYFGAFPQGFDIPAWKLIRLWIAEGLIMSKL
            SGNEIEEIAEYYLNDFANRNLVMVMKKKSNDRIKTCRVHDMLHE
            FCVEEATRLTLFKQVCLTSDQDIQNSITCRRVSIQSSVPQNFISKKT
            VEEHVRSLLCFSSKQKQVDFSNIDVKLIPTAFPLMRVLDIESVKFSI
            PREFYQLLHLRYIAMSGDFEQLPKLFTSFCNAQTLILNTSKPTLDIK
            ADIWNMPRLRHLHTNKPAILPPPTSSSSSSTNSCLLQTLSLVTPESC
            KGNVLSKARNVKKMSVKGNLTPFLETSKGEFFSNFQVLKLLESLT
            LLNDDKSNKSLHLPSAFSECLPNLKKLTLSKTRFDWNQAYRLGQ
            VKNLQVLKLKENAFTGPSWRMEPGGFKKLQVLWIEMADFVSWE
            ASNCPFPRLRSLFLISCLNLEAVPLDLSHLDNLQEMTLENTSKASK
            SAREIECEKKKKQADHPETGKFKLTIPY SEQ ID NO:   ATGGATCCGTTTACGGCGGCTGCATTAACCACTGCGGTGACAG
24: CDS      CCACGGTGAGCCTTCTGGTGGAGAACTTGTCGCATCTTATAAG
NRC6-2b      TTATAATTGGAAGTTGTATACAGGATTGAAGAAATCATGCGAA
            GATTTGTATGATGAAGTGAAGCGATTAAATGCATTTTTAGTCG
            ATAACGCGAATCAGAGAAGTAATAGTACGCAATGGGATGTATT
            AGTCGATAAAATTCGACGTACAGTATATAAAGCAGAGGATGTT
            GTTGATAAAATTATTGATTCAGGGCAAGTTAGACCAAGAGAGTA
            ATATAGCTAAAAAGATGTTTCACAAAACTTACAAAAACAGGA
            ATTTTACTGAGGAAATCAATGAGATACTTGTAGAGGTGAGGAA
            AATCCTTGAGGAAAATCAACATCTGTTTGAGGCAAACCCGACG
            ATTGATCATCATCAGCCTGAAAAAGTTGTCCAGGAGGAACAGG
            GTTCGTCATTGGAAAATCACGAAGTGGTTGGATTTGATGAAGA
            AGCAACGAAAGTGATCAATCGTCTGGTTGAAGGAGCAGAGTG
            TCTAGATGTTATCCCGGTTGTAGGAATGCCGGGACTTGGTAAA
            ACCACACTGGCAAGAAAAATCTTTAATGATCCTAAGATTTCGC
            GAGAATTTTTCAGCTACATTTGGGTTTTCATCGGACAATCAACG
            TGTGTAAAAAGGGATATCCTTTTTAATATTCTGAAAGGGTTCA
            CAAATTCATTTGATGAATTCAAAAACAGAAATGAGGCAAGCAT
            AACTGATGAAATACGTAAGCGTGTGGCTAATGGAGGTAAATGT
            CTCATTGTCTTGGATGATGTGTGGGATACAAATGTTGTAGATAT
            TGTCAAGACAGTTTTCCCTGATAACAAAAAAGCCCACAGGATC
            ATGATGACCACTCGACACGAAGACATTGCTAGATCTGTCAATA
            AATATCCCCACAATCTGAAATTTCTGGATGGAGATGAAAGTTT
            CCAGCTGCTAGAAAAGAGAGCTTTTGGCGTTAGCCGTTGTCCT
            GTTGAGTTAGTAGAACATGGAGAAGCCATTGTAGCAAAATGTA
            GTGGAGTACCACTTACAATTGTGGTAATTGCAGGAGCTTTAAG
            AGGTCGTACGAGTGAAATTGATTGGAAAGTAGTTAGGGAAAA
            TGTGGGGAAGCATCTTATACAAGAAGACAAACTTCAGAGATGT
            GTGAATGTTGTGAGATTGAGTTACAATCATTTGCCTCAAGAAA
            AAAAATCTTGCTTCTTGTATTTTGGTGCCTTTCCTCAAGGATTT
            GATATCCCCGCTTGGAAATTGATTCGACTCTGGATTGCTGAGG
            GACTCATAATGTCCAAGTTGTCGGGCAACGAAATTGAAGAGAT
            AGCAGAGTATTATCTTAATGACTTTGCCAACAGGAACTTAGTG
            ATGGTGATGAAAAAGAAATCTAATGATCGAATAAAAACATGT
            CGTGTTCACGACATGTTACATGAGTTTTGCGTTGAAGAGGCTA
            CTAGATTGACTCTTTTCAAACAAGTATGTCTCACATCTGATCAA
            GACATACAGAACTCAATTACTTGTCGTCGTGTCTCTATTCAATC
            ATCTGTTCCTCAAAACTTCATCTCAAAAAAGACAGTTGAAGAA
            CATGTTAGGTCATTGTTATGTTTTTCCTCAAAACAAAAACAAGT
            TGACTTTTCTAATATCGACGTCAAGCTCATCCCTACCGCATTTC
            CACTTATGAGAGTCTTAGACATTGAATCCGTCAAGTTTAGTATT
```

TABLE 1-continued

Sequence information
The genomic sequences correspond to the mRNA with +2 kb upstream and downstream
from the start and the end.

```
CCCAGGGAATTTTACCAGCTATTGCACTTGAGGTATATCGCTAT
GTCAGGTGATTTCGAGCAACTTCCTAAACTCTTTACTTCTTTCT
GTAATGCACAAACTCTCATTCTAAATACTTCCAAGCCCACCCTT
GATATAAAAGCTGACATATGGAACATGCCACGTTTGCGTCATC
TGCACACCAACAAACCTGCAATCTTACCACCCCCTACAAGTAG
TAGTAGTAGTAGTAGTACAAATTCTTGTTTGTTGCAAACTCTAT
CTCTGGTTACACCAGAAAGCTGCAAGGGAAACGTTCTTTCAAA
GGCTCGTAATGTCAAAAAAATGAGTGTTAAAGGTAATTTGACG
CCTTTTCTTGAAACTAGCAAGGGTGAATTTTTCAGCAATTTTCA
AGTGCTAAAGCTCCTGGAAAGTTTAACACTGCTAAATGATGAT
AAGAGTAATAAATCTCTTCACCTTCCGTCAGCATTCTCCGAATG
TTTACCAAATTTGAAGAAGTTAACTCTATCAAAAACAAGGTTT
GACTGGAATCAGGCATATAGATTAGGGCAGGTGAAAAATCTCC
AGGTCCTAAAACTGAAAGAAAATGCATTCACGGGGCCGTCCTG
GAGGATGGAGCCAGGAGGTTTCAAGAAACTTCAGGTCTTGTGG
ATTGAAATGGCAGATTTCGTGTCGTGGGAGGCATCAAACTGTC
CTTTCCCAAGACTTAGGAGCCCTTTTCCTGATCTCCTGTCTTAAT
CTTGAGGCTGTGCCACTCGATCTTTCCCATTTGGATAACCTTCA
AGAGATGACGTTGGAAAACACAAGCAAAGCAAGCAAATCTGC
AAGAGAAATAGAATGCGAGAAAAAGAAGAAGCAAGCTGATCA
TCCAGAAACTGGCAAATTCAAGCTCACTATTCCCTACTGA
```

```
SEQ ID NO:    MDPFTAAALTTAVTATVSLLVENLSHLISYNWKLYTGLKKSCEDL
25:           YDEVKRLNAFLVDNANQRSNSTQWDVLVDKIRRTVYKAEDVVD
Protein       KLLIQGKLDQESNIAKKMFHKTYKNRNFTEEINEILVEVRKILEEN
NRC6-2b       QHLFEANPTIDHHQPEKVVQEEQGSSLENHEVVGFDEEATKVINR
              LVEGAECLDVIPVVGMPGLGKTTLARKIFNDPKISREFFSYIWVFI
              GQSTCVKRDILFNILKGFTNSFDEFKNRNEASITDEIRKRVANGGK
              CLIVLDDVWDTNVVDIVKTVFPDNKKAHRIMMTTRHEDIARSVN
              KYPHNLKFLDGDESFQLLEKRAFGVSRCPVELVEHGEAIVAKCSG
              VPLTIVVIAGALRGRTSEIDWKVVRENVGKHLIQEDKLQRCVNVV
              RLSYNHLPQEKKSCFLYFGAFPQGFDIPAWKLIRLWIAEGLIMSKL
              SGNEIEEIAEYYLNDFANRNLVMVMKKKSNDRIKTCRVHDMLHE
              FCVEEATRLTLFKQVCLTSDQDIQNSITCRRVSIQSSVPQNFISKKT
              VEEHVRSLLCFSSKQKQVDFSNIDVKLIPTAFPLMRVLDIESVKFSI
              PREFYQLLHLRYIAMSGDFEQLPKLFTSFCNAQTLILNTSKPTLDIK
              ADIWNMPRLRHLHTNKPAILPPPTSSSSSSSTNSCLLQTLSLVTPES
              CKGNVLSKARNVKKMSVKGNLTPFLETSKGEFFSNFQVLKLLESL
              TLLNDDKSNKSLHLPSAFSECLPNLKKLTLSKTRFDWNQAYRLGQ
              VKNLQVLKLKENAFTGPSWRMEPGGFKKLQVLWIEMADFVSWE
              ASNCPFPRLRSLFLISCLNLEAVPLDLSHLDNLQEMTLENTSKASK
              SAREIECEKKKKQADHPETGKFKLTIPY
```

```
SEQ ID NO:    ATGGATCCGTTTACGGCCGCTGCCTTAACCACTGCAGTGACAG
26: CDS       CCACGGTGAGTCTTCTGGTGGAGAACTTGTCGCATCTTATAAG
NRC6-3        TTATAATTGGAAGTTGTATACAGGATTGAAGAAATCATGCGAA
              GATTTGTATGATGAAGTGAAGCGATTAAATGCATTTTTAGTCG
              ATAACGCGAATCAGAGAAGTAATAGTACGCAATGGGATGTATT
              AGTCGATAAAATTCGACGTACAGTATATAAAGCAGAGGATGTT
              GTTGATAAAATTATTGATTCAGGGCAAGTTAGACCAAGAGAGTA
              ATATAGCTAAAAAGATGTTTCACAAAACTTACAAAAACAGGA
              ATTTTACTGAGGAAATCAATGAGATACTTGTAGAGGTGAGGAA
              AATCCTTGAGGAAAATCAACATCTGTTTGAGGCAAACCCGACG
              ATTGATCATCATCAGCCTGAAAAAGTTGTCCAGGAGGAACAGG
              GTTCATCGTTGGAAAATCACGAAGTGGTAGGATTTGATGAAGA
              AGCAACGAAAGTGATCAATCGTCTGGTTGAAGGAGCAGAGCG
              TCTAGATGTTATCCCGGTTGTAGGAATGCCGGGACTTGGTAAA
              ACCACACTGGCAAGAAAAATCTTTAATGATCCGAAGATTTCGC
              GAGAATTTTTCAGCTACATTTGGGTTTTCATCGGACAATCAACG
              TGTGTAAAAAGGGATATCCTTTTTAATATTCTGAAAGGGTTCA
              CAAATTCATTTGATGAATTCAAAAACAGAAATGAGGCAGACAT
              AACTGATGAAATACGTAAGCGTGTGGCTAATGGAGGTAAATGT
              CTCATTGTCTTGGATGATGTGTGGGATCCAAATGTTGTAGATAT
              TGTCAAGACAGTTTTCCCTGATAACAAAAAAGCCCACAGGATC
              ATGATGACCACTCGACACGAAGACATTGCTAGATCTGTCAATA
              AATATCCTCACAATCTGAAATTTCTGGATGGAGATGAAAGTTT
              CCAGCTGCTAGAAAAGAGAGCTTTTGGCGTTAGCCGTTGTCCA
              GTTGAGTTAGTAGAACATGGAGAAGCCATTGTAGCAAAATGTA
              GTGGAGTACCACTTACAATTGTGGTAATTGCAGGAGCTTTAAG
              AGGTCGTACGAGTGAAATTGATTGGAAAGTAGTTAGGGAAAA
              TGTGGGGAAGCATCTTATACAAGAAGACAAACTTCAGAGATGT
              GTGAATGTTGTGAGATTGAGTTACAATCATTTGCCTCAAGAAA
              AAAAATCTTGCTTCTTGTATTTTGGTGCCTTTCCTCAAGGATTC
              GATATCCCCGCTTGGAAGTTGATTCGACTCTGGATTGCTGAGG
              GACTCATAATGTCCAAGTTGTCAGGCAACGAAATTGAAGAGAT
              AGCAGAGTATTATCTTAATGACTTTGCCAACAGGAACTTAGTG
```

TABLE 1-continued

Sequence information
The genomic sequences correspond to the mRNA with +2 kb upstream and downstream
from the start and the end.

```
                  ATGGTGATGAAAAAGAAATCTAATGATCGAATAAAAACATGT
                  CGTGTTCACGACATGTTACATGAGTTTTGCGTTGAAGAGGCTA
                  CTAGATTGACTCTTTTCAAACAAGTATGTCTCACATCTGATCAA
                  GACATACAAAACTCAATTGCTTGTCGTCGTGTCTCTATTCAATC
                  ATCTGTTCCTCAAAACTTCATCTCAAAAAAGACAGTTGAAGAG
                  CATGTTAGGTCATTTTTATGTTTTTCCTCAAAACAAAAACAAGT
                  TGACTTTTCTAATATCGACGTCAAGCTCATCCCTGCCGCATTTC
                  CACTTATGAGAGTCTTAGACATTGAATCCGTCAAGTTTAGTATT
                  CCCAGGGAATTTTACCAGCTATTGCACTTGAGGTATATCGCTAT
                  CTCAGGTGATTTCGAGCAACTTCCTAAACTCTTTACTTCTTTCT
                  GTAATGCACAAACTCTCATTCTAAATACTTCCAAGCCCACCCTT
                  GATATAAAAGCTGACATATGGAACATGCCACGTTTGCGTCATC
                  TGCGCACCAACAAACCTGCAATCTTACCACCCCCTACAAGTAG
                  TAGTAGTAGTAGTAGTACAAATTCTTGTTTTTTGCAAACTCTAT
                  CTCTGGTTACACCAGAAAGCTGCAAGGGAAATGTTCTTTCAAA
                  AGCTCGTAATGTCAAAAAAATGAGTGTTAAAGGTAATTTGACG
                  CCTTTTCTTGAAACTAGCAAGGGTGAATTTTTCAGCAATTTTCA
                  AGTGCTAAAGCTCCTGGAAAGTTTAACACTGCTAAATGATGAT
                  AAGAGTAACAAATCTCTTCACCTTCCGTCAGCATTCTCCGAAT
                  GTTTACCAAATTTGAAGAAGTTAACTCTATCAAAAACAAGGTT
                  TGACTGGAATCAGGCATATAGATTGGGGCAGGTGAAAAATCTC
                  CAGGTCCTAAAACTGAAAGAAAATGCATTCATGGGGCCGTCCT
                  GGAGGATGGAGCCAGGAGGTTTCAAGAAACTTCAGGTCTTGTG
                  GATTGAAATGGCAGATTTCGTGTCGTGGGAGGCATCAAACTGT
                  CCTTTCCCAAGACTTAGGAGCCTTTTCCTGATCTCCTGTCTTAA
                  TCTTGAGGCTGTGCCACTCGATCTTGCCCATTTGGATAACCTTC
                  AAGAGATGACGTTGGAAAACACAAGCAAAGCAAGCAAATCTG
                  CAAGAGAAATAGAATGCGAGAAAAAGAAGAAGCAAGCTGATC
                  ATCCAGAAAGTGGCAAATTCAAGCTCACTATTCCCTACTGA
```

```
SEQ ID NO:       MDPFTAAALTTAVTATVSLLVENLSHLISYNWKLYTGLKKSCEDL
27:              YDEVKRLNAFLVDNANQRSNSTQWDVLVDKIRRTVYKAEDVVD
Protein          KLLIQGKLDQESNIAKKMFHKTYKNRNFTEEINEILVEVRKILEEN
NRC6-3           QHLFEANPTIDHHQPEKVVQEEQGSSLENHEVVGFDEEATKVINR
                 LVEGAERLDVIPVVGMPGLGKTTLARKIFNDPKISREFFSYIWVFI
                 GQSTCVKRDILFNILKGFTNSFDEFKNRNEADITDEIRKRVANGGK
                 CLIVLDDVWDPNVVDIVKTVFPDNKKAHRIMMTTRHEDIARSVN
                 KYPHNLKFLDGDESFQLLEKRAFGVSRCPVELVEHGEAIVAKCSG
                 VPLTIVVIAGALRGRTSEIDWKVVRENVGKHLIQEDKLQRCVNVV
                 RLSYNHLPQEKKSCFLYFGAFPQGFDIPAWKLIRLWIAEGLIMSKL
                 SGNEIEEIAEYYLNDFANRNLVMVMKKKSNDRIKTCRVHDMLHE
                 FCVEEATRLTLFKQVCLTSDQDIQNSIACRRVSIQSSVPQNFISKKT
                 VEEHVRSFLCFSSKQKQVDFSNIDVKLIPAAFPLMRVLDIESVKFSI
                 PREFYQLLHLRYIAISGDFEQLPKLFTSFCNAQTLILNTSKPTLDIK
                 ADIWNMPRLRHLRTNKPAILPPPTSSSSSSSTNSCFLQTLSLVTPES
                 CKGNVLSKARNVKKMSVKGNLTPFLETSKGEFFSNFQVLKLLESL
                 TLLNDDKSNKSLHLPSAFSECLPNLKKLTLSKTRFDWNQAYRLGQ
                 VKNLQVLKLKENAFMGPSWRMEPGGFKKLQVLWIEMADFVSWE
                 ASNCPFPRLRSLFLISCLNLEAVPLDLAHLDNLQEMTLENTSKASK
                 SAREIECEKKKKQADHPESGKFKLTIPY
```

```
SEQ ID NO:       ATGGATCCGTTTACGGCCGCTGCATTAACCACTGCGGTGACAG
28: CDS          CCACGGTGAGCCTTCTGGTGGAGAACTTGTCGCATCTTATAAG
NRC6-1a          TTATAATTGGAAGTTGTATACAGGATTGAAGAAATCATGCGAA
                 GATTTGTATGATGAAGTGAAGCGATTAAATGCATTTTTAGTCG
                 ATAACGCGAATCAGAGAAGTAATAGTACGCAATGGGATGTAC
                 TAGTCGATAAAATTCGACGTACAGTATATAAAGCAGAGGATGT
                 TGTTGATAAATTATTGATTCAGGGCAAGTTAGACCAAGAGAGT
                 AATATAGCTAAAAAGATGTTTCACAAAACTTACAAAAACAGG
                 AATTTTACTGAGGAAATCAATGAGATACTTGTAGAGGTGAGGA
                 AAATCCTTGAGGAAATCAACATCTGTTTGAGGCAAACCCGAC
                 GATTGATCATCATCAGCCTGAAAAAGTTGTCCAGGAGGAACAG
                 GGTTCGTCATTGGAAAATCACGAAGTGGTTGGATTTGATGAAG
                 AAGCAACGAAAGTGATCAATCGTCTGGTTGAAGGAGCAGAGT
                 GTCTAGATGTTATCCCGGTTGTAGGAATGCCGGGACTTGGTAA
                 AACCACACTGGCAAGAAAAATCTTTAATGATCCTAAGATTTCG
                 CGAGAATTTTTCAGCTACATTTGGGTTTTCATCGGACAATCAAC
                 GTGTGTAAAAAGGGATATCCTTTTTAATATTCTGAAAGGGTTC
                 ACAAATTCATTTGATGAATTCAAAAACAGAAATGAGGCAAGC
                 ATAACTGATGAAATACGTAAGCGTGTGGCTAATGGAGGTAAAT
                 GTCTCATTGTCTTGGATGATGTGTGGGATCCAAATGTTGTAGAT
                 ATTGTCAAGACAGTTTTCCCTGATAACAAAAAAGCCCACAGGA
                 TCATGATGACCACTCGACACGAAGACATTGCTAGATCTGTCAA
                 TAAATATCCCCACAATCTGAAATTTCTGGATGGAGATGAAAGT
                 TTCCAGCTGCTAGAAAAGAGAGCTTTTGGCGTTAGCCGTTGTC
                 CTGTTGAGTTAGTAGAACATGGAGAAGCCATTGTAGCAAAATG
```

TABLE 1-continued

Sequence information
The genomic sequences correspond to the mRNA with +2 kb upstream and downstream
from the start and the end.

```
TAGTGGAGTACCACTTACAATTGTGGTAATTGCAGGAGCTTTA
AGAGGTCGTACGAGTGAAATTGATTGGAAAGTAGTTAGGGAA
AATGTGGGGAAGCATCTTATACAAGAAGACAAACTTCAGAGA
TGTGTGAATGTTGTGAGATTGAGTTACAATCATTTGCCTCAAG
AAAAAAAATCTTGCTTCTTGTATTTTGGTGCCTTTCCTCAAGGA
TTTGATATCCCCGCTTGGAAATTGATTCGACTCTGGATTGCTGA
GGGACTCATAATGTCCAAGTTGTCAGGCAACGAAATTGAAGAG
ATAGCAGAGTATTATCTTAATGACTTTGCCAACAGGAACTTAG
TGATGGTGATGAAAAGAAATCTAATGATCGAATAAAAACAT
GTCGTGTTCACGACATGTTACATGAGTTTTGCGTTGAAGAGGC
TACTAGATTGACTCTTTTCAAACAAGTATGTCTCACATCTGATC
AAGACATACAGAACTCAATTACTTGTCGTCGTGTCTCTATTCAA
TCATCTGTTCCTCAAAACTTCATCTCAAAAAAGACAGTTGAAG
AACATGTTAGGTCATTGTTATGTTTTTCCTCAAAACAAAAACA
AGTTGACTTTTCTAATATCGACGTCAAGCTCATCCCTACCGCAT
TTCCACTTATGAGAGTCTTAGACATTGAATCCGTCAAGTTTAGT
ATTACCAGGGAATTTTACCAGCTATTGCACTTGAGGTATATCG
CTATCTCAGGTGATTTCGAGCAACTTCCTAAACTCTTTACTTCT
TTCTGTAATGCACAAACTCTCATTCTAAATACTTCCAAGCCCAC
CCTTGATATAAAAGCTGACATATGGAACATGCCACGTTTGCGT
CATCTGCGCACCAACAAACCTGCAATCTTACCACCCCCTACAA
GTAGTAGTAGTAGTAGTAGTACAAATTCTTGTTTTTTGCAAACT
CTATCTCTGGTTACACCAGAAAGCTGCAAGGGAAATGTTCTTT
CAAAAGCTCGTAATGTCAAAAAAAATGAGTGTTAAAGGTAATTT
GACGCCTTTTCTTGAAACTAGCAAGGGTGAATTTTTCAGCAATT
TTCAAGTGCTAAAGCTCCTGGAAAGTTTAACACTGCTAAATGA
TGATAAGAGTAACAAATCTCTTCACCTTCCGTCAGCATTCTCCG
AATGTTTACCAAATTTGAAGAAGTTAACTCTATCAAAAACAAG
GTTTGACTGGAATCAGGCATATAGATTGGGGCAGGTGAAAAAT
CTCCAGGTCCTAAAAATGAAAGAAAATGCATTCATGGGGCCGT
CCTGGAGGATGGAGCCAGGAGGTTTCAAGAAACTTCAGGTCTT
GTGGATTGAAATGGCAGATTTCGTGTCGTGGGGAGGCATCAAAC
TGTCCTTTCCCAAGACTTAGGAGCCTTTTCCTGATCTCCTGTCT
TAATCTTGAGGCTGTGCCACTCGATCTTGCCCATTTGGATAACC
TTCAAGAGATGACGTTGGAAAACACAAGCAAAGCAAGCAAAT
CTGCAAGAGAAATAGAATGCGAGAAAAAGAAGAAGCAAGCTG
ATCATCCAGAAAGTGGCAAATTCAAGCTCACTATTCCCTACTG
A
```

| SEQ ID NO:<br>29:<br>Protein<br>NRC6-1a | MDPFTAAALTTAVTATVSLLVENLSHLISYNWKLYTGLKKSCEDL<br>YDEVKRLNAFLVDNANQRSNSTQWDVLVDKIRRTVYKAEDVVD<br>KLLIQGKLDQESNIAKKMFHKTYKNRNFTEEINEILVEVRKILEEN<br>QHLFEANPTIDHHQPEKVVQEEQGSSLENHEVVGFDEEATKVINR<br>LVEGAECLDVIPVVGMPGLGKTTLARKIFNDPKISREFFSYIWVFI<br>GQSTCVKRDILFNILKGFTNSFDEFKNRNEASITDEIRKRVANGGK<br>CLIVLDDVWDPNVVDIVKTVFPDNKKAHRIMMTTRHEDIARSVN<br>KYPHNLKFLDGDESFQLLEKRAFGVSRCPVELVEHGEAIVAKCSG<br>VPLTIVVIAGALRGRTSEIDWKVVRENVGKHLIQEDKLQRCVNVV<br>RLSYNHLPQEKKSCFLYFGAFPQGFDIPAWKLIRLWIAEGLIMSKL<br>SGNEIEEIAEYYLNDFANRNLVMVMKKKSNDRIKTCRVHDMLHE<br>FCVEEATRLTLFKQVCLTSDQDIQNSITCRRVSIQSSVPQNFISKKT<br>VEEHVRSLLCFSSKQKQVDFSNIDVKLIPTAFPLMRVLDIESVKFSI<br>TREFYQLLHLRYIAISGDFEQLPKLFTSFCNAQTLILNTSKPTLDIK<br>ADIWNMPRLRHLRTNKPAILPPPTSSSSSSSTNSCFLQTLSLVTPES<br>CKGNVLSKARNVKKMSVKGNLTPFLETSKGEFFSNFQVLKLLESL<br>TLLNDDKSNKSLHLPSAFSECLPNLKKLTLSKTRFDWNQAYRLGQ<br>VKNLQVLKMKENAFMGPSWRMEPGGFKKLQVLWIEMADFVSW<br>EASNCPFPRLRSLFLISCLNLEAVPLDLAHLDNLQEMTLENTSKAS<br>KSAREIECEKKKKQADHPESGKFKLTIPY |

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: *M. enterolobii* Disease Testing

Determining resistance of a tomato plant was done by counting egg masses. The tomato plants to be tested were sown in trays in a greenhouse, after 2 weeks the plants were transferred to 660 cc pots filled with a sandy soil mixture. As a susceptible control plant Dometica RZ was introduced in the test and as a positive control plants grown from the deposit NCIMB 43515 were introduced in the test. Next to the roots, holes were made with a 1 ml pipet tip and filled with 1 ml of suspension comprising 500J2 of the *M. enterolobii* inoculum. After inoculation the plants were grown in a growth chamber (23° C., 14 h. light) and watered three times a week. Six weeks after inoculation the plants were removed from the soil and the roots were washed with tap water in order to remove the soil. The egg masses were counted and the scoring was done according to the symptoms as presented in Table 2. An *M. enterolobii* resistant tomato plant has a score of 0, 1 or 2, preferably 0 or 1, when scoring according to Table 2 is used.

TABLE 2

| scales *M. enterolobii* resistance scores | | |
|---|---|---|
| Score | Number of Egg Masses | Type of resistance |
| 0 | 0 | Highly resistant |
| 1 | 1-3 | Resistant |
| 2 | 4-20 | Intermediate resistant |
| 3 | 21-100 | Susceptible |
| 4 | >100 | Highly Susceptible |

Example 2: Identification of the Nucleic Acid Molecule Capable of Conferring *M. enterolobii* Resistance Various internally developed *Solanum lycopersicum* populations that segregated for *M. enterolobii* resistance were finemapped to a small region on chromosome 4 that contained only 10 potential genes, which were likely to contribute to the *M. enterolobii* resistance. Whole genome sequences were available in-house for the backgrounds of the resistant and susceptible lines that were used in the development of these populations. Some of the genes had a premature stop codon and therefore a functional protein was not expressed. Only the genes present in the region of interest and expressing a functional protein were considered to be candidate genes. Among the remaining genes in the region of interest was the MeR1 gene of the invention, which had various polymorphisms between susceptible and resistant material. Segregating material showed that the MeR1 gene of the invention segregates together with resistance. Through analysis of the correlation in segregation of phenotypes and genotypes it was determined that the specific MeR1 gene was the cause of the *M. enterolobii* resistance of the resistant *Solanum lycopersicum* plants. During the analysis it was also seen that NRC6 segregates together with the MeR1 gene of the invention for the resistance to the *M. enterolobii* resistance. NRC6 comprise the MADA motif as disclosed in Adachi et al. ((2019) An N-terminal motif in NLR immune receptors is functionally conserved across distantly related plant species; Elife. 27; 8) and was therefore considered to be NLR helper protein.

The expression of the MeR1 protein encoded by the MeR1 gene of the invention was determined by RNA sequencing of material of the leaves and the roots of infected plants as well as non-infected plants of *Solanum lycopersicum* plants that are susceptible to *M. enterolobii* and plants of the invention. This lead to the conclusion that the MeR1 protein is expressed in the roots of the plant and is not present in the leaves of the plant.

Example 3: Modifying the MeR1 Gene of the Invention

A functional MeR1 protein in a plant is required for having the resistance to nematodes and in particular the resistance to *M. enterolobii*. Therefore, inhibiting the expression of the MeR1 protein by mutating the MeR1 gene of the invention of a resistant plant will lead to a plant which is susceptible to *M. enterolobii*.

For the inhibition of the expression of the MeR1 protein a CRISPR/Cas experiment was performed. Two designed guide RNAs were incorporated in a plasmid. The two guide RNAs were designed to target two different locations in the coding sequence of the MeR1 gene. An *Agrobacterium tumefaciens*-mediated transformation with the CRISPR/Cas construct was performed on young tomato (*Solanum lycopersicum*) plantlets after growing them in a sterile environment for 6 days. The transformation was performed on plantlets which are resistant and which were obtained by crossing the *Solanum pimpinellifolium* source with a susceptible *Solanum lycopersicum* line to obtain a F1 generation. Subsequently, the F1 plants were back-crossed 3 times to obtain a BC3 population and finally selfed two times to obtain a F3BC3 population.

In the resistant plantlets, one mutant plant with a 236 bp deletion in the coding sequence of the MeR1 gene was found and selected. The deletion led to the expression of a nonfunctional MeR1 protein, thereby inhibiting its expression. The selected plant was selfed in order to obtain a segregating population. Confirmation of the deletion was performed by using a simple PCR experiment. For the PCR experiment, the isolated genomic DNA was used together with the forward primer AGGAATGTATAAATACTCTGACA (SEQ ID NO:31) and reverse primer GCCTAGCAACTAATGTATCT (SEQ ID NO:32). Said primer pair has been designed to amplify the MeR1 amplicon with and without the mutation. The conditions were as follows:

Primer pair with SEQ ID NO:31 and SEQ ID NO:32:
3 minutes at 95° C. (initial denaturing step)
40 amplification cycles, each cycle consisting of 30 seconds denaturation at 95° C., 30 seconds annealing at 60° C., and 75 seconds extension at 75° C.
10 minutes at 72° C. (final extension step).

The PCR products were visualized on agarose gel; plants with the mutation showed an amplicon size of 820 bp and plants without the mutation showed an amplicon of 1100 bp.

By this PCR experiment, 9 plants homozygous for the mutation and 16 plants with a wild-type version of the MeR1 gene were selected for the experiment.

Mutant plants comprising the deletion in the MeR1 gene homozygously as well as plants comprising a functional MeR1 gene in the same genetic background were tested for resistance by counting the number of root knots. Counting the number of root knots is different of counting egg masses as described in Example 1 as it is performed at a different time after inoculation. The tomato plants to be tested were sown in trays in a greenhouse, after 2 weeks the plants were transferred to 900 cc square pots filled with a sandy soil mixture. Next to the roots, holes were made with a 1 ml pipet tip and filled with 1 ml of suspension comprising 500J2 of the *M. enterolobii* inoculum. After inoculation the plants were grown in a controlled greenhouse (23° C., minimum 14 h. light) and watered three times a week. 28 days after inoculation the plants were removed from the soil and the roots were tapped free of soil as much as possible. Plants with the deletion had a significant increase in susceptibility to *M. enterolobii* i.e. an increase in numbers of root knots, as compared to a plant with the same background but without the deletion in the MeR1 gene. The results represented in FIG. 1 show that the inhibition of the expression of a functional MeR1 gene of a resistant plant leads to a more susceptible plant. Therefore the MeR1 gene of the invention confers resistance to *M. enterolobii* to tomato plants. A resistant tomato plant can for example be grown from the deposit NCIMB 43515.

The invention is further described by the following numbered paragraphs:

1. A nucleic acid molecule encoding an MeR1 protein, which confers resistance to root-knot nematode when present in a plant of the Solanaceae family, wherein said nucleic acid molecule has a nucleotide sequence which is:

a) a nucleotide sequence comprising a coding sequence according to SEQ ID NO: 2, 3, 4, 5, 6, 7, 8 or 9, or a coding sequence which has at least 90% sequence identity with the sequence according to SEQ ID NO: 2, 3, 4, 5, 6, 7, 8 or 9; or b) a nucleotide sequence encoding a protein having an amino acid sequence according to SEQ ID NO: 10, 11, 12, 13, 14, 15, 16 or 17, or a protein having an amino acid sequence which has at least 85% sequence identity with the amino acid sequence according to SEQ ID NO: 10, 11, 12, 13, 14, 15, 16 or 17.

2. The nucleic acid of paragraph 1, wherein the sequence identity with the sequence according to SEQ ID NO: 2, 3, 4, 5, 6, 7, 8 or 9 in order of increased preference is 91%, 92%, 93%, 94%, 95%, 96%, 97%, 98%, 99%.

3. The nucleic acid of paragraph 1 or paragraph 2, wherein the sequence identity with the amino acid sequence according to SEQ ID NO: 10, 11, 12, 13, 14, 15, 16 or 17 in order of increased preference is 85%, 86%, 87%, 88%, 89%, 90%, 91%, 92%, 93%, 94%, 95%, 96%, 97%, 98%, 99%.

4. A nucleic acid molecule encoding a NRC6 protein, which contributes to resistance to root-knot nematode when present in a plant of the Solanaceae family together with the nucleic acid molecule of any one on the paragraphs 1-3, wherein said nucleic acid molecule has a nucleotide sequence which is:

a) a nucleotide sequence comprising a coding sequence according to SEQ ID NO: 19, or a coding sequence having at least 98% sequence identity with the sequence according to SEQ ID NO: 19; or b) a nucleotide sequence encoding a protein having an amino acid sequence according to SEQ ID NO: 20, or a protein having an amino acid sequence which has at least 98% sequence identity with the amino acid sequence according to SEQ ID NO: 20.

5. The nucleic acid molecule of any one of the paragraphs 1-4, which confers resistance to root-knot nematode when present in a *Solanum lycopersicum* plant.

6. A plant of the Solanaceae family, in particular a *Solanum lycopersicum* plant, comprising the nucleic acid molecule of any one of the paragraphs 1-3 or 5, wherein the plant is resistant to a root-knot nematode.

7. A plant of the Solanaceae family, in particular a *Solanum lycopersicum* plant, comprising the nucleic acid molecule of any one of the paragraphs 1-3 or 5 and at least one nucleic acid molecule of paragraph 4 or 5, wherein the plant is resistant to a root-knot nematode.

8. A plant of the Solanaceae family, in particular a *Solanum lycopersicum* plant, comprising the nucleic acid molecule of any one of the paragraphs 1-3 or 5 and two nucleic acid molecules of paragraph 4 or 5, wherein the plant is resistant to a root-knot nematode.

9. The plant of any one of the paragraphs 6-8, wherein the plant is resistant to *Meloidogyne enterolobii.*

10. The plant of paragraph 8 or 9, which is a *Solanum lycopersicum* plant, wherein the nucleic acid molecules are as comprised in the genome of a *Solanum lycopersicum* plant representative seed of which was deposited with the NCIMB under deposit number NCIMB 43515.

11. A rootstock of a plant of the Solanaceae family comprising the nucleic acid molecule of any one of the paragraphs 1-3 or 5, and optionally a nucleic acid molecule of paragraph 4 or 5.

12. A seed, wherein a plant of the Solanaceae family, in particular a *Solanum lycopersicum* plant, grown from the seed comprises the nucleic acid molecule as defined in any one of the paragraphs 1-3 or 5, and optionally a nucleic acid molecule of any one of the paragraphs 4 and 5.

13. The seed of paragraph 11, wherein the *Solanum lycopersicum* plant grown from the seed is resistant to *Meloidogyne enterolobii,*

14. Method for selecting a plant of the Solanaceae family carrying the nucleic acid molecule of in any one of the paragraphs 1-3 or 5 and optionally a nucleic acid molecule of paragraph 4 or 5, comprising determining the presence of the nucleic acid molecule as defined in any one of the paragraphs 1-3 or 5 and optionally a nucleic acid molecule of paragraph 4 or 5, or parts thereof, in the plant of the Solanaceae family, and selecting the Solanaceae plant if it comprises the nucleic acid molecule of any one of the paragraphs 1-3 or 5 and optionally the nucleic acid molecule of paragraph 4 or 5.

15. The method of paragraph 14, further comprising the step of determining whether the plant shows resistance against a root-knot nematode.

16. The method of paragraph 14 or 15, wherein the plant is a *Solanum lycopersicum* plant.

17. The method of any one of the paragraphs 14 to 16, wherein the root-knot nematode is *Meloidogyne enterolobii.*

18. A method for producing a plant of the Solanaceae family, in particular a *Solanum lycopersium* plant, having resistance to root-knot nematode comprising:

(a) crossing a plant comprising the nucleic acid molecule of any one of the paragraphs 1-3 and 5 and optionally a nucleic acid molecule of paragraph 4 or 5, with another plant;

(b) optionally performing one or more rounds of selfing and/or crossing;

(c) selecting after one or more rounds of selfing and/or crossing for a plant that comprises said nucleic acid molecule of any one of the paragraphs 1-3 or 5 and optionally a nucleic acid molecule of paragraph 4 or 5.

19. The method of paragraph 18, wherein the selection of a plant of the Solanaceae family which is resistant to root-knot nematode and comprises the nucleic acid molecule of any one of the paragraphs 1-3 or 5 and optionally a nucleic acid molecule of paragraph 4 or 5, further comprises determining the presence of the nucleic acid molecule according the method of paragraph 14.

20. The method of any one of the paragraphs 18 to 19, wherein the root-knot nematode is *Meloidogyne enterolobii.*

21. Use of the nucleic acid molecule of any one of the paragraphs 1-3 or 5 and optionally together with a nucleic acid molecule of paragraph 4 or 5 for producing a plant of the Solanaceae family, in particular a *Sola-num lycopersium* plant, which in resistant to root-knot nematode.

22. Use of paragraph 21, wherein the plant that is resistant is produced by introducing the nucleic acid molecule of any one of the paragraphs 1-3 or 5 optionally together with a nucleic acid molecule of paragraph 4 or 5 into its genome, in particular by means of introgression.

23. Use of any one of the paragraphs 21 or 22, wherein the root-knot nematode is *Meloidogyne enterolobii*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. *Solanum lycopersicum* plant comprising a *Meloidogyne* enterolobii resistant 1 (MeR1) gene encoding an MeR1 protein, and an allele of NLR (Nucleotide-binding domain and leucine-rich repeat) required for cell death 6 (NRC6) gene, wherein the NRC6 gene encodes a NRC6 protein, wherein the MeR1 gene comprises:

a) a nucleotide sequence comprising a coding sequence according to SEQ ID NO: 2, 3, 4, 5, 6, 7, 8 or 9; or b) a nucleotide sequence encoding the MeR1 protein, wherein the MeR1 protein has an amino acid sequence according to SEQ ID NO: 10, 11, 12, 13, 14, 15, 16 or 17;

wherein the allele of the NRC6 gene comprises:

c) a coding sequence according to SEQ ID NO: 19, 22, 24, 26, or 28; or d) a nucleotide sequence encoding the NRC6 protein, wherein the NRC6 protein has an amino acid sequence according to SEQ ID NO: 20, 23, 25, 27, or 29; and wherein the MeR1 gene and the allele of the NRC6 gene confer to the *Solanum lycopersicum* plant resistance to *Meloidogyne* enterolobii.

2. The *Solanum lycopersicum* plant of claim 1, wherein the MeR1 gene is as present in a *Solanum lycopersicum* plant, representative seed of which was deposited under deposit number NCIMB 43515.

3. A rootstock resulting from an interspecific cross, wherein one parent plant is the *Solanum lycopersicum* plant of claim 1 comprising the MeR1 gene and the allele of the NRC6 gene.

4. A seed of, or from, or that produces the plant of claim 1, and comprises the MeR1 gene and the allele of the NRC6 gene.

5. Propagation material for producing the plant of claim 1, wherein the propagation material is for sexual reproduction, and comprises a microspore, pollen, ovary, ovule, embryo sac or an egg cell, or the propagation material is for vegetative reproduction and comprises a cutting, root, stem cell, or a protoplast, or the propagation material is for tissue culture of regenerable cells or protoplasts and comprises a leaf, pollen, embryo, cotyledon, hypocotyl, meristematic cell, root, root tip, anther, flower or a stem, and wherein the propagation material comprises the MeR1 gene and the allele of the NRC6 gene.

6. A method for producing a *Solanum lycopersicum* plant comprising a MeR1 gene and an allele of the NRC6 gene comprising:

(I) crossing a first Solanaceae parent plant with a second *Solanum lycopersicum* plant to obtain an F1 population;

(II) optionally performing one or more rounds of selfing and/or crossing with a F1 *Solanum lycopersicum* plant to obtain a further generation population;

(III) selecting from the population resulting from the cross of step al), or from the further generation population of step II), a *Solanum lycopersicum* plant that comprises the MeR1 gene and the allele of the NRC6 gene; wherein said MeR1 gene:

encodes an MeR1 protein; and a) comprises a nucleotide sequence comprising a coding sequence according to SEQ ID NO: 2, 3, 4, 5, 6, 7, 8 or 9; or b) comprises a nucleotide sequence encoding the MeR1 protein, wherein the MeR1 protein has an amino acid sequence according to SEQ ID NO: 10, 11, 12, 13, 14, 15, 16 or 17; and wherein said NRC6 gene:

encodes a NRC6 protein; and c) comprises a nucleotide sequence comprising a coding sequence according to SEQ ID NO: 19, 22, 24, 26, or 28; or d) comprises a nucleotide sequence encoding the NRC6 protein, wherein the NRC6 protein has an amino acid sequence according to SEQ ID NO: 20, 23, 25, 27, or 29;

(IV) additionally testing the selected plant for resistance to *Meloidogyne enterolobii*; and (V) selecting the additionally tested plant that exhibits resistance to *Meloidogyne enterolobii*.

7. The plant of claim 1, wherein the MeR1 gene comprises:

a) the nucleotide sequence having the coding sequence according to SEQ ID NO: 2; or b) the nucleotide sequence encoding the MeR1 protein, wherein the MeR1 protein has the amino acid sequence of SEQ ID NO: 10.

8. The plant of claim 1, wherein the allele of the NRC6 gene comprises:

c) the coding sequence according to SEQ ID NO: 19; or d) the nucleotide sequence encoding the NRC6 protein, wherein the NRC6 protein has the amino acid sequence of SEQ ID NO: 20.

9. The plant of claim 1, wherein the MeR1 gene comprises:

a) the nucleotide sequence having the coding sequence according to SEQ ID NO: 2; or b) the nucleotide sequence encoding the MeR1 protein, wherein the MeR1 protein has the amino acid sequence of SEQ ID NO: 10; and the allele of the NRC6 gene comprises:

c) the coding sequence according to SEQ ID NO: 19; or d) the nucleotide sequence encoding the NRC6 protein, wherein the NRC6 protein has the amino acid sequence of SEQ ID NO: 20.

10. The plant of claim 1, wherein the MeR1 gene comprises:

a) the nucleotide sequence having the coding sequence according to SEQ ID NO: 2; or b) the nucleotide sequence encoding the MeR1 protein, wherein the MeR1 protein has the amino acid sequence of SEQ ID NO: 10; and the allele of the NRC6 gene comprises:

c) the coding sequences according to SEQ ID NO: 19 and 22; or d) the nucleotide sequence encoding the NRC6 protein, wherein the NRC6 protein has the amino acid sequences of SEQ ID NO: 20 and 23.

11. The plant of claim 1, wherein the MeR1 gene comprises:

a) the nucleotide sequence having the coding sequence according to SEQ ID NO: 2; or b) the nucleotide sequence encoding the MeR1 protein, wherein the MeR1 protein has the amino acid sequence of SEQ ID NO: 10; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

12. The plant of claim 1, wherein the MeR1 gene comprises:

a) the nucleotide sequence having the coding sequence according to SEQ ID NO: 3; or b) the nucleotide sequence encoding the MeR1 protein, wherein the MeR1 protein has the amino acid sequence of SEQ ID NO: 11; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

13. The plant of claim 1, wherein the MeR1 gene comprises:

a) the nucleotide sequence having the coding sequence according to SEQ ID NO: 4; or b) the nucleotide sequence encoding the MeR1 protein, wherein the MeR1 protein has the amino acid sequence of SEQ ID NO: 12; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

14. The plant of claim 1, wherein the MeR1 gene comprises:

a) the nucleotide sequence having the coding sequence according to SEQ ID NO: 5; or b) the nucleotide sequence encoding the MeR1 protein, wherein the MeR1 protein has the amino acid sequence of SEQ ID NO: 13; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

15. The plant of claim 1, wherein the MeR1 gene comprises:

a) the nucleotide sequence having the coding sequence according to SEQ ID NO: 6; or b) the nucleotide sequence encoding the MeR1 protein, wherein the MeR1 protein has the amino acid sequence of SEQ ID NO: 14; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

16. The plant of claim 1, wherein the MeR1 gene comprises:

a) the nucleotide sequence having the coding sequence according to SEQ ID NO: 7; or b) the nucleotide sequence encoding the MeR1 protein, wherein the MeR1 protein has the amino acid sequence of SEQ ID NO: 15; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

17. The plant of claim 1, wherein the MeR1 gene comprises:

a) the nucleotide sequence having the coding sequence according to SEQ ID NO: 8; or b) the nucleotide sequence encoding the MeR1 protein, wherein the MeR1 protein has the amino acid sequence of SEQ ID NO: 16; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

18. The plant of claim 1, wherein the MeR1 gene comprises:

a) the nucleotide sequence having the coding sequence according to SEQ ID NO: 9; or b) the nucleotide sequence encoding the MeR1 protein, wherein the MeR1 protein has the amino acid sequence of SEQ ID NO: 17; and the allele of the NRC6 gene comprises:

c) the coding sequence according to SEQ ID NO: 19, 22, 24, 26, or 28; or d) the nucleotide sequence encoding the NRC6 protein, wherein the NRC6 protein has the amino acid sequence of SEQ ID NO: 20, 23, 25, 27, or 29.

* * * * *

SEQUENCE LISTING

```
Sequence total quantity: 32
SEQ ID NO: 1            moltype = DNA  length = 9591
FEATURE                Location/Qualifiers
misc_feature           1..9591
                       note = genomic MeR1
source                 1..9591
                       mol_type = genomic DNA
                       organism = Solanum lycopersicum
SEQUENCE: 1
tttcgcactt cactgaaaca ttaaattggg caacattact ctgttatact aataatacag   60
attttaggtg ccttgatatc aaacatagag taaattcaat tattttcgtg ttcatcacat  120
tcctcatcta tttttctctt acttattttc ctccttttta gcaggagagt atcgaggcat  180
ggtgatgcat ttgcagtctc agttttgatt acctgttcca ataaagaaac ttgttacaag  240
tatgttttgt tgattcaaac atgccaagtt tgaaaacgaa gtttttatatt aatgtttttg  300
cgttttcttt cagtgctgaa taatttgtct aatctgtagt tgatgtttgg atatctatgt  360
attgttcgat tgcacacgagt tgtttatact atcatttgtt gtttatgaat atgtaaaaca  420
tatttgattt atgtttgcaa cgtcaacgtg aacattcaat tagtctaatc aaagtctaga  480
tctaaaattg attaatttaa gttcataatt tattttgaat tattatctaa aaccgaagac  540
tttctactcg aaaatcgaaa tcatagctga cagtctccat aaatatattt gcaattgaat  600
aacataataa gcatttatca gttaatttta tggagtttct ggatttacgt gatattcaaa  660
catctcccgc gcatattaat tatgtgaagt aatgaagtgt gtaacataag tcaaaaggtg  720
cataaataaa gagtcaaggg taataagact ttagtttact ttaggtgtgt ctctgaaatt  780
tcgattataa tctacgatat attgtgtctt gtcccaacat ttaaataaaa tgaacaaata  840
attttaatta ccaaatggat ccatagtctg tttagttgac taatggaaag atttatagga  900
aggtgagatt gtttttatccc tgattagagg ttttggttcg agttttgtgt atacgaaaaa  960
attgtgttga aagcgtcact tatgaatagg ccctataatg tatgattcga atttagtctg 1020
agttctaata tgaattttga acacattgaa aaattatatc ctttgttaaa tttcatggtt 1080
ttaacatctt ggaagtaaag aaaaaggtaa aatatttttt ttttctattt catttttta 1140
catgtaaatat ttgaattcaa aggctgagag agtaataccc ccctttatt tttatttgtg 1200
gattacatat atacataaga actagaaaaa tgtttatatt ttcgacttga caatgataga 1260
atgtaaatgt tggatatata gaataaatttg ttggagcttc taccattttt tgcttaccgt 1320
cttaaggttg aaggcgtaga tgtttattat ccgaataatt ccttttttgtc gataatcaag 1380
catcaatatt agattagtag ccgaccctct tctcttacct ctctaaacaa tttttcaata 1440
tttccatttt ggttggtaaa aatattagag aacatttttct ctatagaaat atcatgtgtt 1500
tattcagaat tgttattgac tccatatatt tttaataatc caaaacctat aaatttaata 1560
gtttacattc acaattattg cttgttgctg ttcttttacc ttgtgtttct aatttttacc 1620
gttattaaat atgcatgtga ttagttgaaa tattaaatct ctagaaattg aaggctggct 1680
cgaggttaga gattaaatgg aaaaatgaaa gtcaacgaag catggtagct gtcaaatacg 1740
ctccaactca aagcattact gtcatgatgg agttcctatt gatccatcgt gaaaaattga 1800
acgatatgtt ggcacatgtc ggaatactta aaatatcgaa ttaatataat tgaatttaac 1860
tttgaaaatt aatcaaatta actttcgaaa agcgctacct gacaattaaa aatacaagga 1920
gtgagcagtg aacttaaact aatctatttc agatctctag gctttgataa actaattgac 1980
agttcaacat ttgcagatct aacttcaacg tttgcttctt gtagatctgc aacaaggcaa 2040
actaccattt gagagtaaag aaaaaggtat aatataatgt tttttctagtt ttcattttac 2100
atgtattttt gtgattcact tgatttgaat gaaacataca ttacaagaac tagaaaacga 2160
atttgtattt ttgacttaga taattataaa atgttagatg attttgtcat aatttgtagt 2220
attcactctt gttttttagta aatatacctc tttcttaaat gtgattgatt tacagattat 2280
atattttaga atttttgctt attaaaagaa aaattaatta gtggcggaaa tttgaggtga 2340
atttgtgaag aatggaagaa gttggaaatt cgagagtttg ttcatgtgtt ttttaaggta 2400
gaagaaacaa aaaaaatcca tttgatctaa aattccaatt gaaatgtatt acaagttgtt 2460
tggggtaaaa aataatgaca tgaatgtgtt tttctcaaat gataatgaca tagatgagcc 2520
aaagtttaa ctgatgacat aaatgaacct ttctttttct acaaagttcg ataacatatt 2580
tgagccaaaa tttagaattt ataacagctg acattcttct aactctttct tcttgctgtt 2640
acttttactt gtgtttctaa ttcttttatc cttattaaat gtggatgtga ttagtttgaa 2700
aaatcaaatt ttgtagatat tgaaggctgg ttggatggaa aaaggagaaa aatcattggt 2760
atgtctattg tctaccaata ctgtagtttc tagcgttaag agccaatatt ttcaactgaa 2820
ttttgctgat gcatatgttt ttgatttagc agctactatt tgaggaacaa aaaacaagaa 2880
tcacgaatct tattgatgat ttcttgattc gcttgaagca aataaagaat gaattcattg 2940
cttcaaaatt ggatgccttt gaaaatctaa gaatggaact gagattccta agaacatttg 3000
tcctgtttgg gaattcgatg aatttggatg acttttatga gaggatgtca ctgagtataa 3060
gcaaattcga tcaatctacg gagtacgtag ataaaataat cctagagaaa tacaacatgg 3120
aatgtcttgc ccctctgctg cttgaagaga taagaaatta tttgagtttg aagaatgatt 3180
atgtagccac aactacagag ataaaattgt ttgaatacct catcagaaac ctccatgatc 3240
taccaaagta ttgttctgat ttgcttctac cactcatgag tgaatacaag attcttcggc 3300
aagtatgcac acatctcaga gatttctatc agttggaatg caacaaaaca acaaaaacag 3360
aatttctcta tactcggtat caagtgacag ccgatagagt aacacaattc tgtttttgatc 3420
tttggacagg aatgtataaa tactctgaca atgagtatgc cttctctgaa tgttcttcca 3480
```

```
agatcacttc tctactcatt gacataatcc ctcttgagtt ggaggttcta tacatttcta   3540
cttctaagct catcaaagag tcaacgtcaa aagaactaga aggatttgtt aagcaaatct   3600
taaaagcatc tccaaggatt cttcaacatt atctcattca tctccaagga cgcatggccg   3660
gtgtagaagc cgtcaatttc gctccaactc gaagcattag tgtcatgatg gagttcctat   3720
tgatctttct caccgatatg ccaaagcggt ttatccatcg tgaaaaattg aacgatatgt   3780
tggcacatgt cagaatactt acaaggaaaa tatctactct ggtgagtaaa ctgttggagg   3840
agatctctga ggataaatatc aatgaagcgg acttttcagc tccggacttt ttgcaagaaa   3900
ttgaacaaat gaagggagat atcagacaca tcttttttaaa agctcctgag tcatctcaac   3960
ttcggtttcc tatggatgat ggtttcctct tcatgaatct tctactcaga catttaaatg   4020
atttactcat ttccaatgct tattcagttt ttctcataaa aaaagaaatt gggatggtga   4080
aagaaagcct tgaattccta atatcatctt tcaggaaagt caggcaaaca ttggatgaga   4140
gtactagtgg agtagttaaa aattgttggg tgcgtgcttt ggatgtggca tatgaggcag   4200
aacatatcat taattccatt cttgtcagag ataaagctct ctcacatctc ctcttctcac   4260
ttccgagtgt cactgataag atcaaactta tcgtggaaca agtcaccagg tttcagctgg   4320
aggataagaa tggggatggc cccttgatg caaagtcttc cttcgagcca actcagtcaa   4380
cttcatcacc ttttgttgag gtaacagtag gtcacgagaa agaagaatcc cagatcattg   4440
accagctcct tgatgaacat gaatctgagc ttgatgtcat ttccattgtc ggaatgccag   4500
gactcggtaa aactactctg gccaacaaag tgtataaaga tacattagtt gctaggcatt   4560
tccatgtccg tgcttggtgc actgtttcgc aaaagtataa caagtcaaag tgtgttgcggg   4620
agattcttca gcaagttact ggctcgggag gaaaagaaag tgaagatgac ctggctgaaa   4680
agctacgaag agcactactc gataaaaggt acctaatcgt cttggatgat gtgtgggata   4740
ttgcaacagg ggagatgtta atagcatgtt ttcctaaggg taagagagga aatagaatca   4800
tcttaactag ccgaagtaga aaggtaggtt tgaaagttaa atgccgtagt gatcctctcg   4860
accttaaaact tttaacatct gaagaaagtt gggatttatt cgaaaaaagg gtatttggag   4920
atgaaggaag ctgccctgct gaactgtccg aagttggaca ccaaatagtt gagaaatgta   4980
agggtcttcc cttggctatt gttttaattg ctggagtaat tgttagaggg aagaaaaagg   5040
aaaaggattt ttggcttaag atactgcata atctggattc ctttatttct accaacatca   5100
atttggttat gcaattaagt tatgaccatt taccatgcca cctgaagccg ttgctgcttt   5160
actttgcaac aactcaaaag agccaacaaa ctccagtctc tacattgatg cagttgtgga   5220
tggccgaagg gtttgtggat catgatagtt tagaggaagt aactcaaagt tacttggatg   5280
ctctaatttc cagtagcctg ataatggtgg atcatatccc ctccaagagt tattggtgga   5340
cgtctttaat gatcaaggtt tgctatgtgc atgatgttgt gcacgatttt tgttcagaaa   5400
aagccaaaaa ggagaagttt ctcaagttaa tcaattcagg tgatccattt catgcttcag   5460
atttcctaca ccatcgtcta accattcata ctgacaacgg ccaactccac aaaaaatgtg   5520
ttttattcaa ttctaataag tgcttagctg ttagtaagca tgtcatatct ttgaaagtga   5580
gtggtccact agatgagttc aggtatatct gtcacacaag acactttgga cttgttagag   5640
tgttgcaact ggatgacatc attctggaag attctttaat ggaagaaata gggtccctat   5700
ttcatttgag gttcttaagc attgagactg ctgtaggtgt aatagctatc ccagtgtcgt   5760
ggttgaacct ccagaatctg gaaacgctgt tgatttatac gaaaattaag gaatgttctt   5820
tactgcccag aatattgcaa ctgtcaaagc tgaaacatgt gaaaattaag gaatgttctt   5880
tctttgaaga gaaagaggat atccaacgta gaatattgga agctgggaat tcttcaaact   5940
tgacaactct atccggagtt gttatctcat attctgaagg catgagtgat gatgctctgg   6000
agaagttccc aattcttcag caccttgatt gcatcatcat ggaatcgcag aatgctccta   6060
cacacgacta ttggtttctc aagcttgatg tacttaataa actcgaatca ttcgtagcaa   6120
gatacaagcg caatggacat ccctcgttaa accgacaacc gtatggattt cacttcccta   6180
caagcttgaa agagttacgg ttgactggtt tttttcctgag acctgatttg ttgtcagtaa   6240
tcgcagcgtt gcctgagctt gagattatgg agttttcgcg ctgttatttc gtggatacta   6300
aatgggacgc aagtgaggac atctatctaa gtcttaagac tttgattttg cgagatgtcc   6360
atttatcaga atggcaagtt gagggggga cttttcccaa gcttgagaaa ttaatactaa   6420
aattttgttc cacacttggg gagatccctt gtgcatttat ggatgtagaa actttaaagt   6480
ccattgattt aagtttttgtt gggcgtaagc ttcgagattc agccattgag attaagaaaa   6540
atgtagcaga tttcacagga gaggacagag ttgatgtcca cacatcacat ttgtttgcaa   6600
ccaacgtgaa agaacagatt atgagaatga cgggtatggg aaatatacag ggaaggagag   6660
gaatttaaaa agtttagaac ttgaaaggtt gggaacttga aaagtactct aatgcttat   6720
tgaaaaagat aatagtccct catcggtaat ggaaatgaaa ataggagagt ttaaataaat   6780
aaacactcct attaaaattat ttttttttac aaataaattt ctgttcatct tatttactgg   6840
ttctaaaaat ctcagttact tcgtgtttct gaattattta ttataaccag taacttctga   6900
ttttcttaac acagattggc aacagagata actaagttcg tttaatttat ataatttgca   6960
tttgtgtagt gtgttcattg aagttgttag tagagttcat tcttctttct gcacacacta   7020
ccacaaaaac aactttttag aggcaataaa caaatcatcc actgatttga ctagtcgtaa   7080
cattatgaga aaaattcaatg gatttgtttt gtattgcagg tggagaatgt acttgtgaag   7140
aactataata cttagatcct gaatgtttga tttgtgctta tacatagttg gtggagtgat   7200
tgcactgatt ctcgtggtta tgaatcgcag tggttgatga agttggattt ctcatggaaa   7260
aatcacaaca atgaagaacg aaacaacgca acgcctccat ctgattactg cttccaataa   7320
acaaacttgt tactggtttt ctcattgctg gttctggacg tattttgatc taatgtgtcg   7380
tgtgttttct ttcctgtttt tttgttagtt atgaatctta tttcgtctgt aatctctcat   7440
ataagattcc agtttgtttg tttttttaat tggaaggttt caatgccaaa ttgtgaatca   7500
atataggtcc catttggcat gaaaaaggca actaactatc actattgata tggacagtta   7560
attagataac tactgtgcca acaagcattg tggtggagag gcagtactct ctgatcctta   7620
atcagaggtc tcgcgttcga gccctaccag atatagaatc gcctatgtat gtcttactct   7680
caatgtgata ctatttttca atattaaata tgtatcaaat atagaatata attatcgaaa   7740
ctatcttaaa tccttgcaat taggtcctaa actattatta ttattattat ataataaact   7800
aataaagtaa catcaaactt gccattttttt attcttgtca cctaattaca tgattgaata   7860
atgtttttc ccgactatta ttgatccact agcaaatatt tatatggaca gtaggaaatt   7920
atatagaaag actttgcttt aataattcaa aatcatagta aactttgctt aaactaatct   7980
atttcacatc tagtctttaa ttgcttcttg cttttgctca ctcaattttg tcagtgaaag   8040
ttttgtaaat ctgcaaacta ccatttagga tgaagtaact cttttaacag ctgacattcc   8100
tttaactctt tcttcttgct gttactttta cttgtgtttc taattctttt atccttatta   8160
caagtgcatg tgattagttt gaaaaatcaa attttgtaga tattgaaggc tggttggatg   8220
```

-continued

```
gaaaagggag aaaaatcatt ggtatgtcta ttgtctacca atactgtagt ttctagcgtt   8280
aagagccaat attttcaact gaattttgct gatgaatatg tttttgattt agcagctact   8340
atttgaggaa caaaaaacaa gaatcacgaa tcttattgat gatttcttga ttcgcttgaa   8400
gcaaataaag aatgaattca ttgcttcaaa attggatgcc tttgaaaatc taagaatgga   8460
actgagattc ctaagaacat ttgtcctgtt tgggaattcg atgaatttgg atgacttta   8520
tgagaggatg tcactgagta taagcaaatt cgatcaatct acggagtacg tagataaaat   8580
aatcctagag aaatacaaca tggaatgcct tgcccctctg ctgcttgaag agataagaaa   8640
ttatttgagt ttgaagaatg attatgtagc cacaactaca gagataaaat tgtttgaata   8700
cctcatcaga aacctccatg atctaccaaa gtattgttct gatttgcttc taccactcat   8760
gagtgaatac aagattcttc ggcaagtatg cacacatctc agagatttct atcagttgga   8820
atgcaacaaa acaacaaaaa cagaatttct ctatactcgg tatcaagtga cagttaatag   8880
agtaacacaa ttctgtttg atctttggac aagaaagtat aaagactttg caatgagta   8940
tgccttctct gaatgttctt ccaagatcac ttctctatc atcgacataa tccctcttga   9000
gttggaggtt ctacacattt ctacacattg ttaagcaaat cctaaaagca tctccaagga   9060
ttcttcaaaa gcatctcatt catctccaag gacgcatggt agccgtcagt tactctacaa   9120
ctcaaagcat taatgtcatg atggagttcc tattgatctt tctcactgat ataccaaagc   9180
gctttatcca tcgtggcaaa ttgaactcta tgttggcaca tgtcggacta cttacaagga   9240
agatatctat tctcatggaa gagagctcta atatgaatga agcagacttt tcagctacat   9300
acttgttgca agaaatcgaa cgaatgaaga gagatatcaa acagattatt ttgaaagcgc   9360
cagagtcatc ccaactttgc cttcctatgg atgatggttt cctcttcatg aatcttctac   9420
tccgacattt aaatgattta ctcacttcca attcttattc agtttctctg ataaaaaaag   9480
aaattgagat ggtgaaacaa tgccttgaat tcctaacaac atctttcagg caaacattgg   9540
atgagagcac tagtggagtt gttaaagatt gttggatgcg tgctttggat g             9591
```

```
SEQ ID NO: 2            moltype = DNA   length = 3840
FEATURE                 Location/Qualifiers
misc_feature            1..3840
                        note = CDS MeR1 (isoform 1)
source                  1..3840
                        mol_type = genomic DNA
                        organism = Solanum lycopersicum
SEQUENCE: 2
atggaaaaag gagaaaaatc attgctacta tttgaggaac aaaaaacaag aatcacgaat   60
cttattgatg atttcttgat tcgcttgaag caaataaaga atgaattcat tgcttcaaaa   120
ttggatgcct ttgaaaatct aagaatggaa ctgagattcc taagaacatt tgtcctgttt   180
gggaattcga tgaatttgga tgactttat gagaggatgt cactgagtat aagcaaattc   240
gatcaatcta cggagtacgt agataaaata atcctagaga aatacaacat ggaatgtctt   300
gcccctctgc tgcttgaaga gataagaaat tatttgagtt tgaagaatga ttatgtagcc   360
acaactcag agataaaatt gtttgaatac ctcatcagaa acctccatga tctaccaaag   420
tattgttctg atttgcttct accactcatg agtgaataca agattcttcg gcaagtatgc   480
acacatctca gagatttcta tcagttggaa tgcaacaaaa caacaaaaac agaatttctc   540
tatactcggt atcaagtgac agccgataga gtaacacaat tctgttttga tctttggaca   600
ggaatgtata aatactctga caatgagtat gccttctctg aatgttcttc caagatcact   660
tctctactca ttgacataat ccctcttgag ttggaggttc tatacatttc tacttctaag   720
ctcatcaaag agtcaacgtc aaaagaacta gaaggatttg ttaagcaaat cttaaaagca   780
tctccaagga ttcttcaaca ttatctcatt catctccaag gacgcatggc cggtgtagaa   840
gccgtcaatt tcgctccaac tcgaagcatt agtgtcatga tggagttcct attgatcttt   900
ctcaccgata tgccaaagcg gtttatccat cgtgaaaaat tgaacgatat gttggcacat   960
gtcagaatac ttacaaggaa aatatctact ctggtgagta aactgttgga ggagatctct   1020
gaggataata tcaatgaagc ggactttca gctccggact ttttgcaaga aattgaacaa   1080
atgaagggag atatcagaca catctttta aaagctcctg agtcatctca acttcggttt   1140
cctatggatg atggtttcct cttcatgaat cttctactca gacatttaaa tgatttactc   1200
atttccaatg cttattcagt ttttctcata aaaaagaaa ttgggatggt gaaagaaagc   1260
cttgaattcc taatatcatc tttcaggaaa gtcaggcaaa cattggatga gagtactagt   1320
ggagtagtta aaaattgttg ggtgcgtgct ttggatgtgg catatgaggc agaacatatc   1380
attaattcca ttcttgtcag agataaagct ctctcacatc tcctcttctc acttccgagt   1440
gtcactgata agatcaaact tatcgtggaa caagtcacca ggtttcagct ggaggataag   1500
aatggggatg gccccttga tgcaaagtct tccttcgagc caactcagtc aacttcatca   1560
cctttgttg aggtaacagt aggtcacgag aaagaagaat cccagatcat tgaccagctc   1620
cttgatgaac atgaatctga gcttgatgtc atttccattg tcggaatgcc aggactcggt   1680
aaaactactc tggccaacaa agtgtataaa gatacattag ttgctaggca tttccatgtc   1740
cgtgcttggt gcactgtttc gcaaaagtat aacaagtcaa aggtgttgcg ggagattctt   1800
cagcaagtta ctggctcggg aggaaaagaa agtgaagatg acctggctga aaagctacga   1860
agagcactac tcgataaaag gtacctaatc gtcttggatg atgtgttgga tattgcaaca   1920
ggggagatgt taatagcatg ttttcctaag ggtaagagag aaatagaat catcttaact   1980
agccgaagta gaaggtagg tttgaaagtt aaatgccgta gtgatcctct cgaccttaaa   2040
cttttaacat ctgaagaaag ttgggattta ttcgaaaaaa gggtatttgg agatgaagga   2100
agctgccctg ctgaactgtc cgaagttgga caccaaatag ttgagaaatg taagggtctt   2160
cccttggcta ttgttttaat tgctggagta attgttagag ggaagaaaag aagaaggat   2220
ttttggctta agatactgca taatctggat tcctttattt ctaccaacat caatttggtt   2280
atgcaattaa gttatgacca tttaccatgc cacctgaagc cgttgctgct ttactttgca   2340
acaactcaaa agagccaaca aactccagtc tctacattga tgcagttgtg gatggccgaa   2400
gggtttgtgg atcatgatag tttagaggaa gtaactcaaa gttacttgga tgctctaatt   2460
tccagtagcc tgataatggt ggatcatatc ccctccaaga ttattggtg gacgtcttta   2520
atgatcaagg tttgctatgt gcatgatgtt gtgcacgatt tttgttcaga aaaagccaaa   2580
aaggagaagt ttctcaagtt aatcaattca ggtgatccat ttcatgcttc agatttccta   2640
caccatcgtc taaccattca tactgacaac ggccaactcc acaaaaaatg tgttttattc   2700
aattctaata agtgcttagc tgttagtaag catgtcatat ctttgaaagt gagtggtcca   2760
ctagatgagt tcaggtatat ctgtcacaca agacactttg gacttgttag agtgttgcaa   2820
```

```
ctggatgaca tcattctgga agattcttta atggaagaaa tagggtccct atttcatttg  2880
aggttcttaa gcattgagac tgctgtaggt gtaatagcta tcccagtgtc gtggttgaac  2940
ctccagaatc tggaaacgct gttgatttat acaacttatt ccaccatggt attactgccc  3000
agaatattgc aactgtcaaa gctgaaacat gtgaaaatta aggaatgttc tttctttgaa  3060
gagaaagagg atatccaacg tagaatattg gaagctgaga attcttcaaa cttgacaact  3120
ctatccggag ttgttatctc atattctgaa ggcatgagtg atgatgctct ggagaagttc  3180
ccaattcttc agcaccttga ttgcatcatc atggaatcgc agaatgctcc tacacacgac  3240
tattggtttc tcaagcttga tgtacttaat aaactcgaat cattcgtagc aagatacaag  3300
cgcaatggac atccctcgtt aaaccgacaa ccgtatggat ttcacttccc tacaagcttg  3360
aaagagttac ggttgactgg tttttcctg agacctgatt tgttgtcagt aatcgcagcg  3420
ttgcctgagc ttgagattat ggagtttttcc ggctgttatt tcgtggatac taaatgggac  3480
gcaagtgagg acatctatct aagtcttaag actttgattt tgcgagatgt ccatttatca  3540
gaatggcaag ttgaggggggg aacttttccc aagcttgaga aattaatact aaaattttgt  3600
tccacacttg gggagatccc ttgtgcattt atggatgtag aaactttaaa gtccattgat  3660
ttaagtttttg ttgggcgtaa gcttcgagat tcagccattg agattaagaa aaatgtagca  3720
gatttcacag gagaggacag agttgatgtc cacacatcac atttgtttgc aaccaacgtg  3780
aaagaacaga ttatgagaat gacgggtatg ggaaatatac agggaaggag aggaatttaa  3840
```

SEQ ID NO: 3              moltype = DNA   length = 3843
FEATURE                  Location/Qualifiers
misc_feature             1..3843
                         note = CDS MeR1 (isoform 2)
source                   1..3843
                         mol_type = genomic DNA
                         organism = Solanum lycopersicum
SEQUENCE: 3

```
atggaaaaag gagaaaaatc attgcagcta ctatttgagg aacaaaaaac aagaatcacg  60
aatcttattg atgatttctt gattcgcttg aagcaaataa agaatgaatt cattgcttca  120
aaattggatg cctttgaaaa tctaagaatg gaactgagat tcctaagaac atttgtcctg  180
tttgggaatt cgatgaattt ggatgacttt tatgagagga tgtcactgag tataagcaaa  240
ttcgatcaat ctacggagta cgtagataaa ataatcctag agaaatacaa catggaatgt  300
cttgcccctc tgctgcttga agagataaga aattatttga gtttgaagaa tgattatgta  360
gccacaacta cagagataaa attgtttgaa tacctcatca gaaacctcca tgatctacca  420
aagtattgtt ctgatttgct tctaccactc atgagtgaat acaagattct tcggcaagta  480
tgcacacatc tcagagattt ctatcagttg gaatgcaaca aaacaacaaa aacagaattt  540
ctctatactc ggtatcaagt gacagccgat agagtaacac aattctgttt tgatctttgg  600
acaggaatgt ataaatactc tgacaatgag tatgccttct ctgaatgttc ttccaagatc  660
acttctctac tcattgacat aatccctctt gagttggagg ttctatacat ttctacttct  720
aagctcatca aagagtcaac gtcaaaagaa ctagaaggat ttgttaagca aatcttaaaa  780
gcatctccaa ggattcttca acattatctc attcatctcc aaggacgcat ggccggtgta  840
gaagccgtca atttcgctcc aactcgaagc attagtgtca tgatggagtt cctattgatc  900
tttctcaccg atatgccaaa gcggtttatc catcgtgaaa aattgaacga tatgttggca  960
catgtcagaa tacttacaag gaaaaatatct actctggtga gtaaactgtt ggaggagatc  1020
tctgaggata atatcaatga agcggacttt tcagctccgg acttttttgca agaaattgaa  1080
caaatgaagg gagatatcag acacatcttt ttaaaagctc ctgagtcatc tcaacttcgg  1140
tttcctatgg atgatggttt cctcttcatg aatcttctac tcagacattt aaatgattta  1200
ctcatttcca atgcttattc agtttttctc ataaaaaaag aaattgggat ggtgaaagaa  1260
agccttgaat tcctaatatc atctttcagg aaagtcaggc aaacattgga tgagagtact  1320
agtggagtag ttaaaaattg ttgggtgcgt gctttggatg tggcatatga ggcagaacat  1380
atcattaatt ccattcttgt cagagataaa gctctctcac atctcctctt ctcacttccg  1440
agtgtcactg ataagatcaa acttatcgtg gaacaagtca ccaggtttca gctggaggat  1500
aagaatgggg atggcccct tgatgcaaag tcttccttcg agccaactca gtcaacttca  1560
tcacctttttg ttgaggtaac agtaggtcac gagaaagaag aatcccagat cattgaccag  1620
ctccttgatg aacatgaatc tgagcttgat gtcatttcca ttgtcggaat gccaggactc  1680
ggtaaaacta ctctggccaa caaagtgtat aaagatacat tagttgctag gcatttccat  1740
gtccgtgctt ggtgcactgt ttcgcaaaag tataacaagt caaaggtgtt gcgggagatt  1800
cttcagcaag ttactggctc gggaggaaaa gaaagtgaag atgacctggc tgaaaagcta  1860
cgaagagcac tactcgataa aaggtaccta atcgtcttgg atgatgtgtg ggatattgca  1920
acaggggaga tgttaatagc atgtttttcct aagggtaaga gaggaaatag aatcatctta  1980
actagccgaa gtagaaaggt aggtttgaaa gttaaatgcc gtagtgatcc tctcgacctt  2040
aaacttttaa catctgaaga aagttgggat ttattcgaaa aaaggggtatt tggagatgaa  2100
ggaagctgcc ctgctgaact gtccgaagtt ggacaccaaa tagttgagaa atgtaagggt  2160
cttcccttgg ctattgtttt aattgctgga gtaattgtta gagggaagaa aaaggaaaag  2220
gatttttggc ttaagatact gcataatctg gattccttta tttctaccaa catcaatttg  2280
gttatgcaat taagttatga ccatttacca tgccacctga agccgttgct gctttacttt  2340
gcaacaactc aaaagagcca acaaactcca gtctctacat tgatgcagtt gtggatggcc  2400
gaagggtttg tggatcatga tagtttagag gaagtaactc aaagttactt ggatgctcta  2460
atttccagta gcctgataat ggtggatcat atcccctcca agagttattg gtggacgtct  2520
ttaatgatca aggtttgcta tgtgcatgat gttgtgcacg attttttgttc agaaaaagcc  2580
aaaaaggaga agtttctcaa gttaatcaat tcaggtgatc catttcatgc ttcagatttc  2640
ctacaccatc gtctaaccat tcatactgac aacggccaac tccacaaaaa atgtgttta  2700
ttcaattcta ataagtgctt agctgttagt aagcatgtca tatctttgaa agtgagtggt  2760
ccactagatg agttcaggta tatctgtcac acaagacact ttggacttgt tagagtgttg  2820
caactggatg acatcattct ggaagattct ttaatgtggag aaatagggtc ctatttcat  2880
ttgaggttct taagcattga gactgctgta ggtgtaatag ctatcccagt ctcgtggttg  2940
aacctccaga atctggaaac gctgttgatt tatacaactt attccaccat ggtattactg  3000
cccagaatat tgcaactgtc aaagctgaaa catgtgaaaa ttaaggaatg ttctttcttt  3060
gaagagaaag aggatatcca acgtagaata ttggaagctg gaattcttc aaacttgaca  3120
actctatccg gagttgttat ctcatattct gaaggcatga gtgatgatgc tctggagaag  3180
```

-continued

```
ttcccaattc ttcagcacct tgattgcatc atcatggaat cgcagaatgc tcctacacac  3240
gactattggt ttctcaagct tgatgtactt aataaactcg aatcattcgt agcaagatac  3300
aagcgcaatg gacatccctc gttaaaccga caaccgtatg gatttcactt ccctacaagc  3360
ttgaaagagt tacggttgac tggtttttttc ctgagacctg atttgttgtc agtaatcgca  3420
gcgttgcctg agcttgagat tatggagttt tccggctgtt atttcgtgga tactaaatgg  3480
gacgcaagtg aggacatcta tctaagtctt aagactttga ttttgcgaga tgtccattta  3540
tcagaatggc aagttgaggg gggaactttt cccaagcttg agaaattaat actaaaattt  3600
tgttccacac ttggggagat cccttgtgca tttatggatg tagaaacttt aaagtccatt  3660
gatttaagtt ttgttgggcg taagcttcga gattcagcca ttgagattaa gaaaaatgta  3720
gcagatttca caggagagga cagagttgat gtccacacat cacatttgtt tgcaaccaac  3780
gtgaaagaac agattatgag aatgacgggt atgggaaata tacagggaag gagaggaatt  3840
taa                                                                 3843

SEQ ID NO: 4             moltype = DNA   length = 3834
FEATURE                  Location/Qualifiers
misc_feature             1..3834
                         note = CDS MeR1 (isoform 3)
source                   1..3834
                         mol_type = genomic DNA
                         organism = Solanum lycopersicum
SEQUENCE: 4
atggaaaaag gagaaaaatc attgctacta tttgaggaac aaaaaacaag aatcacgaat  60
cttattgatg atttcttgat tcgcttgaag caaataaaga atgaattcat tgcttcaaaa  120
ttggatgcct ttgaaaatct aagaatggaa ctgagattcc taagaacatt tgtcctgttt  180
gggaattcga tgaatttgga tgactttttat gagaggatgt cactgagtat aagcaaattc  240
gatcaatcta cggagtacgt agataaaata atcctagaga aatacaacat ggaatgtctt  300
gcccctctgc tgcttgaaga gataagaaat tatttgagtt tgaagaatga ttatgtagcc  360
acaactacag agataaaatt gtttgaatac ctcatcagaa acctccatga tctaccaaag  420
tattgttctg atttgcttct accactcatg agtgaataca agattcttcg gcaagtatgc  480
acacatctca gagatttcta tcagttggaa tgcaacaaaa caacaaaaac agaatttctc  540
tatactcggt atcaagtgac agccgataga gtaacacaat tctgtttttga tctttggaca  600
ggaatgtata aatactctga caatgagtat gccttctctg aatgttcttc caagatcact  660
tctctactca ttgacataat ccctcttgag ttggaggttc tatacatttc tacttctaag  720
ctcatcaaag agtcaacgtc aaaagaacta gaaggatttg ttaagcaaat cttaaaagca  780
tctccaagga ttcttcaaca ttatctcatt catctccaag gacgcatggc cggtgtagaa  840
gccgtcaatt tcgctccaac tcgaagcatt agtgtcatga tggagttcct attgatctttt  900
ctcaccgata tgccaaagcg gtttatccat cgtgaaaaat tgaacgatat gttggcacat  960
gtcagaaatac ttacaaggaa aatatctact ctggtgagta aactgttgga ggagatctct  1020
gaggataata tcaatgaagc ggactttttca gctccggact ttttgcaaga aattgaacaa  1080
atgaagggag atatcagaca catcttttta aaagctcctg agtcatctca acttcggtttt  1140
cctatggatg atggtttcct cttcatgaat cttctactca gacatttaaa tgatttactc  1200
atttccaatg cttattcagt tttttctcata aaaaaagaaa ttgggatggt gaaagaaagc  1260
cttgaattcc taatatcatc cttcaggaaa gtcaggcaaa cattcgatga gagtactagt  1320
ggagtagtta aaaattgttg ggtgcgtgct ttggatgtgg catatgaggc agaacatatc  1380
attaattcca ttcttgtcag agataaagct ctctcacatc tcctcttctc acttccgagt  1440
gtcactgata agatcaaact tatcgtgaaa caagtcacca ggtttcagct ggaggataag  1500
aatggggatg gccccttga tgcaaagtct tccttcagac caactcagtc aacttcatca  1560
ccttttgttg aggtaacagt aggtcacgag aaagaagaat cccagatcat tgaccagctc  1620
cttgatgaac atgaatctga gcttgatgtc atttccattg tcggaatgcc aggactcggt  1680
aaaactactc tggccaacaa agtgtataaa gatacattag ttgctaggca tttccatgtc  1740
cgtgcttggt gcactgtttc gcaaaagtat aacaagtcaa aggtgttgcg gggagattctt  1800
cagcaagtta ctggctcggg aggaaaagaa agtgaagatg acctggctga aaagctacga  1860
agagcactac tcgataaaag gtacctaatc gtcttggatg atgtgtggga tattgcaaca  1920
ggggagatgt taatagcatg ttttttcctaag ggtaagagag gaaatagaat catcttaact  1980
agccgaagta gaaaggtagg tttgaaagtt aaatgccgta ggtgatcctct cgacctttaaa  2040
cttttttaacat ctgaagaaag ttgggattta ttcgaaaaaa gggtatttgg agatgaagga  2100
agctgccctg ctgaactgtc cgaagttgga caccaaatag ttgagaaatg taagggtctt  2160
ccccttggcta ttgtttttaat tgctggagta attgttagag ggaagaaaaa ggaaaaggat  2220
ttttggctta agatactgca taatctggat tcctttattt ctaccaacat caatttggtt  2280
atgcaattaa gttatgacca tttaccatgc cacctgaagc cgttgctgct ttactttgca  2340
acaactcaaa agagccaaca aactccagtc tctacattga tgcagttgtg gatggccgaa  2400
gggtttgtgg atcatgatag tttagaggaa gtaactcaaa gttacttgga tgctctaatt  2460
tccagtagcc tgataatggt ggatcatatc ccctccaaga gttattggtg gacgtctttta  2520
atgatcaagg tttgctatgt gcatgatgtt gttgcacgatt tttcaga aaaagccaaa  2580
aaggagaagt ttctcaagtt aatcaattca ggtgatccat ttcatgcttc agatttccta  2640
caccatcgtc taaccattca tactgacaac ggccaactcc acaaaaaatg tgtttttattc  2700
aattctaata agtgcttagc tgttagtaag catgtcatat ctttgaaagt gagtggtcca  2760
ctagatgagt tcaggtatat ctgtcacaca agacactttg gacttgttag agtgttgcaa  2820
ctggatgaca tcattctgga agattcttta atggaagaaa tagggtccct atttcatttg  2880
aggttcttaa gcattgagac tgctgtaggg gtaatagcta tcccagtgtc gtggttgaac  2940
ctccagaatc tggaaacgct gttgatttat acaacttatt ccaccatggt attactgccc  3000
agaatattgc aactgtcaaa gctgaaacat gtgaaaatta aggaatgttc tttctttgaa  3060
gagaaagagg atatccaacg tagaatattg gaagctggga attcttcaaa cttgacaact  3120
ctatccggag ttgttatctc atattctgaa ggcatgagtg atgtgtctct gggagagttc  3180
ccaattcttc agcaccttga ttgcatcatc atggaatcgc agaatgctcc tacacacgac  3240
tattggtttc tcaagcttga tgtacttaat aaactcgaat cattcgtagc aagatacaag  3300
cgcaatggac atccctcgtt aaaccgacaa ccgtatggat ttcacttccc tacaagcttg  3360
aaagagttac ggttgactgg tttttttcctg agacctgatt tgttgtcagt aatcgcagcg  3420
ttgcctgagc ttgagattat ggagtttttcc ggctgttatt tcgtggatac taaatgggac  3480
```

```
gcaagtgagg acatctatct aagtcttaag actttgattt tgcgagatgt ccatttatca   3540
gaatggcaag ttgaggggg aacttttccc aagcttgaga aattaatact aaaatttgt    3600
tccacacttg gggagatccc ttgtgcattt atggatgtag aaactttaaa gtccattgat   3660
ttaagttttg ttgggcgtaa gcttcgagat tcagccattg agattaagaa aaatgtagca   3720
gatttcacag gagaggacag agttgatgtc cacacatcac atttgtttgc aaccaacgtg   3780
aaagaacaga ttatgagaat gacgggtgga gaatgtactt gtgaagaact ataa        3834
```

SEQ ID NO: 5             moltype = DNA   length = 3837
FEATURE                Location/Qualifiers
misc_feature          1..3837
                            note = CDS MeR1 (isoform 4)
source                  1..3837
                            mol_type = genomic DNA
                            organism = Solanum lycopersicum
SEQUENCE: 5

```
atggaaaaag gagaaaaatc attgcagcta ctatttgagg aacaaaaaac aagaatcacg   60
aatcttattg atgatttctt gattcgcttg aagcaaataa agaatgaatt cattgcttca   120
aaattggatg cctttgaaaa tctaagaatg gaactgagat tcctaagaac atttgtcctg   180
tttgggaatt cgatgaattt ggatgacttt tatgagagga tgtcactgag tataagcaaa   240
ttcgatcaat ctacggagta cgtagataaa ataatcctag agaaatacaa catggaatgt   300
cttgcccctc tgctgcttga agagataaga aattatttga gtttgaagaa tgattatgta   360
gccacaacta cagagataaa attgtttgaa tacctcatca gaaacctcca tgatctacca   420
aagtattgtt ctgatttgct tctaccactc atgagtgaat acaagattct tcggcaagta   480
tgcacacatc tcagagattt ctatcagttg gaatgcaaca aaacaacaaa aacagaattt   540
ctctatactc ggtatcaagt gacagccgat agagtaacac aattctgttt tgatctttgg   600
acaggaatgt ataaatactc tgacaatgag tatgccttct ctgaatgttc ttccaagatc   660
acttctctac tcattgacat aatccctctt gagttggagg ttctatacat ttctacttct   720
aagctcatca aagagtcaac gtcaaaagaa ctagaaggat ttgttaagca aatcttaaaa   780
gcatctccaa ggattcttca acattatctc attcatctcc aaggacgcat ggccggtgta   840
gaagccgtca atttcgctcc aactcgaagc attagtgtca tgatggagtt cctattgatc   900
tttctcaccg atatgccaaa gcggtttatc catcgtgaaa aattgaacga tatgttggca   960
catgtcagaa tacttacaag gaaaatatct actctggtga gtaaactgtt ggaggagatc   1020
tctgaggata atatcaatga agcggacttt tcagctccgg acttttgca agaaattgaa    1080
caaatgaagg gagatatcag acacatcttt ttaaaagctc ctgatgtcatc tcaacttcgg  1140
tttcctatgg atgatggttt cctcttcatg aatcttctac tcagacattt aaatgattta   1200
ctcatttcca atgcttattc agttttttctc ataaaaaaag aaattgggat ggtgaaagaa   1260
agccttgaat tcctaatatc atctttcagg aaagtcaggc aaacattgga tgagagtact   1320
agtggagtag ttaaaaattg ttgggtgcgt gctttggatg tggcatatga ggcagaacat   1380
atcattaatt ccattcttgt cagagataaa gctctctaac atctcctctt ctcacttccg   1440
agtgtcactg ataagatcaa acttatcgtg gaacaagtca ccaggtttca gctggaggat   1500
aagaatgggg atggcccct tgatgcaaag tcttccttcg agccaactca gtcaacttca   1560
tcaccttttg ttgaggtaac agtaggtcac gagaaagaag aatcccagat cattgaccag   1620
ctccttgatg aacatgaatc tgagcttgat gtcatttcca ttgtcggaat gccaggactc   1680
ggtaaaacta ctctggccaa caaagtgtat aaagatacat tagttgctag gcatttccat   1740
gtccgtgctt ggtgcactgt ttcgcaaaag tataacaagt caaaggtgtt gcgggagatt   1800
cttcagcaag ttactggctc gggaggaaaa gaaagtgaag atgacctggc tgaaaagcta   1860
cgaagagcac tactcgataa aaggtaccta atcgtcttgg atggatgtgg ggatattgca   1920
acaggggaga tgttaatagc atgttttcct aagggtaaga gaggaaatag aatcatctta   1980
actagccgaa gtagaaaggt aggtttgaaa gttaaatgcc gtagtgatcc tctcgacctt   2040
aaacttttaa catctgaaga aagttgggat ttattcgaaa aaagggtatt tggagatgaa   2100
ggaagctgcc ctgctgaact gtccgaagtt ggacaccaaa tagttgagaa atgtaagggt   2160
cttcccttgg ctattgtttt aattgctgga gtaattgtta gagggaagaa aaaggaaaag   2220
gatttttggc ttaagatact gcataatctg gattccttta tttctaccaa catcaatttg   2280
gttatgcaat taagttatga ccatttacca tgccacctga agccgttgct gctttactttt   2340
gcaacaactc aaaagagcca acaaactcca gtctctacat tgatgcagtt gtggatggcc   2400
gaaggggtttg tggatcatga tagtttagag gaagtaactc aaagttactt ggatgctcta   2460
atttccagta gcctgataat ggtggatcat atcccctcca agagttattg gtggacgtct   2520
ttaatgatca aggtttgcta tgtgcatgat gttgtgcacg atttttgttc agaaaaagcc   2580
aaaaaggaga agtttctcaa gttaatcaat tcaggtgatc catttcatgc ttcagatttc   2640
ctacaccatc gtctaaccat tcatactgac aacggccaac tccacaaaaa atgtgtttta   2700
ttcaattcta ataagtgctt agctgttagt aagcatgtca tatctttgaa agtgagtggt   2760
ccactagatg agttcaggta tatctgtcac acaagacact ttggacttgt tagagtgttg   2820
caactggatg acatcattct ggaagattct ttaatggaag aaatagggtc cctatttcat   2880
ttgaggttct taagcattga gactgctgta ggtgtaatag ctatcccagt gccaggttg    2940
aacctccaga atctgaaac gctgttgatt tatacaactt attccaccat ggtgattactg    3000
cccagaatat tgcaactgtc aaagctgaaa catgtgaaaa ttaaggaatg ttcttttctt    3060
gaagagaaag aggatatcca acgtagaata ttggaagctg ggaattcttc aaacttgaca   3120
actctatccg gagttgttat ctcatattct gaaggcatga gtgatgatgc tctggagaag   3180
ttcccaattc ttcagcacct tgattgcatc atcatggaat cgcagaatgc tcctacacac   3240
gactattggt ttctcaagct tgatgtactt aataaactcg aatcattcgt agcaagatac   3300
aagcgcaatg gacatccctc gttaaaccga caaccgtatg gatttcactt ccctacaagc   3360
ttgaaagagt tacggttgac tggttttttc ctgagacctg atttgttgtc agtaatcgca   3420
gcgttgcctg agcttgagat tatggagttt tccggctgtt atttcgtgga tactaaatgg   3480
gacgcaagtg aggacatctc tcttaagtct aagactttga tttgcgaga tgtccatttta   3540
tcagaatggc aagttgaggg gggaactttt cccaagcttg agaaattaat actaaaattt   3600
tgttccacac ttggggagat cccttgtgca tttatggatg tagaaacttt aaagtccatt   3660
gatttaagtt ttgttgggcg taagcttcga gattcagcca ttgagattaa gaaaaatgta   3720
gcagatttca caggagagga cagagttgat gtccacacat cacatttgtt tgcaaccaac   3780
gtgaaagaac agattatgag aatgacgggt ggagaatgta cttgtgaaga actataa      3837
```

-continued

```
SEQ ID NO: 6            moltype = DNA  length = 1899
FEATURE                 Location/Qualifiers
misc_feature            1..1899
                        note = CDS MeR1 (isoform 5)
source                  1..1899
                        mol_type = genomic DNA
                        organism = Solanum lycopersicum
SEQUENCE: 6
atggaaaaag gagaaaaatc attgctacta tttgaggaac aaaaaacaag aatcacgaat   60
cttattgatg atttcttgat tcgcttgaag caaataaaga atgaattcat tgcttcaaaa  120
ttggatgcct ttgaaaatct aagaatggaa ctgagattcc taagaacatt tgtcctgttt  180
gggaattcga tgaatttgga tgactttat gagaggatgt cactgagtat aagcaaattc   240
gatcaatcta cggagtacgt agataaaata atcctagaga aatacaacat ggaatgtctt  300
gcccctctgc tgcttgaaga gataagaaat tatttgagtt tgaagaatga ttatgtagcc  360
acaactacag agataaaatt gtttgaatac ctcatcagaa acctccatga tctaccaaag  420
tattgttctg atttgcttct accactcatg agtgaataca agattcttcg gcaagtatgc  480
acacatctca gagatttcta tcagttggaa tgcaacaaaa caacaaaac agaatttctc   540
tatactcggt atcaagtgac agccgataga gtaacacaat tctgttttga tctttggaca  600
ggaatgtata aatactctga caatgagtat gccttctctg aatgttcttc caagatcact  660
tctctactca ttgacataat ccctcttgag ttggaggttc tatacatttc tacttctaag  720
ctcatcaaag agtcaacgtc aaaagaacta gaaggatttg ttaagcaaat cttaaaagca  780
tctccaagga ttcttcaaca ttatctcatt catctccaag gacgcatggc cggtgtagaa  840
gccgtcaatt tcgctccaac tcgaagcatt agtgtcatga tggagttcct attgatcttt  900
ctcaccgata tgccaaagcg gtttatccat cgtgaaaat tgaacgatat gttggcacat   960
gtcagaatac ttacaaggaa aatatctact ctggtgacta actgttgga ggagatctct   1020
gaggataata tcaatgaagc ggactttca gctccggact ttttgcaaga aattgaacaa  1080
atgaagggag atatcagaca catcttttta aaagctcctg agtcatctca acttcggttt  1140
cctatggatg atggtttcct cttcatgaat cttctactca gacatttaaa tgatttactc  1200
atttccaatg cttattcagt ttttctcata aaaaaagaaa ttgggatggt gaaagaagaa  1260
cttgaattcc taatatcatc tttcaggaaa gtcaggcaaa cattggatga gagtactagt  1320
ggagtagtta aaaattgttg ggtgcgtgct ttggatgtgg catatgaggc agaacatatc  1380
attaattcca ttcttgtcag agataaagct ctctcacatc tcctcttctc acttccgagt  1440
gtcactgata gatcaaact tatcgtggaa caagtcacca ggtttcagct ggaggataag  1500
aatgggatg gccccttga tgcaaagtct tccttcgagc caactcagtc aacttcatca  1560
cctttttgttg aggtaacagt aggtcacgag aaagaagaat cccagatcat tgaccagctc  1620
cttgatgaac atgaatctga gcttgatgtc atttccattg tcggaatgcc aggactcggt  1680
aaaactactc tggccaacaa agtgtataaa gatacattag ttgctaggca tttccatgtc  1740
cgtgcttggt gcactgtttc gcaaaagtat aacaagtcaa aggtgttgcg ggagattctt  1800
cagcaagtta ctggctcggg aggaaaagaa agtgaagatg acctggctga aaagctacga  1860
agagcactac tcgataaaag gtggagaatg tacttgtga                           1899

SEQ ID NO: 7            moltype = DNA  length = 1902
FEATURE                 Location/Qualifiers
misc_feature            1..1902
                        note = CSD MeR1 (isoform 6)
source                  1..1902
                        mol_type = genomic DNA
                        organism = Solanum lycopersicum
SEQUENCE: 7
atggaaaaag gagaaaaatc attgcagcta ctatttgagg aacaaaaaac aagaatcacg   60
aatcttattg atgatttctt gattcgcttg aagcaaataa agaatgaatt cattgcttca  120
aaattggatg cctttgaaaa tctaagaatg gaactgagat tcctaagaac atttgtcctg  180
tttgggaatt cgatgaattt ggatgacttt atgagagga tgtcactgag tataagcaaa   240
ttcgatcaat ctacggagta cgtagataaa ataatcctag aaaatacaa catggaatgt   300
cttgccctc tgctgcttga agagataaga aattatttga gtttgaagaa tgattatgta   360
gccacaacta cagagataaa attgtttgaa tacctcatca gaaacctcca tgatctacca  420
aagtattgtt ctgatttgct tctaccactc atgagtgaat acaagattct tcggcaagta  480
tgcacacatc tcagagattt ctatcagttg gaatgcaaca aacaacaaa aacagaattt   540
ctctatactc ggtatcaagt gacagccgat agagtaacac aattctgttt tgatctttgg  600
acaggaatgt ataaatactc tgacaatgag tatgccttct ctgaatgttc ttccaagatc  660
acttctctac tcattgacat aatccctctt gagttggagg ttctatacat ttctacttct  720
aagctcatca aagagtcaac gtcaaaagaa ctagaaggat tgttaagca atcttaaaa   780
gcatctccaa ggattcttca acattatctc attcatctcc aaggacgcat ggccggtgta  840
gaagccgtca atttcgctcc aactcgaagc attagtgtca tgatggagtt cctattgatc  900
tttctcaccg atatgccaaa gcggtttatc catcgtgaaa aattgaacga tatgttggca  960
catgtcagaa tacttacaag gaaaatatct actctggtga gtaaactgtt ggaggagatc  1020
tctgaggata tatcaatga agcggacttt cagctccgg acttttttgg agaaattgaa  1080
caaatgaagg gagatatcag acacatcttt taaaagctc ctgagtcatc tcaacttcgg  1140
tttcctatgg atgatggttt cctcttcatg aatcttctac tcagacattt aaatgattta  1200
ctcatttcca atgcttattc agttttctc ataaaaaag aaattgggat ggtgaaagaa   1260
agccttgaat cctaatatc atctttcagg aaagtcaggc aaacattgga tgagagtact  1320
agtggagtag ttaaaaattg ttgggtgcgt gctttggatg tggcatatga ggcagaacat  1380
atcattaatt ccattcttgt cagagataaa gctctctcac atctcctctt ctcacttcgg  1440
agtgtcactg ataagatcaa acttatcgtg gaacaagtca ccaggtttca gctggaggat  1500
aagaatgggg atggccccct tgatgcaaag tcttccttcg agccaactca gtcaacttca  1560
tcaccttttt tgaggtaac agtaggtcac gagaaagaag aatcccagat cattgaccag  1620
ctccttgatg aacatgaatc tgagcttgat gtcatttcca ttgtcggaat gccaggactc  1680
ggtaaaacta ctctggccaa caaagtgtat aaagatacat tagttgctag gcatttccat  1740
```

```
gtccgtgctt ggtgcactgt ttcgcaaaag tataacaagt caaaggtgtt gcgggagatt  1800
cttcagcaag ttactggctc gggaggaaaa gaaagtgaag atgacctggc tgaaaagcta  1860
cgaagagcac tactcgataa aaggtggaga atgtacttgt ga                      1902

SEQ ID NO: 8             moltype = DNA  length = 3849
FEATURE                  Location/Qualifiers
misc_feature             1..3849
                         note = CDS MeR1 (isoform 7)
source                   1..3849
                         mol_type = genomic DNA
                         organism = Solanum lycopersicum SEQUENCE: 8
atggaaaaag gagaaaaatc attgctacta tttgaggaac aaaaaacaag aatcacgaat  60
cttattgatg atttcttgat tcgcttgaag caaataaaga atgaattcat tgcttcaaaa  120
ttggatgcct ttgaaaatct aagaatggaa ctgagattcc taagaacatt tgtcctgttt  180
gggaattcga tgaatttgga tgactttat gagaggatgt cactgagtat aagcaaattc  240
gatcaatcta cggagtacgt agataaaata atcctagaga aatacaacat ggaatgtctt  300
gcccctctgc tgcttgaaga gataagaaat tatttgagtt tgaagaatga ttatgtagcc  360
acaactacag agataaaatt gtttgaatac ctcatcagaa acctccatga tctaccaaag  420
tattgttctg atttgcttct accactcatg agtgaataca agattcttcg gcaagtatgc  480
acacatctca gagatttcta tcagttggaa tgcaacaaaa caacaaaaac agaatttctc  540
tatactcggt atcaagtgac agccgataga gtaacacaat tctgttttga tctttggaca  600
ggaatgtata aatactctga caatgagtat gccttctctg aatgttcttc caagatcact  660
tctctactca ttgacataat ccctcttgag ttggaggttc tatacatttc tacttctaag  720
ctcatcaaag agtcaacgtc aaaagaacta gaaggatttg ttaagcaaat cttaaaagca  780
tctccaagga ttcttcaaca ttatctcatt catctccaag gacgcatggc cggtgtagaa  840
gccgtcaatt tcgctccaac tcgaagcatt agtgtcatga tggagttcct attgatcttt  900
ctcaccgata tgccaaagcg gtttatccat cgtgaaaaat tgaacgatat gttggcacat  960
gtcagaatac ttacaaggaa aatatctact ctggtgagta aactgttgga gggagatctct  1020
gaggataata tcaatgaagc ggactttca gctccggact ttttgcaaga aattgaacaa  1080
atgaagggag atatcagaca catcttttta aaagctcctg agtcatctca acttcggttt  1140
cctatggatg atggtttcct cttcatgaat cttctactca gacatttaaa tgatttactc  1200
atttccaatg cttattcagt ttttctcata aaaaaagaaa ttgggatggt gaaagaaagc  1260
cttgaattcc taatatcatc tttcaggaaa gtcaggcaaa cattggatga gagtactagt  1320
ggagtagtta aaaattgttg ggtgcgtgct ttggatgtgg catatgaggc agaacatatc  1380
attaattcca ttcttgtcag agataaagct ctctcacatc tcctcttctc acttccgagt  1440
gtcactgata agatcaaact tatcgtggaa caagtcacca ggtttcagct ggaggataag  1500
aatggggatg gcccccttga tgcaaagtct tccttcgagc caactcagtc aacttcatca  1560
cctttgttg aggtaacagt aggtcacgag aaagaagaat cccagatcat tgaccagctc  1620
cttgatgaac atgaatctga gcttgatgtc atttccattg tcggaatgcc aggactcggt  1680
aaaactactc tggccaacaa agtgtataaa gatacattag ttgctaggca tttccatgtc  1740
cgtgcttggt gcactgtttc gcaaaagtat aacaagtcaa aggtgttgcg ggagattctt  1800
cagcaagtta ctggctcggg aggaaaagaa gtgaagatga cctggctgaa aagctagcc  1860
agagcactac tcgataaaag gtacctaatc gtcttggatg atgtgtggga tattgcaaca  1920
ggggagatgt taatagcatg tttttcctaag ggtaagagag gaaatagaat catcttaact  1980
agccgaagta gaaaggtagg tttgaaagtt aaatgccgta gtgatcctct cgaccttaaa  2040
cttttaacat ctgaagaaag ttgggattta ttcgaaaaaa gagtgatttgg agatgaagga  2100
agctgccctg ctgaactgtc cgaagttgga caccaaatag ttgagaaatg taagggtctt  2160
cccttggcta ttgtttttaat tgctggagta attgttagag ggaagaaaaa ggaaaaggat  2220
ttttggctta agatactgca taatctggat tcctttattt ctaccaacat caatttggtt  2280
atgcaattaa gttatgacca tttaccatgc cacctgaagc cgttgctgct ttactttgca  2340
acaactcaaa agagccaaca aactccagtc tctacattga tgcagttgtg gatggccgaa  2400
gggtttgtgg atcatgatag tttagaggaa gtaactcaaa gttacttgga tgctctaatt  2460
tccagtagcc tgataatggt ggatcatatc ccctccaaga gttattggtg gacgtctta  2520
atgatcaagg tttgctatgt gcatgatgtt gtgcacgatt tttgttcaga aaaagccaaa  2580
aaggagaagt ttctcaagtt aatcaattca ggtgatccat ttcatgcttc agatttccta  2640
caccatcgtc taaccattca tactgacaac ggccaactcc acaaaaaatg tgttttattc  2700
aattctaata agtgcttagc tgttagtaag catgtcatat cttttgaaagt gagtggtcca  2760
ctagatgaac tcaggtatat ctgtcacaca agacactttg gacttgttag agtgttgcaa  2820
ctggatgaca tcattctgga agattctta atggaagaaa tagggtccct atttcatttg  2880
aggttcttaa gcattgagac tgctgtaggg gtaaatagcta tcccagtgtc gtggttgaac  2940
ctccagaatc tggaaacgct gttgatttat acaacttatt ccaccatggt attactgccc  3000
agaatattgc aactgtcaaa gctgaaacat gtgaaaatta aggaatgttc tttctttgaa  3060
gagaaagagg atatccaacg tagaatattg gaagctgcaa attcttcaaa cttgacaact  3120
ctatccggag ttgttatctc atattctgaa ggcatgagtg atgatgctct ggagaagttc  3180
ccaattcttc agcaccttga ttgcatcatc atggaatcgc agaatgctcc tacacacgac  3240
tattggtttc tcaagcttga tgtacttaat aaactcgaat cattcgtagc aagatacaag  3300
cgcaatggac atccctcgtt aaaccgacaa ccgtatggat ttcacttccc tacaagcttg  3360
aaagagttac ggttgactgg ttttttcctg agacctgatt tgttgtcagt aatcgcagcg  3420
ttgcctgagc ttgagattat ggagttttcc ggctgttatt tcgtggatac taaatgggac  3480
gcaagtgagg acatctatct aagtcttaag actttgattt tgcgagatgt ccatttatca  3540
gaatggcaag ttgagggggg aacttttccc aagcttgaga aattaatact aaaatttgt  3600
tccacacttg gggagatccc ttgtgcattt atggatgtag aaactttaaa gtccattgat  3660
ttaagttttg ttgggcgtaa gcttcgagat tcagccattg agattaagaa aaatgtagca  3720
gatttcacag gagaggacag agttgatgtc cacacatcac atttgtttgc aaccaacgtg  3780
aaagaacaga ttatgagaat gacggtggtt gatgaagttg gatttctcat ggaaaaatca  3840
caacaatga                                                           3849

SEQ ID NO: 9             moltype = DNA  length = 3852
```

-continued

```
FEATURE              Location/Qualifiers
misc_feature         1..3852
                     note = CDS MeR1 (isoform 8)
source               1..3852
                     mol_type = genomic DNA
                     organism = Solanum lycopersicum SEQUENCE: 9
atggaaaaag gagaaaaatc attgcagcta ctatttgagg aacaaaaaac aagaatcacg    60
aatcttattg atgatttctt gattcgcttg aagcaaataa agaatgaatt cattgcttca   120
aaattggatg cctttgaaaa tctaagaatg gaactgagat tcctaagaac atttgtcctg   180
tttgggaatt cgatgaattt ggatgacttt tatgagagga tgtcactgag tataagcaaa   240
ttcgatcaat ctacggagta cgtagataaa ataatcctag agaaatacaa catggaatgt   300
cttgcccctc tgctgcttga agagataaga aattatttga gtttgaagaa tgattatgta   360
gccacaacta cagagataaa attgtttgaa tacctcatca gaacctcca tgatctacca   420
aagtattgtt ctgatttgct tctaccactc atgagtgaat acaagattct tcggcaagta   480
tgcacacatc tcagagattt ctatcagttg gaatgcaaca aaacaacaaa aacagaattt   540
ctctatactc ggtatcaagt gacagccgat agagtaacac aattctgttt tgatctttgg   600
acaggaatgt ataaatactc tgacaatgag tatgccttct ctgaatgttc ttccaagatc   660
acttctctac tcattgacat aatccctctt gagttggagg ttctatacat ttctacttct   720
aagctcatca aagagtcaac gtcaaaagaa ctagaaggat ttgttaagca aatcttaaaa   780
gcatctccaa ggattcttca acattatctc attcatctcc aaggacgcat ggccggtgta   840
gaagccgtca atttcgctcc aactcgaagc attagtgtca tgatggagtt cctattgatc   900
tttctcaccg atatgccaaa gcggtttatc catcgtgaaa aattgaacga tatgttggca   960
catgtcagaa tacttacaag gaaaatatct actctggtga gtaaactgtt ggaggagatc  1020
tctgaggata atatcaatga agcggacttt tcagctccgg acttttttgca agaaattgaa  1080
caaatgaagg gagatatcag acacatcttt ttaaaagctc ctgatgcatc tcaacttcgg  1140
tttcctatgg atgatggttt cctcttcatg aatcttctac tcagacattt aaatgattta  1200
ctcatttcca atgcttattc agttttttctc ataaaaaaag aaattgggat ggtgaaagaa  1260
agccttgaat tcctaatatc atctttcagg aaagtcaggc aaacattgga tgagagtact  1320
agtggagtag ttaaaaattg ttgggtgcgt gctttggatg tggcatatga ggacgaaacat  1380
atcattaatt ccattcttgt cagagataaa gctctctcca atctcctctt ctcacttccg  1440
agtgtcactg ataagatcaa acttatcgtg gaacaagtca ccaggtttca gctggaggat  1500
aagaatgggg atggcccct tgatgcaaag tcttccttcg agccaactca gtcaacttca  1560
tcacctttttg ttgaggtaac agtaggtcac gagaaagaag aatcccagat cattgaccag  1620
ctccttgatg aacatgaatc tgagcttgat gtcatttcca ttgtcggaat gccaggactc  1680
ggtaaaacta ctctgccaa caaagtgtat aaagatacat tagttgctag gcatttccat  1740
gtccgtgctt ggtgcactgt ttcgcaaaag tataacaagt caaaggtgtt gcgggagatt  1800
cttcagcaag ttactggctc gggaggaaaa gaaagtgaag atgacctggc tgaaaagcta  1860
cgaagagcac tactcgataa aaggtaccta atcgtcttgt atgatgtgtg ggatattgca  1920
acaggggaga tgttaatagc atgtttttcct aagggtaaga gaggaaatag aatcatctta  1980
actagccgaa gtagaaaggt aggtttgaaa gttaaatgcc gtagtgatcc tctcgacctt  2040
aaactttttaa catctgaaga aagttgggat ttattcgaaa aaagggtatt tggagatgaa  2100
ggaagctgcc ctgctgaact gtccgaagtt ggacaccaaa tagttgagaa atgtaagggt  2160
cttcccttgg ctattgtttt aattgctgga gtaattgtta gagggaagaa aaaggaaaag  2220
gattttttggc ttaagatact gcataatctg gattccttta tttctaccaa catcaatttg  2280
gttatgcaat taagttatga ccatttacca tgccacctga agccgttgct gctttacttt  2340
gcaacaactc aaaagagcca acaaactcca gtctctacat tgatgcagtt gtggatggcc  2400
gaagggtttg tggatcatga tagtttagag gaagtaactc aaagttactt ggatgctcta  2460
atttccagta gcctgataat ggtggatcat atccctcca agagttattg gtggacgtct  2520
ttaatgatca aggtttgcta tgtgcatgat gttgtgcacg atttttgttc agaaaaagcc  2580
aaaaaggaga agtttctcaa gttaatcaat tcaggtgatc catttcatgc ttcagatttc  2640
ctacaccatc gtctaaccat tcatactgac aacggccaac tccacaaaaa atgtgtttta  2700
ttcaattcta ataagtgctt agctgttagt aagcatgtca tatctttgaa agtgagtggt  2760
ccactagatg agttcaggta tatctgtcac acaagacact ttggacttgt tagagtgttg  2820
caactggatg acatcattct ggaagattct ttaatggaag aaataggtc cctatttcat  2880
ttgaggttct taagcattga gactgctgta ggtgtaatag ctatcccagt gtcgtggttg  2940
aacctccaga atctggaaac gctgttgatt tatacaactt attccaccat ggtattactg  3000
cccagaatat tgcaactgtc aaagctgaaa catgtgaaaa ttaaggaatg ttctttctttt  3060
gaagagaaag aggatatcca acgtagaata ttggaagctg ggaattcttc aaacttgaca  3120
actctatccg gagttgttat ctcatattct gaaggcatga gtgatgatgc tctgggagaag  3180
ttcccaattc ttcagcacct tgattgcatc atcatggaat cgcagaatgc tcctacacac  3240
gactattggt ttctcaagct tgatgtactt aataaactcg aatcattcgt agcaagatac  3300
aagcgcaatg gacatccctc gttaaaccga caaccgtatg gatttcactt ccctacaagc  3360
ttgaaagagt tacggttgac tggttttttc ctgagacctg atttgtttgtc agtaatccga  3420
gcgttgcctg agcttgagat tatggagttt tccggctgtt atttcgtgga tactaaatgt  3480
gacgcaagtg aggacatcta tctaagtctt aagactttga ttttgcgaga tgtccattta  3540
tcagaatggc aagttgaggg gggaacttttt cccaagcttg agaaattaat actaaaattt  3600
tgttccacac ttggggagat ccctgtgca tttatggatg tagaaactttt aaagtccatt  3660
gatttaagtt ttgttgggcg taagcttcga gattcagcca ttgagattaa gaaaaatgta  3720
gcagatttca caggagagga cagagttgat gtccacacat cacatttgtt tgcaaccaac  3780
gtgaaagaac agattatgag aatgacggtg gttgatgaag ttggattttct catggaaaaa  3840
tcacaacaat ga                                                      3852

SEQ ID NO: 10       moltype = AA  length = 1279
FEATURE             Location/Qualifiers
REGION              1..1279
                    note = protein MeR1 (isoform 1)
source              1..1279
                    mol_type = protein
```

```
                                   organism = Solanum lycopersicum
SEQUENCE: 10
MEKGEKSLLL FEEQKTRITN LIDDFLIRLK QIKNEFIASK LDAFENLRME LRFLRTFVLF  60
GNSMNLDDFY ERMSLSISKF DQSTEYVDKI ILEKYNMECL APLLLEEIRN YLSLKNDYVA  120
TTTEIKLFEY LIRNLHDLPK YCSDLLLPLM SEYKILRQVC THLRDFYQLE CNKTTKTEFL  180
YTRYQVTADR VTQFCFDLWT GMYKYSDNEY AFSECSSKIT SLLIDIIPLE LEVLYISTSK  240
LIKESTSKEL EGFVKQILKA SPRILQHYLI HLQGRMAGVE AVNFAPTRSI SVMMEFLLIF  300
LTDMPKRFIH REKLNDMLAH VRILTRKIST LVSKLLEEIS EDNINEADFS APDFLQEIEQ  360
MKGDIRHIFL KAPESSQLRF PMDDGFLFMN LLLRHLNDLL ISNAYSVFLI KKEIGMVKES  420
LEFLISSFRK VRQTLDESTS GVVKNCWVRA LDVAYEAEHI INSILVRDKA LSHLLFSLPS  480
VTDKIKLIVE QVTRFQLEDK NGDGPLDAKS SFEPTQSTSS PFVEVTVGHE KEESQIIDQL  540
LDEHESELDV ISIVGMPGLG KTTLANKVYK DTLVARHFHV RAWCTVSQKY NKSKVLREIL  600
QQVTGSGGKE SEDDLAEKLR RALLDKRYLI VLDDVWDIAT GEMLIACFPK GKRGNRIILT  660
SRSRKVGLKV KCRSDPLDLK LLTSEESWDL FEKRVFGDEG SCPAELSEVG HQIVEKCKGL  720
PLAIVLIAGV IVRGKKKEKD FWLKILHNLD SFISTNINLV MQLSYDHLPC HLKPLLLYFA  780
TTQKSQQTPV STLMQLWMAE GFVDHDSLEE VTQSYLDALI SSSLIMVDHI PSKSYWWTSL  840
MIKVCYVHDV VHDFCSEKAK KEKFLKLINS GDPFHASDFL HHRLTIHTDN GQLHKKCVLF  900
NSNKCLAVSK HVISLKVSGP LDEFRYICHT RHFGLVRVLQ LDDIILEDSL MEEIGSLFHL  960
RFLSIETAVG VIAIPVSWLN LQNLETLLIY TTYSTMVLLP RILQLSKLKH VKIKECSFFE  1020
EKEDIQRRIL EAGNSSNLTT LSGVVISYSE GMSDDALEKF PILQHLDCII MESQNAPTHD  1080
YWFLKLDVLN KLESFVARYK RNGHPSLNRQ PYGFHFPTSL KELRLTGFFL RPDLLSVIAA  1140
LPELEIMEFS GCYFVDTKWD ASEDIYLSLK TLILRDVHLS EWQVEGGTFP KLEKLILKFC  1200
STLGEIPCAF MDVETLKSID LSFVGRKLRD SAIEIKKNVA DFTGEDRVDV HTSHLFATNV  1260
KEQIMRMTGM GNIQGRRGI                                                 1279

SEQ ID NO: 11            moltype = AA  length = 1280
FEATURE                  Location/Qualifiers
REGION                   1..1280
                         note = protein MeR1 (isoform 2)
source                   1..1280
                         mol_type = protein
                         organism = Solanum lycopersicum
SEQUENCE: 11
MEKGEKSLQL LFEEQKTRIT NLIDDFLIRL KQIKNEFIAS KLDAFENLRM ELRFLRTFVL  60
FGNSMNLDDF YERMSLSISK FDQSTEYVDK IILEKYNMEC LAPLLLEEIR NYLSLKNDYV  120
ATTTEIKLFE YLIRNLHDLP KYCSDLLLPL MSEYKILRQV CTHLRDFYQL ECNKTTKTEF  180
LYTRYQVTAD RVTQFCFDLW TGMYKYSDNE YAFSECSSKI TSLLIDIIPL ELEVLYISTS  240
KLIKESTSKE LEGFVKQILK ASPRILQHYL IHLQGRMAGV EAVNFAPTRS ISVMMEFLLI  300
FLTDMPKRFI HREKLNDMLA HVRILTRKIS TLVSKLLEEI SEDNINEADF SAPDFLQEIE  360
QMKGDIRHIF LKAPESSQLR FPMDDGFLFM NLLLRHLNDL LISNAYSVFL IKKEIGMVKE  420
SLEFLISSFR KVRQTLDEST SGVVKNCWVR ALDVAYEAEH IINSILVRDK ALSHLLFSLP  480
SVTDKIKLIV EQVTRFQLED KNGDGPLDAK SSFEPTQSTS SPFVEVTVGH EKEESQIIDQ  540
LLDEHESELD VISIVGMPGL GKTTLANKVY KDTLVARHFH VRAWCTVSQK YNKSKVLREI  600
LQQVTGSGGK ESEDDLAEKL RRALLDKRYL IVLDDVWDIA TGEMLIACFP KGKRGNRIIL  660
TSRSRKVGLK VKCRSDPLDL KLLTSEESWD LFEKRVFGDE GSCPAELSEV GHQIVEKCKG  720
LPLAIVLIAG VIVRGKKKEK DFWLKILHNL DSFISTNINL VMQLSYDHLP CHLKPLLLYF  780
ATTQKSQQTP VSTLMQLWMA EGFVDHDSLE EVTQSYLDAL ISSSLIMVDH IPSKSYWWTS  840
LMIKVCYVHD VVHDFCSEKA KKEKFLKLIN SGDPFHASDF LHHRLTIHTD NGQLHKKCVL  900
FNSNKCLAVS KHVISLKVSG PLDEFRYICH TRHFGLVRVL QLDDIILEDS LMEEIGSLFH  960
LRFLSIETAV GVIAIPVSWL NLQNLETLLI YTTYSTMVLL PRILQLSKLK HVKIKECSFF  1020
EEKEDIQRRI LEAGNSSNLT TLSGVVISYS EGMSDDALEK FPILQHLDCI IMESQNAPTH  1080
DYWFLKLDVL NKLESFVARY KRNGHPSLNR QPYGFHFPTS LKELRLTGFF LRPDLLSVIA  1140
ALPELEIMEF SGCYFVDTKW DASEDIYLSL KTLILRDVHL SEWQVEGGTF PKLEKLILKF  1200
CSTLGEIPCA FMDVETLKSI DLSFVGRKLR DSAIEIKKNV ADFTGEDRVD VHTSHLFATN  1260
VKEQIMRMTG MGNIQGRRGI                                                1280

SEQ ID NO: 12            moltype = AA  length = 1277
FEATURE                  Location/Qualifiers
REGION                   1..1277
                         note = protein MeR1 (isoform 3)
source                   1..1277
                         mol_type = protein
                         organism = Solanum lycopersicum
SEQUENCE: 12
MEKGEKSLLL FEEQKTRITN LIDDFLIRLK QIKNEFIASK LDAFENLRME LRFLRTFVLF  60
GNSMNLDDFY ERMSLSISKF DQSTEYVDKI ILEKYNMECL APLLLEEIRN YLSLKNDYVA  120
TTTEIKLFEY LIRNLHDLPK YCSDLLLPLM SEYKILRQVC THLRDFYQLE CNKTTKTEFL  180
YTRYQVTADR VTQFCFDLWT GMYKYSDNEY AFSECSSKIT SLLIDIIPLE LEVLYISTSK  240
LIKESTSKEL EGFVKQILKA SPRILQHYLI HLQGRMAGVE AVNFAPTRSI SVMMEFLLIF  300
LTDMPKRFIH REKLNDMLAH VRILTRKIST LVSKLLEEIS EDNINEADFS APDFLQEIEQ  360
MKGDIRHIFL KAPESSQLRF PMDDGFLFMN LLLRHLNDLL ISNAYSVFLI KKEIGMVKES  420
LEFLISSFRK VRQTLDESTS GVVKNCWVRA LDVAYEAEHI INSILVRDKA LSHLLFSLPS  480
VTDKIKLIVE QVTRFQLEDK NGDGPLDAKS SFEPTQSTSS PFVEVTVGHE KEESQIIDQL  540
LDEHESELDV ISIVGMPGLG KTTLANKVYK DTLVARHFHV RAWCTVSQKY NKSKVLREIL  600
QQVTGSGGKE SEDDLAEKLR RALLDKRYLI VLDDVWDIAT GEMLIACFPK GKRGNRIILT  660
SRSRKVGLKV KCRSDPLDLK LLTSEESWDL FEKRVFGDEG SCPAELSEVG HQIVEKCKGL  720
PLAIVLIAGV IVRGKKKEKD FWLKILHNLD SFISTNINLV MQLSYDHLPC HLKPLLLYFA  780
TTQKSQQTPV STLMQLWMAE GFVDHDSLEE VTQSYLDALI SSSLIMVDHI PSKSYWWTSL  840
MIKVCYVHDV VHDFCSEKAK KEKFLKLINS GDPFHASDFL HHRLTIHTDN GQLHKKCVLF  900
```

```
NSNKCLAVSK HVISLKVSGP LDEFRYICHT RHFGLVRVLQ LDDIILEDSL MEEIGSLFHL  960
RFLSIETAVG VIAIPVSWLN LQNLETLLIY TTYSTMVLLP RILQLSKLKH VKIKECSFFE 1020
EKEDIQRRIL EAGNSSNLTT LSGVVISYSE GMSDDALEKF PILQHLDCII MESQNAPTHD 1080
YWFLKLDVLN KLESFVARYK RNGHPSLNRQ PYGFHFPTSL KELRLTGFFL RPDLLSVIAA 1140
LPELEIMEFS GCYFVDTKWD ASEDIYLSLK TLILRDVHLS EWQVEGGTFP KLEKLILKFC 1200
STLGEIPCAF MDVETLKSID LSFVGRKLRD SAIEIKKNVA DFTGEDRVDV HTSHLFATNV 1260
KEQIMRMTGG ECTCEEL                                                1277

SEQ ID NO: 13            moltype = AA   length = 1278
FEATURE                  Location/Qualifiers
REGION                   1..1278
                         note = protein MeR1 (isoform 4)
source                   1..1278
                         mol_type = protein
                         organism = Solanum lycopersicum
SEQUENCE: 13
MEKGEKSLQL LFEEQKTRIT NLIDDFLIRL KQIKNEFIAS KLDAFENLRM ELRFLRTFVL   60
FGNSMNLDDF YERMSLSISK FDQSTEYVDK IILEKYNMEC LAPLLLEEIR NYLSLKNDYV  120
ATTTEIKLFE YLIRNLHDLP KYCSDLLLPL MSEYKILRQV CTHLRDFYQL ECNKTTKTEF  180
LYTRYQVTAD RVTQFCFDLW TGMYKYSDNE YAFSECSSKI TSLLIDIIPL ELEVLYISTS  240
KLIKESTSKE LEGFVKQILK ASPRILQHYL IHLQGRMAGV EAVNFAPTRS ISVMMEFLLI  300
FLTDMPKRFI HREKLNDMLA HVRILTRKIS TLVSKLLEEI SEDNINEADF SAPDFLQEIE  360
QMKGDIRHIF LKAPESSQLR FPMDDGFLFM NLLLRHLNDL LISNAYSVFL IKKEIGMVKE  420
SLEFLISSFR KVRQTLDEST SGVVKNCWVR ALDVAYEAEH IINSILVRDK ALSHLLFSLP  480
SVTDKIKLIV EQVTRFQLED KNGDGPLDAK SSFEPTQSTS SPFVEVTVGH EKEESQIIDQ  540
LLDEHESELD VISIVGMPGL GKTTLANKVY KDTLVARHFH VRAWCTVSQK YNKSKVLREI  600
LQQVTGSGGK ESEDDLAEKL RRALLDKRYL IVLDDVWDIA TGEMLIACFP KGKRGNRIIL  660
TSRSRKVGLK VKCRSDPLDL KLLTSEESWD LFEKRVFGDE GSCPAELSEV GHQIVEKCKG  720
LPLAIVLIAG VIVRGKKKEK DFWLKILHNL DSFISTNINL VMQLSYDHLP CHLKPLLLYF  780
ATTQKSQQTP VSTLMQLWMA EGFVDHDSLE EVTQSYLDAL ISSSLIMVDH IPSKSYWWTS  840
LMIKVCYVHD VVHDFCSEKA KKEKFLKLIN SGDPFHASDF LHHRLTIHTD NGQLHKKCVL  900
FNSNKCLAVS KHVISLKVSG PLDEFRYICH TRHFGLVRVL QLDDIILEDS LMEEIGSLFH  960
LRFLSIETAV GVIAIPVSWL NLQNLETLLI YTTYSTMVLL PRILQLSKLK HVKIKECSFF 1020
EEKEDIQRRI LEAGNSSNLT TLSGVVISYS EGMSDDALEK FPILQHLDCI IMESQNAPTH 1080
DYWFLKLDVL NKLESFVARY KRNGHPSLNR QPYGFHFPTS LKELRLTGFF LRPDLLSVIA 1140
ALPELEIMEF SGCYFVDTKW DASEDIYLSL KTLILRDVHL SEWQVEGGTF PKLEKLILKF 1200
CSTLGEIPCA FMDVETLKSI DLSFVGRKLR DSAIEIKKNV ADFTGEDRVD VHTSHLFATN 1260
VKEQIMRMTG GECTCEEL                                               1278

SEQ ID NO: 14            moltype = AA   length = 632
FEATURE                  Location/Qualifiers
REGION                   1..632
                         note = protein MeR1 (isoform 5)
source                   1..632
                         mol_type = protein
                         organism = Solanum lycopersicum
SEQUENCE: 14
MEKGEKSLLL FEEQKTRITN LIDDFLIRLK QIKNEFIASK LDAFENLRME LRFLRTFVLF   60
GNSMNLDDFY ERMSLSISKF DQSTEYVDKI ILEKYNMECL APLLLEEIRN YLSLKNDYVA  120
TTTEIKLFEY LIRNLHDLPK YCSDLLLPLM SEYKILRQVC THLRDFYQLE CNKTTKTEFL  180
YTRYQVTADR VTQFCFDLWT GMYKYSDNEY AFSECSSKIT SLLIDIIPLE LEVLYISTSK  240
LIKESTSKEL EGFVKQILKA SPRILQHYLI HLQGRMAGVE AVNFAPTRSI SVMMEFLLIF  300
LTDMPKRFIH REKLNDMLAH VRILTRKIST LVSKLLEEIS EDNINEADFS APDFLQEIEQ  360
MKGDIRHIFL KAPESSQLRF PMDDGFLFMN LLLRHLNDLL ISNAYSVFLI KKEIGMVKES  420
LEFLISSFRK VRQTLDESTS GVVKNCWVRA LDVAYEAEHI INSILVRDKA LSHLLFSLPS  480
VTDKIKLIVE QVTRFQLEDK NGDGPLDAKS SFEPTQSTSS PFVEVTVGHE KEESQIIDQL  540
LDEHESELDV ISIVGMPGLG KTTLANKVYK DTLVARHFHV RAWCTVSQKY NKSKVLREIL  600
QQVTGSGGKE SEDDLAEKLR RALLDKRWRM YL                                632

SEQ ID NO: 15            moltype = AA   length = 633
FEATURE                  Location/Qualifiers
REGION                   1..633
                         note = protein MeR1 (isoform 6)
source                   1..633
                         mol_type = protein
                         organism = Solanum lycopersicum
SEQUENCE: 15
MEKGEKSLQL LFEEQKTRIT NLIDDFLIRL KQIKNEFIAS KLDAFENLRM ELRFLRTFVL   60
FGNSMNLDDF YERMSLSISK FDQSTEYVDK IILEKYNMEC LAPLLLEEIR NYLSLKNDYV  120
ATTTEIKLFE YLIRNLHDLP KYCSDLLLPL MSEYKILRQV CTHLRDFYQL ECNKTTKTEF  180
LYTRYQVTAD RVTQFCFDLW TGMYKYSDNE YAFSECSSKI TSLLIDIIPL ELEVLYISTS  240
KLIKESTSKE LEGFVKQILK ASPRILQHYL IHLQGRMAGV EAVNFAPTRS ISVMMEFLLI  300
FLTDMPKRFI HREKLNDMLA HVRILTRKIS TLVSKLLEEI SEDNINEADF SAPDFLQEIE  360
QMKGDIRHIF LKAPESSQLR FPMDDGFLFM NLLLRHLNDL LISNAYSVFL IKKEIGMVKE  420
SLEFLISSFR KVRQTLDEST SGVVKNCWVR ALDVAYEAEH IINSILVRDK ALSHLLFSLP  480
SVTDKIKLIV EQVTRFQLED KNGDGPLDAK SSFEPTQSTS SPFVEVTVGH EKEESQIIDQ  540
LLDEHESELD VISIVGMPGL GKTTLANKVY KDTLVARHFH VRAWCTVSQK YNKSKVLREI  600
LQQVTGSGGK ESEDDLAEKL RRALLDKRWR MYL                              633
```

```
SEQ ID NO: 16            moltype = AA   length = 1282
FEATURE                  Location/Qualifiers
REGION                   1..1282
                         note = protein MeR1 (isoform 7)
source                   1..1282
                         mol_type = protein
                         organism = Solanum lycopersicum
SEQUENCE: 16
MEKGEKSLLL FEEQKTRITN LIDDFLIRLK QIKNEFIASK LDAFENLRME LRFLRTFVLF   60
GNSMNLDDFY ERMSLSISKF DQSTEYVDKI ILEKYNMECL APLLLEEIRN YLSLKNDYVA  120
TTTEIKLFEY LIRNLHDLPK YCSDLLLPLM SEYKILRQVC THLRDFYQLE CNKTTKTEFL  180
YTRYQVTADR VTQFCFDLWT GMYKYSDNEY AFSECSSKIT SLLIDIIPLE LEVLYISTSK  240
LIKESTSKEL EGFVKQILKA SPRILQHYLI HLQGRMAGVE AVNFAPTRSI SVMMEFLLIF  300
LTDMPKRFIH REKLNDMLAH VRILTRKIST LVSKLLEEIS EDNINEADFS APDFLQEIEQ  360
MKGDIRHIFL KAPESSQLRF PMDDGFLFMN LLLRHLNDLL ISNAYSVFLI KKEIGMVKES  420
LEFLISSFRK VRQTLDESTS GVVKNCWVRA LDVAYEAEHI INSILVRDKA LSHLLFSLPS  480
VTDKIKLIVE QVTRFQLEDK NGDGPLDAKS SFEPTQSTSS PFVEVTVGHE KEESQIIDQL  540
LDEHESELDV ISIVGMPGLG KTTLANKVYK DTLVARHFHV RAWCTVSQKY NKSKVLREIL  600
QQVTGSGGKE SEDDLAEKLR RALLDKRYLI VLDDVWDIAT GEMLIACFPK GKRGNRIILT  660
SRSRKVGLKV KCRSDPLDLK LLTSEESWDL FEKRVFGDEG SCPAELSEVG HQIVEKCKGL  720
PLAIVLIAGV IVRGKKKEKD FWLKILHNLD SFISTNINLV MQLSYDHLPC HLKPLLLYFA  780
TTQKSQQTPV STLMQLWMAE GFVDHDSLEE VTQSYLDALI SSSLIMVDHI PSKSYWWTSL  840
MIKVCYVHDV VHDFCSEKAK KEKFLKLINS GDPFHASDFL HHRLTIHTDN GQLHKKCVLF  900
NSNKCLAVSK HVISLKVSGP LDEFRYICHT RHFGLVRVLQ LDDIILEDSL MEEIGSLFHL  960
RFLSIETAVG VIAIPVSWLN LQNLETLLIY TTYSTMVLLP RILQLSKLKH VKIKECSFFE 1020
EKEDIQRRIL EAGNSSNLTT LSGVVISYSE GMSDDALEKF PILQHLDCII MESQNAPTHD 1080
YWFLKLDVLN KLESFVARYK RNGHPSLNRQ PYGFHFPTSL KELRLTGFFL RPDLLSVIAA 1140
LPELEIMEFS GCYFVDTKWD ASEDIYLSLK TLILRDVHLS EWQVEGGTFP KLEKLILKFC 1200
STLGEIPCAF MDVETLKSID LSFVGRKLRD SAIEIKKNVA DFTGEDRVDV HTSHLFATNV 1260
KEQIMRMTVV DEVGFLMEKS QQ                                         1282

SEQ ID NO: 17            moltype = AA   length = 1283
FEATURE                  Location/Qualifiers
REGION                   1..1283
                         note = protein MeR1 (isoform 8)
source                   1..1283
                         mol_type = protein
                         organism = Solanum lycopersicum
SEQUENCE: 17
MEKGEKSLQL LFEEQKTRIT NLIDDFLIRL KQIKNEFIAS KLDAFENLRM ELRFLRTFVL   60
FGNSMNLDDF YERMSLSISK FDQSTEYVDK IILEKYNMEC LAPLLLEEIR NYLSLKNDYV  120
ATTTEIKLFE YLIRNLHDLP KYCSDLLLPL MSEYKILRQV CTHLRDFYQL ECNKTTKTEF  180
LYTRYQVTAD RVTQFCFDLW TGMYKYSDNE YAFSECSSKI TSLLIDIIPL ELEVLYISTS  240
KLIKESTSKE LEGFVKQILK ASPRILQHYL IHLQGRMAGV EAVNFAPTRS ISVMMEFLLI  300
FLTDMPKRFI HREKLNDMLA HVRILTRKIS TLVSKLLEEI SEDNINEADF SAPDFLQEIE  360
QMKGDIRHIF LKAPESSQLR FPMDDGFLFM NLLLRHLNDL LISNAYSVFL IKKEIGMVKE  420
SLEFLISSFR KVRQTLDEST SGVVKNCWVR ALDVAYEAEH IINSILVRDK ALSHLLFSLP  480
SVTDKIKLIV EQVTRFQLED KNGDGPLDAK SSFEPTQSTS SPFVEVTVGH EKEESQIIDQ  540
LLDEHESELD VISIVGMPGL GKTTLANKVY KDTLVARHFH VRAWCTVSQK YNKSKVLREI  600
LQQVTGSGGK ESEDDLAEKL RRALLDKRYL IVLDDVWDIA TGEMLIACFP KGKRGNRIIL  660
TSRSRKVGLK VKCRSDPLDL KLLTSEESWD LFEKRVFGDE GSCPAELSEV GHQIVEKCKG  720
LPLAIVLIAG VIVRGKKKEK DFWLKILHNL DSFISTNINL VMQLSYDHLP CHLKPLLLYF  780
ATTQKSQQTP VSTLMQLWMA EGFVDHDSLE EVTQSYLDAL ISSSLIMVDH IPSKSYWWTS  840
LMIKVCYVHD VVHDFCSEKA KKEKFLKLIN SGDPFHASDF LHHRLTIHTD NGQLHKKCVL  900
FNSNKCLAVS KHVISLKVSG PLDEFRYICH TRHFGLVRVL QLDDIILEDS LMEEIGSLFH  960
LRFLSIETAV GVIAIPVSWL NLQNLETLLI YTTYSTMVLL PRILQLSKLK HVKIKECSFF 1020
EEKEDIQRRI LEAGNSSNLT TLSGVVISYS EGMSDDALEK FPILQHLDCI IMESQNAPTH 1080
DYWFLKLDVL NKLESFVARY KRNGHPSLNR QPYGFHFPTS LKELRLTGFF LRPDLLSVIA 1140
ALPELEIMEF SGCYFVDTKW DASEDIYLSL KTLILRDVHL SEWQVEGGTF PKLEKLILKF 1200
CSTLGEIPCA FMDVETLKSI DLSFVGRKLR DSAIEIKKNV ADFTGEDRVD VHTSHLFATN 1260
VKEQIMRMTV VDEVGFLMEK SQQ                                         1283

SEQ ID NO: 18            moltype = DNA   length = 8391
FEATURE                  Location/Qualifiers
misc_feature             1..8391
                         note = Genomic NRC6-2a
source                   1..8391
                         mol_type = genomic DNA
                         organism = Solanum lycopersicum
SEQUENCE: 18
attcaatttt aaaaaattat tcagtaaaat tattaaattt tattttgtat cgttaaaatt   60
actcaatttg gatatattta aatcagtgaa attattaaac taaatttatc attaaaataa  120
taaaataatt ttttaaatat ataattacaa ataaaataat aaataaatac ttaaaattac  180
tactttatta tatattgtaa gataaaataa taaaagataa ttttatcaat ttcatttggt  240
acactgcttc attattgcaa tgacgactgt cgattttgct ccggtagttt aatcaatttg  300
tagtggttta atcaattttt tgtttgtgtg aatcccttat ttaatttttt tttaaaaaaa  360
ataaataaag tgaggtttca tgtatcaatg gtagtttgga caattttgag tagtttgata  420
aatttatttt ttgtttttgaa tttttattat tttataatga aatagtaatt tcgagtcatg  480
tactatgtag tttaatcata aacatagatt gagtgatttt aatgatataa aaacctaaat  540
```

-continued

```
tgagtatttt actggtacaa aatgaagttt agttgctaga tatatttcaa aagttgagtg  600
acctttttgag aaattaactc ctctgtcaga tctcctaatt tgataaattt tcaaaacttc  660
ataaatataac attttccttt tttataatga ttacaaacta tatcaaacga cgagttcccc  720
ctgtcactta tactttttaat tcacaaattc ctcttatcag tgtgaccaca tccccacaac  780
catacttgtt acgatccaaa aatgagcgtg atgacactcg tcttattcac atagattagt  840
cagcctaaaa ctcaattatt atgaagaaga gaggaaataa actataaagt ggaatcagat  900
tcatgagttg tgtttgagtc tgaattattg aatattaaag tctgatcaat taaagtcgag  960
agtaattagt ctgtataatt tgttctatgt ttattactga gttgtaataa tttctatatt 1020
ttgtaaccaa aaacggattt gactttttga agagagttg agagaattgt aacaagaaat 1080
gtgtttgact tatcgcagag tagagttaag agagagttag agagaattgt aataagaaat 1140
gagtttgact tcttagtgag tagagagttg agagagagtt tgagagaatt ataacaagaa 1200
gtttgacttc ttggagaata gagtttccga ttataattaa tcgttgaaga gtaaagatac 1260
tagacttagt ccctttgatg attgaattgt tattgaagtt aataaaattg tgatgtgatt 1320
ttttccttcc ttgagggagg aaggcttcca cggtaaatta agtgttgttt aaattctgtt 1380
ctaaacgact ataggaacca ggttcctaga aataattgtt ggcgcatagt atctttcaag 1440
gaaaaatgca gaatgccacg taagctcgaa aagggtagaa aattatctat aaaataagtt 1500
cgggtggaag gataataaga gttgtataag tgtgtctctg aaatttgaga catagattag 1560
gaggtactta tgtattttcc cttcttccag ttatttgtt cacctcttcc ataatgtcaa 1620
atccttaatt atatatgtct acctctgtac gtcatattat agatagagaa acaatttaaa 1680
tgtgtcttta taatcaatat cactgaaagc tctagcgacg ttaaatacaa caatattatt 1740
tttttatttt gctaccttga ataataattc tcaattgttt acaagctttc caacaacacc 1800
catttatttc aaccaatgtg aacctctttc caacaacact taatttgttt tctagtaatt 1860
tttcaatcaa catgaactta attattcaaa tgttagctgt cattggatta ttaaattgtt 1920
aatgttgtaa ggtgatggtg tattatatta agaattaaca aataatactt aaagacttgg 1980
ttaatctaat tcagagtcaa cttgaagtta tttcattcca catgtttata aacacacaac 2040
tatggcaata acaacatagc aattgtcatc tctaaattac tactactatt cttcttctcc 2100
atcaatttaa tcctcagaaa tggatccgtt tacggcggct gcattaacca ctgcggtgac 2160
agccacggtg agccttctgg tggagaactt gtcgcatctt ataagttata attggaagtt 2220
gtatacagga ttgaagaaat catgcgaaga tttgtatgat gaagtgaagc gattaaatgc 2280
attttttagtc gataacgcga atcagagaag taatagtacg caatgggatg tattagtcga 2340
taaaattcga cgtacagtat ataaagcaga ggatgttgtt gataaattat tgattcaggg 2400
caagttagac caagagagta atatagctaa aaagatgttt cacaaaactt acaaaaacag 2460
gaattttact gaggaaatca atgagatact tgtagaggtg aggaaaatcc ttgaggaaaa 2520
tcaacatctg tttgaggcaa acccgacgat tgatcatcat cagcctgaaa aagttgtcca 2580
ggaggaacag gtacgtttac acgaaatttc gattttaatg tgatttattg aaatatgaaa 2640
tgaactatga tttgctcgtt cagtaaaact gtataagagt tggagaaata gtacttcctc 2700
tgtttttaata tgcattattt gtttgaactt agttaaagtt taatctaaat tattcagatc 2760
taggacaagg cattaggcat aagtaaggca aagggtagaa gtacctttct agattatgac 2820
tcaaattccg tagaatttta ctttagttaa ggtgtgtctc tgaaattcag acaattaaag 2880
gtcaccacca accattatta catgcacaaa tcactatcga taattgccac cattggtcaa 2940
cattatatat cgctgacctc catctatcat taactgtcag tatgattcca ctattaatta 3000
tcaaatggtc atcaacaaca accacaatta atcactaagg ccaatcacta tactgtccac 3060
aaccactatc atctgtcaac actatctaaa atcgatacac acaatcacta tcattagtca 3120
ttaccaccac cgattgtcac attttcttgt agtgaatgat ggggattgaa aatatgaaga 3180
ataaaataga catgcatagg ataagggac atatttttca tagttgaatg ggacattgaa 3240
aattaataac tttcacatga tcataactca tttggtacct gatggaataa tttcttgtta 3300
tgatgataca atcaagacaa gtagccttaa taacttgtt aatttgtcca tcttacaggg 3360
ttcgtcattg gaaaatcacg aagtggttgg atttgatgaa gaagcaacga aagtgatcaa 3420
tcgtctggtt gaaggagcag agtgtctaga tgttatcccg gttgtaggaa tgccgggact 3480
tggtaaaacc acactggcaa gaaaaatctt taatgatcct aagatttcgc gagaattttt 3540
cagctacatt tgggtttca tcggacaatc aacgtgtgta aaaagggata tcctttttaa 3600
tattctgaaa gggttcacaa attcatttga tgaattcaaa aacagaaatg aggcaagcat 3660
aactgatgaa atacgtaagc gtgtggctaa tggaggtaaa tgtctcattg tcttggatga 3720
tgtgtgggat acaaatgttg tagatattgt caagacagtt ttccctgata acaaaaaagc 3780
ccacaggatc atgatgacca ctcgacacga agacattgct agatctgtca ataaatatcc 3840
ccacaatctg aaatttctgg atggagacga aagtttccag ctgctagaaa agagagcttt 3900
tggcgttagc cgttgtcctg ttgagttagt agaacatgga gaagccattg tagcaaaatg 3960
tagtggagta ccacttacaa ttgtggtaat tgcaggagct ttaagaggtc gtacgagtga 4020
aattgatgca aaagtagtta gggaaaatgt ggggaagcat cttatacaag aagacaaact 4080
tcagagatgt gtgaatgttg tgagattgag ttacaatcat ttgcctcaag aaaaaaaatc 4140
ttgcttcttg tattttggtg cctttcctca aggatttgat atccccgctt ggaaattgat 4200
tcgactctgg attgctgagg gactcataat gtccaagttg tcgggcaacg aaattgaaga 4260
gatagcagag tattatctta atgactttgc caacaggaac ttagtgatgg tgatgaaaaa 4320
gaaatctaat gatcgaataa aaacatgtcg tgttcacgac atgttacatg agtttttgcg 4380
tgaagaggct actagattga ctcttttcaa acaagtatgt ctcacatctg atcaagacat 4440
acagaactca attacttgtc gtcgtgtctc tattcaatca tctgttcctc aaaacttcat 4500
ctcaaaaaag acagttgaag aacatgttag gtcattgtta tgtttttcct caaaacaaaa 4560
acaagttgac ttttctaata tcgacgtcaa gctcatccct accgcatttc cacttatgag 4620
agtcttagac attgaatccg tcaagtttag tattcccagg gaattttacc agctattgca 4680
cttgaggtat atcgctatgt caggtgattt cgagcaactt cctaaactct ttacttcttt 4740
ctgtaatgca caaactctca ttctaaatac ttccaagccc acccttgata taaaagctga 4800
catatggaac atgccacgtt tgcgtcatct gcacaccaac aaacctgcaa tcttaccacc 4860
ccctacaagt agtagtagta gtagtacaaa ttcttgtttg ttgcaaactc tatctctggt 4920
tacaccagaa agctgcaagg gaaacgttct ttcaaaggct cgtaatgtca agaaaatgag 4980
tgttaaaggt aatttgacac cttttcttga aactagcaag ggtgaatttt tcagcaattt 5040
tcaagtgcta aagctcctgg aaagtttaac actgctaaat gatgataaga gtaataaatc 5100
tcttcacctt ccgtcagcat tctccgaatg tttaccaaat ttgaagaagt taactctatc 5160
aaaaacaagg tttgactgga atcaggcata tagattaggc caggtgaaaa atctccaggt 5220
cctaaaactg aaagaaaatg cattcacggg gccgtcctgg aggatggagc caggaggttt 5280
```

```
caagaaactt caggtcttgt ggattgaaat ggcagatttc gtgtcgtggg aggcatcaaa  5340
ctgtcctttc ccaagactta ggagcctttt cctgatctcc tgtcttaatc ttgaggctgt  5400
gccactcgat ctttcccatt tggataacct tcaagagatg acgttggaaa acacaagcaa  5460
agcaagcaaa tctgcaagag aaatagaatg cgagaaaaag aagaagcaag ctgatgatcc  5520
agaaactggc aaattcaagc tcactattcc ctactgagtc tgatttcaat gccacaaagt  5580
gaagttgtta taaggttagt ccaattctct ccctctcgta tcagtaaata tcgaataaga  5640
tatttttcaa taagattgca tctatcccta tagtctctcc acgcagaatt agtaggtagc  5700
agtgtgttgt cttgctgtct cgttcatatc aatagtcata gtattgctcc tatagtttct  5760
tatccttcga tttttcgtta ctatacgttg tcccttatac ctcgatatta gtaatgcttg  5820
ttgtagtttc tcttatgtta ctatctgctg tttttgttat tacctgttgt ttcttgtatt  5880
tccgtcattt ctttttggga ctcctttgaa ctttctcctt gagacaaagg tcaatcggaa  5940
acaacctacc tctctttctt tgagataagg ttcctccccg actctatttt gtgggactac  6000
actgagtata ttgttttggg tttcgcactt cactgaaaca ttaaattggg caacattact  6060
ctgttatact aataatacag attttaggtg ccttgatatc aaacatagag taaattcaat  6120
tattttcgtg ttcatcacat tcctcatcta ttttttctctt acttattttc ctcctttta  6180
gcaggagagt atcgaggcat ggtgatgcat ttgcagtctc agttttgatt acctgttcca  6240
ataaagaaac ttgttacaag tatgttttgt tgattcaaac atgccaagtt tgaaaacgaa  6300
gttttatatt aatgttttg cgttttcttt cagtgctgaa taatttgtct aatctgtagt  6360
tgatgtttgg atatctatgt attgttcgat tgacacgagt tgtttatact atcatttgtt  6420
gtttatgaat atgtaaaaca tatttgattt atgtttgcaa cgtcaacgtg aacattcaat  6480
tagtctaatc aaagtctaga tctaaaattg attaatttaa gttcataatt tattttgaat  6540
tattatctaa aaccgaagac tttctactcg aaaatcgaaa tcatagctga cagtctccat  6600
aaatatattt gcaattgaat aacataataa gcatttatca gttaattta tggagtttct  6660
ggatttacgt gatattcaaa catctcccgc gcatattaat tatgtgaagt aatgaagtgt  6720
gtaacataag tcaaaggtg cataaataaa gagtcaaggg taataagact ttagtttact  6780
ttaggtgtgt ctctgaaatt tcgattataa tctacgatat attgtgtctt gtcccaacat  6840
ttaaataaaa tgaacaaata attttaatta ccaaatggat ccatagtctg tttagttgac  6900
taatggaaag atttatagga aggtgagatt gttttatccc tgattagagg ttttggttcg  6960
agttttgtgt atacgaaaaa attgtgttga aagcgtcact tatgaatagg ccctataatg  7020
tatgattcga atttagtctg agttctaata tgaattttga acacattgaa aaattatatc  7080
ctttgttaaa tttcatggtt ttaacatctt ggaagtaaag aaaaaggtaa aatatttttt  7140
ttttctattt cattttttta catgtaatat ttgaattcaa aggctgagag agtaataccc  7200
cccttttatt tttatttgtg gattacatat atacataaga actagaaaaa tgtttatatt  7260
ttcgacttga caatgataga atgtaaatgt tggatatata gaataatttg ttggagcttc  7320
taccattttt tgcttaccgt cttaaggttg aaggcgtaga tgtttattat ccgaataatt  7380
cctttttgtc gataatcaag catcaatatt agattagtag ccgaccctct tctcttacct  7440
ctctaaacaa tttttcaata tttccatttt ggttggtaaa aatattagag aacattttct  7500
ctatagaaat atcatgtgtt tattcagaat tgttattgac tccatatatt tttaataatc  7560
caaaacctat aaatttaata gtttacattc acaattattg cttgttgctg ttctttttacc  7620
ttgtgtttct aattttttacc gttattaaat atgcatgtga ttagttgaaa tattaaatct  7680
ctagaaattg aaggctggct cgaggttaga gattaaatgg aaaaatgaaa gtcaacgaag  7740
catggtagct gtcaaaatacg ctccaactca aagcattact gtcatgatgg agttcctatt  7800
gatccatcgt gaaaaattga acgatatgtt ggcacatgtc ggaatactta aaatatcgaa  7860
ttaatataat tgaatttaac tttgaaaatt aatcaaatta actttcgaaa agcgctacct  7920
gacaattaaa aatacaagga gtgagcagtg aacttaaact aatctatttc agatctctag  7980
gctttgataa actaattgac agttcaacat ttgcagatct aacttcaacg tttgcttctt  8040
gtagatctgc aacaaggcaa actaccattt gagagtaaag aaaaaggtat aatataagt  8100
ttttctagtt ttcattttac atgtattttt gtgattcact tgatttgaat gaaacataca  8160
ttacaagaac tagaaaacga atttgtattt ttgacttaga taattataaa atgttagatg  8220
attttgtcat aatttgtagt attcactctt gtttttagta aatatacctc tttcttaaat  8280
gtgattgatt tacagattat atattttaga atttttgctt attaaaagaa aaattaatta  8340
gtggcggaaa tttgaggtga atttgtgaag aatggaagaa gttggaaatt c            8391
```

```
SEQ ID NO: 19              moltype = DNA   length = 2670
FEATURE                    Location/Qualifiers
misc_feature               1..2670
                           note = CDS NRC6-2a
source                     1..2670
                           mol_type = genomic DNA
                           organism = Solanum lycopersicum
SEQUENCE: 19
atggatccgt ttacggcggc tgcattaacc actgcggtga cagccacggt gagccttctg  60
gtggagaact tgtcgcatct tataagttat aattggaagt tgtatacagg attgaagaaa  120
tcatcgcgaag atttgtatga tgaagtgaag cgattaaatg cattttttagt cgataacgcg  180
aatcagagaa gtaatagtac gcaatgggat gtattagtcg ataaaattcg acgtacagta  240
tataaagcag aggatgttgt tgataaatta ttgattcagg gcaagttaga ccaagagagt  300
aatatagcta aaaagatgtt tcacaaaact tacaaaaaca ggaattttac tgaggaaatc  360
aatgagatac ttgtagaggt gaggaaaatc cttgaggaaa atcaacatct gtttgaggca  420
aacccgacga ttgatcatca tcagcctgaa aaagttgtcc aggaggaaca gggttcgtca  480
ttggaaaatc acgaagtggt tggatttgat gaagaagcaa cgaaagtgat caatcgtctg  540
gttgaaggag cagagtgtct agatgttatc ccggttgtag gaatgccggg acttggtaaa  600
accacactgg caagaaaaat ctttaatgat cctaagattt cgcgagaatt tttcagctac  660
atttgggttt tcatcggaca atcaacgtgt gtaaaaaggg atatcctttt taatattctg  720
aaagggttca caattcatt tgatgaattc aaaaacagaa atagggaag cataactgat  780
gaaatacgta agcgtgtggc taatggaggt aaatgtctca ttgtcttgga tgatgtgtgg  840
gatacaaatg ttgtagatat tgtcaagaca gttttccctg ataacaaaaa agcccacagg  900
atcatgatga ccactcgaca cgaagacatt gctagatctg tcaataaata tccccacaat  960
ctgaaatttc tggatggaga cgaaagtttc cagctgctag aaaagagagc ttttggcgtt  1020
agccgttgtc ctgttgagtt agtagaacat ggagaagcca ttgtagcaaa atgtagtgga  1080
```

```
gtaccactta caattgtggt aattgcagga gctttaagag gtcgtacgag tgaaattgat    1140
tggaaagtag ttagggaaaa tgtgggggaag catcttatac aagaagacaa acttcagaga   1200
tgtgtgaatg ttgtgagatt gagttacaat catttgcctc aagaaaaaaa atcttgcttc    1260
ttgtattttg gtgcctttcc tcaaggattt gatatccccg cttggaaatt gattcgactc    1320
tggattgctg agggactcat aatgtccaag ttgtcgggca acgaaattga agagatagca    1380
gagtattatc ttaatgactt tgccaacagg aacttagtga tggtgatgaa aaagaaatct    1440
aatgatcgaa taaaaacatg tcgtgttcac gacatgttac atgagtttgtg cgttgaagag   1500
gctactagat tgactctttt caaacaagta tgtctcacat ctgatcaaga catacagaac    1560
tcaattactt gtcgtcgtgt ctctattcaa tcatctgttc ctcaaaactt catctcaaaa    1620
aagacagttg aagaacatgt taggtcattg ttatgttttt cctcaaaaca aaaacaagtt    1680
gacttttcta atatcgacgt caagctcatc cctaccgcat ttccacttat gagagtctta    1740
gacattgaat ccgtcaagtt tagtattccc agggaatttt accagctatt gcacttgagg    1800
tatatcgcta tgtcaggtga tttcgagcaa cttcctaaac tctttacttc tttctgtaat    1860
gcacaaactc tcattctaaa tacttccaag cccacccttg atataaaagc tgacatatgg    1920
aacatgccac gtttgcgtca tctgcacacc aacaaacctg caatcttacc accccctaca    1980
agtagtagta gtagtagtac aaattcttgt ttgttgcaaa ctctatctct ggttacacca    2040
gaaagctgca agggaaacgt tctttcaaag gctcgtaatg tcaagaaaat gagtgttaaa    2100
ggtaatttga caccttttct tgaaactagc aagggtgaat ttttcagcaa ttttcaagtg    2160
ctaaagctcc tggaaagttt aacactgcta aatgatgata agagtaataa atctcttcac    2220
cttccgtcag cattctccga atgtttacca aatttgaaga agttaactct atcaaaaaca    2280
aggtttgact ggaatcaggc atatagatta gggcaggtga aaaatctcca ggtcctaaaa    2340
ctgaaagaaa atgcattcac ggggccgtcc tggaggatgg agccaggagg tttcaagaaa    2400
cttcaggtct tgtggattga aatggcagat ttcgtgtcgt gggaggcatc aaactgtcct    2460
ttcccaagac ttaggagcct tttcctgatc tcctgtctta atcttgaggc tgtgccactc    2520
gatctttccc atttggataa ccttcaagag atgacgttgg aaaacacaag caaagcaagc    2580
aaatctgcaa gagaaatag atgcgagaaa aagaagaagc aagctgatga tccagaaact    2640
ggcaaattca agctcactat tccctactga                                     2670
```

SEQ ID NO: 20            moltype = AA   length = 889
FEATURE                  Location/Qualifiers
REGION                   1..889
                         note = Protein NRC6-2a
source                   1..889
                         mol_type = protein
                         organism = Solanum lycopersicum
SEQUENCE: 20
```
MDPFTAAALT TAVTATVSLL VENLSHLISY NWKLYTGLKK SCEDLYDEVK RLNAFLVDNA    60
NQRSNSTQWD VLVDKIRRTV YKAEDVVDKL LIQGKLDQES NIAKKMFHKT YKNRNFTEEI    120
NEILVEVRKI LEENQHLFEA NPTIDHHQPE KVVQEEQGSS LENHEVVGFD EEATKVINRL    180
VEGAECLDVI PVVGMPGLGK TTLARKIFND PKISREFFSY IWVFIGQSTC VKRDILFNIL    240
KGFTNSFDEF KNRNEASITD EIRKRVANGG KCLIVLDDVW DTNVVDIVKT VFPDNKKAHR    300
IMMTTRHEDI ARSVNKYPHN LKFLDGDESF QLLEKRAFGV SRCPVELVEH GEAIVAKCSG    360
VPLTIVVIAG ALRGRTSEID WKVVRENVGK HLIQEDKLQR CVNVVRLSYN HLPQEKKSCF    420
LYFGAFPQGF DIPAWKLIRL WIAEGLIMSK LSGNEIEEIA EYYLNDFANR NLVMVMKKKS    480
NDRIKTCRVH DMLHEFCVEE ATRLTLFKQV CLTSDQDIQN SITCRRVSIQ SSVPQNFISK    540
KTVEEHVRSL LCFSSKQKQV DFSNIDVKLI PTAFPLMRVL DIESVKFSIP REFYQLLHLR    600
YIAMSGDFEQ LPKLFTSFCN AQTLILNTSK PTLDIKADIW NMPRLRHLHT NKPAILPPPT    660
SSSSSSTNSC LLQTLSLVTP ESCKGNVLSK ARNVKKMSVK GNLTPFLETS KGEFFSNFQV    720
LKLLESLTLL NDDKSNKSLH LPSAFSECLP NLKKLTLSKT RFDWNQAYRL GQVKNLQVLK    780
LKENAFTGPS WRMEPGGFKK LQVLWIEMAD FVSWEASNCP FPRLRSLFLI SCLNLEAVPL    840
DLSHLDNLQE MTLENTSKAS KSAREIECEK KKKQADDPET GKFKLTIPY              889
```

SEQ ID NO: 21            moltype = DNA   length = 8421
FEATURE                  Location/Qualifiers
misc_feature             1..8421
                         note = Genomic NRC6-2c
source                   1..8421
                         mol_type = genomic DNA
                         organism = Solanum lycopersicum
SEQUENCE: 21
```
agtttgtcaa atcatcaaaa ctacaaataa cagttttgat tttggactct ctttttttta    60
aaaaaatttt aatattatat tatattttta aattaatttt ttattggccc acgggccggc    120
cctaccaata tttctcaagc ccccaaatg agcaggctta ttcaggctgg acaaaaaaat     180
cattttctta aatgggtcc aaaaatctta gcccaatcct attaaatctc gggttaggcc     240
aggccgaccc aacggaccta gcccatattg acggctctag ttagaaccat gaaaattatg    300
tgatatattt tggtcaaatg tttctcacaa tgaaacttaa aaacctaatg aaggctagct    360
tgaatatatg gccatacaac aaaataaaat gacaaaactg atcccttatc tttgctagta    420
gtttcaatat agtcctttta agtatcaatc aaatactttt gatcattttt agtaagataa    480
attttgtaga taaataacaa attcgttgct aattctgttt agtgataaat tatcaaagat    540
attttttaac cacaagcaat ttaacgatga aattcgtacc taattctatt ttattttat    600
ataaaatatt atcgaaactt taatgtttta aattcaattt aaactgtgaa aatatttta    660
aaaaatctat ttattttatt cttctatatt ttgtgctcaa tatagttgga tgtagttcac    720
acttcacaat tgtattacat aatttttctta tatccttaat cttctttgca ttgtttttggg   780
aaaaaaatgc aattttataa taataattat cgtcataata ataataatta gtcaagtgaa    840
taataaaaat aatttctgtt aagaattatt ttaatcaaat tatccacctt cttaagaatc    900
tcatcatttc aagtaaacgt ggatctgcca ataagataaa ggacctagga agtgatgata    960
aaaaatattt atttcaaatt gggatgattt caataaacga ataaaattct tgtaacttag    1020
gaattaattt tttaactttt tcttttataa caactctatt ataagactga ataaaataat    1080
gactacatta cccccccacta tattaattaa ttctattta tataaacttt acagaaaaac    1140
```

```
ctcggcaaag cgaacacctt gtttcccgtg ctcaccaacc acaacaatta cgcggttaat   1200
atctcaaatg gttatacaat tttaaaaaat tattcggtaa aatcattaaa ttttatttta   1260
tattattaga gttactcaat ttaagtatat ttaaatcggt gaaatcacta aactaaattt   1320
atcgataaat taagtgttgt taaaattttg ttctaaacga ctataggaaa taggtttcta   1380
caaataactg tcggcgcata gtttctttca aggaaaaatg cagagtgcca agtaaggccg   1440
aaaaggggtaa aaaattatct ataaaataag tccggatggg ggaataataa gacttgtata   1500
agtgtgtctc tgaaatttcg gacataaatt aggagatact tatgtatttt cctttgtttc   1560
agttatttgt ttcacctctt ccataatgtt aaatccttaa ttatatatgt ctacctctgt   1620
acgtcatatt atagatagaa aaaaaaatta aatatgtgtc tttataatca acactctata   1680
taagtatcac tgaaagatct agcgacgtta aatacaacta aatatttttt attttgctac   1740
cttgaataat aattctcaat tgtttacaag ctttccaaca acacccattt attttcaacc   1800
aatgtgaacc tctttccaac aacacttaat ttttctatca atatgaactt aattattcaa   1860
atgttagctg tcattggatt attaaattgt taatgttgta aggtgatggt gtattatatt   1920
aagaattaac taataatact taaagacttg gttaatctaa ttcagagtca acataaagtt   1980
aattcattcc acatctttat atacacacaa ctatggcaat aacaacatag caattgtcat   2040
ctctaaatta ctactactat tcttcttctt catcaattta atcctcagaa atggatccgt   2100
ttacggccgc tgccttaacc actgcagtga cagccacggt gagtcttctg gtggagaact   2160
tgtcgcatct tataagttat aattggaagt tgtatacagg attgaagaaa tcatgcgaag   2220
atttgtatga tgaagtgaag cgattaaatg catttttagc cgataacgcg aatcagagaa   2280
gtaatagtac gcaatgggat gtattagtcg ataaaattcg acgtacagta tataaagcag   2340
aggatgttgt tgataaatta ttgattcagg gcaagttaga ccaagagagt aatatagcta   2400
gaaaaatgtt tcacaaaact tacaaaaaca ggaattttac tgaggaaatc aatgagatac   2460
ttgtagaggt gaggaaaatc cttgatgaaa atcaacatct gtttgaggca aacccgacga   2520
ttgatcatca tcagcctgaa aaagttgtcc aggaggaaca ggtacgttta cacgaaattt   2580
cgattttaat gtgatttatt gaaatatgaa atgaactatg atttgctcgt ttagtaaaac   2640
tgtataagag ttggagaaat agtacttcct ctgtttaat atgcattatt tgtttgaact   2700
tagttaaagt ttaatctaaa ttattcagat ctaggacaag gcataagtaa ggcaaaggat   2760
agaagtacct ttctagatta tgactcaaat tccgtagaat tttactttag ttaaggtgtg   2820
tctctgaaat tcagacaatt aaaggtcacc accaaccatt attacatgca caaatcacta   2880
tcgataattg ccaccattgg tcaacattat atatcgctga cctccatcta tcattaactg   2940
tcagtatgat tccactatta attatcaaat ggtcaccaac aacaaccaca attaatcact   3000
aaggccaatc actatactgt tcacaaccac tatcatctgt caacactatc taaaatcgat   3060
acacacaatc actatcatta gtcattacca ccaccgattg tcacattttc ttgtagtgaa   3120
tgatggggat tgaaaatatg aagaataaaa tagacatgca taggataagg ggacatattt   3180
ttcatagttg aatggacat tgaaaattaa taacttcac atgatcataa ctcatttggt   3240
acctgatgga ataatttctt gttatgatga tacaatcaag acaagtagcc ttaataaatt   3300
gtttaatttg tccatcttac agggttcgtc attggaaaat cacgaagtgg ttggatttga   3360
tgaagaagca acgaaagtga tcaatcgtct ggttgaagga gcagagtgtc tagatgttat   3420
cccggttgta ggaatgccgg gacttggtaa aaccacactg gcaagaaaaa tctttaatga   3480
tcctaagatt tcgcgagaat ttttcagcta catttgggtt ttcatcggac aatcaacgtg   3540
tgtaaaaagg gatatccttt ttaatattct gaaagggttc acaaattcat ttgatgaatt   3600
caaaaacaga aatgaggcaa gcataactga tgaaatacgt aagcgtgtgg ctaatggagg   3660
taaatgtctc attgtcttgg atgatgtgtg ggatacaaat gttgtagata ttgtcaagac   3720
agttttccct gataacaaaa aagcccacag gatcatgatg accactcgac acgaagacat   3780
tgctagatct gtcaataaat atccccacaa tctgaaattt ctggatggag atgaaagttt   3840
ccagctgcta gaaaagagag cttttggcgt tagccgttgt cctgttgagt tagtagaaca   3900
tggagaagcc attgtagcaa aatgtagtgg agtaccactt acaattgtgg taattgcagg   3960
agctttaaga ggtcgtacga gtgaaattga ttggaaagta gttagggaaa atgtggggaa   4020
gcatcttata caagaagaca aacttcgagag atgtgtgaat gttgtgagat tgagttacaa   4080
tcatttgcct caagaaaaaa aatcttgctt cttgtatttt ggtgcctttc ctcaaggatt   4140
tgatatcccc gcttggaaat tgattcgact ctggattgct gagggactca taatgtccaa   4200
gttgtcgggc aacgaaattg aagagatagc agagtattat cttaatgact ttgccaacag   4260
gaacttagtg atggtgatga aaaagaaatc taatgatcga ataaaaacat gtcgtgttca   4320
cgacatgtta catgagtttt gcgttgaaga ggctactaga ttgactcttt tcaaacaagt   4380
atgtctcaca tctgatcaag acatacagaa ctcaattact tgtcgtcgtg tctctattca   4440
atcatctgtt cctcaaaact tcatctcaaa aaagacagtt gaagaacatg ttaggtcatt   4500
gttatgtttt tcctcaaaac aaaaacaagt tgactttcct aatatcgacg tcaagctcat   4560
ccctaccgca tttccactta tgagagtctt agacattgaa tccgtcaagt ttagtattcc   4620
cagggaattt taccagctat tgcacttgag gtatatcgct atgtcaggtg atttcgagca   4680
acttcctaaa ctctttactt ctttctgtaa tgcacaaact ctcattctaa atacttccaa   4740
gcccacccct gatataaaag ctgacatatg gaacatgcca cgtttgcgtc atctgcacac   4800
caacaaacct gcaatcttac caccccctac aagtagtagt agtagtagta caaattcttg   4860
tttgttgcaa actctatctc tggttacacc agaaagctgc aagggaaacg ttcttttcaaa   4920
ggctcgtaat gtcaagaaaa tgagtgttaa aggtaatttg acacctttc ttgaaactag   4980
caagggtgaa ttttttcagca attttcaagt gctaaagctc ctggaaagtt taacactgct   5040
aaatgatgat aagagtaata aatctcttca ccttccgtca gcattctccg aatgtttacc   5100
aaatttgaag aagttaactc tatcaaaaac aaggtttgac tggaatcagg catatagatt   5160
agggcaggtg aaaaatctcc aggtcctaaa actgaaagaa aatgcattca cggggccgtc   5220
ctggaggatg gagccaggag gtttcaagaa acttcaggtc ttgtggattg aaatggcaga   5280
tttcgtgtcg tgggaggcat caaactgtcc tttcccaaga cttaggagcc ttttcctgat   5340
ctcctgtctt aatcttgagg ctgtgccact cgatctttcc catttggata accttcaaga   5400
gatgacgttg gaaaacacaa gcaaagcaag caaatctgca agagaaatag aatgcgagaa   5460
aaagaagaag caagctgatc atccagaaac tggcaaattc aagctcacta ttccctactg   5520
aagctgattt caatgccaca aagtgaagtt gttataaggt tagtccaatt ctctccctct   5580
cgtatcagta aatatcgaat aagatatttt tcaataagat tgcatctatc cctatagtct   5640
ctccacgcag aattagtagg tagcagtgtg ttgtcttgct gtctcgttca tatcaatagt   5700
catagtattg ctcctatagt ttcttatcct tcgatttttc gttactatac gttgtccctt   5760
atacctcgat attagtaatg cttgttgtag tttctcttat gttactatct gctgtttttg   5820
ttattacctg ttgtttcttg tatttccgtc atttctttt gggactcctt tgaactttct   5880
```

```
ccttgagaca aaggtcaatc ggaaacaacc tacctctctt tctttgagat aaggttcctc   5940
cccagactct attttgtggg actacactga gtatattgtt ttgggtttcg cacttcactg   6000
aaacattaaa ttgggcaaca ttactctgtt atactaataa tacagatttt aggtgccttg   6060
atatcaaaca tagagtaaat tcaattattt tcgtgttcat cacattcctc atctattttt   6120
ctcttactta ttttcctcct ttttagcagg agagtatcga ggcatggtga tgcatttgca   6180
gtctcagttt tgattacctg ttccaataaa gaaacttgtt acaagtatgt tttgttgatt   6240
caaacatgcc aagtttgaaa acgaagtttt atattaatgt ttttgcgttt tctttcagtg   6300
ctgaataatt tgtctaatct gtagttgatg tttggatatc tatgtattgt tcgattgaca   6360
cgagttgttt atactatcat ttgttgttta tgaatatgta aaacatattt gatttatgtt   6420
tgcaacgtca acgtgaacat tcaattagtc taatcaaagt ctagatctaa aattgattaa   6480
tttaagttta taatttattt tgaattatta tctaaaaccg aagactttct actcgaaaat   6540
cgaaatcata gctgacagtc tccataaata tatttgcaat tgaataacat aataagcatt   6600
tatcagttaa tttttatggag tttttggatt tacgtgatat tcaaacatct cccgcgcata   6660
ttaattatgt gaagtaatga agtgtgtaac ataagtcaaa aggtgcataa ataaagagtc   6720
aagggtaata agactttagt ttacttttagg tgtgtctctg aaatttcgat tataatctac   6780
gagatattgt gtcttgtccc aacatttaaa taaaatgaac aaataatttt aattaccaaa   6840
tggatccata gtctgtttag ttgactaatg gaaagattta taggaaggtg agattgtttt   6900
atccctgatt agaggttttg gttcgagttt tgtgtatacg aaaaaattgt gttgaaagcg   6960
tcacttatga ataggcccta taatgtatga ttcgaattta gtctgagttc taatatgaat   7020
tttgaacaca ttgaaaaatt atatcctttg ttaaatttca tggttttaac atcttggaag   7080
taaagaaaaa ggtaaaatat ttttttttc tatttcattt ttttacatgt aatatttgaa   7140
ttcaaaggca gagagagtaa taccccccctt ttatttttat ttgtggatta catatataca   7200
taagaactag aaaaatgttt atattttcga cttgacaatg atagaatgta aatgttggat   7260
atatagaata atttgttgga gcttctacca ttttttgctt accgtcttaa ggttgaaggc   7320
gtagatgttt attatccgaa taattccttt ttgtcgataa tcaagcatca atattagatt   7380
agtagccgac cctcttctct tacctctcta aacaattttt caatatttcc attttggttg   7440
gtaaaaatat tagagaacat tttctctata gaaatatcat gtgtttattc agaattgtta   7500
tttactacat atattttaa taattaaaaa cctataaatt taatagttta cattcacaat   7560
tattgcttgt tgctgttctt ttgccttgtg tttctaattt ttaccgttat taaatatgca   7620
tgtgattagt tgaaatatca aatctcatat taaatgaaaa aatgaaagtc aacgaagcat   7680
ggtagctgtc aaatacgctc caactcaaag cattactgtc atgatggatt tcctattgat   7740
ccatcgtgaa aaattgaacg atatgttggc acatgtcaga atgcttaaaa tatcgaatta   7800
atataattga atttaacttt gaaaattaat caaattaact ttcgaaaagc gctacctgac   7860
aattaaaaat agaaggagtg agcagtgaac ttaaactaat ctatttcaga tctctagagt   7920
ttgataaact aattgacagt tcaacatttg cagatctaac ttcaacattt gcttcttgta   7980
aatctgcaac aaggcaaact accatttgag agtaaagaaa aagtataat ataatgtttt   8040
tctagttttc attttacatg tattttttgtg attcacttga tttgaatgaa acatacatta   8100
caagaactag aaaacgaatt tgtatttttg acttagataa ttataaaatg ttagatgatt   8160
gtcataattt gtagtattca ctcttgtttt tagtaaatat actctttctt aaatgtgatt   8220
gatttacaga ttatatattt tagaattttt gcttattaaa agaaaaatta attagtggcg   8280
gaaatttgag gtgaattcgt gaagaatgga agaagttgga aatttgagag ttttacatgt   8340
gttttttaag gtagaagaaa caaaaagaat ccatttgatc taaaattcca attgaaaagt   8400
attaaaagtt gtttgggatc t                                              8421
```

```
SEQ ID NO: 22          moltype = DNA   length = 2670
FEATURE                Location/Qualifiers
misc_feature           1..2670
                       note = CDS NRC6-2c
source                 1..2670
                       mol_type = genomic DNA
                       organism = Solanum lycopersicum
SEQUENCE: 22
atggatccgt ttacggccgc tgccttaacc actgcagtga cagccacggt gagtcttctg    60
gtggagaact tgtcgcatct tataagttat aattggaagt tgtatacagg attgaagaaa   120
tcatcgcgaag atttgtatga tgaagtgaag cgattaaatg cattttttagc cgataacgat   180
aatcagagaa gtaatagtac gcaatgggat gtattagtcg ataaaattcg acgtacagta   240
tataaagcag aggatgttgt tgataaatta ttgattcagg gcaagttaga ccaagagagt   300
aatatagcta gaaaaatgtt tcacaaaact tacaaaaaca ggaattttac tgaggaaatc   360
aatgagatac ttgtagaggt gaggaaaatc cttgatgaaa atcaacatct gtttgaggca   420
aacccgacga ttgatcatca tcagcctgaa aaagttgtcc aggaggaaca gggttcgtca   480
ttggaaaatc acgaagtggt tggatttgat gaagaagcaa cgaaagtgat caatcgtctg   540
gttgaaggag cagagtgtct agatgttatc ccggttgtag gaatgccggg acttggtaaa   600
accacactgg caagaaaaat cttaatgat cctaagattt cgcgagaatt tttcagctac   660
atttgggttt tcatcggaca atcaacgtgt gtaaaaaggg atattcctttt taatattctg   720
aaagggttca caaattcatt tgatgaattc aaaaacagaa atgaggcaag cataactgat   780
gaaatacgta agcgtgtggc taatggaggt aaatgtctca ttgtcttgga tgatgtgtgg   840
gatacaaatg ttgtagatat tgtcaagaca gttttcccctg ataacaaaaa agcccacagg   900
atcatgatga ccactcgaca cgaagacatt gctagatgtc tcaataaata tccccacaat   960
ctgaaatttc tggatggaga tgaaagtttc cagctgctag aaaagagagc ttttggcgtt  1020
agccgttgtc ctgttgagtt agtagaacat ggagaagcca ttgtagcaaa atgtagtgga  1080
gtaccactta caattgtggt aattgcagga gctttaagag gtcgtacgag tgaaattgat  1140
tggaaagtag ttagggaaaa tgtgggggaag catcttatac aagaagacaa acttcagaga  1200
tgtgtgaatg ttgtgagatt gagttacaat catttgcctc aagaaaaaaa atcttgcttc  1260
ttgtattttg gtgcctttcc tcaaggattt gatatcccgt gatgaaatt gattcgactc  1320
tggattgctg agggactcat aatgtccaag ttgtcgggca acgaaattga agagatagca  1380
gagtattatc ttaatgactt tgccaacagg aacttagtga tggtgatgaa aaagaaatct  1440
aatgatcgaa taaaaacatg tcgtgttcac gacatgttac atgagtttttg cgttgaagag  1500
gctactagat tgactctttt caaacaagta tgtctcacat ctgatcaaga catacagaac  1560
tcaattactt gtcgtcgtgt ctctattcaa tcatctgttc ctcaaaactt catctcaaaa  1620
```

```
aagacagttg aagaacatgt taggtcattg ttatgttttt cctcaaaaca aaaacaagtt   1680
gacttttcta atatcgacgt caagctcatc cctaccgcat ttccacttat gagagtctta   1740
gacattgaat ccgtcaagtt tagtattccc agggaatttt accagctatt gcacttgagg   1800
tatatcgcta tgtcaggtga tttcgagcaa cttcctaaac tctttacttc tttctgtaat   1860
gcacaaactc tcattctaaa tacttccaag cccacccttg atataaaagc tgacatatgg   1920
aacatgccac gtttgcgtca tctgcacacc aacaaacctg caatcttacc accccctaca   1980
agtagtagta gtagtagtac aaattcttgt ttgttgcaaa ctctatctct ggttacacca   2040
gaaagctgca agggaaacgt tctttcaaag gctcgtaatg tcaagaaaat gagtgttaaa   2100
ggtaatttga caccttttct tgaaactagc aagggtgaat ttttcagcaa ttttcaagtg   2160
ctaaagctcc tggaaagttt aacactgcta aatgatgata agagtaataa atctcttcac   2220
cttccgtcag cattctccga atgtttacca aatttgaaga agttaactct atcaaaaaca   2280
aggtttgact ggaatcaggc atatagatta gggcaggtga aaaatctcca ggtcctaaaa   2340
ctgaaagaaa atgcattcac ggggccgtcc tggaggatga agccaggagg tttcaagaaa   2400
cttcaggtct tgtggattga aatggcagat ttcgtgtcct gggaggcatc aaactgtcct   2460
ttcccaagac ttaggagcct tttcctgatc tcctgtctta atcttgaggc tgtgccactc   2520
gatctttccc atttggataa ccttcaagag atgacgttgg aaaacacaag caaagcaagc   2580
aaatctgcaa gagaaataga atgcgagaaa aagaagaagc aagctgatca tccagaaact   2640
ggcaaattca agctcactat tccctactga                                     2670
```

```
SEQ ID NO: 23          moltype = AA  length = 889
FEATURE                Location/Qualifiers
REGION                 1..889
                       note = Protein NRC6-2c
source                 1..889
                       mol_type = protein
                       organism = Solanum lycopersicum
SEQUENCE: 23
MDPFTAAALT TAVTATVSLL VENLSHLISY NWKLYTGLKK SCEDLYDEVK RLNAFLADNA   60
NQRSNSTQWD VLVDKIRRTV YKAEDVVDKL LIQGKLDQES NIARKMFHKT YKNRNFTEEI   120
NEILVEVRKI LDENQHLFEA NPTIDHHQPE KVVQEEQGSS LENHEVVGFD EEATKVINRL   180
VEGAECLDVI PVVGMPGLGK TTLARKIFND PKISREFFSY IWVFIGQSTC VKRDILFNIL   240
KGFTNSFDEF KNRNEASITD EIRKRVANGG KCLIVLDDVW DTNVVDIVKT VPPDNKKAHR   300
IMMTTRHEDI ARSVNKYPHN LKFLDGDESF QLLEKRAFGV SRCPVELVEH GEAIVAKCSG   360
VPLTIVVIAG ALRGRTSEID WKVVRENVGK HLIQEDKLQR CVNVVRLSYN HLPQEKKSCF   420
LYFGAFPQGF DIPAWKLIRL WIAEGLIMSK LSGNEIEEIA EYYLNDFANR NLVMVMKKKS   480
NDRIKTCRVH DMLHEFCVEE ATRLTLFKQV CLTSDQDIQN SITCRRVSIQ SSVPQNFISK   540
KTVEEHVRSL LCFSSKQKQV DFSNIDVKLI PTAFPLMRVL DIESVKFSIP REFYQLLHLR   600
YIAMSGDFEQ LPKLFTSFCN AQTLILNTSK PTLDIKADIW NMPRLRHLHT NKPAILPPPT   660
SSSSSSTNSC LLQTLSLVTP ESCKGNVLSK ARNVKKMSVK GNLTPFLETS KGEFFSNFQV   720
LKLLESLTLL NDDKSNKSLH LPSAFSECLP NLKKLTLSKT RFDWNQAYRL GQVKNLQVLK   780
LKENAFTGPS WRMEPGGFKK LQVLWIEMAD FVSWEASNCP FPRLRSLFLI SCLNLEAVPL   840
DLSHLDNLQE MTLENTSKAS KSAREIECEK KKKQADHPET GKFKLTIPY                 889
```

```
SEQ ID NO: 24          moltype = DNA  length = 2673
FEATURE                Location/Qualifiers
misc_feature           1..2673
                       note = CDS NRC6-2b
source                 1..2673
                       mol_type = genomic DNA
                       organism = Solanum lycopersicum
SEQUENCE: 24
atggatccgt ttacggcggc tgcattaacc actgcggtga cagccacggt gagccttctg   60
gtggagaact tgtcgcatct tataagttat aattggaagt tgtatacagg attgaagaaa   120
tcatgcgaag atttgtatga tgaagtgaag cgattaaatg catttttagt cgataacgcg   180
aatcagagaa gtaatagtac gcaatgggat gtattagtcg ataaaattcg acgtacagta   240
tataaagcag aggatgttgt tgataaatta ttgattcagg gcaagttaga ccaagagagt   300
aatatagcta aaaagatgtt tcacaaaact tacaaaaaca ggaattttac tgaggaaatc   360
aatgagatac ttgtagaggt gaggaaaatc cttgaggaaa atcaacatct gtttgaggca   420
aacccgacga ttgatcatca tcagcctgaa aaagttgtcc aggaggaaca gggttcgtca   480
ttggaaaatc acgaagtggt tggatttgat gaagaagcaa cgaaagtgat caatcgtctg   540
gttgaaggag cagagtgtct agatgttatc ccggttgtag gaatgccggg acttggtaaa   600
accacactgg caagaaaaat ctttaatgat cctaagattt cgcgagaatt tttcagctac   660
atttgggttt tcatcggaca atcaacgtgt gtaaaaaggg atatcctttt taatattctg   720
aaagggttca caattcatt tgatgaattc aaaaacagga tgaggcaag cataactgat   780
gaaatacgta agcgtgtggc taatggaggt aaatgtctca ttgtcttgga tgatgtgtgg   840
gatacaaatg ttgtagatat tgtcaagaca gttttccctg ataacaaaa agcccacagg   900
atcatgatga ccactcgaca cgaagacatt gctagatctg tcaataaata tccccacaat   960
ctgaaatttc tggatggaga tgaaagtttc cagctgctag aaaagagagc ttttggcgtt   1020
agccgttgtc ctgttgagtt agtagcaaca tgatagtgga ttgtagaaca gcatgagaca   1080
gtaccactta caattgtggt aattgcagga gctttaagag gtcgtacgag tgaaattgat   1140
tggaaagtag ttagggaaaa tgtggggaag catcttatac aagaagacaa acttcagaga   1200
tgtgtgaatg ttgtgagatt gagttacaat catttgcctc aagaaaaaaa atcttgcttc   1260
ttgtattttg gtgcctttcc tcaaggattt gatatccccg cttggaaatt gattcgactc   1320
tggattgctg agggactcat aatgtccaag ttgtcgggca acgaaattga agagatagca   1380
gagtattatc ttaatgactt tgccaacagg aactcagtga tggtgatgaa aaagaaatct   1440
aatgatcgaa taaaaacatg tcgtgttcac gacatgttac atgagttttg cgttgaagag   1500
gctactagat tgactctttt caaacaagta tgtctcacat ctgatcaaga catacagaac   1560
tcaattactt gtcgtcgtgt ctctattcaa tcatctgttc ctcaaaactt catctcaaaa   1620
aagacagttg aagaacatgt taggtcattg ttatgttttt cctcaaaaca aaaacaagtt   1680
```

```
gacttttcta atatcgacgt caagctcatc cctaccgcat ttccacttat gagagtctta  1740
gacattgaat ccgtcaagtt tagtattccc agggaatttt accagctatt gcacttgagg  1800
tatatcgcta tgtcaggtga tttcgagcaa cttcctaaac tctttacttc tttctgtaat  1860
gcacaaactc tcattctaaa tacttccaag cccacccttg atataaaagc tgacatatgg  1920
aacatgccac gtttgcgtca tctgcacacc aacaaacctg caatcttcc accccctaca   1980
agtagtagta gtagtagtag tacaaattct tgtttgttgc aaactctatc tctggttaca  2040
ccagaaagct gcaagggaaa cgttctttca aaggctcgta atgtcaaaaa aatgagtgtt  2100
aaaggtaatt tgacgccttt tcttgaaact agcaagggtg aatttttcag caattttcaa  2160
gtgctaaagc tcctggaaag tttaacactg ctaaatgatg ataagagtaa taaatctctt  2220
caccttccgt cagcattctc cgaatgttta ccaaatttga agaagttaac tctatcaaaa  2280
acaaggtttg actggaatca ggcatataga ttagggcagg tgaaaaatct ccaggtccta  2340
aaactgaaag aaaatgcatt cacggggccg tcctggagga tggagccagg aggtttcaag  2400
aaacttcagg tcttgtggat tgaaatggca gatttcgtgt cgtgggaggc atcaaactgt  2460
cctttcccaa gacttaggag ccttttcctg atctcctgtc ttaatcttga ggctgtgcca  2520
ctcgatcttt cccatttgga taaccttcaa gagatgacgt tggaaaacac aagcaaagca  2580
agcaaatctg caagagaaat agaatgcgag aaaaagaaga agcaagctga tcatccagaa  2640
actggcaaat tcaagctcac tattccctac tga                                2673
```

```
SEQ ID NO: 25           moltype = AA  length = 890
FEATURE                 Location/Qualifiers
REGION                  1..890
                        note = Protein NRC6-2b
source                  1..890
                        mol_type = protein
                        organism = Solanum lycopersicum
SEQUENCE: 25
MDPFTAAALT TAVTATVSLL VENLSHLISY NWKLYTGLKK SCEDLYDEVK RLNAFLVDNA   60
NQRSNSTQWD VLVDKIRRTV YKAEDVVDKL LIQGKLDQES NIAKKMFHKT YKNRNFTEEI   120
NEILVEVRKI LEENQHLFEA NPTIDHHQPE KVVQEEQGSS LENHEVVGFD EEATKVINRL   180
VEGAECLDVI PVVGMPGLGK TTLARKIFND PKISREFFSY IWVFIGQSTC VKRDILFNIL   240
KGFTNSFDEF KNRNEASITD EIRKRVANGG KCLIVLDDVW DTNVVDIVKT VFPDNKKAHR   300
IMMTTRHEDI ARSVNKYPHN LKFLDGDESF QLLEKRAFGV SRCPVELVEH GEAIVAKCSG   360
VPLTIVVIAG ALRGRTSEID WKVVRENVGK HLIQEDKLQR CVNVVRLSYN HLPQEKKSCF   420
LYFGAFPQGF DIPAWKLIRL WIAEGLIMSK LSGNEIEEIA EYYLNDFANR NLVMVMKKKS   480
NDRIKTCRVH DMLHEFCVEE ATRLTLFKQV CLTSDQDIQN SITCRRVSIQ SSVPQNFISK   540
KTVEEHVRSL LCFSSKQKQV DFSNIDVKLI PTAFPLMRVL DIESVKFSIP REFYQLLHLR   600
YIAMSGDFEQ LPKLFTSFCN AQTLILNTSK PTLDIKADIW NMPRLRHLHT NKPAILPPPT   660
SSSSSSSTNS CLLQTLSLVT PESCKGNVLS KARNVKKMSV KGNLTPFLET SKGEFFSNFQ   720
VLKLLESLTL LNDDKSNKSL HLPSAFSECL PNLKKLTLSK TRFDWNQAYR LGQVKNLQVL   780
KLKENAFTGP SWRMEPGGFK KLQVLWIEMA DFVSWEASNC PFPRLRSLFL ISCLNLEAVP   840
LDLSHLDNLQ EMTLENTSKA SKSAREIECE KKKKQADHPE TGKFKLTIPY               890
```

```
SEQ ID NO: 26           moltype = DNA  length = 2673
FEATURE                 Location/Qualifiers
misc_feature            1..2673
                        note = CDS NRC6-3
source                  1..2673
                        mol_type = genomic DNA
                        organism = Solanum lycopersicum
SEQUENCE: 26
atggatccgt ttacggccgc tgccttaacc actgcagtga cagccacggt gagtcttctg  60
gtggagaact tgtcgcatct tataagttat aattggaagt tgtatacagg attgaagaaa  120
tcatgcgaag atttgtatga tgaagtgaag cgattaaatg cattttttagt cgataacgcg  180
aatcagagaa gtaatagtac gcaatgggat gtattagtcg ataaaattcg acgtacagta  240
tataaagcag aggatgttgt tgataaaatta ttgattcagg gcaagttaga ccaagagagt  300
aatatagcta aaaagatgtt tcacaaaact tacaaaaaca ggaattttac tgaggaaatc  360
aatgagatac ttgtagaggt gaggaaaatc cttgaggaaa tcaacatct gtttgaggca   420
aacccgacga ttgatcatca tcagcctgaa aaagttgtcc aggaggaaca gggttcatcg  480
ttggaaaatc acgaagtggt aggatttgat gaagaagcaa cgaaagtgat caatcgtctg  540
gttgaaggag cagagcgtct agatgttatc ccggttgtag aatgccgggg acttggtaaa  600
accacactgg caagaaaaat ctttaatgat ccgaagattt cgcgagaatt tttcagctac  660
atttgggttt tcatcggaca atcaacgtgt gtaaaaaggg atatccttt taatattctg   720
aaagggttca caaattcatt tgatgaattc aaaaacagaa atgaggcaga cataactgat  780
gaaatacgta agcgtgtggc taatggaggt aaatgtctca ttgtcttgga tgatgtgtgg  840
gatccaaatg ttgtagatat tgtcaagaca gttttccctg ataacaaaaa agcccacagg  900
atcatgatga ccactcgaca cgaagacatt gctagatctg tcaataaata tcctcacaat  960
ctgaaatttc tggatggaga tgaaagtttc cagctgctag aaaagagagc ttttggcgtt  1020
agccgttgtc cagttgagtt agtagaacat ggagaagcca ttgtagcaaa atgtagtgga  1080
gtaccactta caattgtggt aattgcagga gctttaagag gtcgtacgag tgaaattgat  1140
tggaaagtag ttagggaaaa tgtggggaag catcttatac aagaagacaa acttcagaga  1200
tgtgtgaatg ttgtgagatt gagttacaat catttgcctc aagaaaaaaa atcttgcttc  1260
ttgtatttttg gtgcctttcc tcaaggattc gatatccccg cttggaagtt gattcgactc  1320
tggattgctg agggactcat aatgtccaag ttgtcaggca acgaaattga agagatagca  1380
gagtattatc ttaatgactt tgccaacagg aacttagtga tggtgataaa gaagaaatct  1440
aatgatcgaa taaaaacatg tcgtgttcac gacatgttac atgagtttgt cgttgaagag  1500
gctactagat tgactctttt caaacaagta tgtctcacat ctgatcaaga catacaaaac  1560
tcaattgctt gtcgtcgtgt ctctattcaa tcatctgttc ctcaaaactt catctcaaaa  1620
aagacagttg aagagcatgt taggtcattt ttatgttttt cctcaaaaca aaaacaagtt  1680
gactttttcta atatcgacgt caagctcatc cctgccgcat ttccacttat gagagtctta  1740
```

```
gacattgaat ccgtcaagtt tagtattccc agggaatttt accagctatt gcacttgagg   1800
tatatcgcta tctcaggtga tttcgagcaa cttcctaaac tctttacttc tttctgtaat   1860
gcacaaactc tcattctaaa tacttccaag cccacccttg atataaaagc tgacatatgg   1920
aacatgccac gtttgcgtca tctgcgcacc aacaaacctg caatcttacc accccctaca   1980
agtagtagta gtagtagtag tacaaattct tgtttttttgc aaactctatc tctggttaca   2040
ccagaaagct gcaagggaaa tgttctttca aaagctcgta atgtcaaaaa aatgagtgtt   2100
aaaggtaatt tgacgccttt tcttgaaact agcaagggtg aatttttcag caattttcaa   2160
gtgctaaagc tcctggaaag tttaacactg ctaaatgatg ataagagtaa caaatctctt   2220
caccttccgt cagcattctc cgaatgttta ccaaatttga agaagttaac tctatcaaaa   2280
acaaggtttg actggaatca ggcatataga ttggggcagg tgaaaaatct ccaggtccta   2340
aaactgaaag aaaatgcatt catggggccg tcctggagga tggagccagg aggttttcaag   2400
aaacttcagg tcttgtggat tgaaatggca gatttcgtgt cgtgggaggc atcaaactgt   2460
cctttcccaa gacttaggag cctttttcctg atctcctgtc ttaatcttga ggctgtgcca   2520
ctcgatcttg cccatttgga taaccttcaa gagatgacgt tggaaaacac aagcaaagca   2580
agcaaatctg caagagaaat agaatgcgag aaaaagaaga agcaagctga tcatccagaa   2640
agtggcaaat tcaagctcac tattccctac tga                                2673
```

```
SEQ ID NO: 27             moltype = AA   length = 890
FEATURE                   Location/Qualifiers
REGION                    1..890
                          note = Protein NRC6-3
source                    1..890
                          mol_type = protein
                          organism = Solanum lycopersicum
SEQUENCE: 27
MDPFTAAALT TAVTATVSLL VENLSHLISY NWKLYTGLKK SCEDLYDEVK RLNAFLVDNA   60
NQRSNSTQWD VLVDKIRRTV YKAEDVVDKL LIQGKLDQES NIAKKMFHKT YKNRNFTEEI   120
NEILVEVRKI LEENQHLFEA NPTIDHHQPE KVVQEEQGSS LENHEVVGFD EEATKVINRL   180
VEGAERLDVI PVVGMPGLGK TTLARKIFND PKISREFFSY IWVFIGQSTC VKRDILFNIL   240
KGFTNSFDEF KNRNEADITD EIRKRVANGG KCLIVLDDVW DPNVVDIVKT VPPDNKKAHR   300
IMMTTRHEDI ARSVNKYPHN LKFLDGDESF QLLEKRAFGV SRCPVELVEH GEAIVAKCSG   360
VPLTIVVIAG ALRGRTSEID WKVVRENVGK HLIQEDKLQR CVNVVRLSYN HLPQEKKSCF   420
LYFGAFPQGF DIPAWKLIRL WIAEGLIMSK LSGNEIEEIA EYYLNDFANR NLVMVMKKKS   480
NDRIKTCRVH DMLHEFCVEE ATRLTLFKQV CLTSDQDIQN SIACRRVSIQ SSVPQNFISK   540
KTVEEHVRSF LCFSSKQKQV DFSNIDVKLI PAAFPLMRVL DIESVKFSIP REFYQLLHLR   600
YIAISGDFEQ LPKLFTSFCN AQTLILNTSK PTLDIKADIW NMPRLRHLRT NKPAILPPPT   660
SSSSSSSTNS CFLQTLSLVT PESCKGNVLS KARNVKKMSV KGNLTPFLET SKGEFFSNFQ   720
VLKLLESLTL LNDDKSNKSL HLPSAFSECL PNLKKLTLSK TRFDWNQAYR LGQVKNLQVL   780
KLKENAFMGP SWRMEPGGFK KLQVLWIEMA DFVSWEASNC PFPRLRSLFL ISCLNLEAVP   840
LDLAHLDNLQ EMTLENTSKA SKSAREIECE KKKKQADHPE SGKFKLTIPY              890
```

```
SEQ ID NO: 28             moltype = DNA   length = 2673
FEATURE                   Location/Qualifiers
misc_feature             1..2673
                          note = NRC6-1a
source                    1..2673
                          mol_type = genomic DNA
                          organism = Solanum lycopersicum
SEQUENCE: 28
atggatccgt ttacggccgc tgcattaacc actgcggtga cagccacggt gagccttctg   60
gtggagaact tgtcgcatct tataagttat aattggaagt tgtatacagg attgaagaaa   120
tcatgcgaag atttgtatga tgaagtgaag cgattaaatg cattttttagt cgataacgcg   180
aatcagagaa gtaatagtac gcaatgggat gtactagtcg ataaaattcg acgtacagta   240
tataaagcag aggatgttgt tgataaatta ttgattcagg gcaagttaga ccaagagagt   300
aatatagcta aaaagatgtt tcacaaaact tacaaaaaca ggaattttac tgaggaaatc   360
aatgagatac ttgtagaggt gaggaaaatc cttgaggaaa atcaacatct gtttgaggca   420
aacccgacga ttgatcatca tcagcctgaa aaagttgtcc aggaggaaca gggttcgtca   480
ttggaaaatc acgaagtggt tggatttgat gaagaagcaa cgaaagtgat caatcgtctg   540
gttgaaggag cagagtgtct agatgttatc ccggttgtag gaatgccggg acttggtaaa   600
accacactgg caagaaaaat ctttaatgat cctaagattt cgcgagaatt tttcagctac   660
atttgggttt tcatcggaca atcaacgtgt gtaaaaaggg atatccttt taatattctg   720
aaagggttca caaattcatt tgatgaattc aaaaacagaa atgaggcaag cataactgat   780
gaaatacgta agcgtgtggc taatggaggt aaatgtctca ttgtcttgga tgatgtgtgg   840
gatccaaatg ttgtagatat tgtcaagaca gttttccctg ataacaaaaa agcccacagg   900
atcatgatga ccactcgaca cgaagacatt gctagatctg tcaataaata tccccacaat   960
ctgaaatttc tggatggaga tgaaagtttc cagctgctag aaaagagagc ttttggcgtt   1020
agccgttgtc ctgttgagtt agtagaacat ggagaagcca ttgtagcaaa atgtagtgga   1080
gtaccactta caattgtggt aattgcagga gctttaagag tcgtacgag tgaaattgat   1140
tggaaagtag ttagggaaaa tgtggggaag catcttatac aagaagacaa acttcagaga   1200
tgtgtgaatg ttgtgagatt gagttacaat catttgcctc aagaaaaaaa atcttcgcttc   1260
ttgtattttg gtgcctttcc tcaaggattt gatatccccg cttggaaatt gattcgactc   1320
tggattgcta agggactcat aatgtccaag ttgtcaggca cgaaattga agagatagca   1380
gagtattatc ttaatgactt tgccaacagg aacttagtga tggtgatgaa aaagaaatct   1440
aatgatcgaa taaaaacatg tcgtgttcac gacatgttac atgagtttttg cgttgaagag   1500
gctactagat tgactctttt caaacaagta tgtctcacat ctgatcaaga catacagaac   1560
tcaattactc gtcgtcgtgt ctctattcaa tcatctgttc ctcaaaactt catctcaaaa   1620
aagacagttg aagaacatgt taggtcattg ttatgttttt cctcaaaaca aaaacaagtt   1680
gactttttcta atatcgacgt caagctcatc cctaccgcat ttccacttat gagagtctta   1740
gacattgaat ccgtcaagtt tagtattacc agggaatttt accagctatt gcacttgagg   1800
```

-continued

```
tatatcgcta tctcaggtga tttcgagcaa cttcctaaac tctttacttc tttctgtaat   1860
gcacaaactc tcattctaaa tacttccaag cccacccttg atataaaagc tgacatatgg   1920
aacatgccac gtttgcgtca tctgcgcacc aacaaacctg caatcttacc acccccct aca 1980
agtagtagta gtagtagtag tacaaattct tgtttttttgc aaactctatc tctggttaca   2040
ccagaaagct gcaagggaaa tgttctttca aaagctcagta atgtcaaaaa aatgagtgtt   2100
aaaggtaatt tgacgccttt tcttgaaact agcaagggtg aatttttcag caattttcaa   2160
gtgctaaagc tcctggaaag tttaacactg ctaaatgatg ataagagtaa caaatctctt   2220
caccttccgt cagcattctc cgaatgttta ccaaatttga agaagttaac tctatcaaaa   2280
acaaggtttg actggaatca ggcatataga ttggggcagg tgaaaaatct ccaggtccta   2340
aaaatgaaag aaaatgcatt catgggggccg tcctggagga tggagccagg aggtttcaag   2400
aaacttcagg tcttgtggat tgaaatggca gatttcgtgt cgtgggaggc atcaaactgt   2460
cctttcccaa gacttaggag ccttttcctg atctcctgtc ttaatcttga ggctgtgcca   2520
ctcgatcttg cccatttgga taaccttcaa gagatgacgt tggaaaacac aagcaaagca   2580
agcaaatctg caagagaaat agaatgcgag aaaaagaaga agcaagctga tcatccagaa   2640
agtggcaaat tcaagctcac tattccctac tga                                2673

SEQ ID NO: 29            moltype = AA  length = 890
FEATURE                  Location/Qualifiers
REGION                   1..890
                         note = Protein NRC6-1a
source                   1..890
                         mol_type = protein
                         organism = Solanum lycopersicum
SEQUENCE: 29
MDPFTAAALT TAVTATVSLL VENLSHLISY NWKLYTGLKK SCEDLYDEVK RLNAFLVDNA   60
NQRSNSTQWD VLVDKIRRTV YKAEDVVDKL LIQGKLDQES NIAKKMFHKT YKNRNFTEEI   120
NEILVEVRKI LEENQHLFEA NPTIDHHQPE KVVQEEQGSS LENHEVVGFD EEATKVINRL   180
VEGAECLDVI PVVGMPGLGK TTLARKIFND PKISREFFSY IWVFIGQSTC VKRDILFNIL   240
KGFTNSFDEF KNRNEASITD EIRKRVANGG KCLIVLDDVW DPNVVDIVKT VFPDNKKAHR   300
IMMTTRHEDI ARSVNKYPHN LKFLDGDESF QLLEKRAFGV SRCPVELVEH GEAIVAKCSG   360
VPLTIVVIAG ALRGRTSEID WKVVRENVGK HLIQEDKLQR CVNVVRLSYN HLPQEKKSCF   420
LYFGAPPQGF DIPAWKLIRL WIAEGLIMSK LSGNEIEEIA EYYLNDFANR NLVMVMKKKS   480
NDRIKTCRVH DMLHEFCVEE ATRLTLFKQV CLTSDQDIQN SITCRRVSIQ SSVPQNFISK   540
KTVEEHVRSL LCFSSKQKQV DFSNIDVKLI PTAFPLMRVL DESVKFSIT REFYQLLHLR    600
YIAISGDFEQ LPKLFTSFCN AQTLILNTSK PTLDIKADIW NMPRLRHLRT NKPAILPPPT   660
SSSSSSSTNS CFLQTLSLVT PESCKGNVLS KARNVKKMSV KGNLTPFLET SKGEFFSNFQ   720
VLKLLESLTL LNDDKSNKSL HLPSAFSECL PNLKKLTLSK TRFDWNQAYR LGQVKNLQVL   780
KMKENAFMGP SWRMEPGGFK KLQVLWIEMA DFVSWEASNC PFPRLRSLFL ISCLNLEAVP   840
LDLAHLDNLQ EMTLENTSKA SKSAREIECE KKKKQADHPE SGKFKLTIPY               890

SEQ ID NO: 30            moltype = AA  length = 4
FEATURE                  Location/Qualifiers
REGION                   1..4
                         note = N-terminal motif
source                   1..4
                         mol_type = protein
                         organism = Solanum lycopersicum
SEQUENCE: 30
MADA                                                                 4

SEQ ID NO: 31            moltype = DNA  length = 23
FEATURE                  Location/Qualifiers
misc_feature             1..23
                         note = Forward primer
source                   1..23
                         mol_type = genomic DNA
                         organism = Lactuca sativa
SEQUENCE: 31
aggaatgtat aaatactctg aca                                           23

SEQ ID NO: 32            moltype = DNA  length = 20
FEATURE                  Location/Qualifiers
misc_feature             1..20
                         note = Reverse primer
source                   1..20
                         mol_type = genomic DNA
                         organism = Lactuca sativa
SEQUENCE: 32
gcctagcaac taatgtatct                                               20
```